(12) United States Patent
Tao

(10) Patent No.: US 9,550,760 B2
(45) Date of Patent: Jan. 24, 2017

(54) SUBSTITUTED INDOL-5-OL DERIVATIVES AND THEIR THERAPEUTIC APPLICATIONS

(71) Applicant: NantBioScience, Inc., Culver City, CA (US)

(72) Inventor: Chunlin Tao, Newport Coast, CA (US)

(73) Assignee: NantBioScience, Inc., Culver City, CA (US)

( * ) Notice: Subject to any disclaimer, the term of this patent is extended or adjusted under 35 U.S.C. 154(b) by 0 days.

(21) Appl. No.: 14/775,434

(22) PCT Filed: Mar. 17, 2014

(86) PCT No.: PCT/US2014/030167
§ 371 (c)(1),
(2) Date: Sep. 11, 2015

(87) PCT Pub. No.: WO2014/145403
PCT Pub. Date: Sep. 18, 2014

(65) Prior Publication Data
US 2016/0016945 A1  Jan. 21, 2016

Related U.S. Application Data

(60) Provisional application No. 61/852,309, filed on Mar. 15, 2013.

(51) Int. Cl.
| C07D 403/14 | (2006.01) |
| A61K 31/506 | (2006.01) |
| C07D 413/14 | (2006.01) |
| A61K 31/5377 | (2006.01) |
| A61K 31/541 | (2006.01) |
| C07D 401/14 | (2006.01) |

(52) U.S. Cl.
CPC ........... *C07D 413/14* (2013.01); *A61K 31/506* (2013.01); *A61K 31/5377* (2013.01); *A61K 31/541* (2013.01); *C07D 401/14* (2013.01); *C07D 403/14* (2013.01)

(58) Field of Classification Search
CPC ... C07D 401/14; C07D 403/14; C07D 413/14; A61K 31/506; A61K 31/5377; A61K 31/541
USPC ...................... 544/295, 317; 514/252.19, 272
See application file for complete search history.

(56) References Cited

U.S. PATENT DOCUMENTS

| 5,916,596 | A  | 6/1999  | Desai et al.   |
| 6,506,405 | B1 | 1/2003  | Desai et al.   |
| 6,537,579 | B1 | 3/2003  | Desai et al.   |
| 2004/0049032 | A1 | 3/2004  | Charrier et al. |
| 2007/0254896 | A1 | 11/2007 | Butler et al.  |

FOREIGN PATENT DOCUMENTS

| JP | 2006-501176 A | 1/2006 |
| JP | 2008-526759 A | 7/2008 |
| JP | 2009-514887 A | 4/2009 |
| JP | 2010-524952 A | 7/2010 |
| WO | WO 00/47212 A1 | 8/2000 |
| WO | WO 2004/009542 A2 | 1/2004 |
| WO | WO 2007/035309 A1 | 3/2007 |
| WO | WO 2009/036055 A1 | 3/2009 |
| WO | WO 2014/071378 A1 | 5/2014 |

OTHER PUBLICATIONS

Bundgaard, Design of Prodrugs, p. 1, 1985.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. I: Principles and Practice, pp. 975-977, 1995.*
Silverman, Prodrugs and Drug Delivery Systems, The Organic Chemistry of Drug Design and Drug Action, pp. 352-399, 1992.*
Ulrich, Crystallization, Kirk-Othmer Encyclopedia of Chemical Technology, pp. 1-7, 2002.*
Vippagunta et al., Crystalline Solids, Advanced Drug Delivery Reviews 48 (2001), pp. 3-26.*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1995.*
Berge et al., *J. Pharmaceutical Sci.*, 66(1), 1-19 (Jan. 1977).
Bhide et al., *J. Med. Chem.*, 49(7), 2143-2146 (Apr. 6, 2006).
Garcia-Bustos et al., *EMBO J.*, 13(10), 2352-2361 (1994).
Gould, Philip L., *Int. J. Pharmaceutics*, 33, 201-217 (1986).
Hanks et al., *FASEB J.*, 9, 576-596 (1995).
Knighton et al., *Science*, 253(5018),407-414 (Jul. 26, 1991).
Schlessinger et al., *Neuron*, 9, 383-391 (Sep. 1992).
Shoemaker, Robert H., *Nat. Rev. Cancer*, 6(10), 813-823 (Oct. 2006).
Yamagishi et al., *Org. Lett*, 10(12), 2369-2372 (2008).
Japanese Patent Application No. 503340/2016, Office Action (Oct. 18, 2016).

* cited by examiner

*Primary Examiner* — Deepak Rao
(74) *Attorney, Agent, or Firm* — Leydig, Voit & Mayer, Ltd.

(57) ABSTRACT

The present invention relates generally to the use of compounds to treat a variety of disorders, diseases and pathologic conditions and more specifically to the use of substituted indol-5-ol derivatives to modulate protein kinases and for treating protein kinase-mediated diseases.

40 Claims, 78 Drawing Sheets

| Targeted Kinase | IC$_{50}$ (nM) |
|---|---|
| Abl(h) | 0.7 |
| Abl(t315I) (h) | 0.9 |
| cKit(h) | 411 |
| cKit(D816H)(h) | 6 |
| cKit(V560G)(h) | 0.7 |
| cKit(V654A)(h) | 26 |
| PDGFRa(h) | 276 |
| PDGFRa (D842V)(h) | 12 |
| PDGFRa (V561D)(h) | 6 |

FIG. 2

| Cancer | Cell line | NTW-3475 |
|---|---|---|
| Leukemia | CCRF-CEM | <10 |
| | K562 | <10 |
| Non-Small Cell Lung Cancer | HOP-92 | <10 |
| | NCI-H226 | <10 |
| Colon Cancer | COLO 205 | <10 |
| | HCT-116 | <10 |
| | KM12 | <10 |
| | SW620 | <10 |
| CNS Cancer | SNB-75 | 17 |
| Melanoma | LOX IMVI | 14 |
| Ovarian Cancer | IGROVI | 58 |
| Renal Cancer | A498 | <10 |
| | RXF393 | 18 |
| Breast Cancer | MCF7 | <10 |
| | HS 578T | 13 |
| | MDA-MB-498 | 26 |

FIG. 3

| Cancer | Cell Line | Kinase status | Proliferation GI$_{50}$ (nM) | Phosphorylation EC$_{50}$ (nM) |
|---|---|---|---|---|
| CML | K562 | Bcr-Abl | 0.81 | 5.00 |
| AML | MV4.11 | Flt3(ITD) | 0.86 | 0.26 |
| Thyroid | TT | Ret (C634W) | 2.00 | - |
| Endometrial | AN3CA | FGFR2 (N549K) | 3.00 | - |
| Gastric | KATO III | FGFR2 amp | 0.33 | - |
| Breast | MDA-MB134 | FGFR1 amp | 0.80 | - |
| Pancreatic | MiaPaca2 | Ras mutant | 29 | 46 (pERK) |
| | Panc-1 | Ras mutant | 256 | - |

FIG. 20

| Cancer | Model | Dose (mg/kg)/route | Dosing Schedule | Efficacy T/C% |
|---|---|---|---|---|
| CML | K562 | 50/PO | QDx10 | -99.1 |
| AML | MV4. 11 | 50/PO | QDx10 | -100 |
| Thyroid cancer | TT | 100/PO | QDx30 | -2.7 |
| Endometrial Adenocarcinoma | AN3CA | 100/PO | QDx14 | -89.5 |
| Pancreatic Carcinoma | MiaPaca2 | NTW-3475, 75/PO | QDx20 | 25.5 |
| | | ABX, 20/IV | QDx3 | 49.4 |
| | | NTW-3475+ABX 75/PO + 20/IV | QDx20+QWx3 | -70.1 |

FIG. 21

| Targeted Kinase | IC$_{50}$ (nM) | |
|---|---|---|
| | Kinase | Cell-based |
| ABL | 1.0 | - |
| AURORA-A | 7 | - |
| AURORA-B | 10 | - |
| ARG | 0.5 | - |
| AXL | 7 | - |
| cSRC | 4 | - |
| FLT3 | 9 | - |
| VEGFR1 (FLT1) | 2 | 30.6 |
| VEGFR2 (KDR) | 11 | 6.3 |
| VEGFR3 (FLT4) | 0.9 | 6.2 |
| FMS | 5 | - |
| FGFR1 | 0.6 | 1.2 |
| FGFR2 | 2 | 0.4 |
| FGFR3 | 0.7 | 0.2 |
| FGFR4 | 21 | 12.3 |
| JAK2 | 5 | - |
| JAK3 | 9 | - |
| MER | 3 | - |
| RET | 3 | 14.4 |
| TIE2 | 9 | 17.1 |
| TRKA | 7 | - |
| TRKB | 7 | - |
| Parental BaF3 | - | >100 |

Chronic Myeloid Leukemia (CML)

Acute Myeloid Leukemia (AML)

Cancers: Endometrial Bladder, Gastric Breast, Lung, Colon, etc.

Medullary Thyroid Carcinoma (MTC) NSCLC

FIG. 22

| Targeted Kinase | $IC_{50}$ (nM) |
|---|---|
| Abl(h) | 1.0 |
| Abl(T315I)(h) | 1.0 |
| Abl(H396P)(h) | 0.2 |
| Abl(M315I)(h) | 0.9 |
| Abl(Q252H)(h) | 0.4 |
| Abl(Y253F)(h) | 0.6 |
| cKit(h) | 461 |
| cKit(D816H)(h) | 3 |
| cKit(V560G)(h) | 4 |
| cKit(V654A)(h) | 8 |
| PDGFRa(h) | 203 |
| PDGFRa(D842V)(h) | 7 |
| PDGFRa(V561D)(h) | 1.0 |

FIG. 23

| Targeted Kinase | $IC_{50}$ (nM) |
|---|---|
| Abl(h) | 1.0 |
| Abl(T315I)(h) | 1.0 |
| Abl(H396P)(h) | 0.2 |
| Abl(M351T)(h) | 0.9 |
| Abl(Q252H)(h) | 0.4 |
| Abl(Y253F)(h) | 0.6 |

FIG. 24

(60 NCI's Cancer Cell Lines, GI50: nM)

| Cancer | Cell line | NTW-3475 |
|---|---|---|
| Leukemia | CCRF-CEM | <10 |
| | K562 | <10 |
| Non-Small Cell Lung Cancer | HOP-92 | <10 |
| | NCI-H226 | <10 |
| Colon Cancer | COLO 205 | <10 |
| | HCT-116 | <10 |
| | KM12 | <10 |
| | SW620 | <10 |
| CNS Cancer | SNB-75 | 17 |
| Melanoma | LOX IMVI | 14 |
| Ovarian Cancer | IGROVI | 58 |
| Renal Cancer | A498 | <10 |
| | RXF393 | 18 |
| Breast Cancer | MCF7 | <10 |
| | HS 578T | 13 |
| | MDA-MB-498 | 26 |

FIG. 25

| Cancer | Cell Line | Kinase status | Proliferation GI$_{50}$ (nM) | Phosphorylation EC$_{50}$ (nM) |
|---|---|---|---|---|
| CML | K562 | Bcr-Abl | 0.67 | 4 |
| AML | MV4.11 | Flt3(ITD) | 0.44 | 1 |
| Thyroid | TT | Ret (C634W) | 0.60 | 1 |
| Endometrial | AN3CA | FGFR2 (N549K) | 0.82 | 0.46 |
| Gastric | KATO III | FGFR2 amp | 0.09 | ND |
| Breast | MDA-MB134 | FGFR1 amp | 4.00 | ND |
| Pancreatic | MiaPaca2 | Ras mutant | 17 | 9 (pERK) |
| Pancreatic | Panc-1 | Ras mutant | 55 | ND |

FIG. 26

| Cancer | Model | Dose (mg/kg)/route | Dosing Schedule | Efficacy T/C% |
|---|---|---|---|---|
| CML | K562 | 50/PO | QDx10 | -98.9 |
| AML | MV4. 11 | 50/PO | QDx10 | -100 |
| | | 20/IV | QDx10 | -100 |
| Thyroid cancer | TT | 100/PO | QDx30 | -50 |
| Endometrial Adenocarcinoma | AN3CA | 100/PO | QDx14 | -93.4 |
| Pancreatic Carcinoma | | NTW-3456, 75/PO | QDx20 | 42.6 |
| | | ABX, 20/IV | QDx3 | 49.4 |
| | | NTW-3456+ABX 75/PO + 20/IV | QDx20+QWx3 | -88.2 |
| | Panc-1 | NTW-3456, 75/PO | QDx15 | 33.8 |
| | | ABX, 20/IV | QDx3 | 4.3 |
| | | NTW-3456+ABX 75/PO + 20/IV | QDx15+QWx3 | -91.3 |

FIG. 50

|  | NTW-3456 | | NTW-3475 | |
|---|---|---|---|---|
|  | MiaPaca2 | BxPC3 | MiaPaca2 | BxPC3 |
| pERK | 9 | 259 | 46 | 322 |
| pAkt | 458 | >1μM | 25 | 308 |
| GI$_{50}$ | 66 | 469 | 58 | 242 |

FIG. 53

|  | K562 cells (nM) | | |
|---|---|---|---|
|  | Proliferation ($GI_{50}$) | phospho-CrkL ($EC_{50}$) | Caspsae 3/7 Inhibition ($EC_{50}$) |
| NTW-3456 | 0.7 | 4 | 4 |
| Nilotinib | 2 | 142 | 18 |
| Ponatinib | 0.2 | 13 | 1 |
| Sunitinib | >100 | >1000 | >100 |
| Imatinib | 37 | ND | 255 |

FIG. 57

| ID | IC$_{50}$ (nM) | | | | |
|---|---|---|---|---|---|
| | Parental | FGFR1 | FGFR2 | FGFR3 | FGFR4 |
| NTW-3456 | >100 | 1.2 | 0.4 | 0.2 | 12.3 |

FIG. 59

☐ Treated Control, QD X 5, Day 12 (20,30), 100% DMSO
○ NSC S764410D, 50.0 mg/kg/dose IP, QD X 5, Day 12 (20,30): 4 Drug Deaths
△ NSC S764410D, 60.0 mg/kg/dose IP, Q2D X 3, Day 12 (20)
◇ NSC S764410D, 60.0 mg/kg/dose IP, Q4D X 3, Day 12 (24)
▭ NSC S764410D, 50.0 mg/kg/dose IV, Q2D X 3, Day 12

Note: NSC S764410D = Compound 53

SUBSTITUTED INDOL-5-OL DERIVATIVES AND THEIR THERAPEUTIC APPLICATIONS

PRIORITY CLAIM

This application is a national phase of International Patent Application No. PCT/US2014/030167, filed Mar. 17, 2014, which claims the benefit of U.S. Provisional Patent Application 61/852,309 (Filed on Mar. 15, 2013), both of which are hereby incorporated by reference in their entireties.

FIELD OF THE INVENTION

The present invention relates generally to the use of compounds to treat a variety of disorders, diseases and pathologic conditions and more specifically to the use of substituted indol-5-ol derivatives to modulate protein kinases and for treating protein kinase-mediated diseases.

BACKGROUND OF THE INVENTION

Protein kinases constitute a large family of structurally related enzymes that are responsible for the control of a variety of signal transduction processes within the cell. Protein kinases, containing a similar 250-300 amino acid catalytic domain, catalyze the phosphorylation of target protein substrates.

The kinases may be categorized into families by the substrates in the phosphorylate (e.g., protein-tyrosine, protein-serine/threonine, lipids, etc.). Tyrosine phosphorylation is a central event in the regulation of a variety of biological processes such as cell proliferation, migration, differentiation and survival. Several families of receptor and non-receptor tyrosine kinases control these events by catalyzing the transfer of phosphate from ATP to a tyrosine residue of specific cell protein targets. Sequence motifs have been identified that generally correspond to each of these kinase families [Hanks et al., FASEB J., (1995), 9, 576-596; Knighton et al., Science, (1991), 253, 407-414; Garcia-Bustos et al., EMBO J., (1994), 13:2352-2361). Examples of kinases in the protein kinase family include, without limitation, abl, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRafl, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, Tie, Tie-2, TRK, Yes, and Zap70.

Studies indicated that protein kinases play a central role in the regulation and maintenance of a wide variety of cellular processes and cellular function. For example, kinase activity acts as molecular switches regulating cell proliferation, activation, and/or differentiation. Uncontrolled or excessive kinase activity has been observed in many disease states including benign and malignant proliferation disorders as well as diseases resulting from inappropriate activation of the immune system (autoimmune disorders), allograft rejection, and graft vs host disease.

It is reported that many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. In addition, endothelial cell specific receptor PTKs, such as VEGF-2 and Tie-2, mediate the angiogenic process and are involved in supporting the progression of cancers and other diseases involving uncontrolled vascularization. Accordingly, there has been a substantial effort in medicinal chemistry to find protein kinase inhibitors that are effective as therapeutic agents.

Many cancers are characterized by disruptions in cellular signaling pathways that lead to uncontrolled growth and proliferation of cancerous cells. Receptor tyrosine kinases (RTKs) play a crucial role in these signaling pathways, transmitting extracellular molecular signals into cytoplasm and/or nucleus of a cell. RTKs are transmembrane proteins that generally include an extracellular ligand-binding domain, a membrane-spanning domain and a catalytic cytoplasmic tyrosine kinase domain. The binding of ligand to the extracellular portion is believed to promote dimerization, resulting in trans-phosphorylation and activation of the intracellular tyrosine kinase domain (Schlessinger et al. Neuron 1992; 9:383-391).

Considering the lack of currently available treatment options for the majority of the conditions associated with protein kinases, there is still a great need for new therapeutic agents that inhibit these protein targets.

SUMMARY OF THE INVENTION

Accordingly, it is an objective of the present invention to provide an antitumor agent comprising a substituted indol-5-ol derivative as described in formula (I), pharmaceutically-acceptable formulations thereof, methods for making novel compounds and compositions for using the compounds. The compounds and compositions comprising the compounds in formula (I) have utility in treatment of a variety of diseases.

The combination therapy described herein may be provided by the preparation of the substituted indol-5-ol derivatives of formula (I) and the other therapeutic agent as separate pharmaceutical formulations followed by the administration thereof to a patient simultaneously, semi-simultaneously, separately or over regular intervals.

The present invention provides methods of use for certain chemical compounds such as kinase inhibitors for treatment of various diseases, disorders, and pathologies, for example, cancer, and vascular disorders, such as myocardial infarction (MI), stroke, or ischemia. The triazine compounds described in this invention may block the enzymatic activity of some or many of the members of the Aurora kinase family, in addition to blocking the activity of other receptor and non-receptor kinase. Such compounds may be beneficial for treatment of the diseases where disorders affect cell motility, adhesion, and cell cycle progression, and in addition, diseases with related hypoxic conditions, osteoporosis and conditions, which result from or are related to increases in vascular permeability, inflammation or respiratory distress, tumor growth, invasion, angiogenesis, metastases and apoptosis.

BRIEF DESCRIPTION OF THE DRAWINGS

FIG. 2 depicts the kinase inhibitory activity of NTW-3475 against a wide range of mutant kinases.

FIG. 3 depicts the in vitro antiproliferation activity of NTW-3475.

FIG. 20 summarizes NTW-3475's in vitro activity.

FIG. 21 summarizes the in vivo (xenografts) pharmacology of NTW-3475.

FIG. 22 depicts the kinase inhibitory activity of NTW-3456 (also referred to herein as compound 87) against a wide range of kinases in a wide range of cancers.

FIG. 23 depicts the kinase inhibitory activity of NTW-3456 against a wide range of mutant kinases.

FIG. 24 depicts the kinase inhibitory activity of NTW-3456 against mutant abl kinases.

FIG. 25 depicts the in vitro antiproliferation activity of NTW-3456.

FIG. 26 depicts exemplary antiproliferative and phosphorylation inhibition activity for NTW-3456.

(FIGS. 27-29 and 30-32 are separate experiments).

FIG. 50 summarizes the in vivo pharmacology of NTW-3456.

FIG. 53 summarizes the inhibitory activities of NTW-3456 and NTW-3475.

FIG. 57 summarizes the inhibitory activities of NTW-3456.

FIG. 59 summarizes the inhibitory activities of NTW-3456 on Fibroblast Growth Factor Receptors.

DETAILED DESCRIPTION OF THE INVENTION

Figure 1:
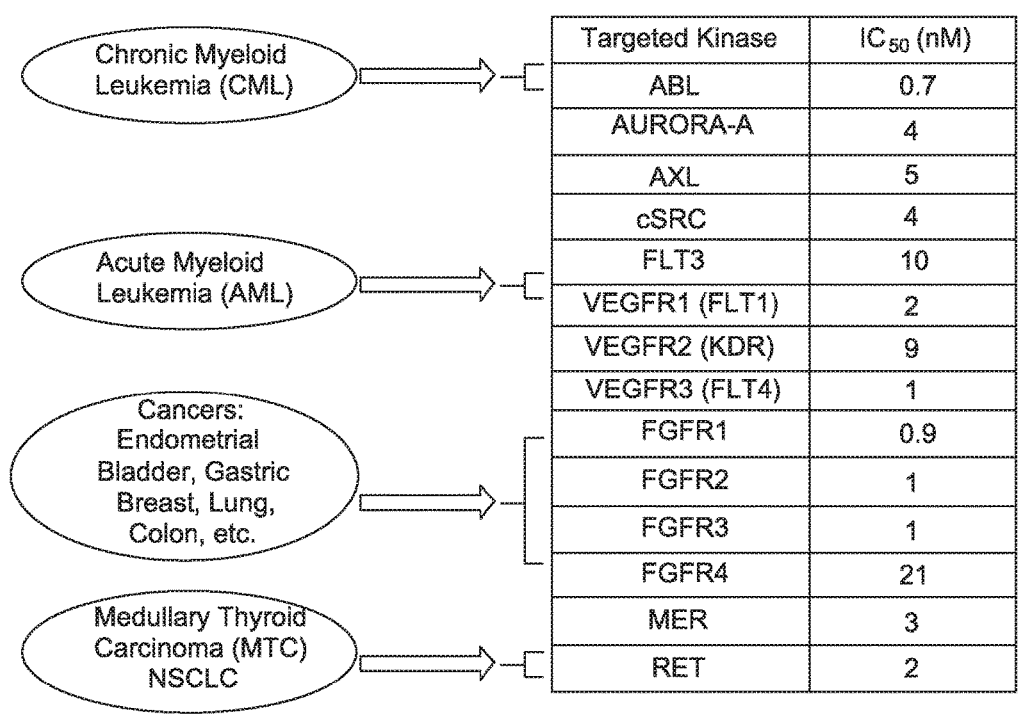
FIG. 1 depicts the kinase inhibitory activity of NTW-3475 (also referred to herein as compound 81) against a wide range of kinases from a wide range of diseases.

The present invention is related to compounds having general Formula (I)

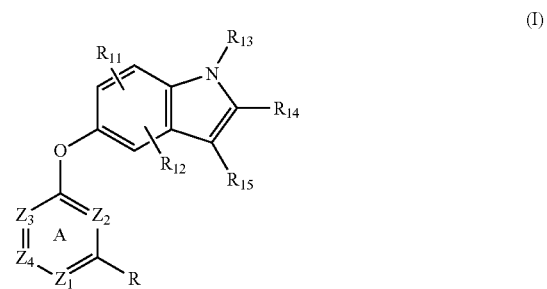

or a pharmaceutically acceptable salt thereof, wherein:
Z1, Z2, Z3, and Z4 is independently N or as described below;
R is selected from:
(i) hydrogen, amino, alkyl amino;
(ii) $C_1$-$C_6$ alkyl, $C_2$-$C_6$ alkenyl, $C_2$-$C_6$ alkynyl;
(iii) K—Ar.

Ar represents heteroaryl or aryl, each of which is substituted with from 0 to 4 substituents independently chosen from:
(1) halogen, hydroxy, amino, amide, cyano, —COOH, —$SO_2NH_2$, oxo, nitro and alkoxycarbonyl; and
(2) $C_1$-$C_6$ alkyl, $C_1$-$C_6$ alkoxy, $C_3$-$C_{10}$ cycloalkyl, $C_2$-$C_6$ alkenyl, $C2$-$C_6$ alkynyl, $C_2$-$C_6$ alkanoyl, $C_1$-$C_6$ haloalkyl, $C_1$-$C_6$ haloalkoxy, mono- and di-($C_1$-$C_6$ alkyl)amino, $C_1$-$C_6$ alkylsulfonyl, mono- and di-($C_1$-$C_6$ alkyl) sulfonamido and mono- and di-($C_1$-$C_6$ alkyl) aminocarbonyl; phenyl$C_0$-$C_4$ alkyl and (4- to 7-membered heterocycle) $C_0$-$C_4$ alkyl, each of which is substituted with from 0 to 4 secondary substituents independently chosen from halogen, hydroxy, cyano, oxo, imino, alkyl, $C_1$-$C_4$ alkoxy and $C_1$-$C_4$ haloalkyl.

K is selected from
a) O, S, SO, $SO_2$;
b) $(CH_2)m$, m=0-3, —$O(CH_2)p$, p=1-3, —$S(CH_2)p$, p=1-3, —$N(CH_2)p$, p=1-3, —$(CH_2)pO$, p=1-3;
c) NR1

R1 represents hydrogen, alkyl, cycloalkyl, alkenyl, alkynyl, alkylthio, aryl, arylalkyl.

(iv) groups of the formula (Ia):

wherein:

R$_2$ represents hydrogen, C$_1$-C$_4$ alkyl, oxo;

X is CH, when R$_3$ is hydrogen; or X—R$_3$ is O; or X is N, R$_3$ represents groups of hydrogen, C$_1$-C$_6$ alkyl, C$_2$-C$_6$ alkenyl, C$_2$-C$_6$ alkynyl, C$_3$-C$_{10}$ aryl or heteroaryl, (C$_3$-C$_7$cycloalkyl)C$_1$-C$_4$ alkyl, C$_1$-C$_6$ haloalkyl, C$_1$-C$_6$ alkoxy, C$_1$-C$_6$ alkylthio, C$_2$-C$_6$ alkanoyl, C$_1$-C$_6$ alkoxycarbonyl, C$_2$-C$_6$ alkanoyloxy, mono- and di-(C$_3$-C$_8$ cycloalkyl)aminoC$_0$-C$_4$alkyl, (4- to 7-membered heterocycle)C$_0$-C$_4$alkyl, C$_1$-C$_6$ alkylsulfonyl, mono- and di-(C$_1$-C$_6$ alkyl) sulfonamido, and mono- and di-(C$_1$-C$_6$ alkyl)aminocarbonyl, each of which is substituted with from 0 to 4 substituents independently chosen from halogen, hydroxy, cyano, amino, —COOH and oxo.

R$_{11}$ and R$_{12}$ are independently selected from: Hydrogen, F, Cl, Br, CN, C$_1$-C$_4$ alkyl, C$_1$-C$_6$ alkoxy.

R$_{13}$, R$_{14}$ and R$_{15}$ are independently selected from Hydrogene, C$_1$-C$_4$ alkyl, C$_2$-C$_6$ alkenyl, CF$_3$, CF$_2$H, CFH$_2$, C$_2$-C$_6$ alkynyl, C$_3$-C$_{10}$ aryl or heteroaryl, C$_1$-C$_6$ alkoxy, C$_1$-C$_6$ alkylthio, C$_2$-C$_6$ alkanoyl, C$_1$-C$_6$ alkoxycarbonyl, C$_2$-C$_6$ alkanoyloxy.

Ring A is selected from the group consisting of:

a
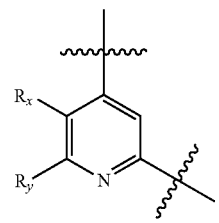

b
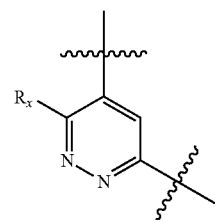

c
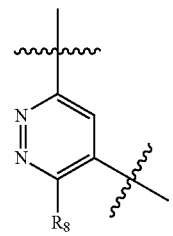

d
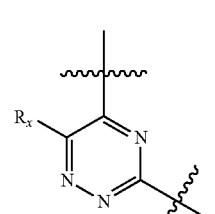

e

f
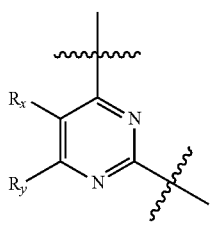

g
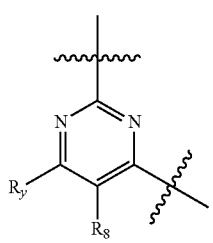

h

i
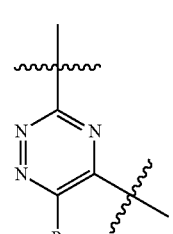

R$_x$ and R$_y$—are independently selected from T-R$_4$, or R$_x$ and —R$_y$ are taken together with their intervening atoms to form a fused, unsaturated or partially unsaturated, 5-7 membered ring having 0-3 ring heteroatoms selected from oxygen, sulfur, or nitrogen, wherein any substitutable carbon on said fused ring formed by R$_x$ and R$_y$ is substituted by oxo or T-R$_4$, and any substitutable nitrogen on said ring formed by R$_x$ and R$_y$ is substituted by R$_5$;

T is a valence bond or a C$_{1-4}$ alkylidene chain;

R4 is selected from —R6, -halo, —OR6, —C(=O)R6, —CO$_2$R6, —COCOR6, —COCH$_2$COR6, —NO$_2$, —CN, —S(O)R6, —S(O)$_2$R6, —SR6, —N(R5)$_2$, —CON(R7)$_2$, —SO$_2$N(R7)$_2$, —OC(=O)R6, —N(R7)COR6, —N(R7)CO$_2$ (optionally substituted C1-6 aliphatic), —N(R5)N(R5)$_2$, —C=NN(R5)$_2$, —C=N—OR6, —N(R7)CON(R7)$_2$, —N(R7) SO$_2$N(R7)$_2$, —N(R4) SO$_2$R6, or —OC(=O)N(R7)$_2$;

Each $R_6$ is independently selected from hydrogen or an optionally substituted group selected from $C_{1-6}$ aliphatic, $C_{6-10}$ aryl, a heteroaryl ring having 5-10 ring atoms, or a heterocyclyl ring having 5-10 ring atoms;

Each $R_5$ is independently selected from —$R_7$, —$COR_7$, —$CO_2(C_{1-6}$ aliphatic), —$CON(R_7)_2$, or —$SO_2R_7$, or two $R_5$ on the same nitrogen are taken together to form a 5-8 membered heterocyclyl or heteroaryl ring;

Each $R_7$ is independently selected from hydrogen or an optionally substituted $C_{1-6}$ aliphatic group, or two $R_7$ on the same nitrogen are taken together with the nitrogen to form a 5-8 membered heterocyclyl or heteroaryl ring;

$R_8$ is selected from —$R_6$, halo, —$OR_6$, —$C(=O)R_6$, —$CO_2R_6$, —$COCOR_6$, —$NO_2$, —$CN$, —$S(O)R_6$, —$SO_2R_6$, —$SR_6$, —$N(R_4)_2$, —$CON(R_5)_2$, —$SO_2N(R_5)_2$, —$OC(=O)R_6$, —$N(R_5)COR_6$, —$N=(R_5)CO_2$ (optionally substituted $C_{1-6}$ aliphatic), —$N(R_5)N(R_5)_2$, —$C=NN(R_5)_2$, —$C=N—OR_6$, —$N(R_5)CON(R_5)_2$, —$N(R_5)SO_2N(R_5)_2$, —$N(R_5)SO_2R_6$, or —$OC(=O)N(R_5)_2$.

$R_x$ and $R_y$ (at positions $Z_3$ and $Z_4$, respectively) may be taken together to form a fused ring, providing a bicyclic ring system containing Ring A. alternatively, R and $Z_2$ also may be taken together to form a fused ring, providing a bicyclic ring system containing Ring A. Preferred $R_x/R_y$ and $R/Z_2$ rings include a 5-, 6-, or 7-, membered unsaturated or partially unsaturated ring having 0-2 heteroatoms, wherein said $R_x/R_y$ and $R/Z_2$ ring is optionally substituted. Examples of Ring A systems are shown below by compounds I-1 through I-26, wherein $Z_1$ to $Z_4$ is nitrogen or $C(R_8)$.

I-1
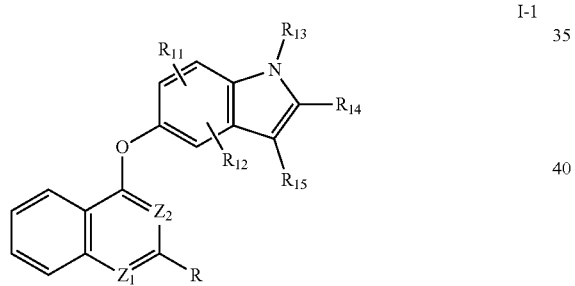

I-2
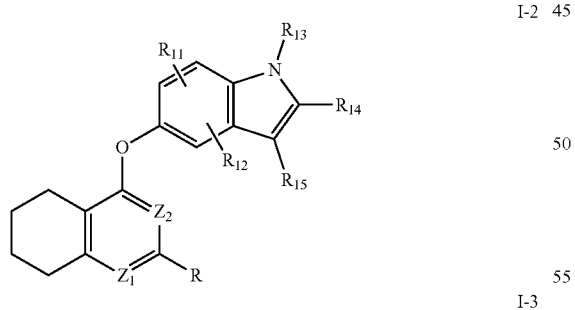

I-3
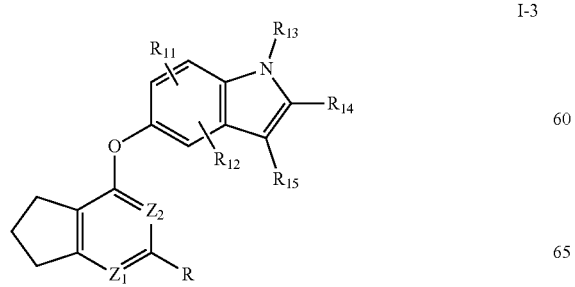

I-4
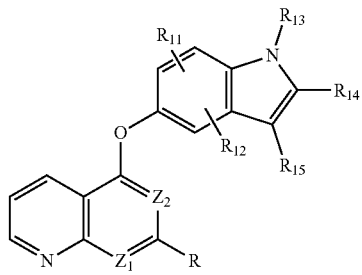

I-5
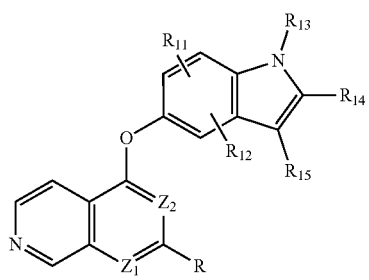

I-6
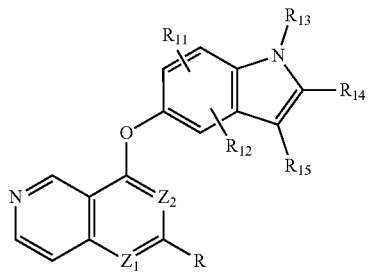

I-7
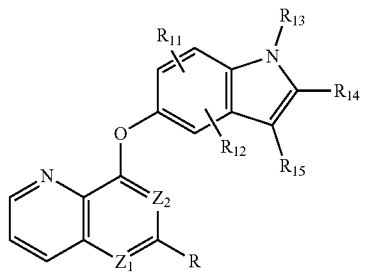

I-8
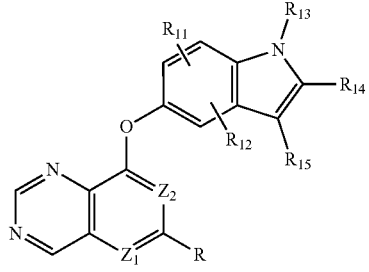

I-9
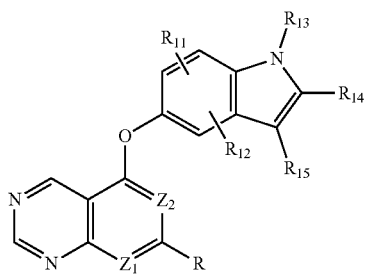
I-10
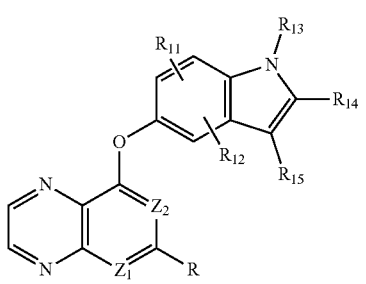
I-11
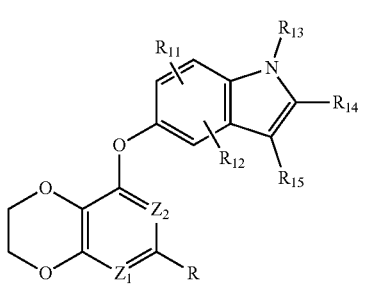
I-12
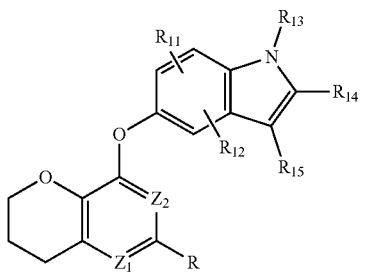
I-13
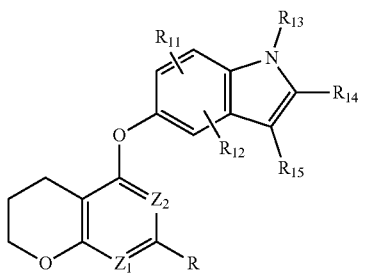
I-14
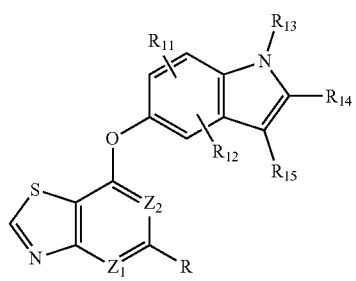
I-15
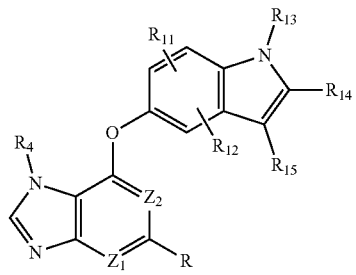
I-16
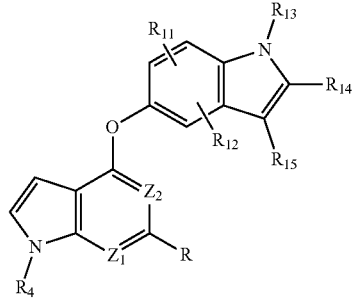
I-17
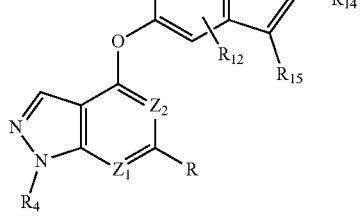
I-18
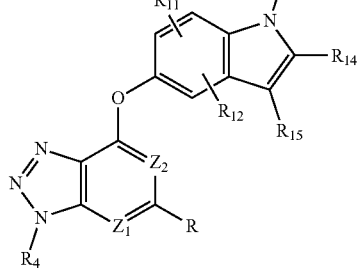

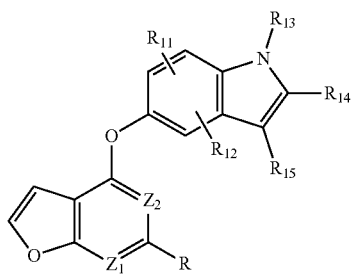

I-19

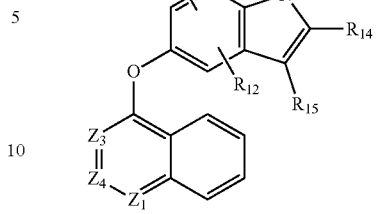

I-24

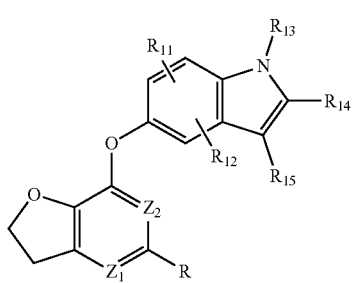

I-20

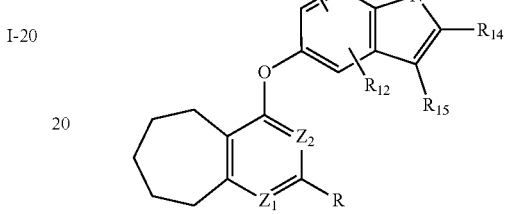

I-25

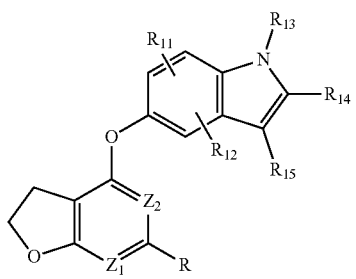

I-21

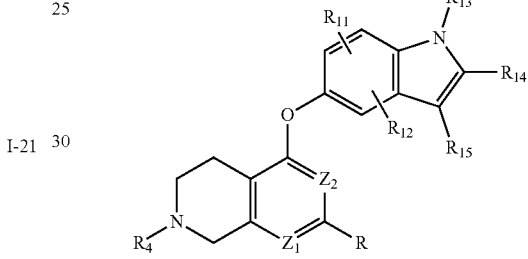

I-26

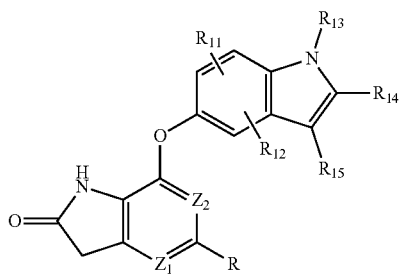

I-22

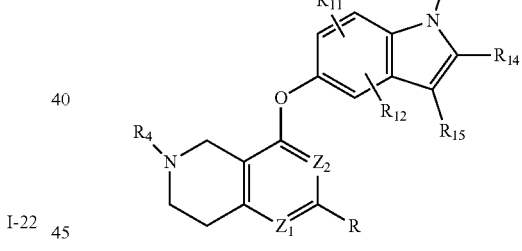

I-27

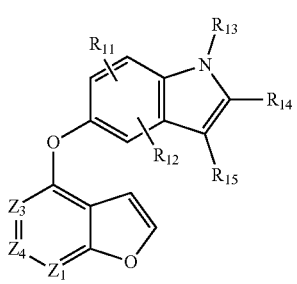

I-23

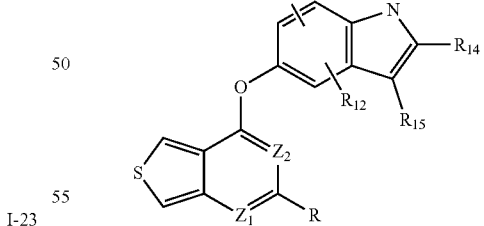

I-28

Preferred bicyclic Ring A systems include I-1, I-2, I-3, I-4, I-5, I-6, I-7, I-8, I-14, I-15 I-16, I-17, I-19, I-23 and I-24, more preferably I-1, I-2, I-3, I-5, I-8, I-14, I-15 I-16, I-17, I-19, I-23 and I-24, and most preferably I-1, I-14, I-16, and I-19.

In the monocyclic Ring A system, preferred $R^x$ groups, when present, include hydrogen, alkyl- or dialkylamino, acetamido, or a $C_{1-4}$ aliphatic group such as methyl, ethyl, cyclopropyl, isopropyl or t-butyl. Preferred $R^y$ groups, when present, include T-$R_4$ wherein T is a valence bond or a methylene, and R₄ is —R₆, —N(R₅)₂, or —OR₆. Examples of preferred R^y include 2-pyridyl, 4-pyridyl, piperidinyl, methyl, ethyl, cyclopropyl, isopropyl, t-butyl, alkyl- or dialkylamino, acetamido, optionally substituted phenyl such as phenyl or halo-substituted phenyl, and methoxymethyl.

In the bicyclic Ring A system, the ring formed when R^x and R^y are taken together may be substituted or unsubstituted. Suitable substituents include —R₆, halo, —OR₆, —C(=O)R₆, —CO₂R₆, —COCOR₆, —NO₂, —CN, —S(O)R₆, —SO₂R₆, —SR₆, —N(R₅)₂, —CON(R₅)₂, —SO₂N(R₅)₂, —OC(=O)R₆, —N(R₄)COR₆, —N(R₅)CO₂ (optionally substituted C₁₋₆ aliphatic), —N(R₅)N(R₅)₂, —C=NN(R₅)₂, —C=N—OR₆, —N(R₅)CON(R₅)₂, —N(R₅)SO₂N(R₅)₂, —N(R₅)SO₂R₆ or —OC(=O)N(R₅)₂, wherein R and R⁵ are as defined above. Preferred R^x/R^y ring substituents include -halo, —R₆, —OR₆, —COR_E, —CO₂R₆, —CON(R₅)₂, —CN, or —N(R₅)₂ wherein R6 is hydrogen or an optionally substituted C₁₋₆ aliphatic group.

An embodiment that is particularly useful for treating kinase-mediated diseases relates to compounds of formula IIa, IIb and IIc:

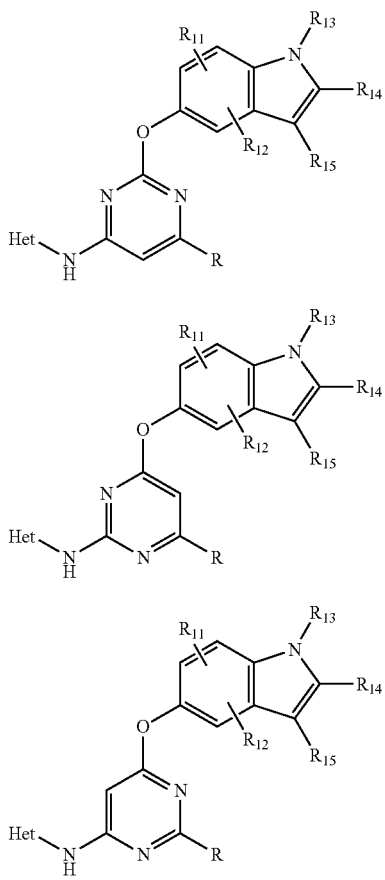

or a pharmaceutically acceptable derivative or prodrug thereof, wherein;

R is selected from:
(i) hydrogen, amino, alkyl amino;
(ii) C₁-C₆ alkyl, C₂-C₆ alkenyl, C₂-C₆ alkynyl;
(iii) K—Ar.

Ar represents heteroaryl or aryl, each of which is substituted with from 0 to 4 substituents independently chosen from:

(1) halogen, hydroxy, amino, amide, cyano, —COOH, —SO₂NH₂, oxo, nitro and alkoxycarbonyl; and
(2) C₁-C₆ alkyl, C₁-C₆ alkoxy, C₃-C₁₀cycloalkyl, C₂-C₆ alkenyl, C₂-C₆ alkynyl, C₂-C₆ alkanoyl, C₁-C₆ haloalkyl, C₁-C₆ haloalkoxy, mono- and di-(C₁-C₆ alkyl)amino, C₁-C₆ alkylsulfonyl, mono- and di-(C₁-C₆ alkyl) sulfonamido and mono- and di-(C₁-C₆ alkyl) aminocarbonyl; phenyl C₀-C₄ alkyl and (4- to 7-membered heterocycle) C₀-C₄ alkyl, each of which is substituted with from 0 to 4 secondary substituents independently chosen from halogen, hydroxy, cyano, oxo, imino, C₁-C₄ alkyl, C₁-C₄ alkoxy and C₁-C₄ haloalkyl.

K is selected from
a) O, S, SO, SO₂;
b) (CH₂)m, m=0-3, —O(CH₂)p, p=1-3, —S(CH₂)p, p=1-3, —N(CH₂)p, p=1-3, —(CH₂)pO, p=1-3;
c) NR1

R₁ represents hydrogen, alkyl, cycloalkyl, alkenyl, alkynyl, alkylthio, aryl, arylalkyl.

(iv) groups of the formula (Ia):

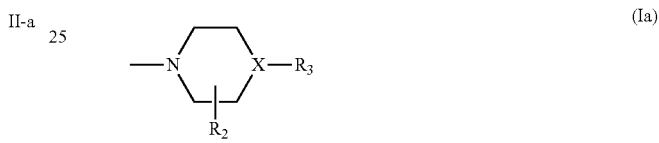

wherein:
R₂ represents hydrogen, C₁-C₄ alkyl, oxo;
X is CH, when R₃ is hydrogen; or X—R₃ is O; or X is N, R₃ represents groups of hydrogen, C₁-C₆ alkyl, C₂-C₆ alkenyl, C₂-C₆ alkynyl, C₃-C₁₀aryl or heteroaryl, (C₃-C₇cycloalkyl)C₁-C₄alkyl, C₁-C₆ haloalkyl, C₁-C₆ alkoxy, C₁-C₆ alkylthio, C₂-C₆ alkanoyl, C₁-C₆ alkoxycarbonyl, C₂-C₆ alkanoyloxy, mono- and di-(C₃-C₈ cycloalkyl)aminoC₀-C₄alkyl, (4- to 7-membered heterocycle)C₀-C₄alkyl, C₁-C₆ alkylsulfonyl, mono- and di-(C₁-C₆ alkyl) sulfonamido, and mono- and di-(C₁-C₆alkyl)aminocarbonyl, each of which is substituted with from 0 to 4 substituents independently chosen from halogen, hydroxy, cyano, amino, —COOH and oxo.

Het is selected from any heterocycle, which is substituted with from 0 to 4 substituents independently chosen from:
(i) C1-C6 alkyl, C2-C6 alkenyl, C2-C6 alkynyl;
(ii) halogen, hydroxy, amino, amide, cyano, —COOH, —SO₂NH₂, oxo, nitro and alkoxycarbonyl,
(iii) aryl.

Substituents on indole are as the following:
R11 and R12 are independently selected from: Hydrogen, F, Cl, Br, CN, C1-C4 alkyl, C1-C6 alkoxy.

R₁₃, R₁₄ and R₁₅ are independently selected from Hydrogene, C₁-C₄ alkyl, C₂-C₆ alkenyl, C₂-C₆ alkynyl, C₃-C₁₀ aryl or heteroaryl, C₁-C₆ alkoxy, C₁-C₆ alkylthio, C₂-C₆ alkanoyl, C₁-C₆ alkoxycarbonyl, C₂-C₆ alkanoyloxy.

Preferred R groups of formula (I) are listed below:

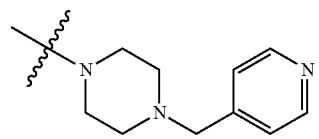

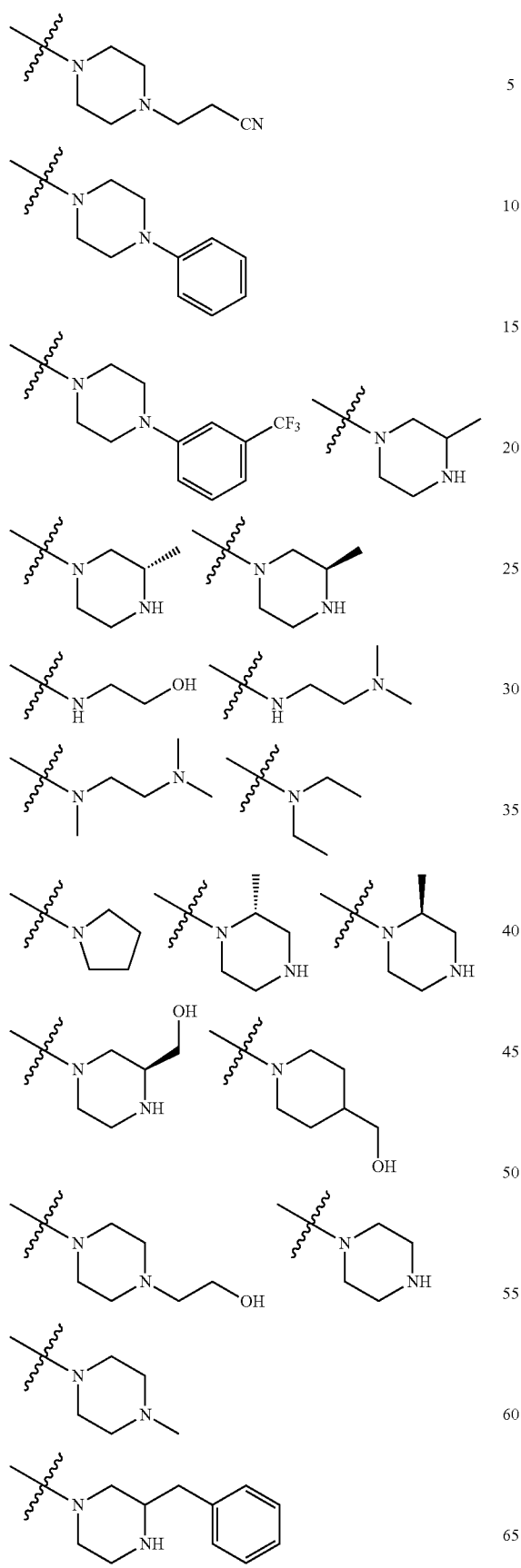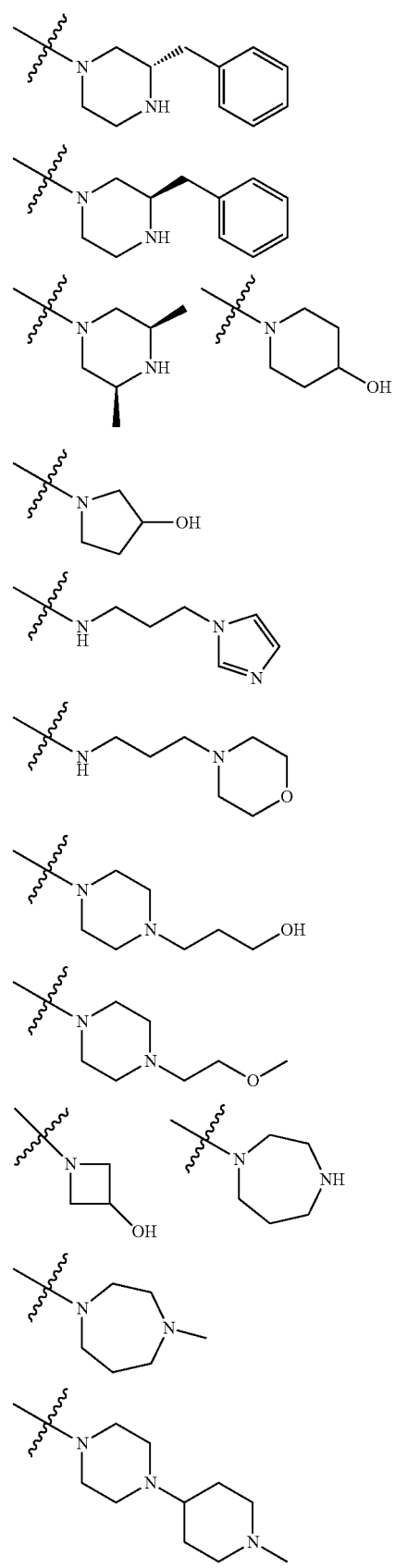

-continued
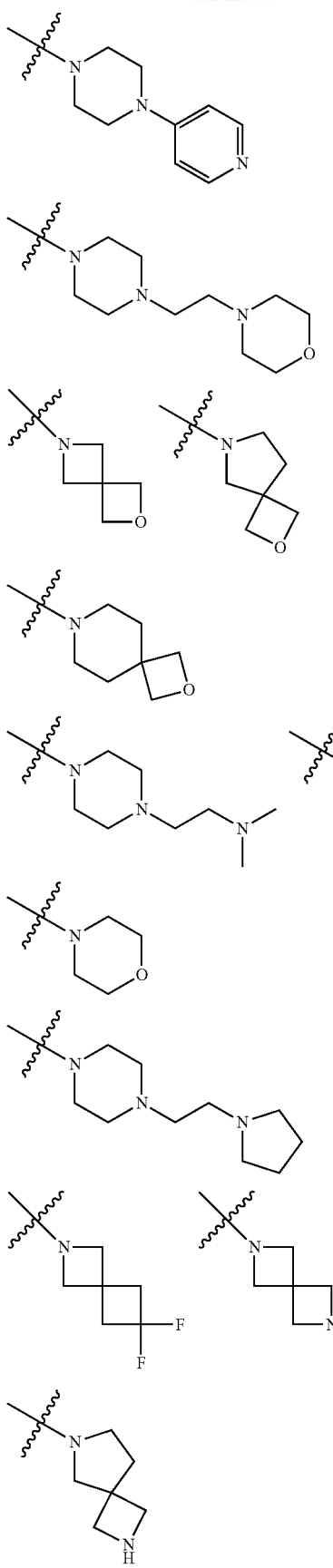
-continued
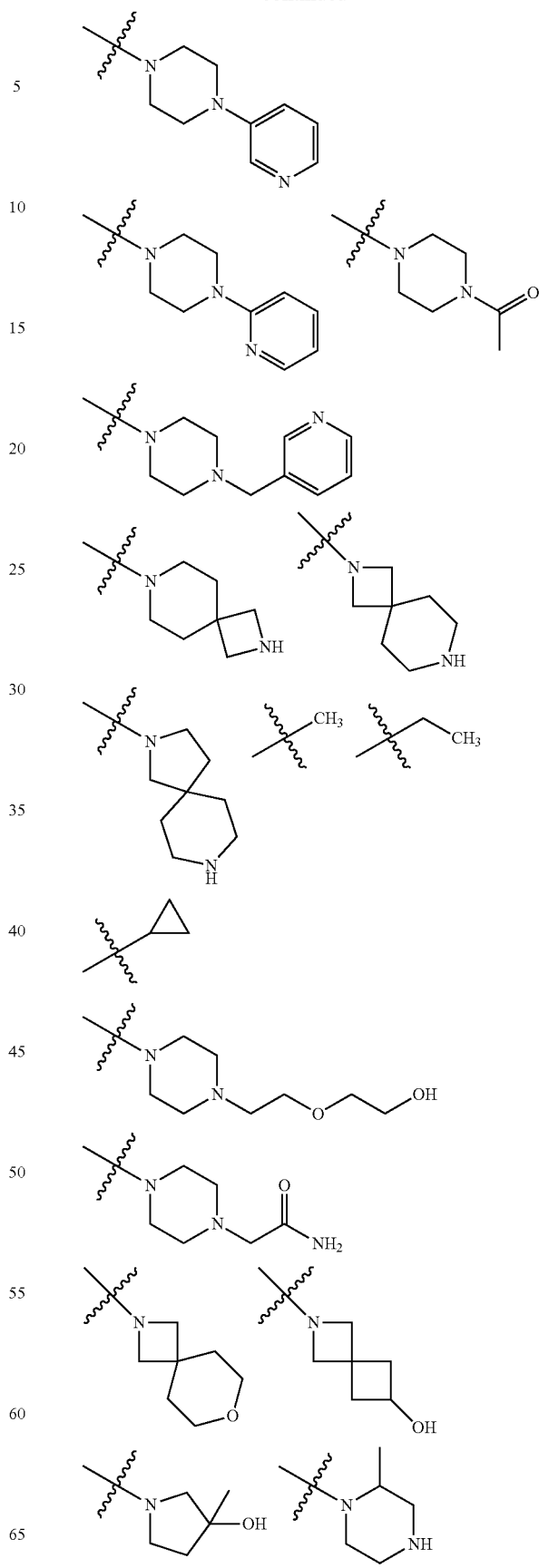

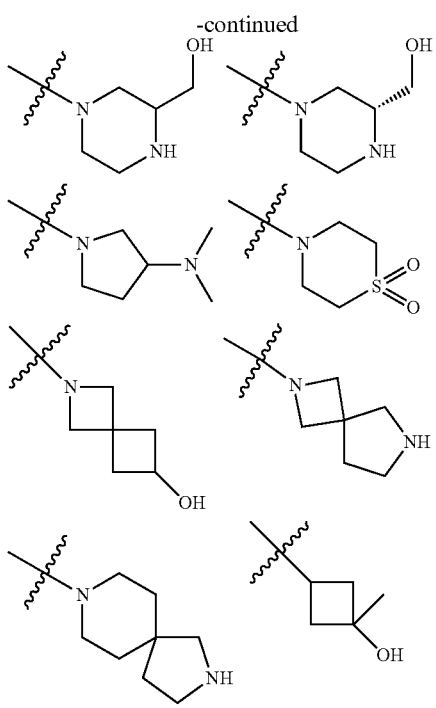

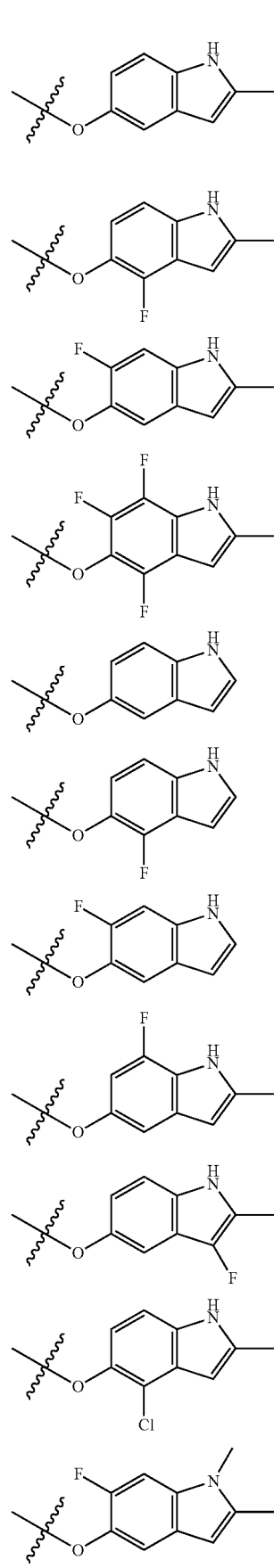

Preferred Het groups of formula (II) are list below, wherein the substitute may be the specific ones as defined here or may be one or multiple substitutes as defined above:

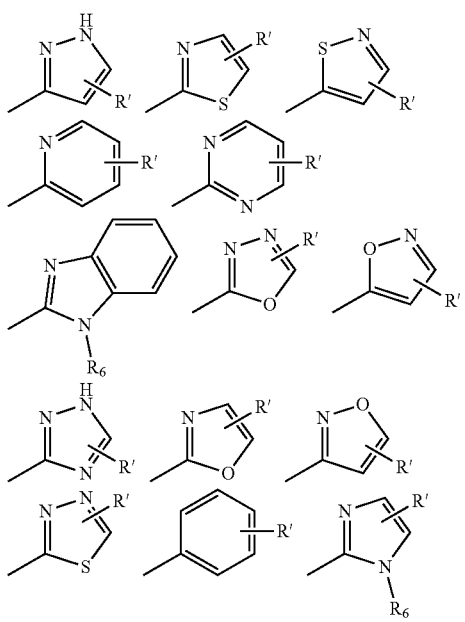

R' is selected from
(i) Hydrogen;
(ii) C1-C6 alkyl, C2-C6 alkenyl, C2-C6 alkynyl;
(iii) aryl, which may have 1-4 optically substituents;
(iii) —C(=O)R6, (R6 is described below).

Preferred substituted indole groups of formula (I) are listed below:

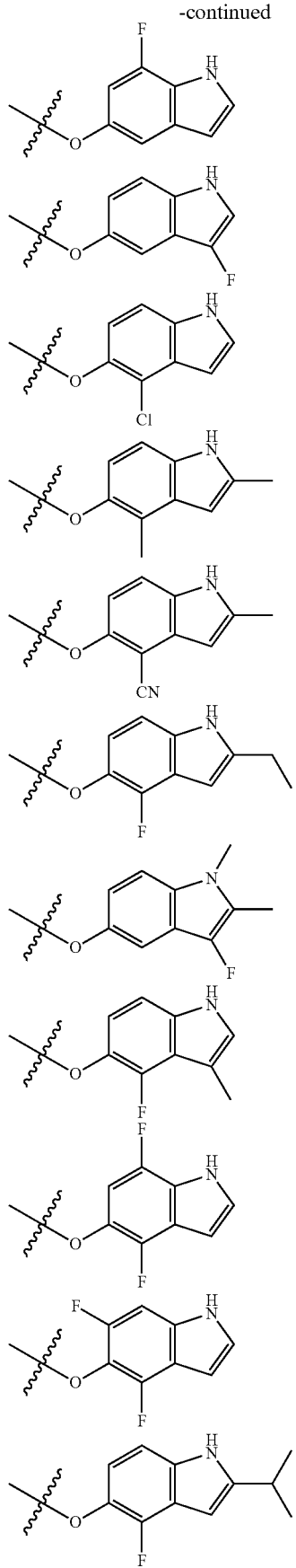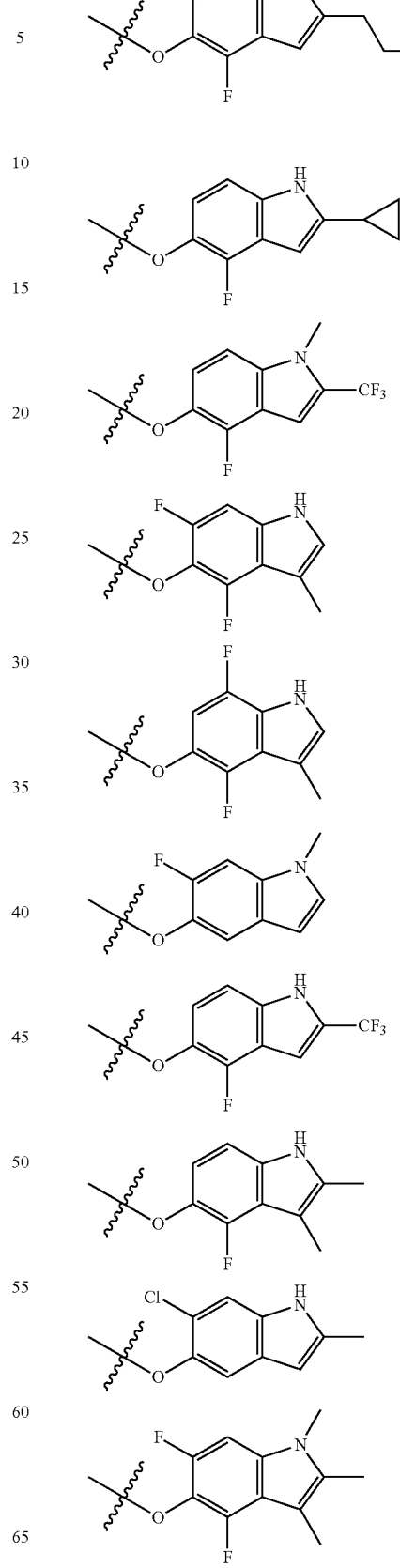

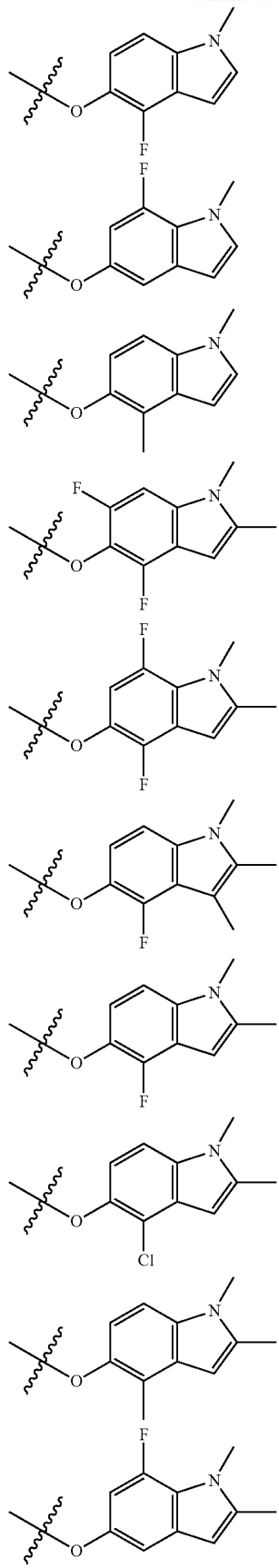
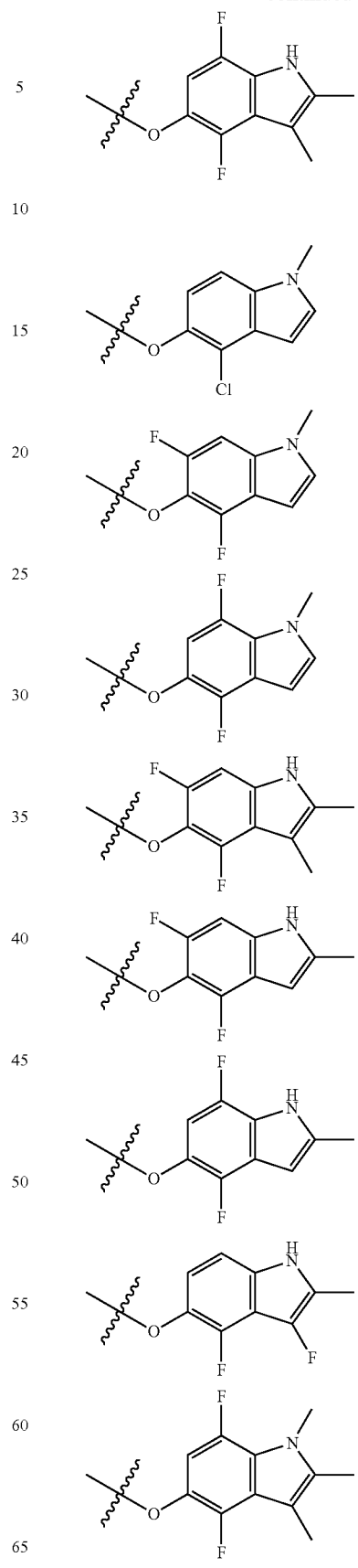

Embodiments of the invention include:
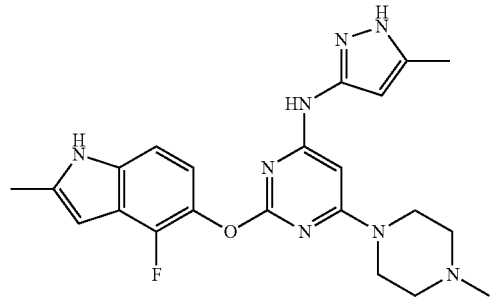
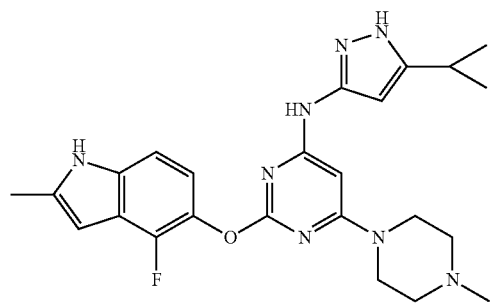
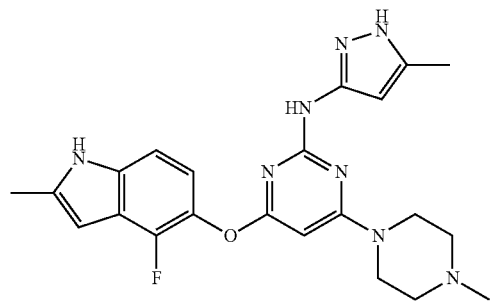
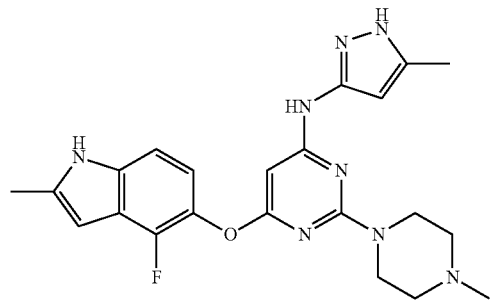
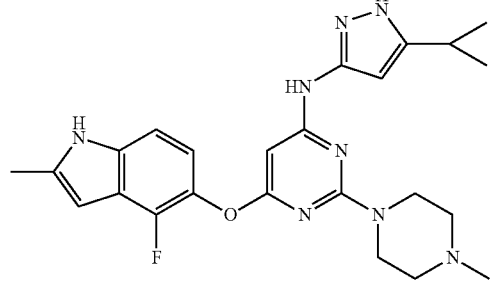
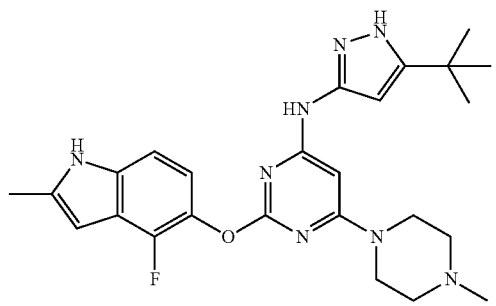
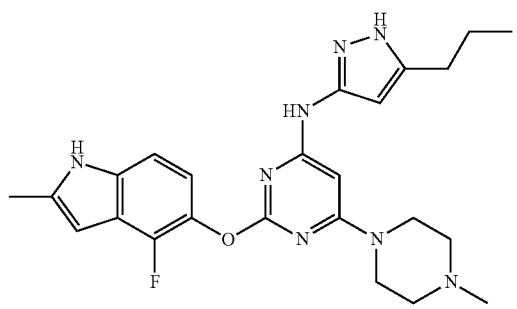
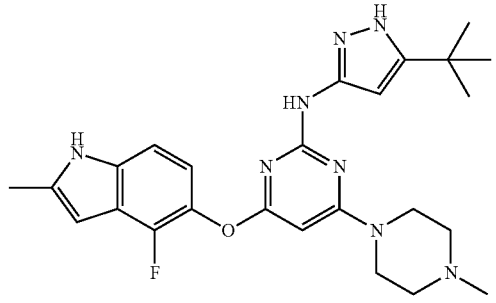
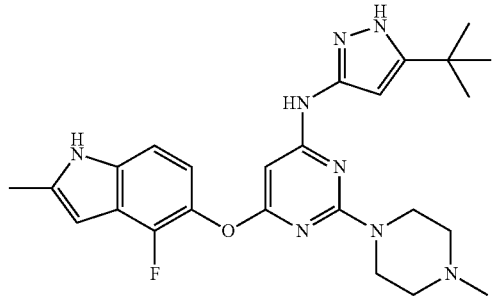
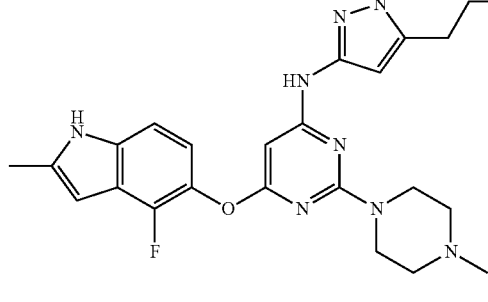

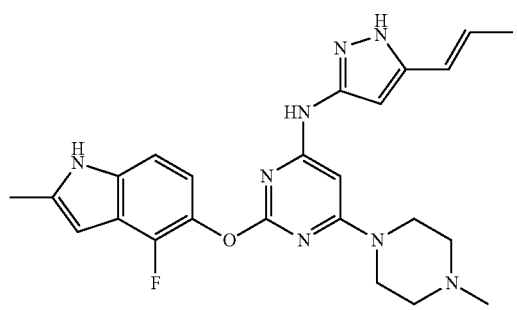
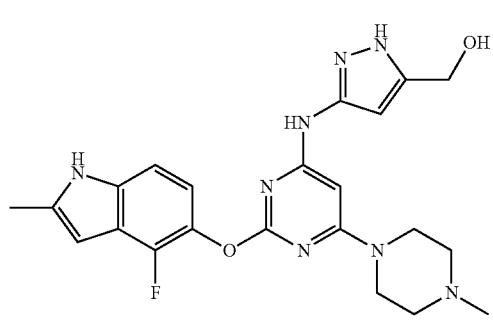
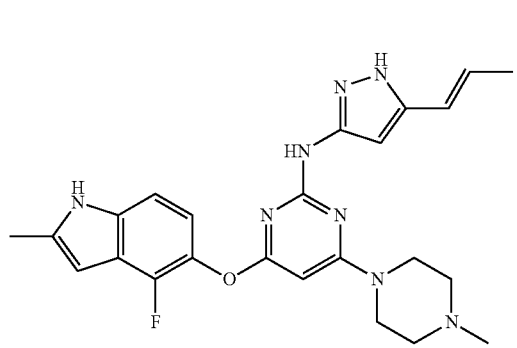
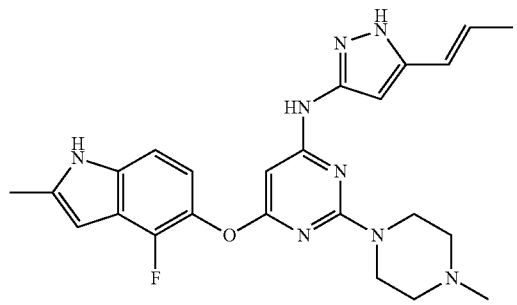
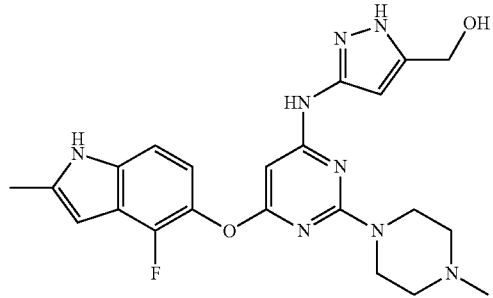
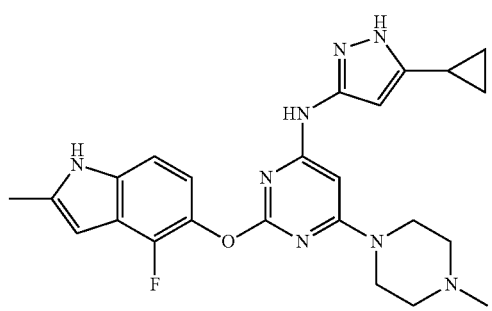
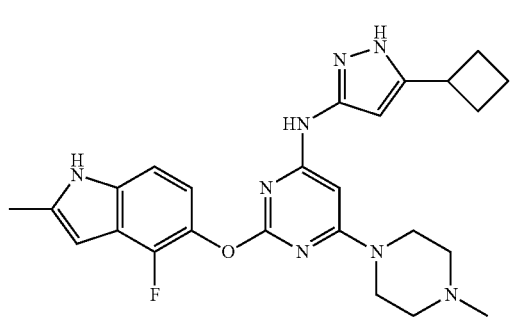
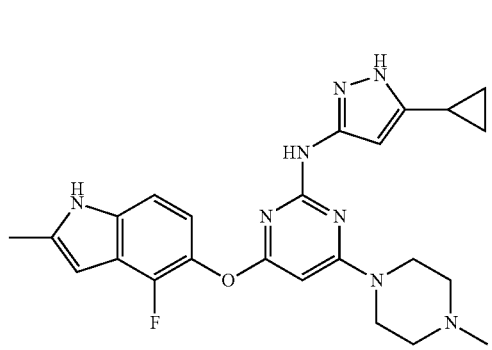
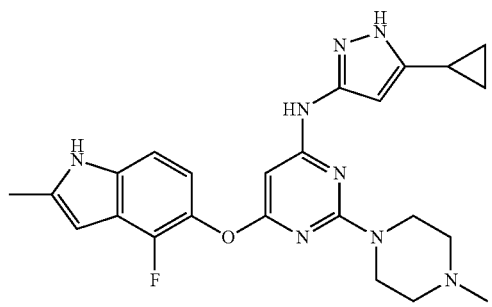
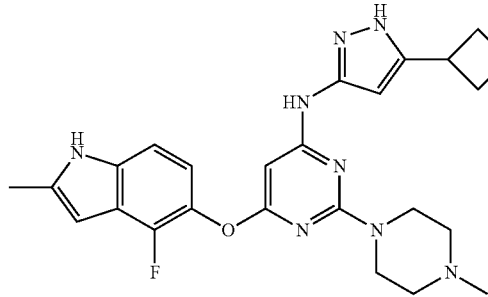

31
-continued
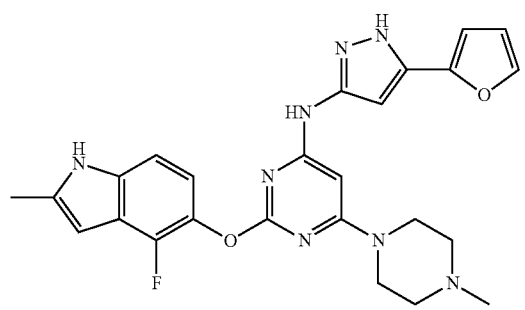
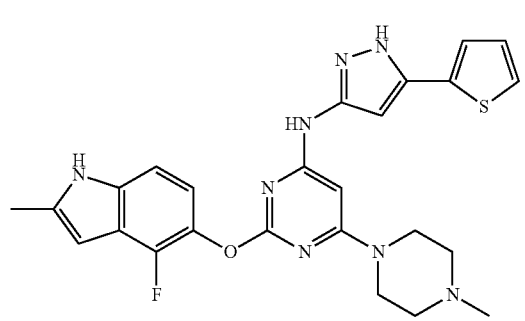
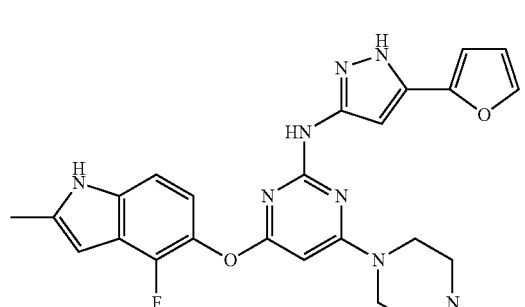
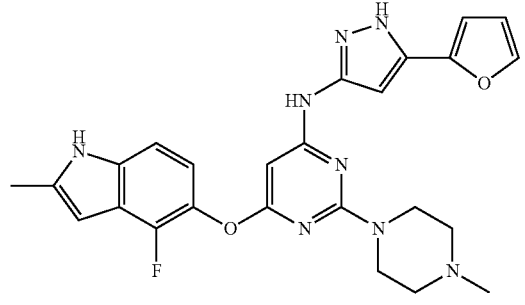
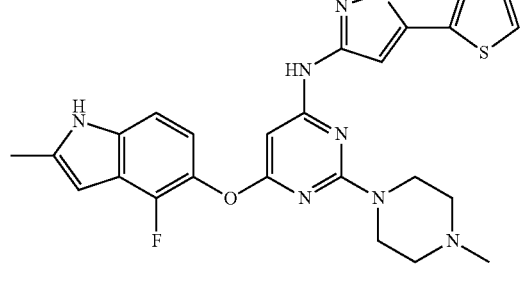
32
-continued
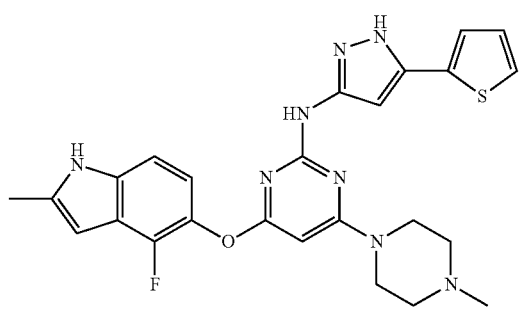
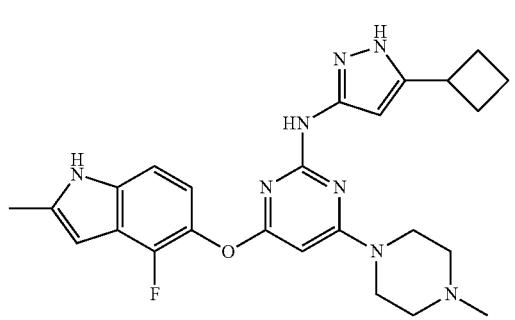
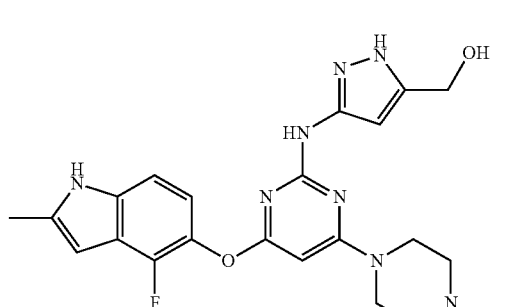
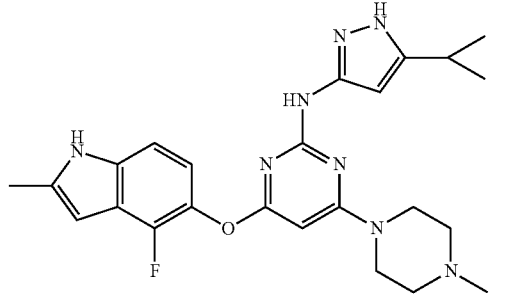
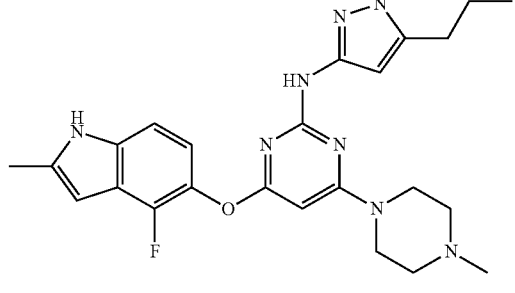

33
-continued
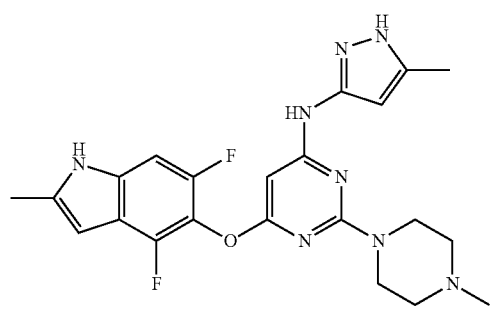
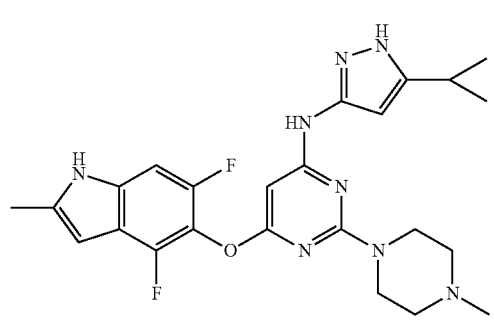
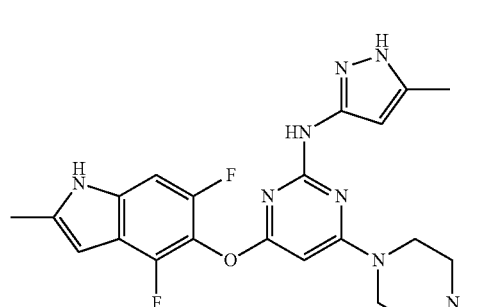
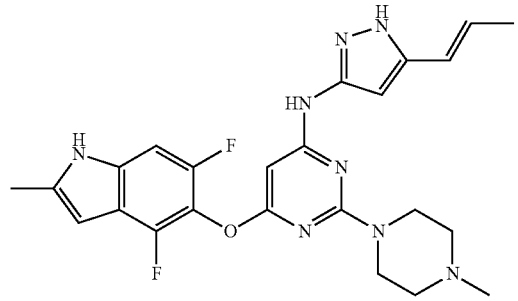
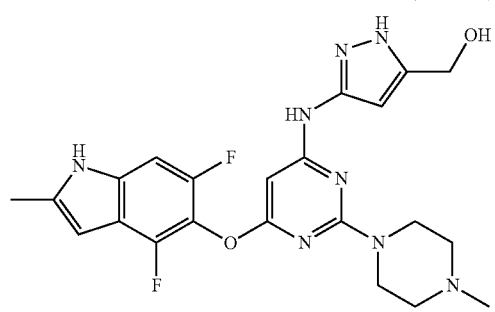
34
-continued
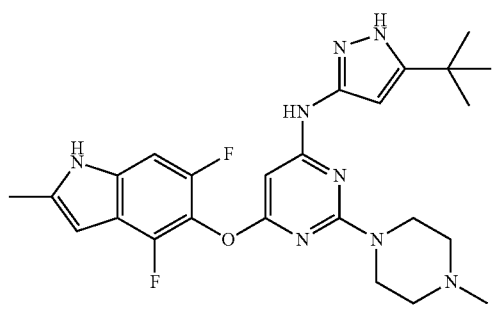
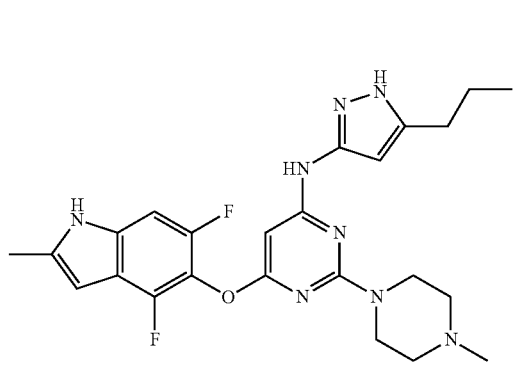
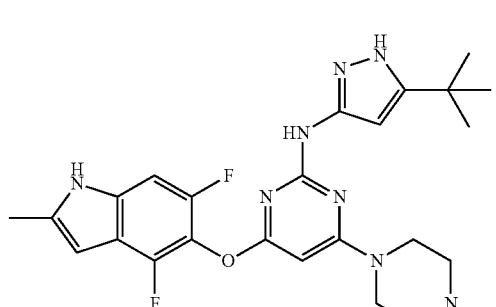
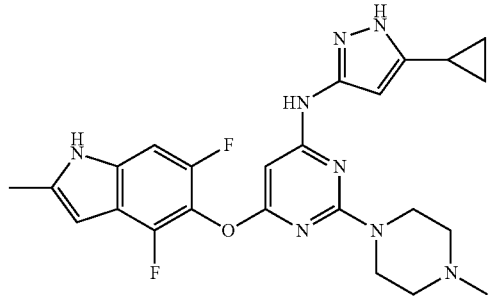
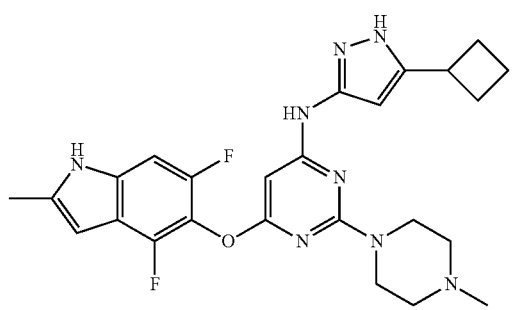

35
-continued
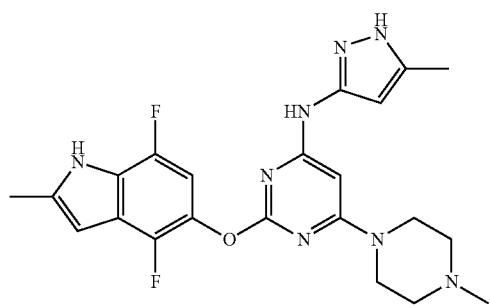
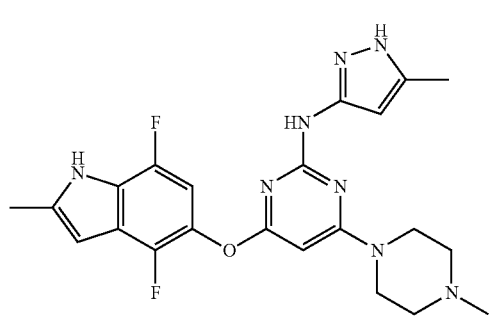
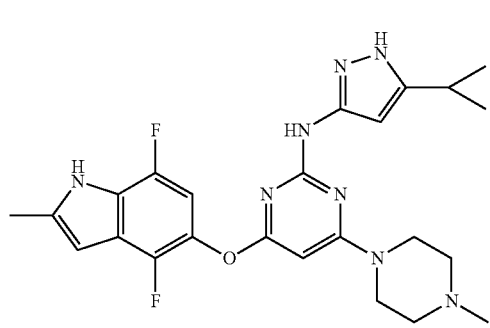
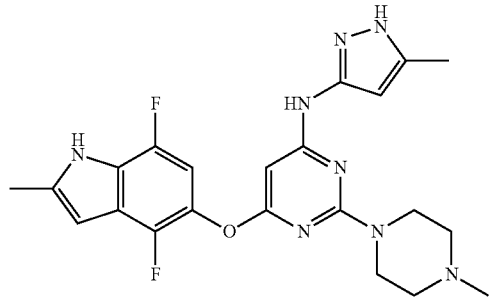
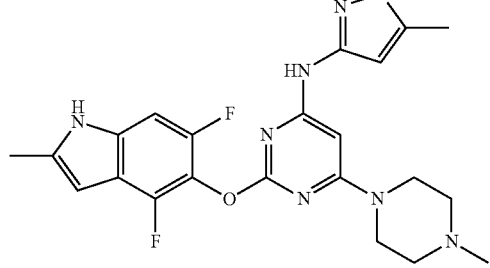
36
-continued
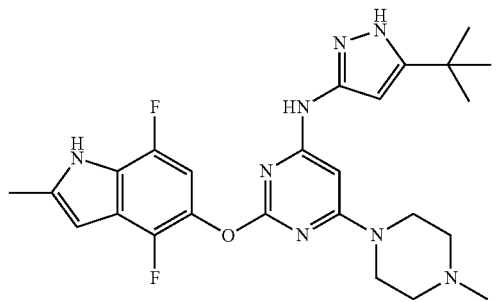
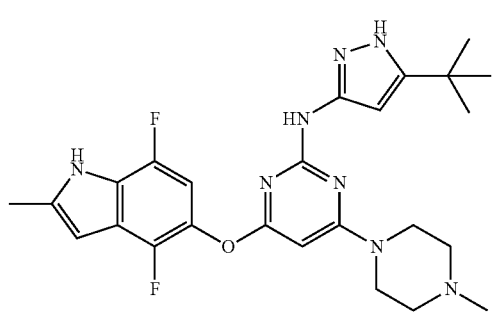
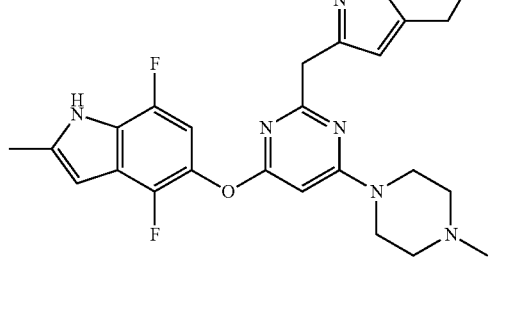
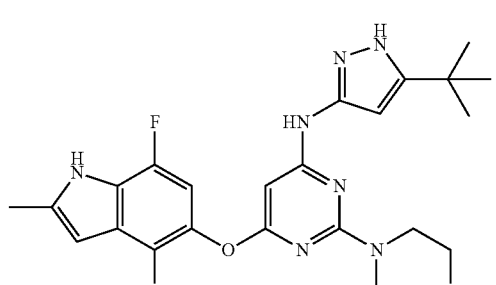
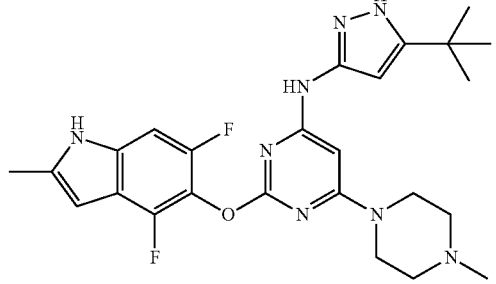

37
-continued
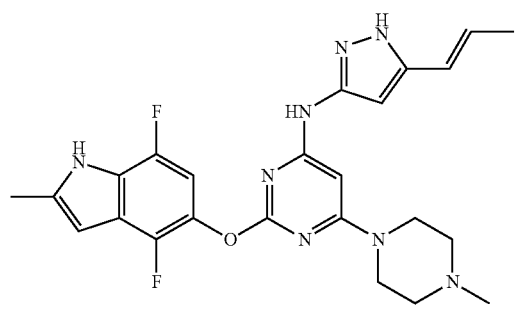
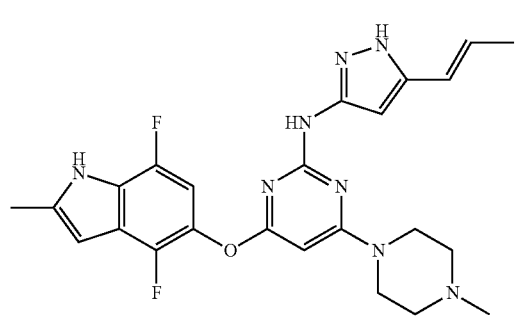
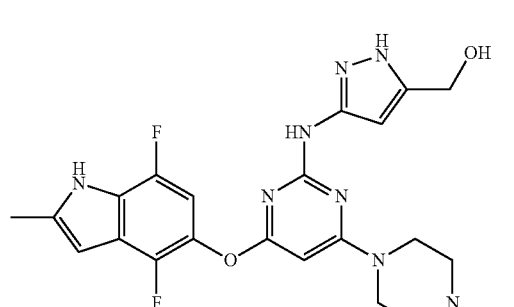
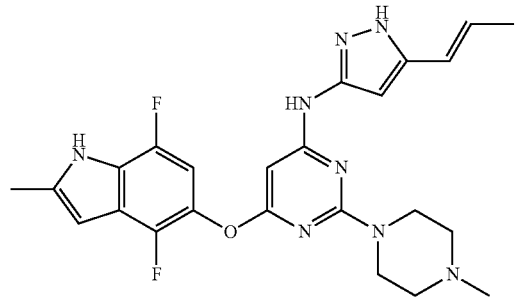
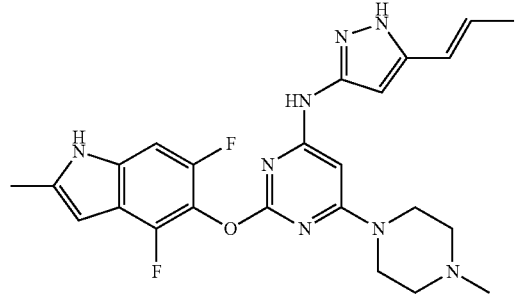
38
-continued
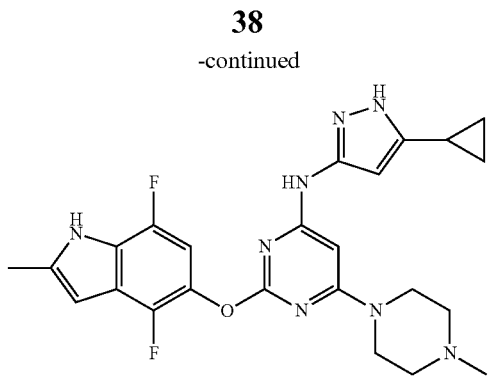
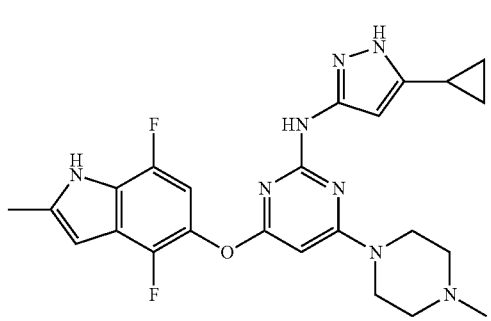
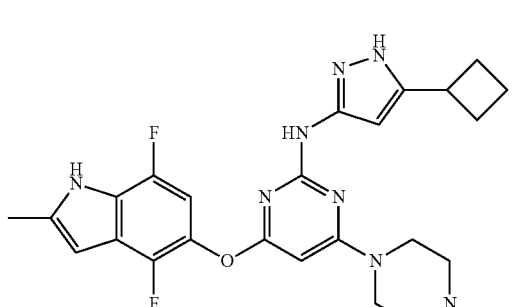
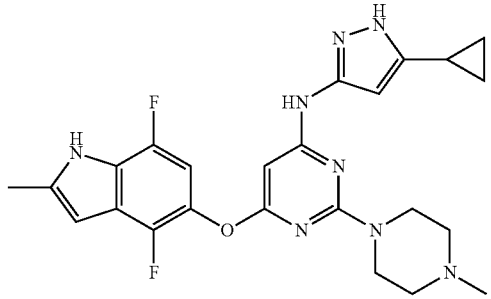
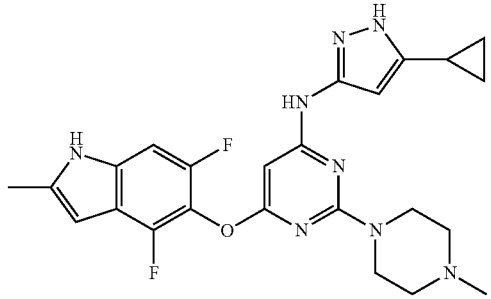

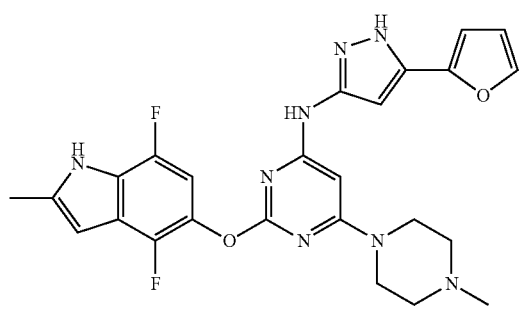
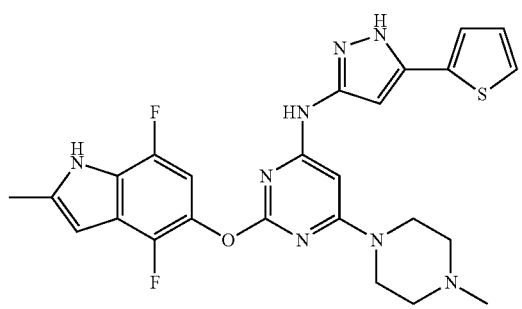
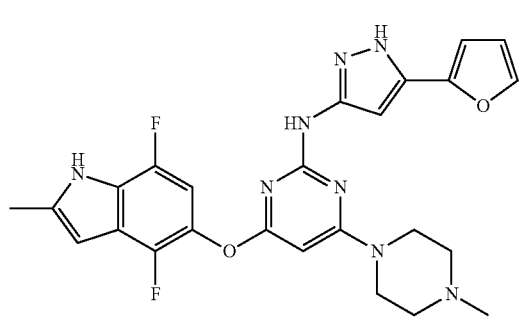
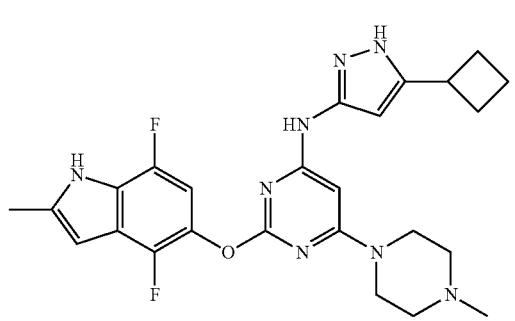
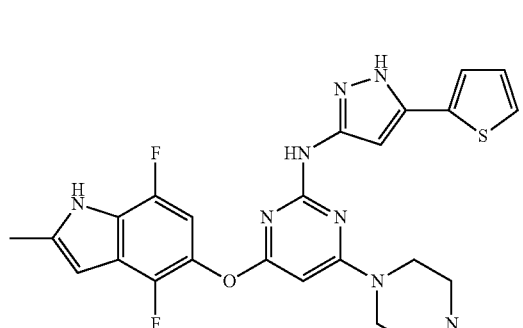
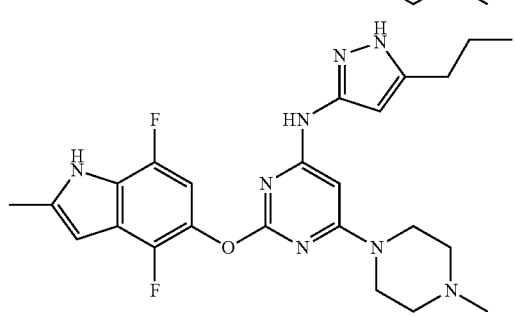
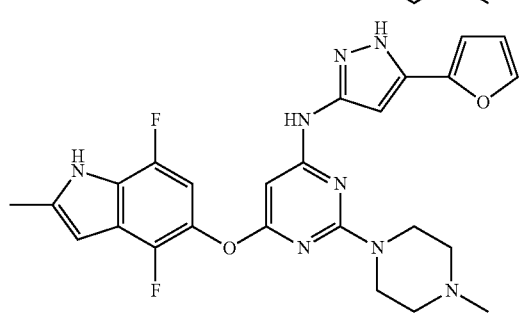
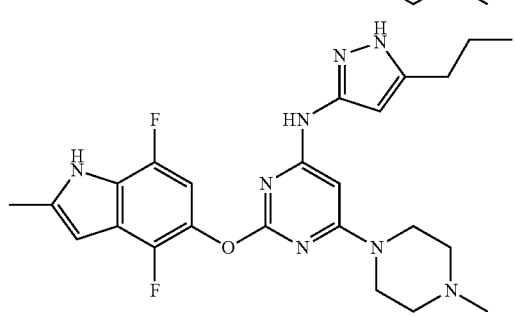
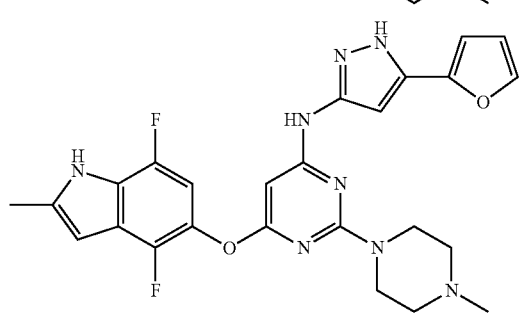
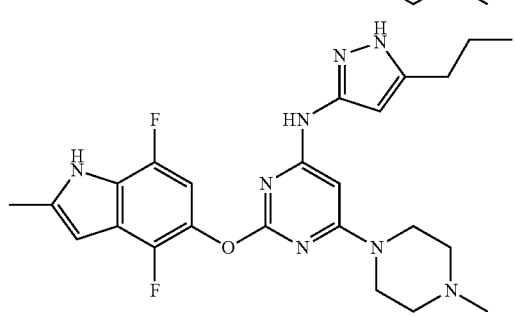

41
-continued
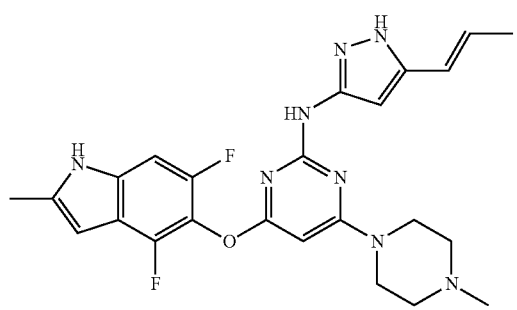
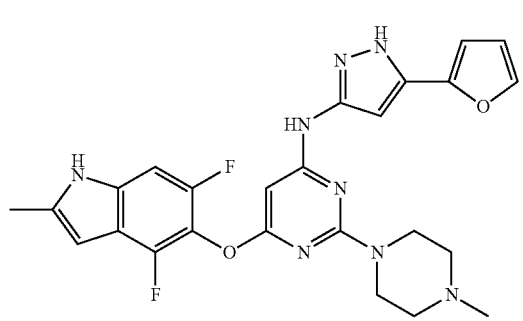
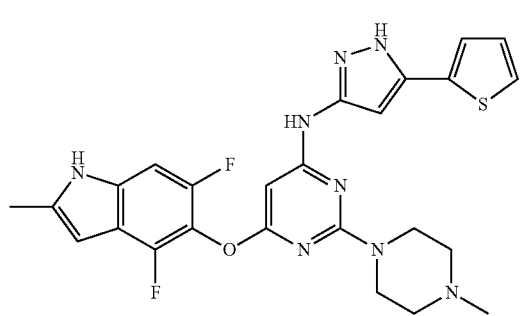
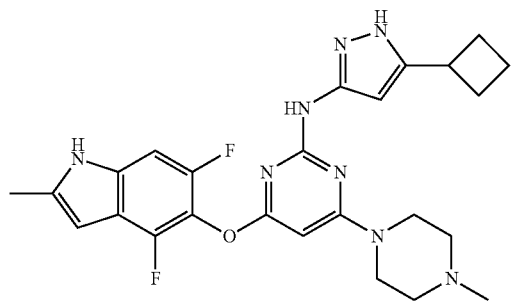
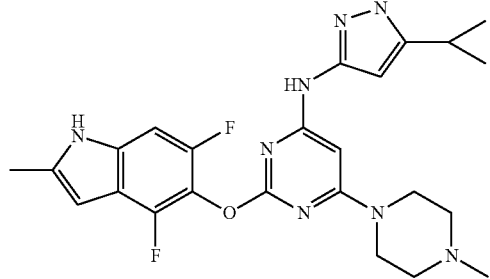
42
-continued
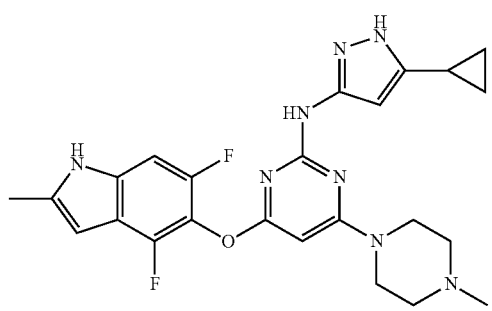
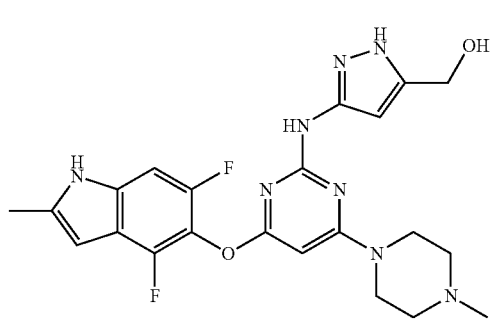
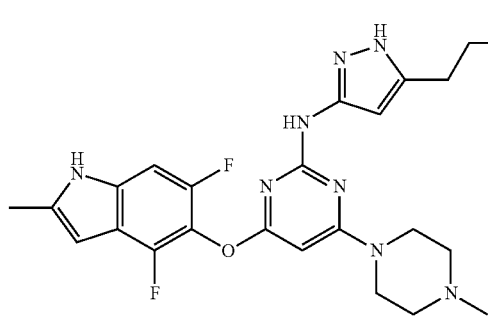
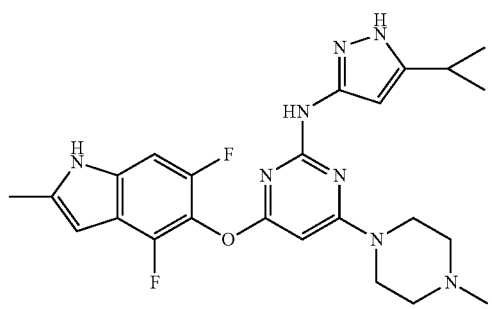
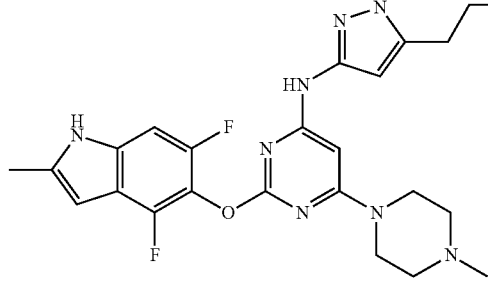

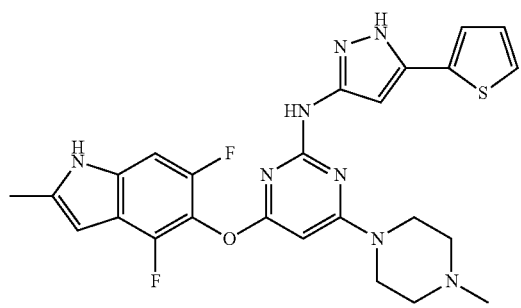
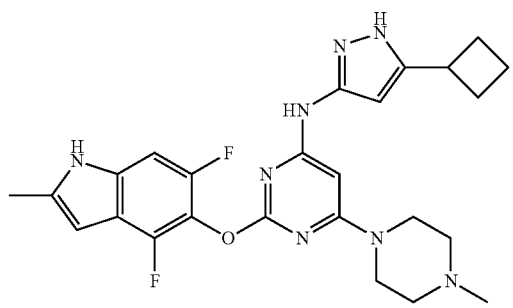
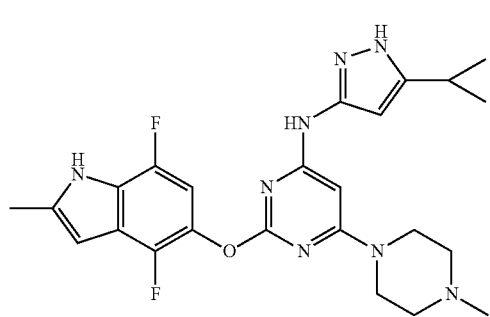
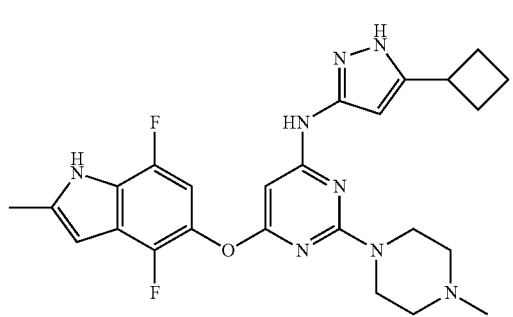
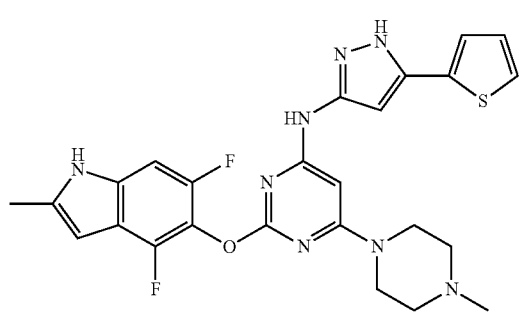
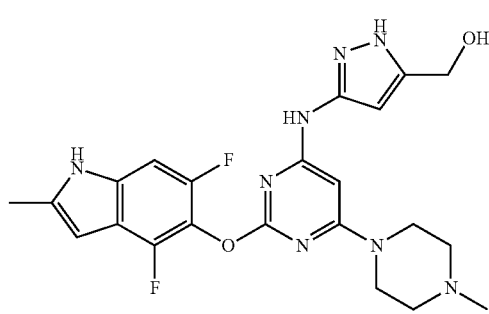
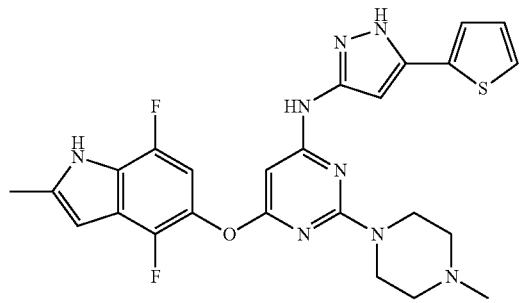
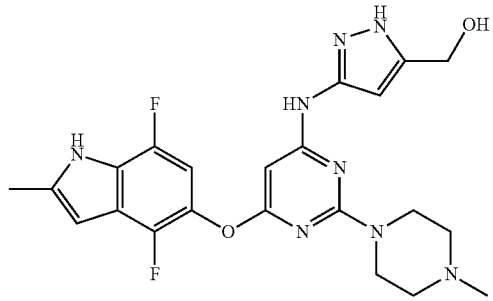
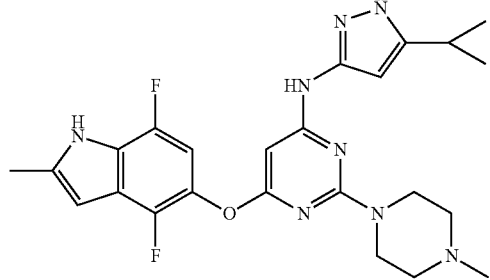
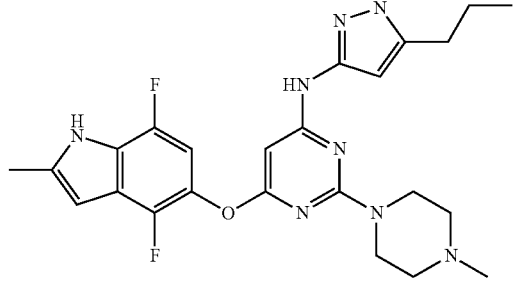

45
-continued
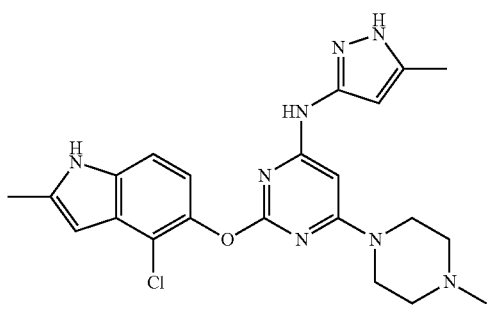
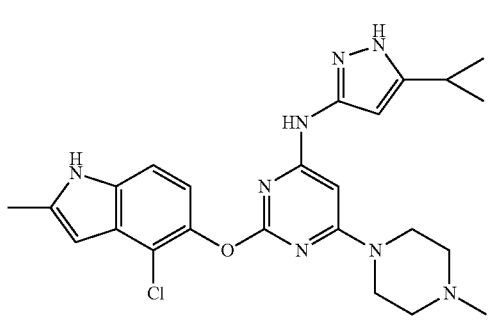
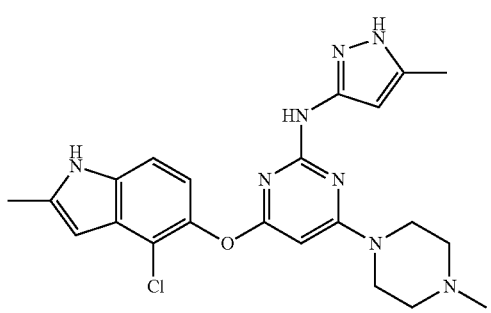
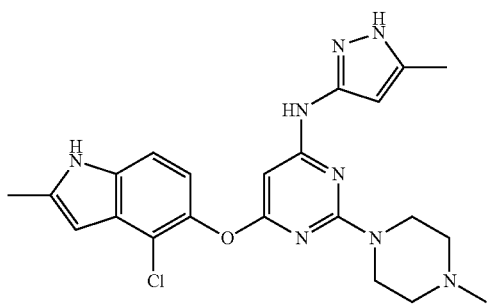
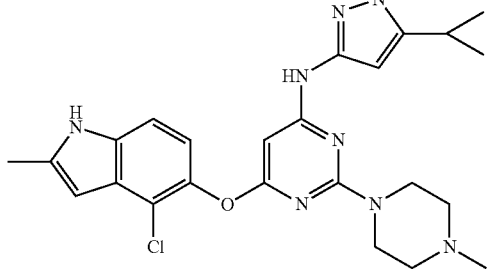
46
-continued
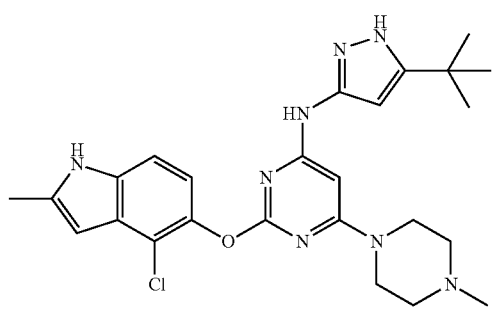
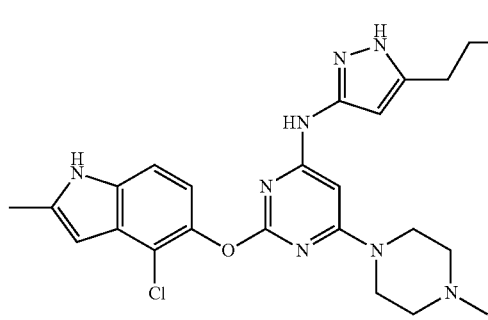
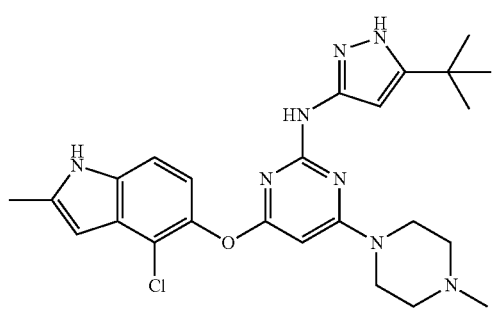
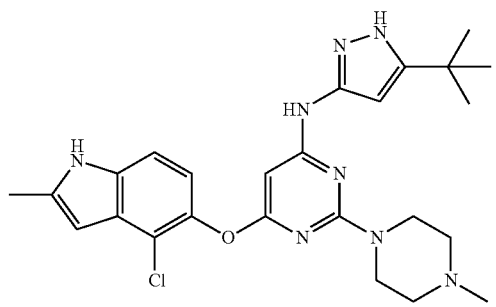
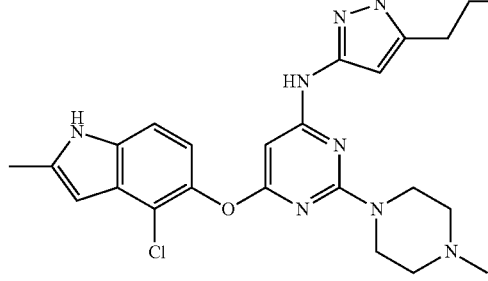

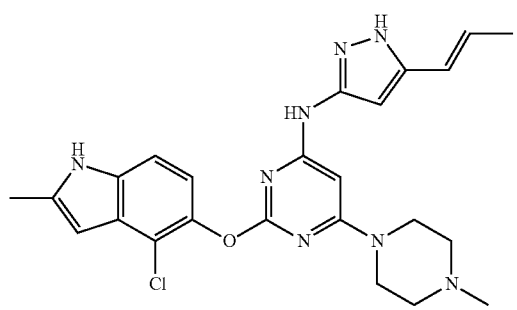
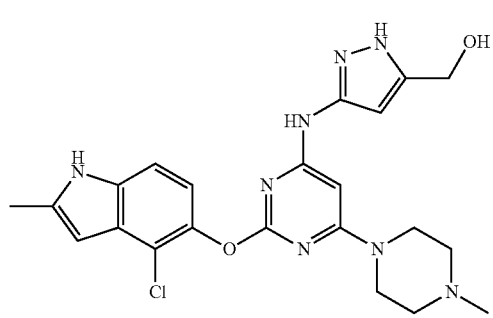
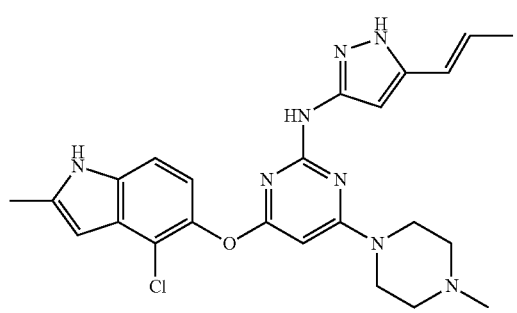
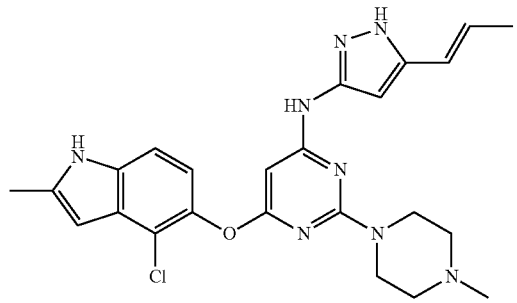
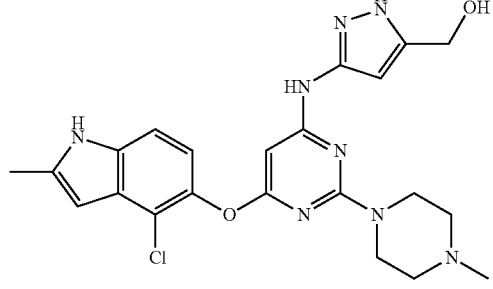
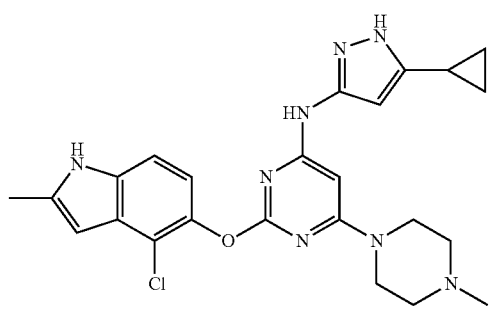
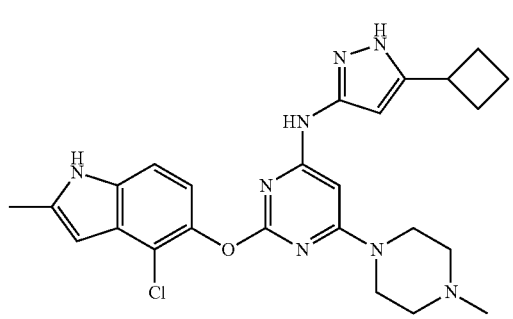
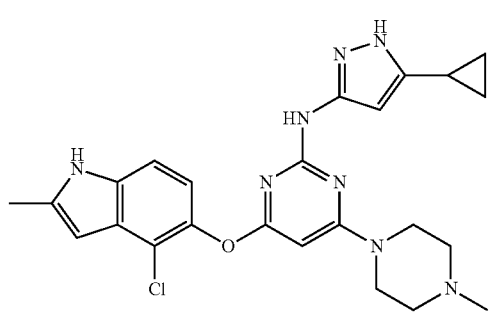
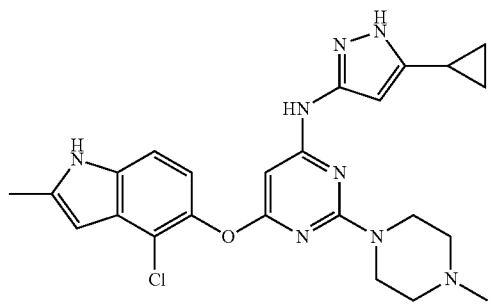
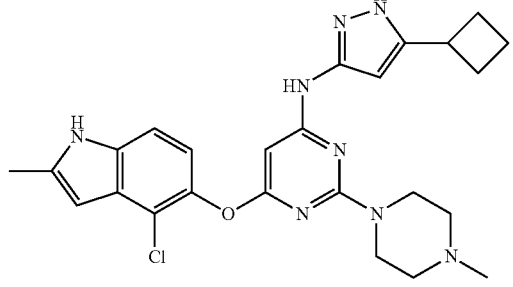

49
-continued
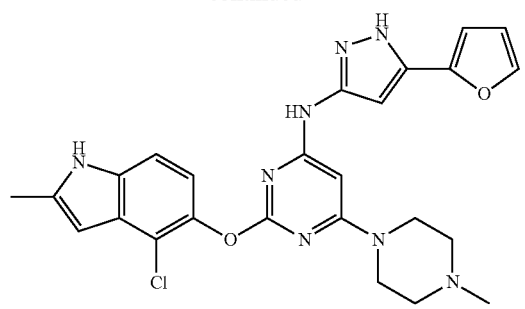
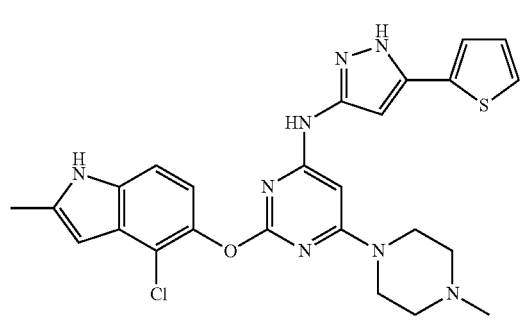
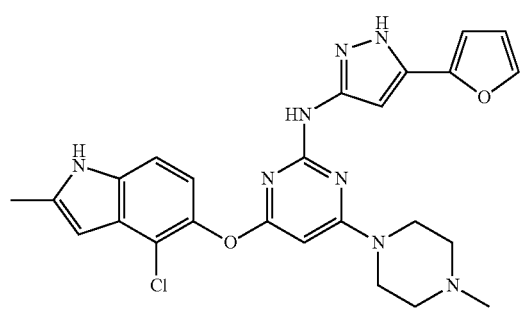
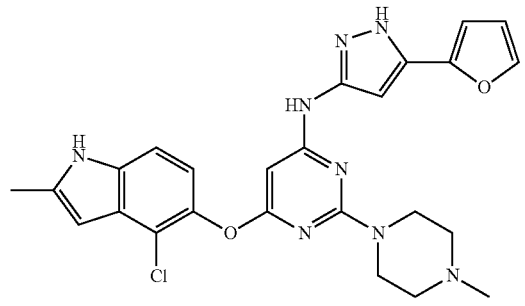
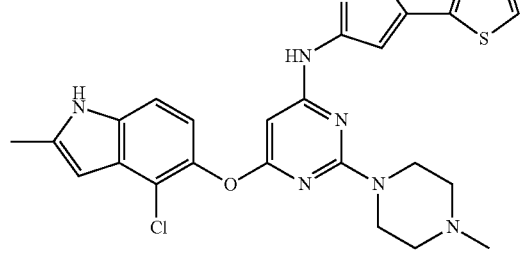
50
-continued
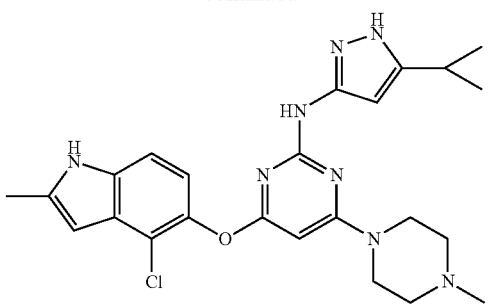
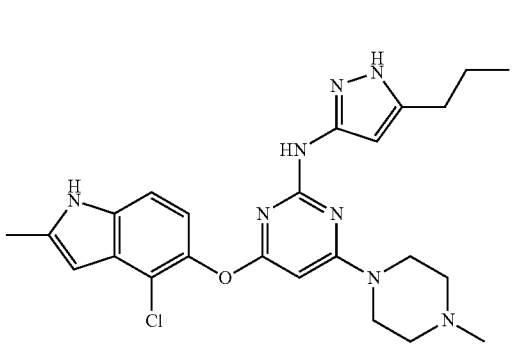
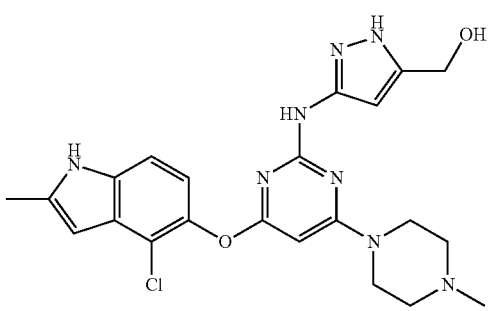
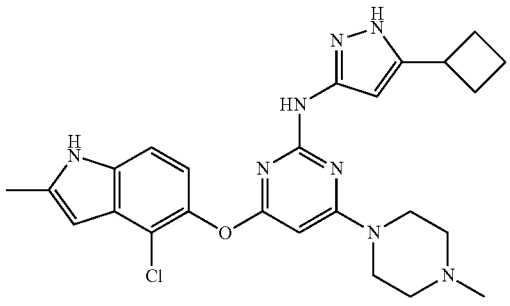
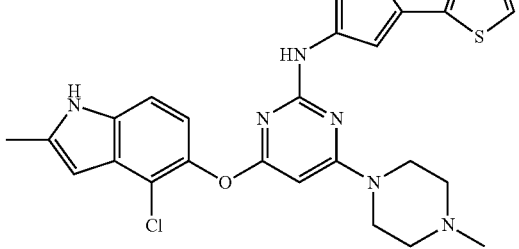

51
-continued
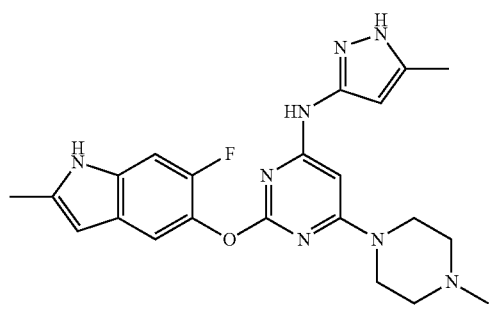
52
-continued
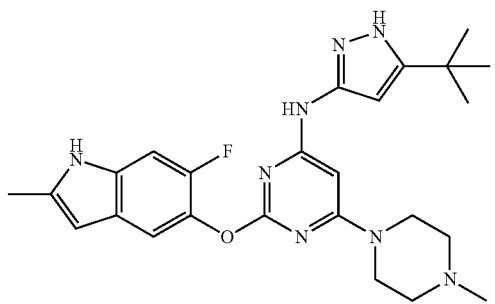
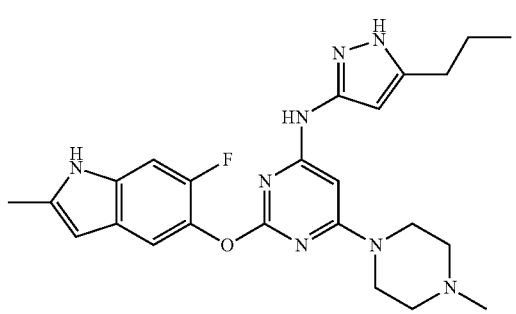
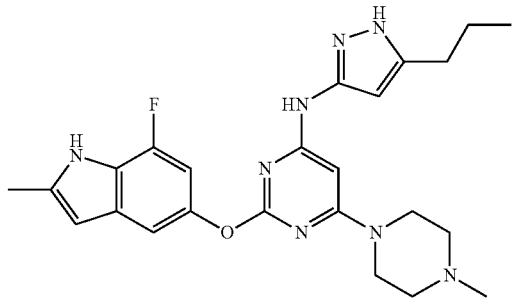
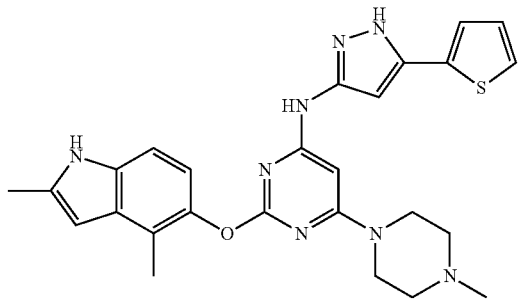
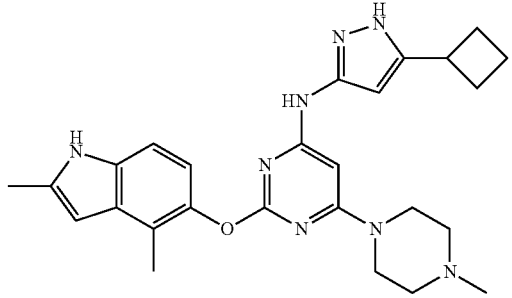

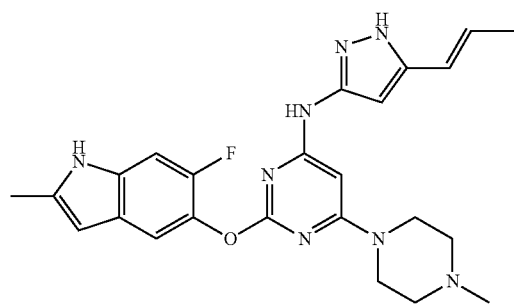
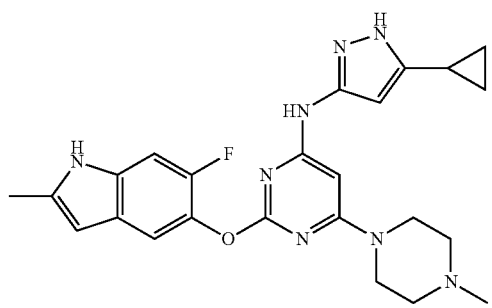
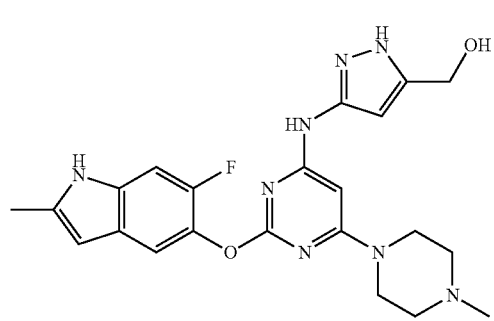
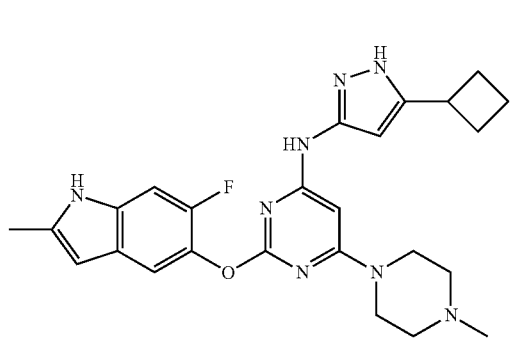
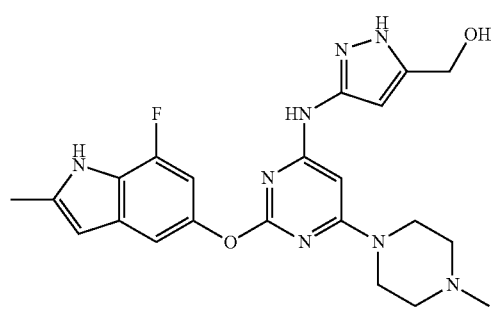
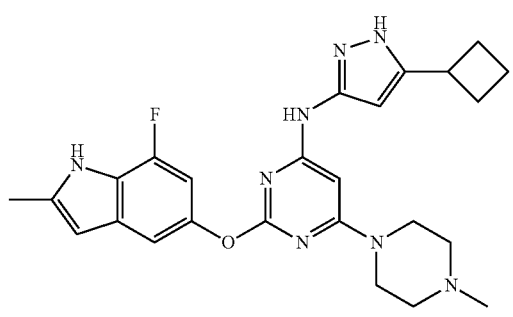
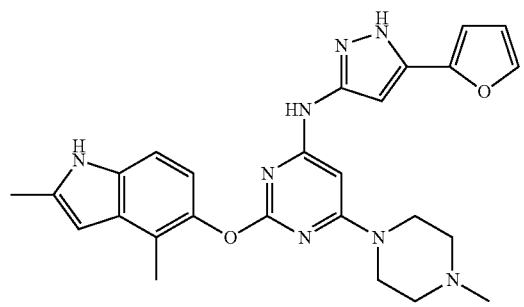
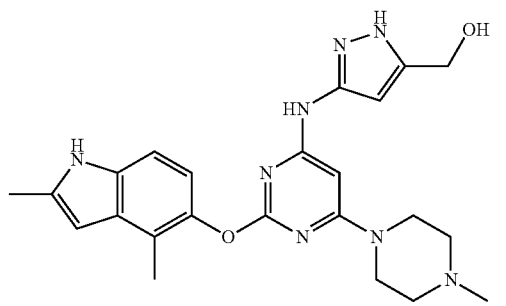
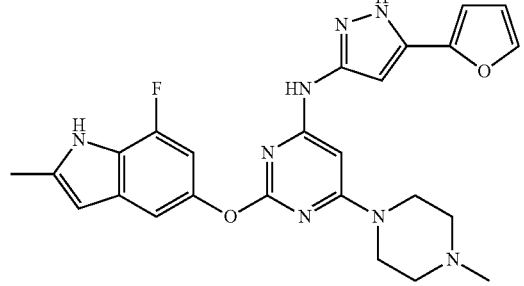
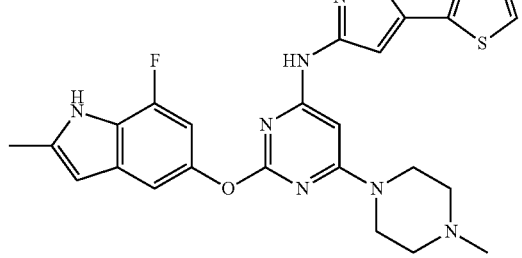

55
-continued
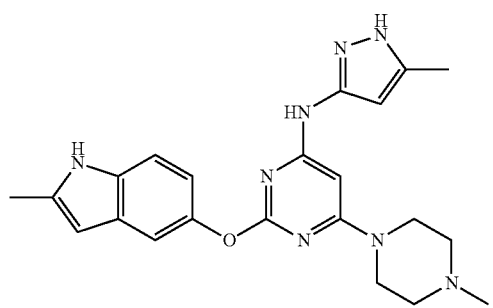
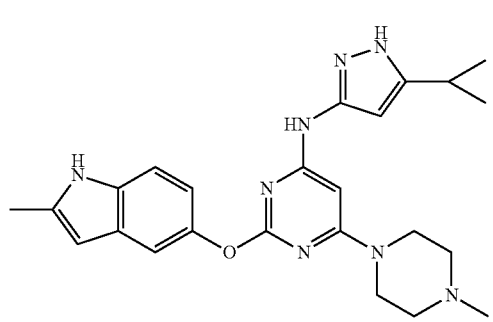
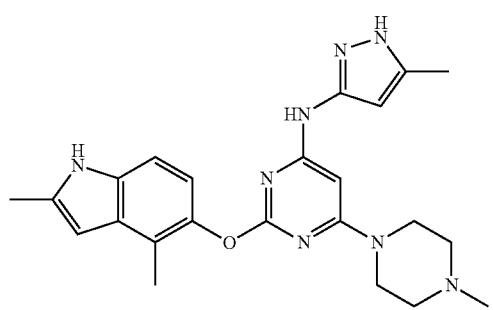
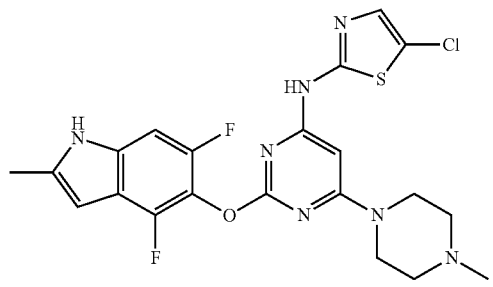
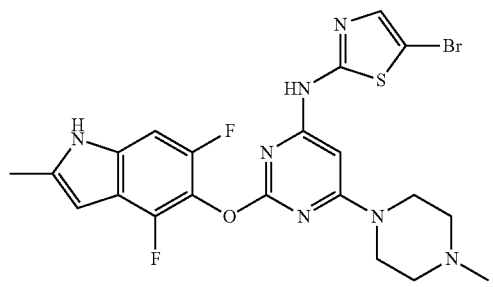
56
-continued
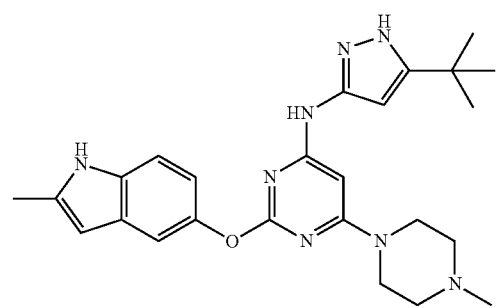
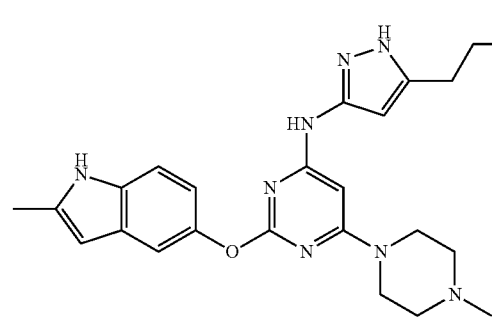
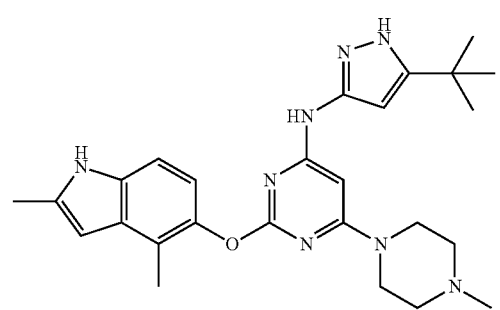
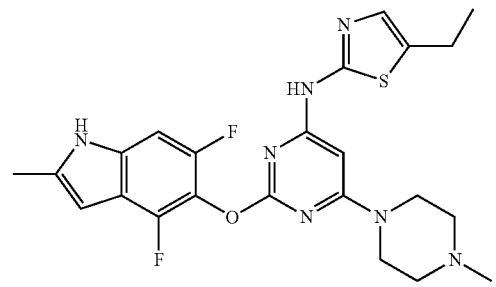
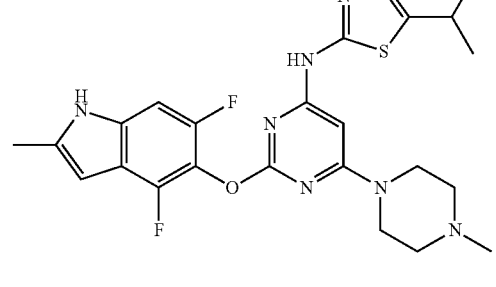

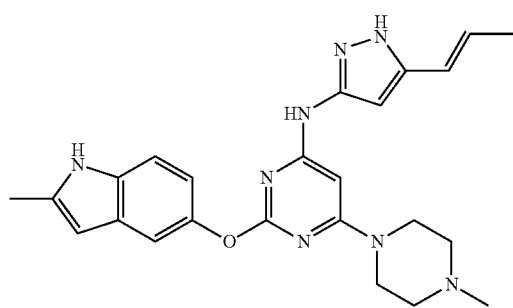
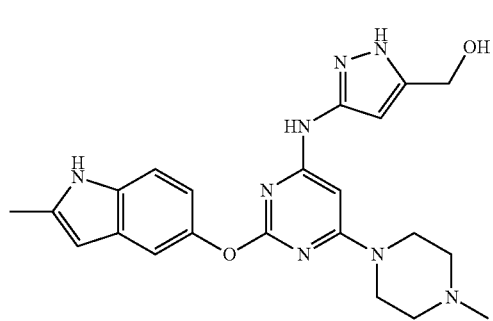
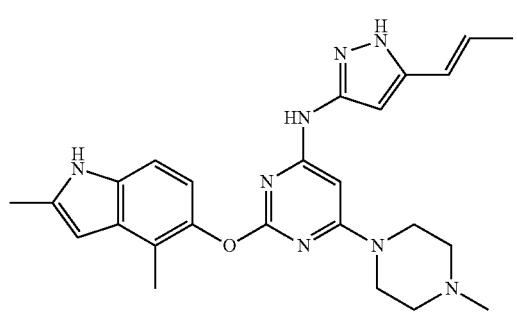
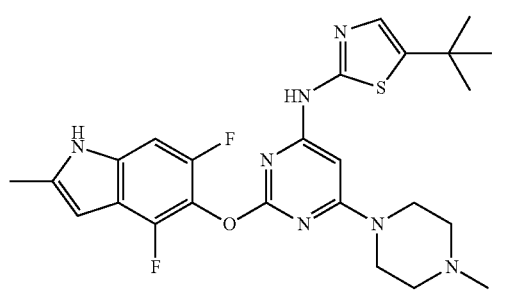
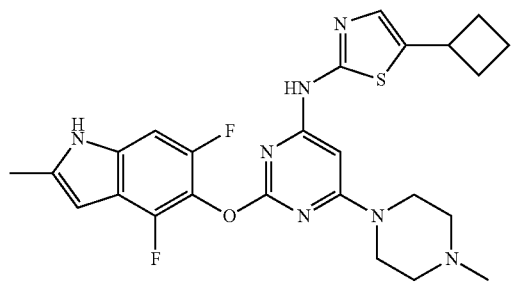
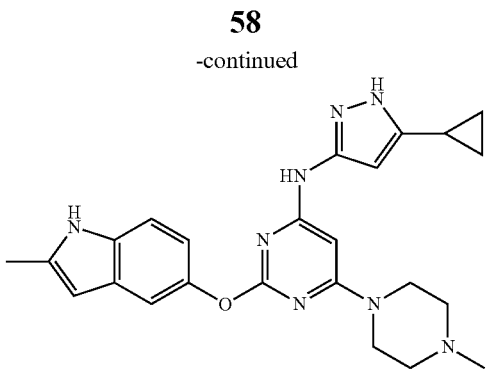
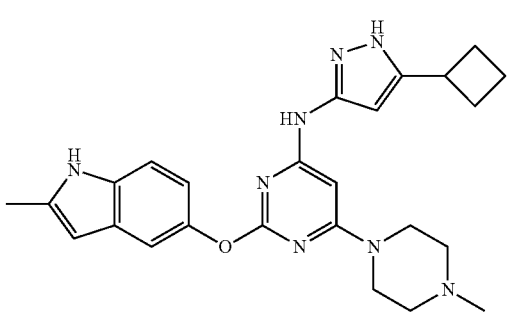
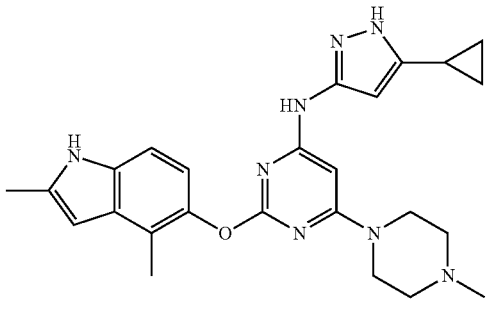
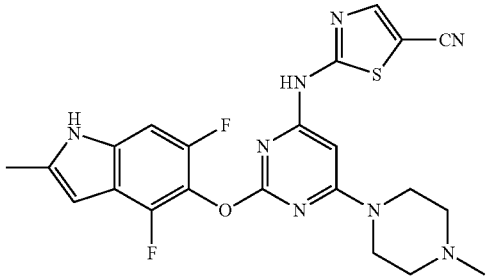
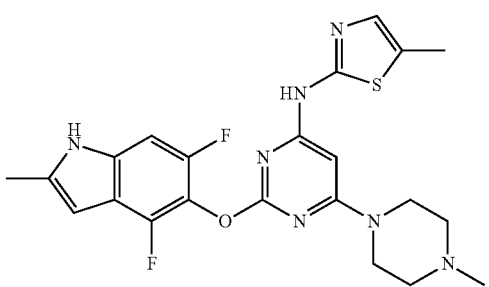

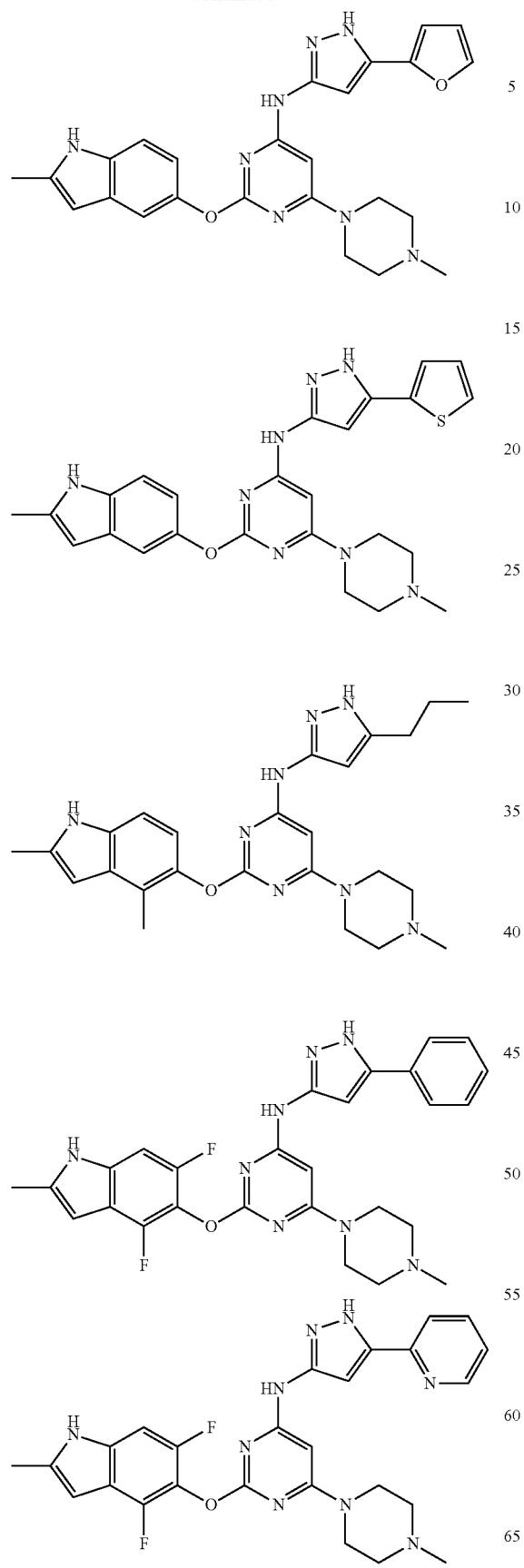
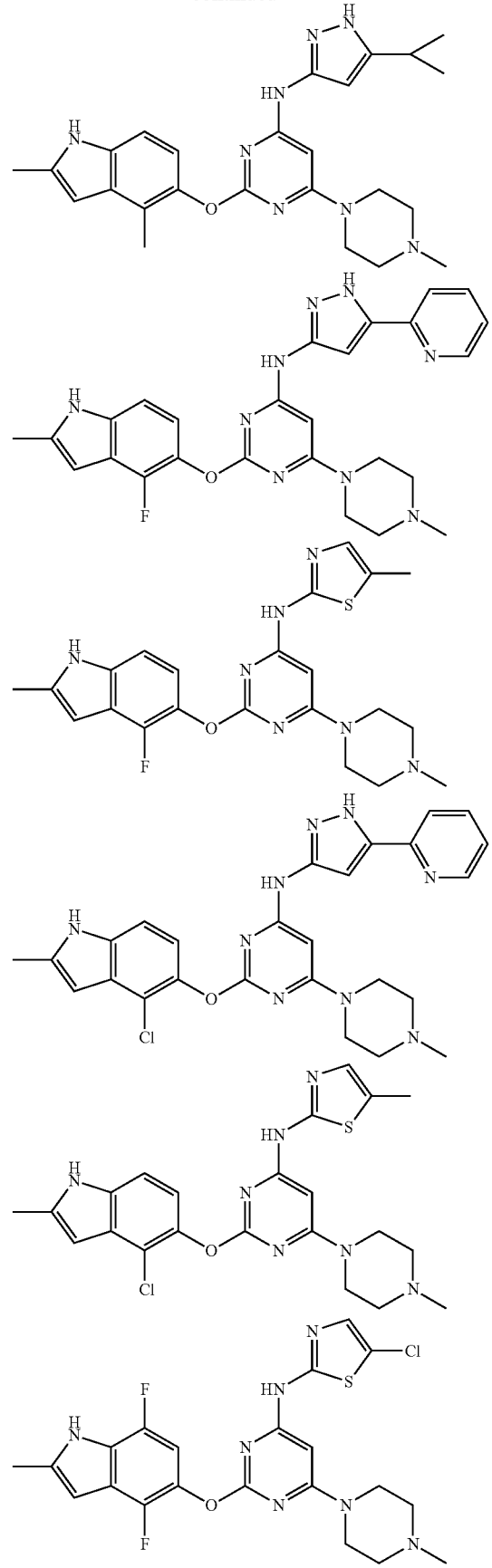

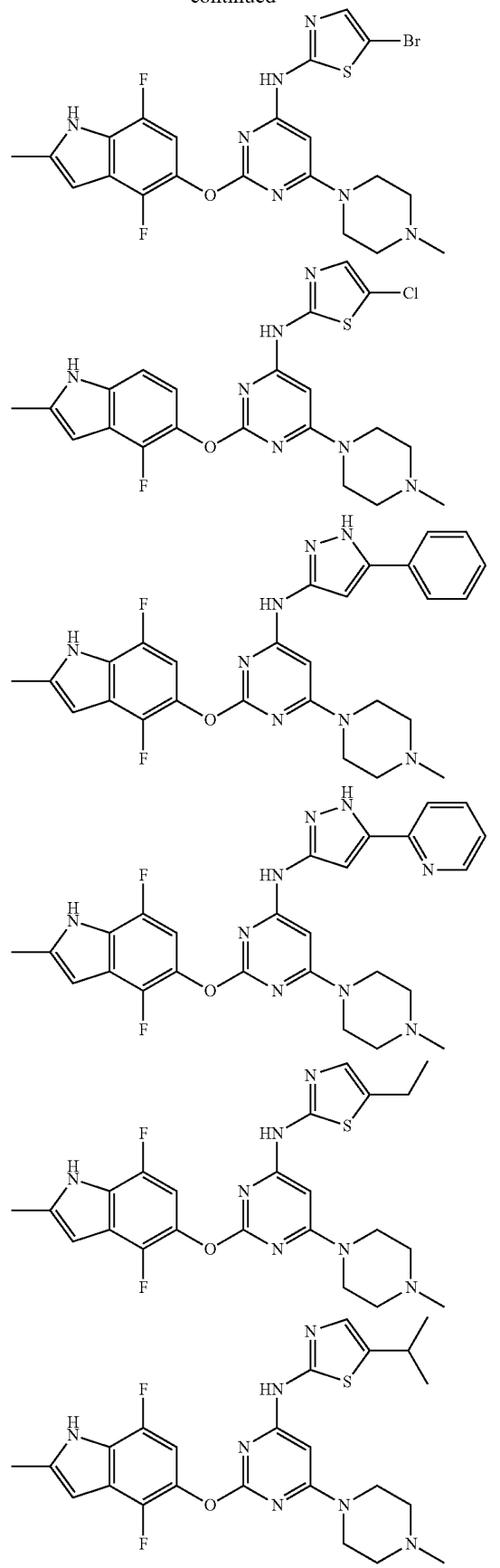
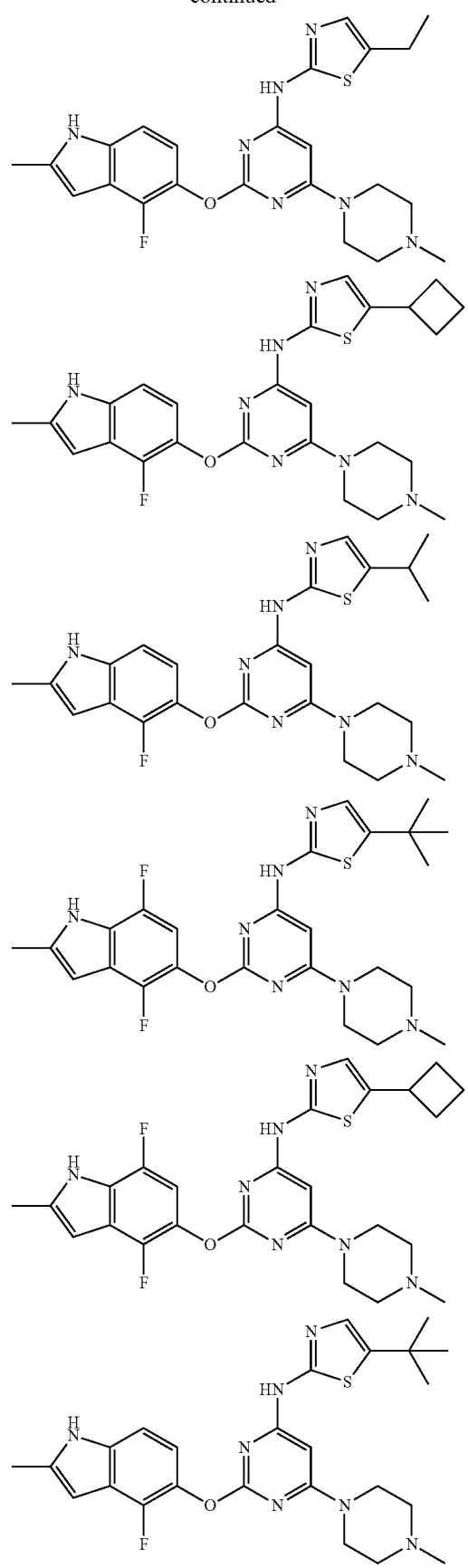

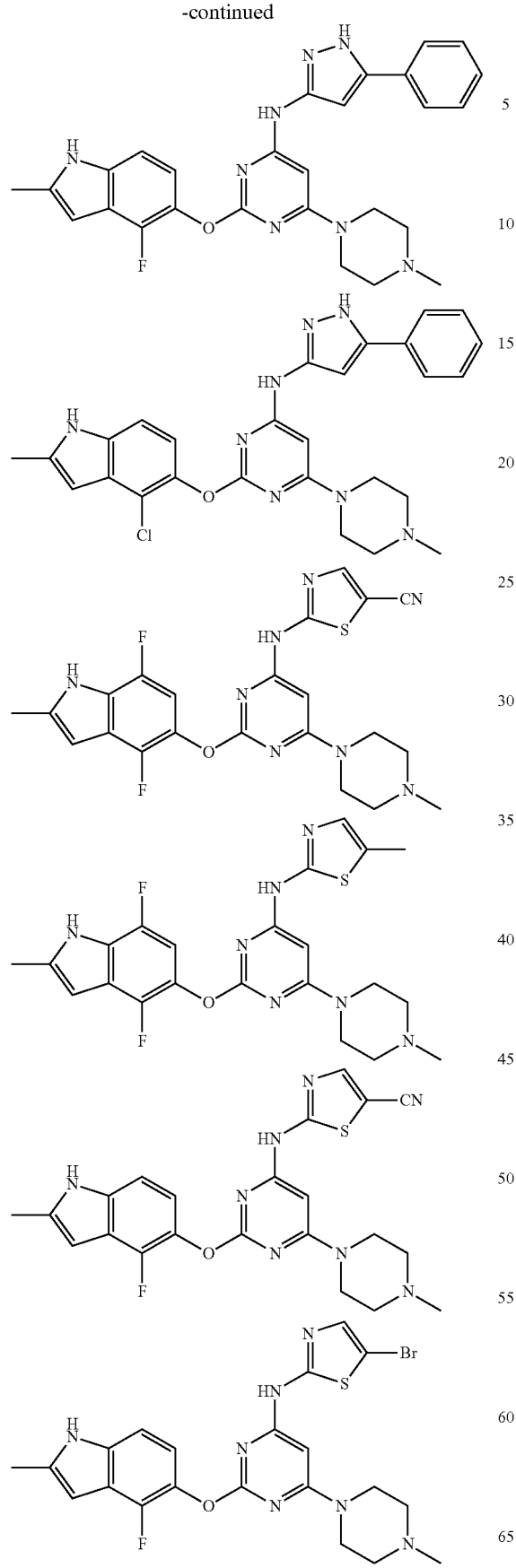
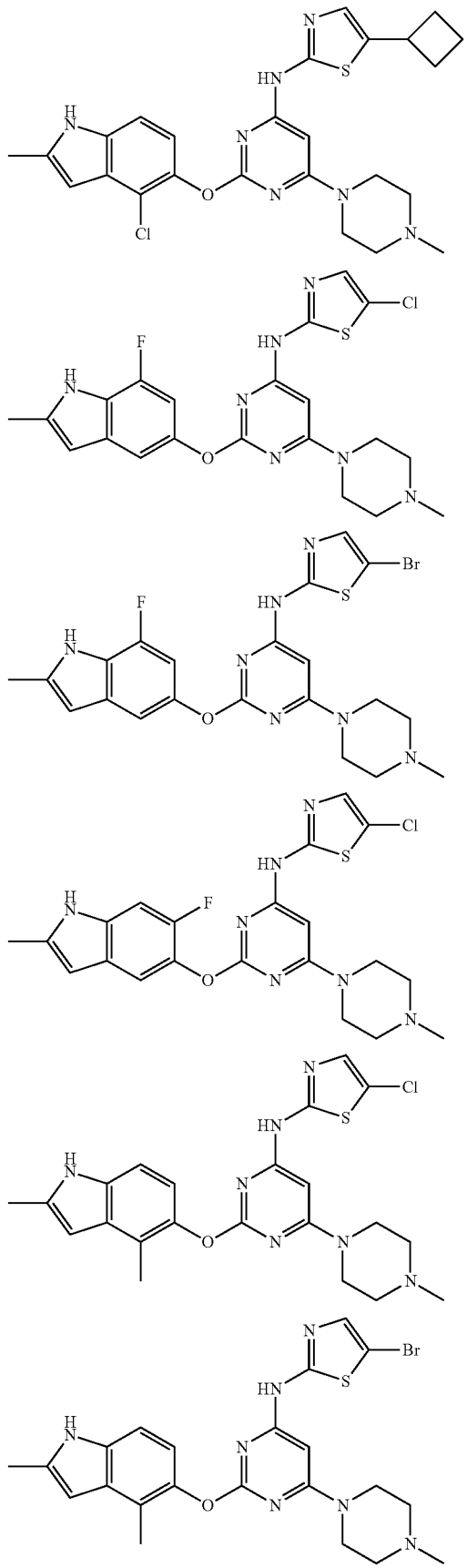

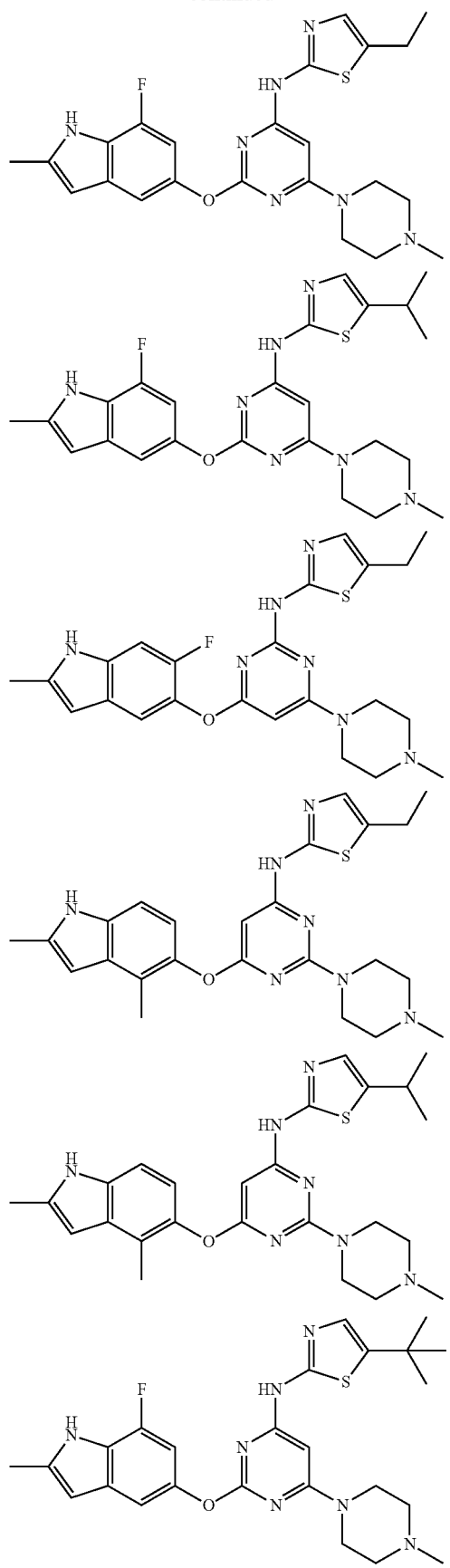
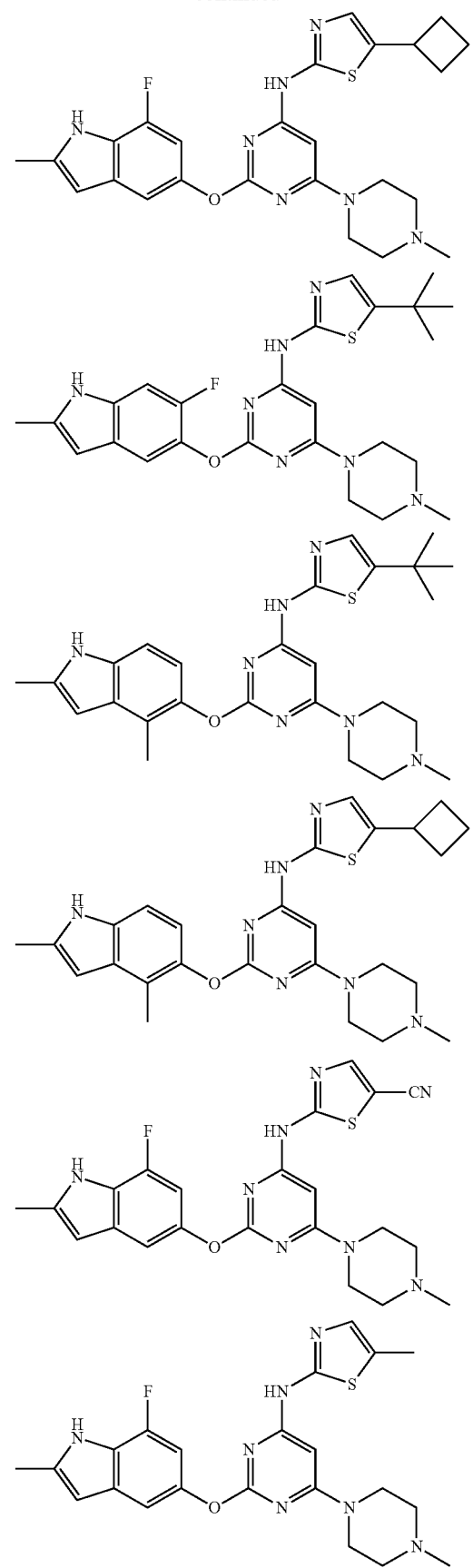

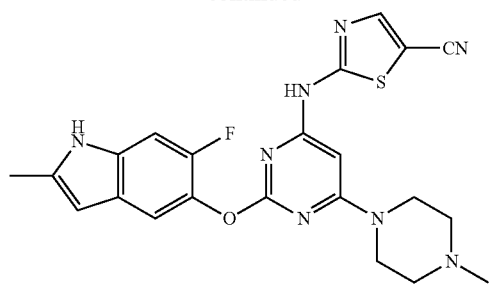
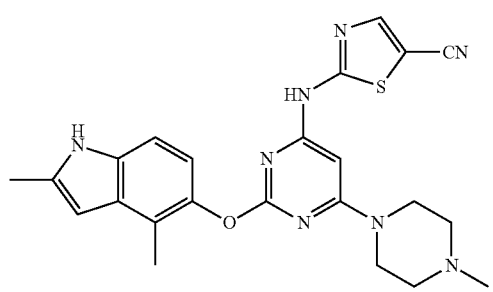
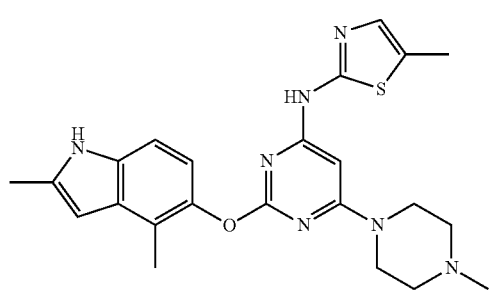
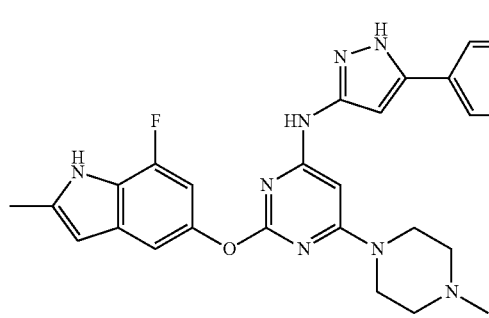
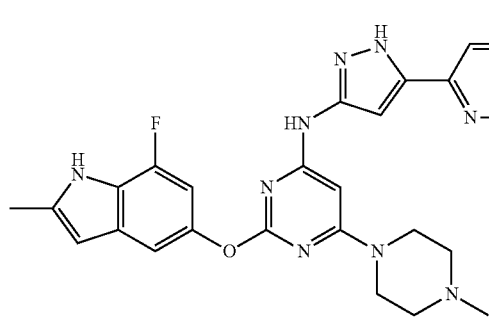
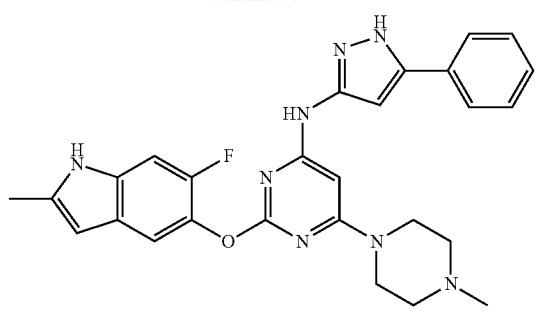
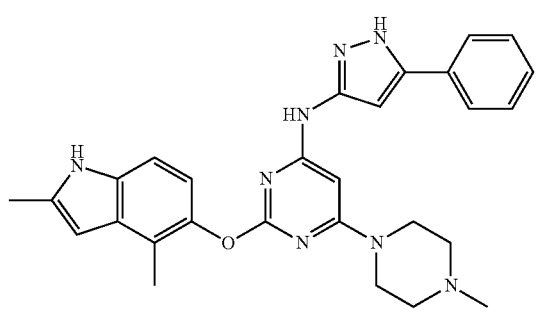
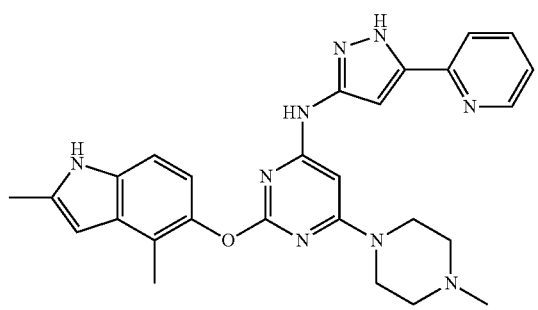
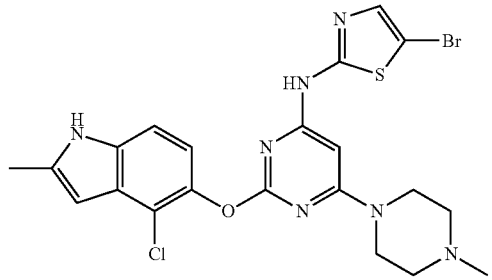
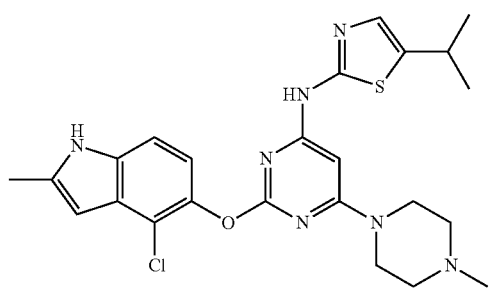

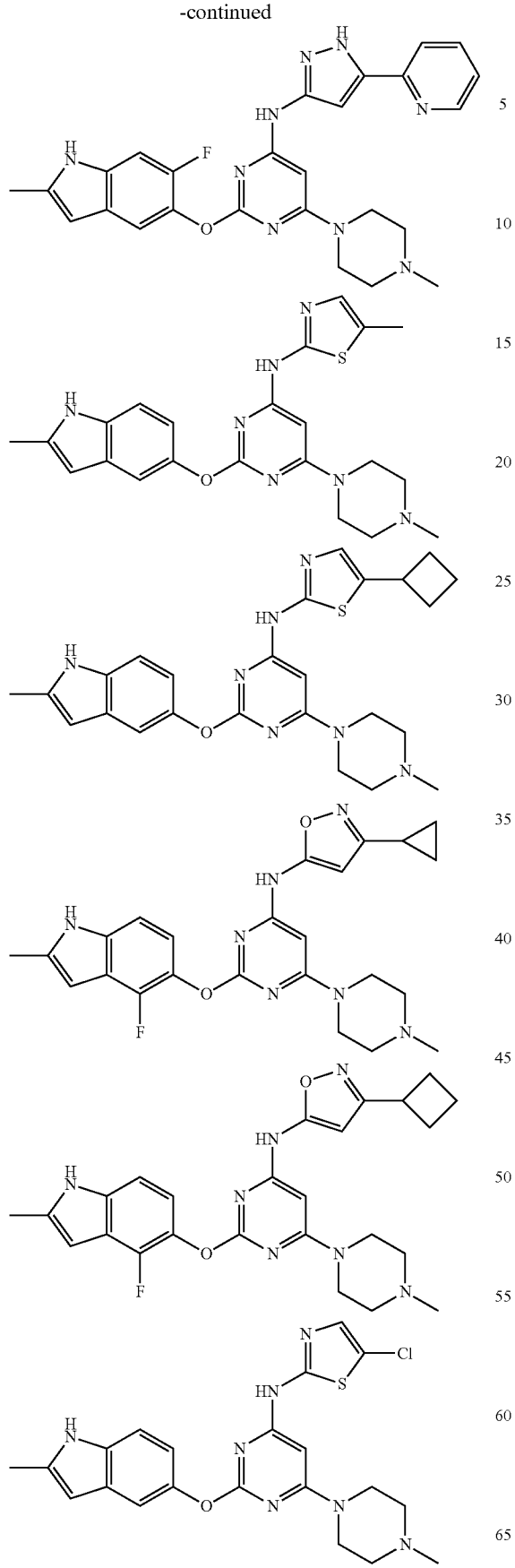
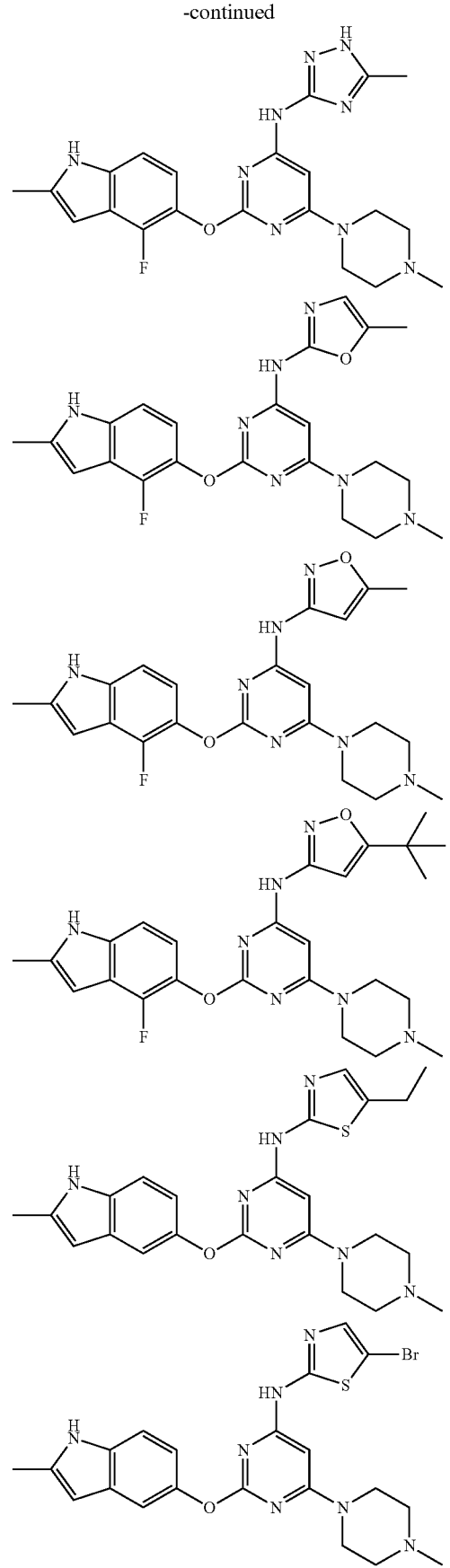

71
-continued
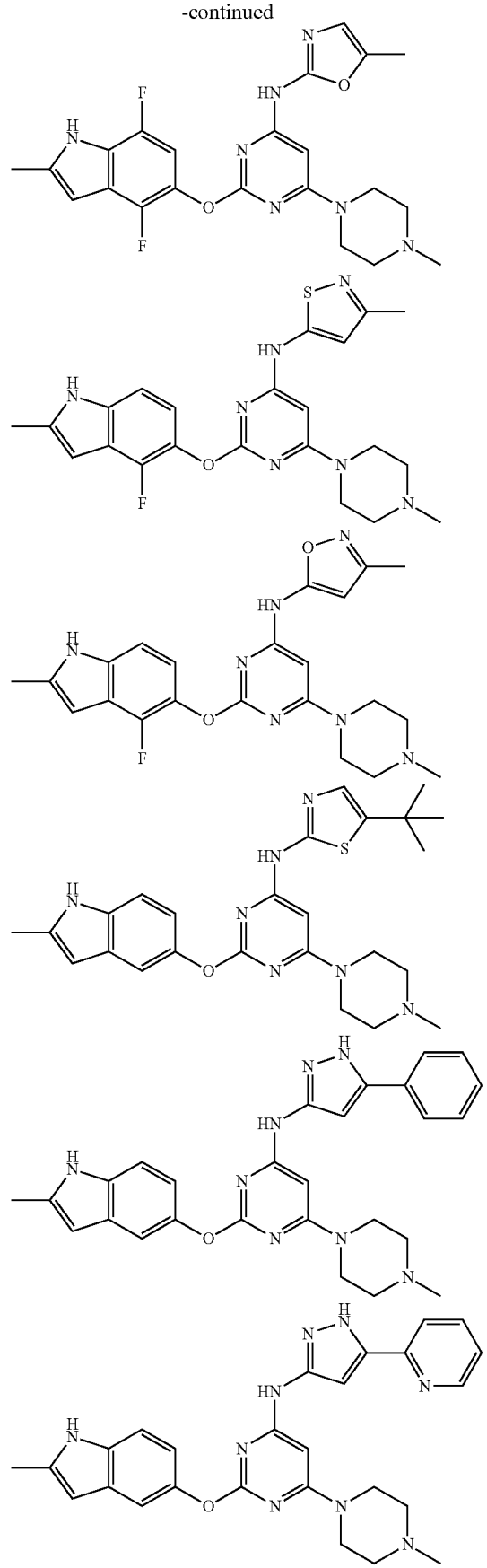
72
-continued
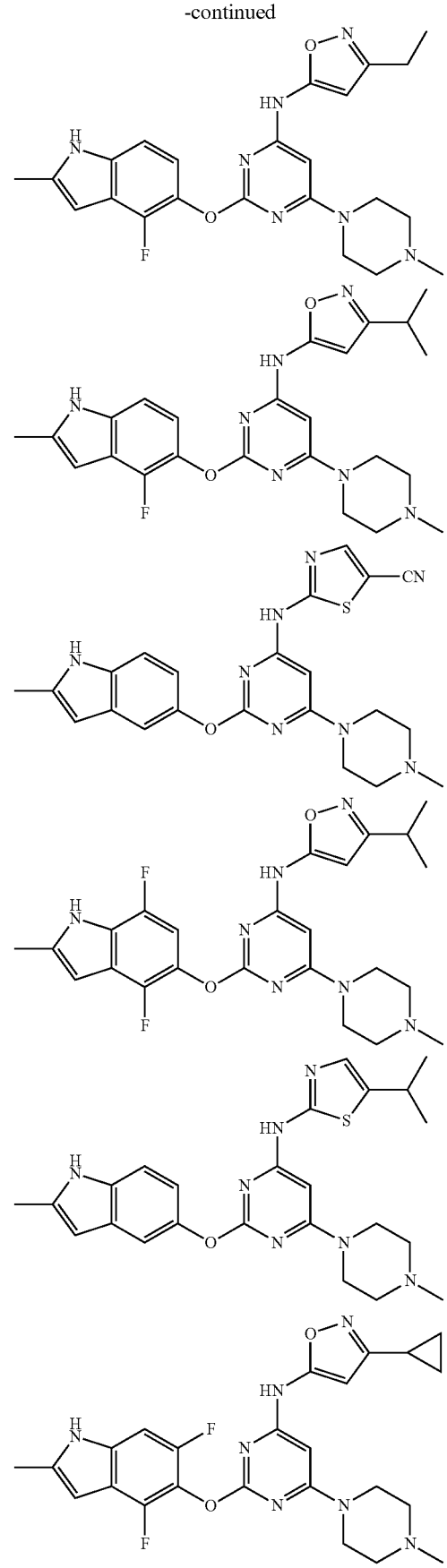

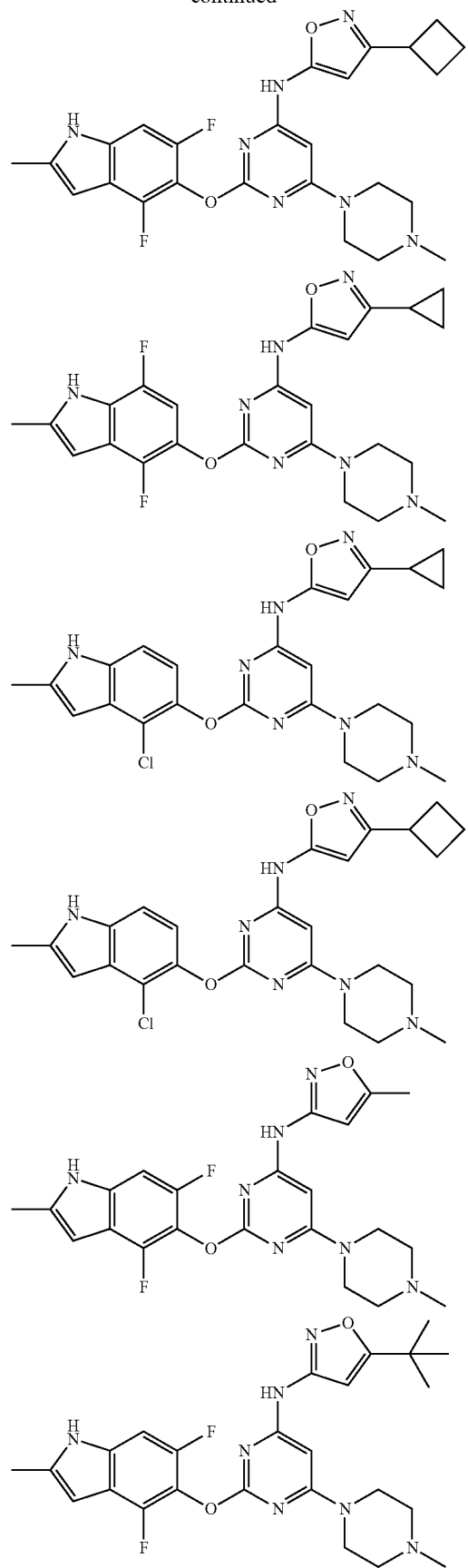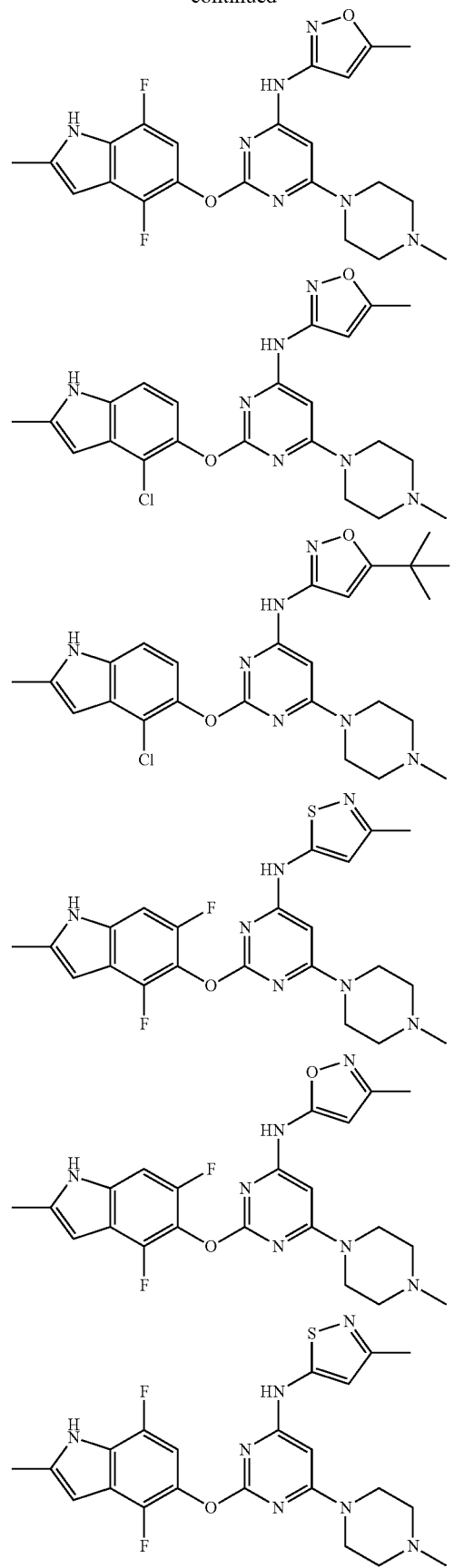

75
-continued
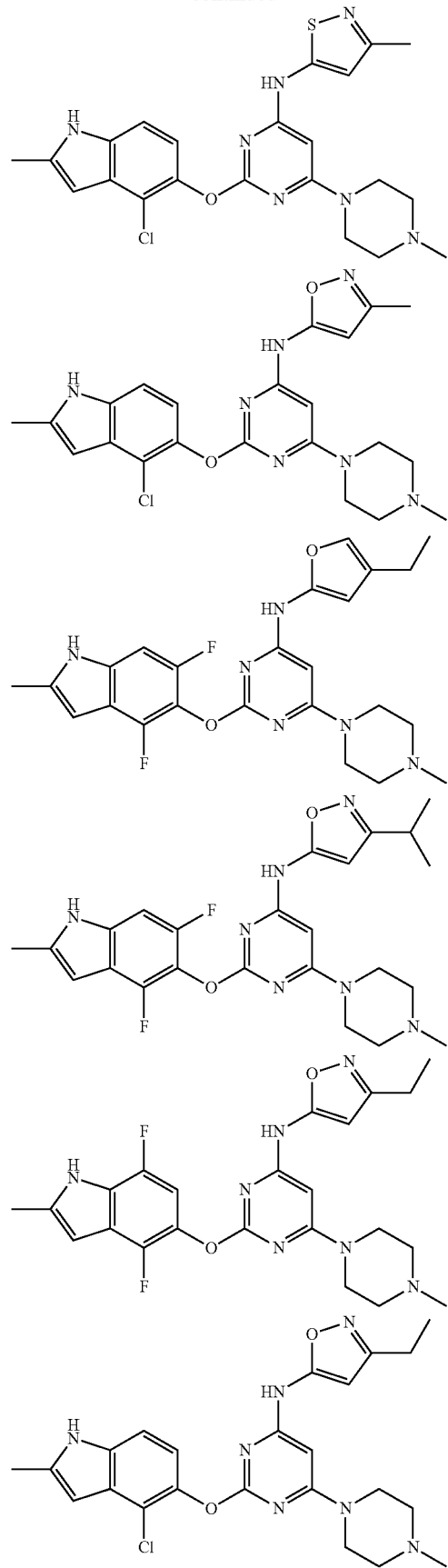
76
-continued
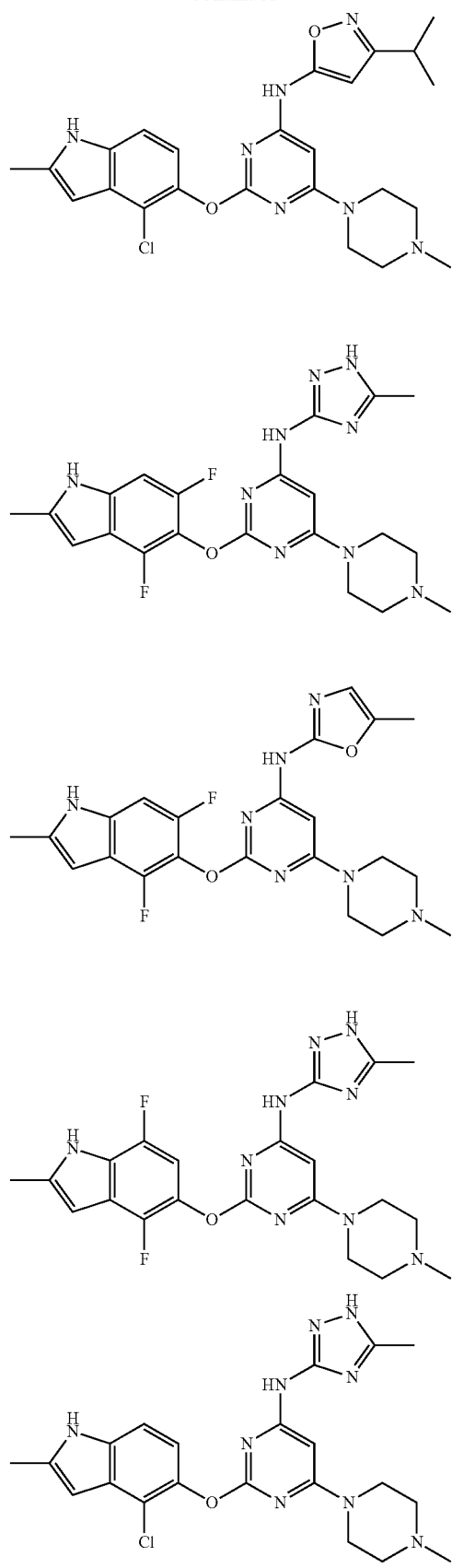

77
-continued
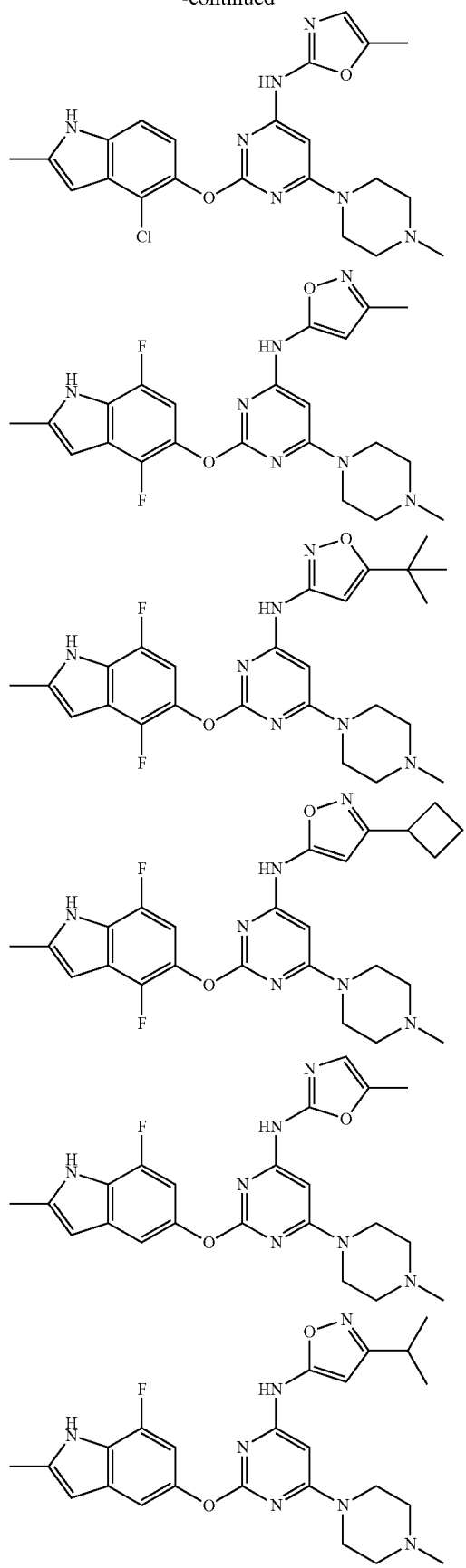
78
-continued
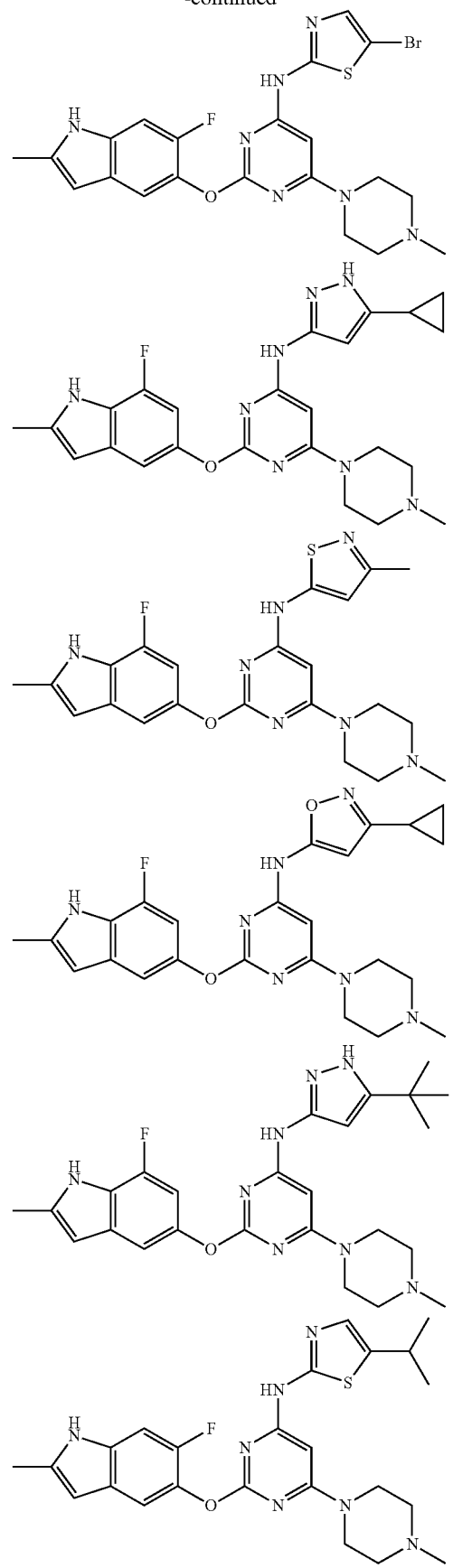

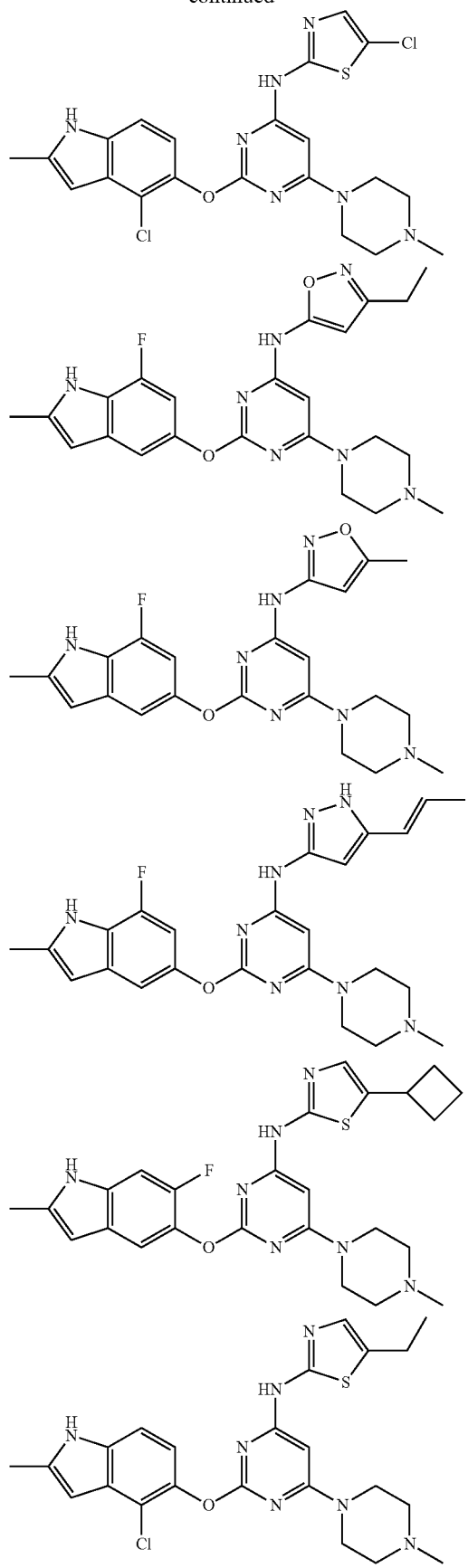
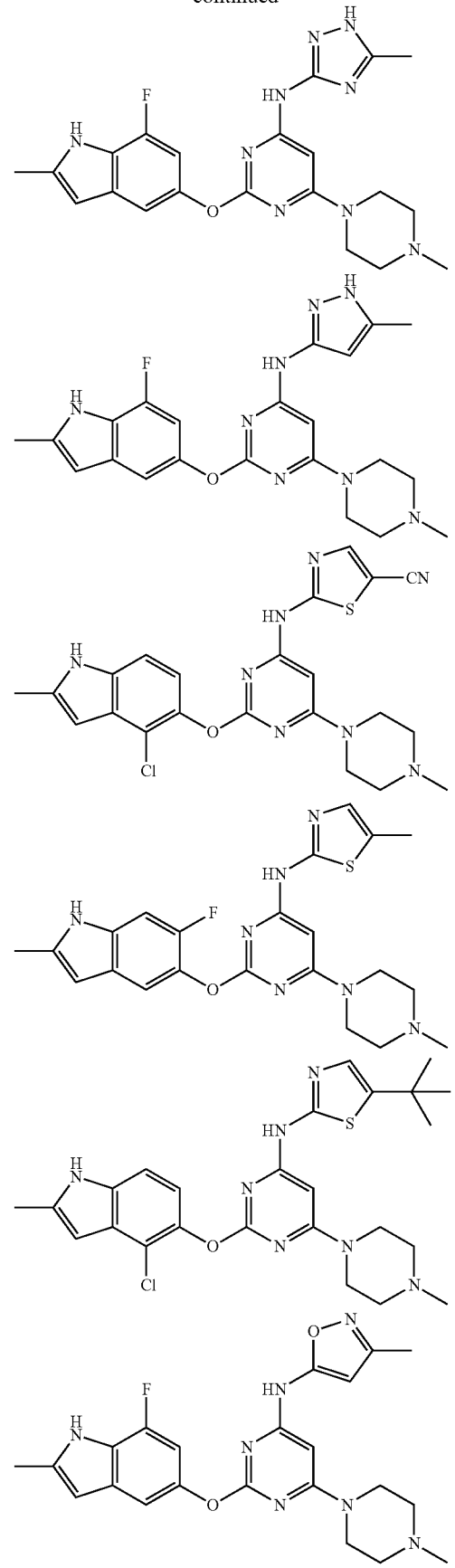

-continued
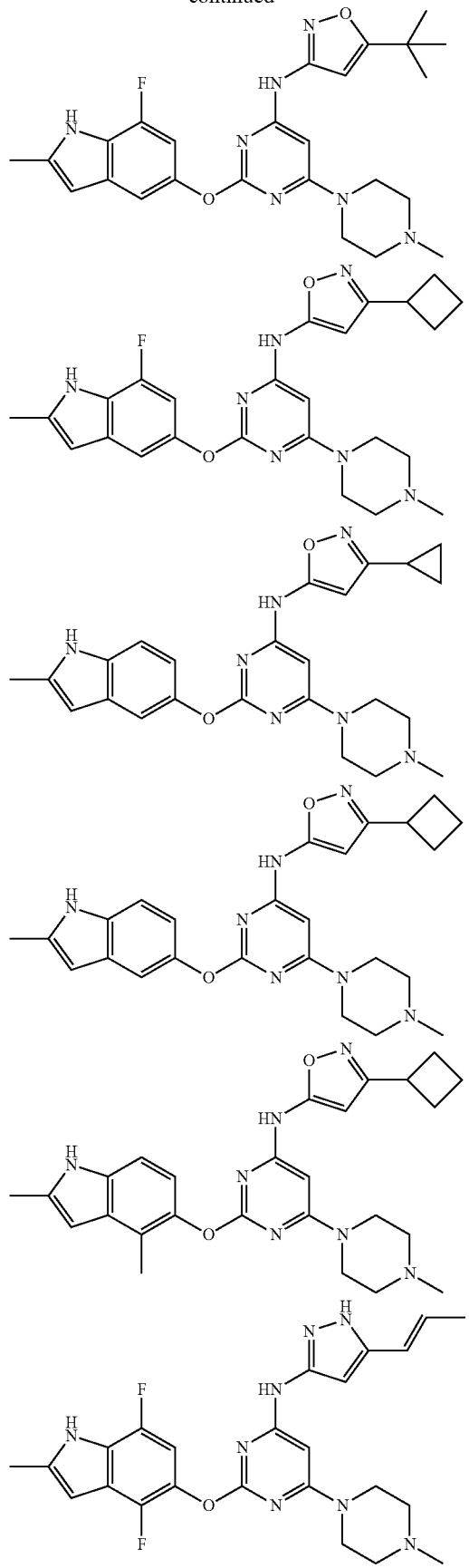
-continued
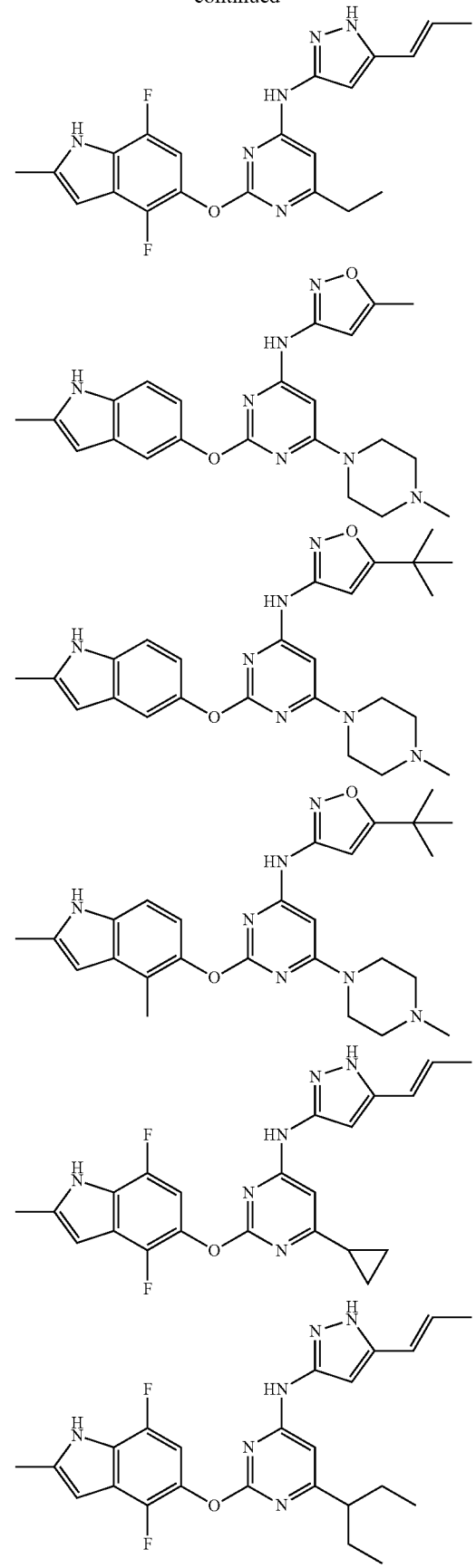

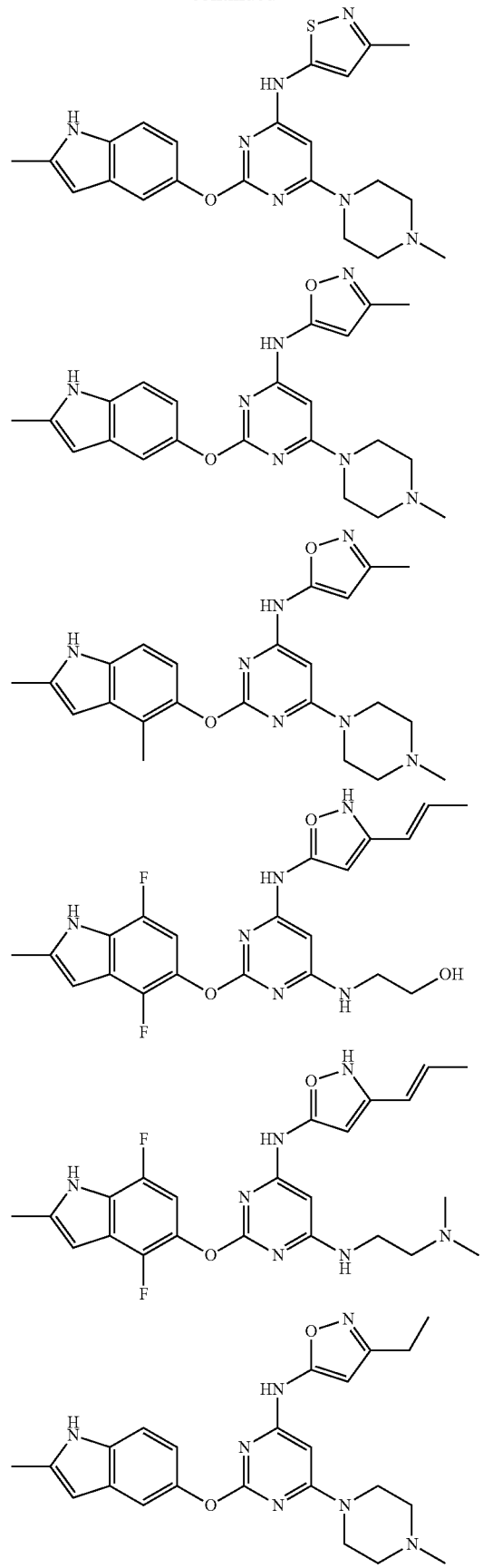
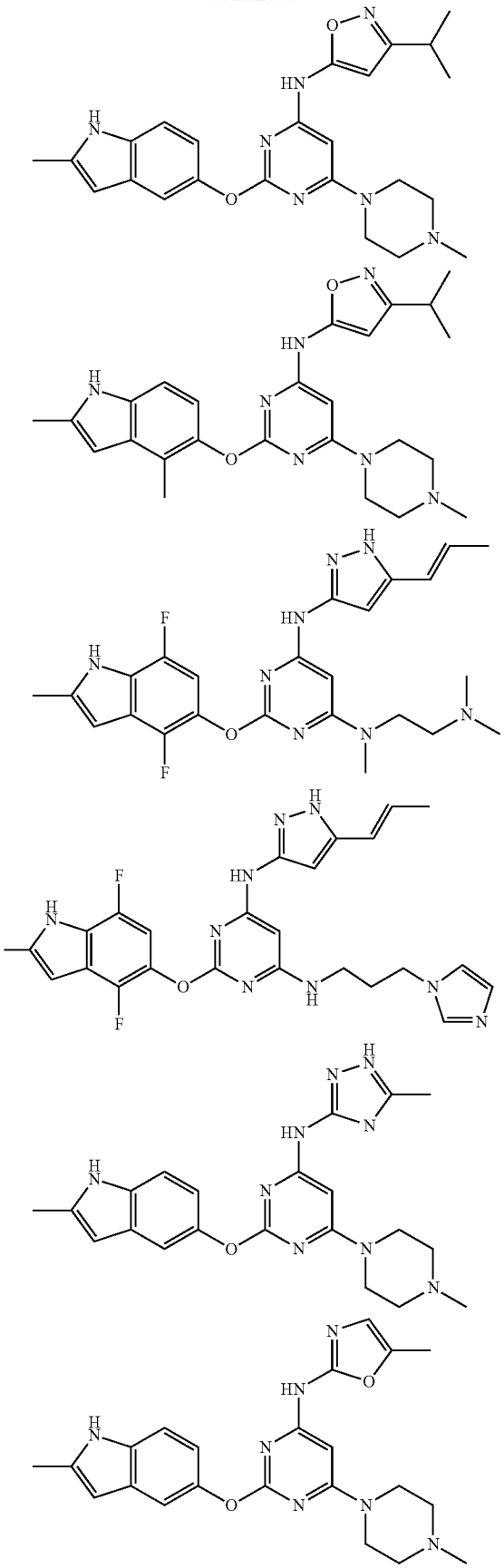

85
-continued
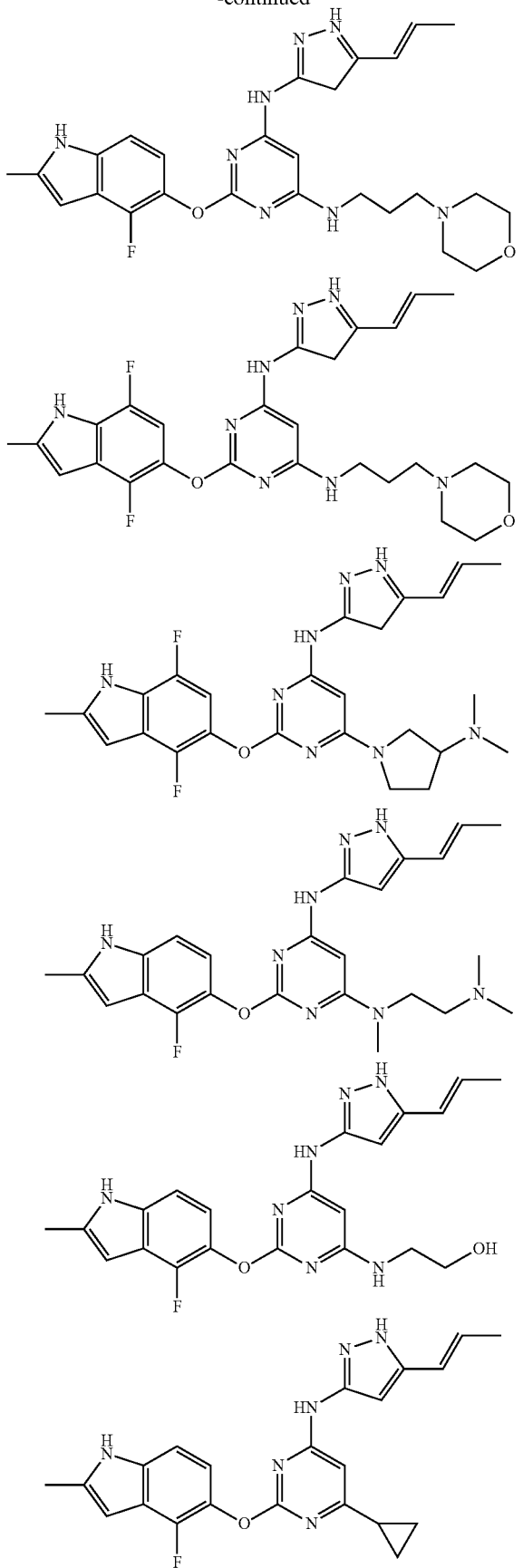
86
-continued
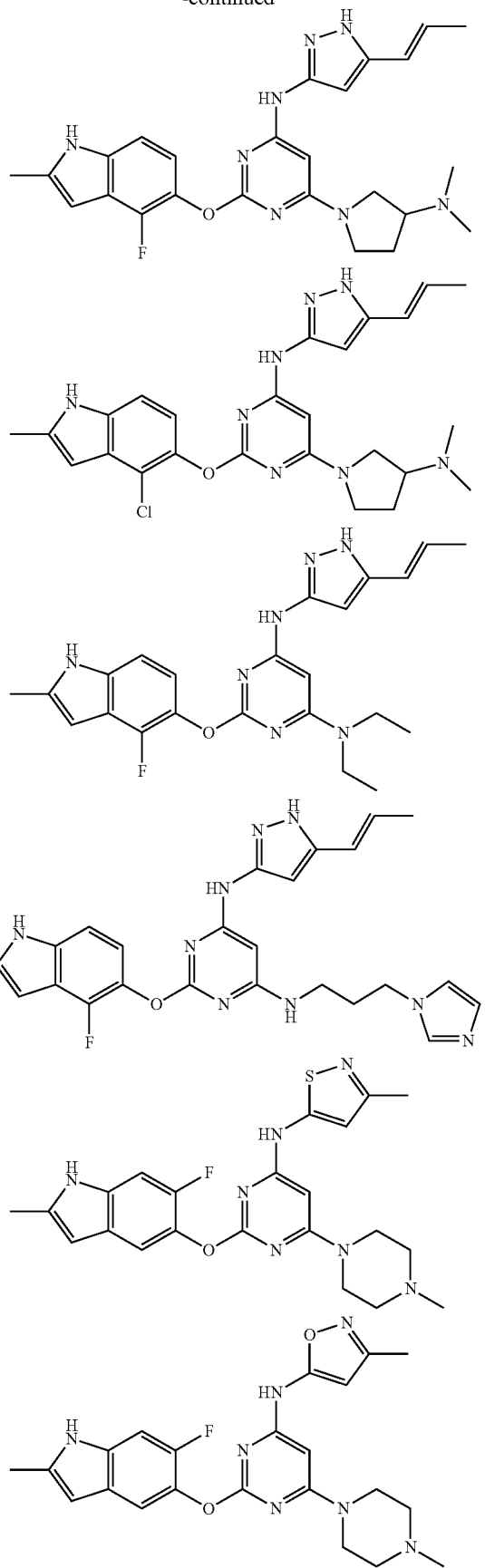

87
-continued
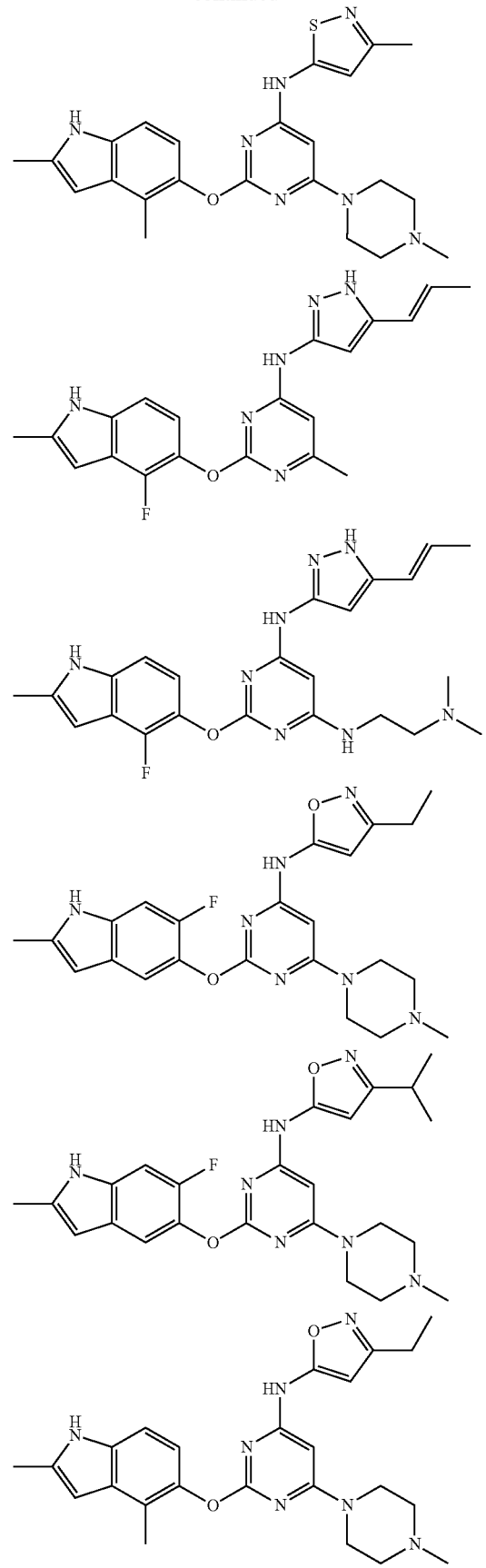
88
-continued
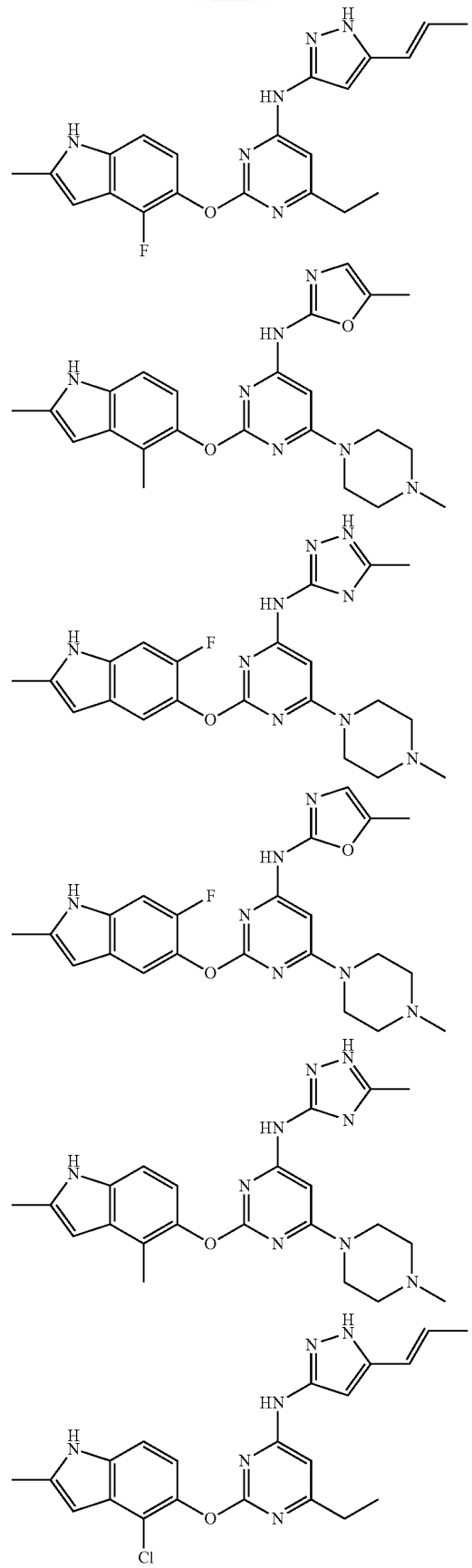

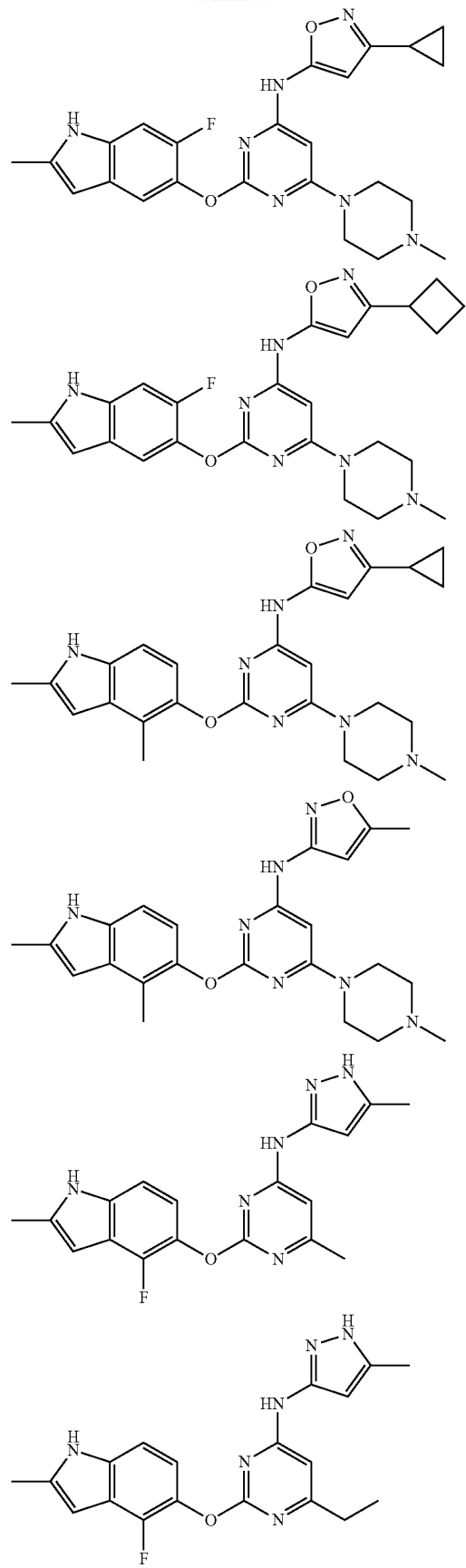
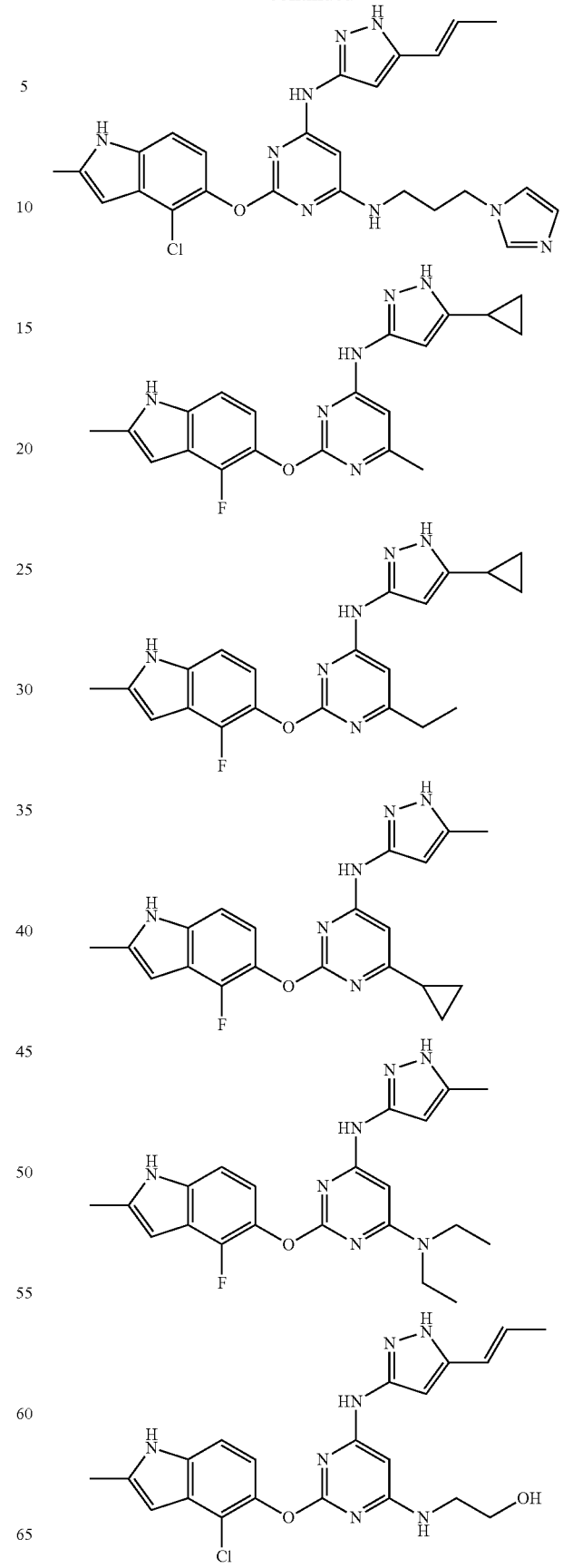

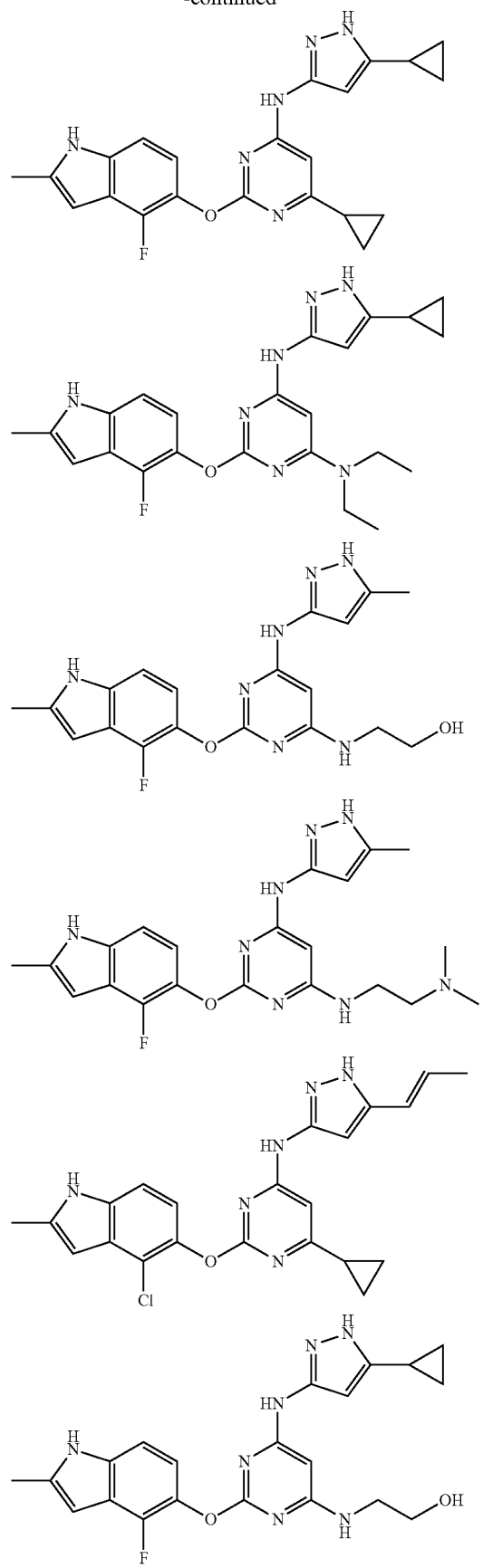
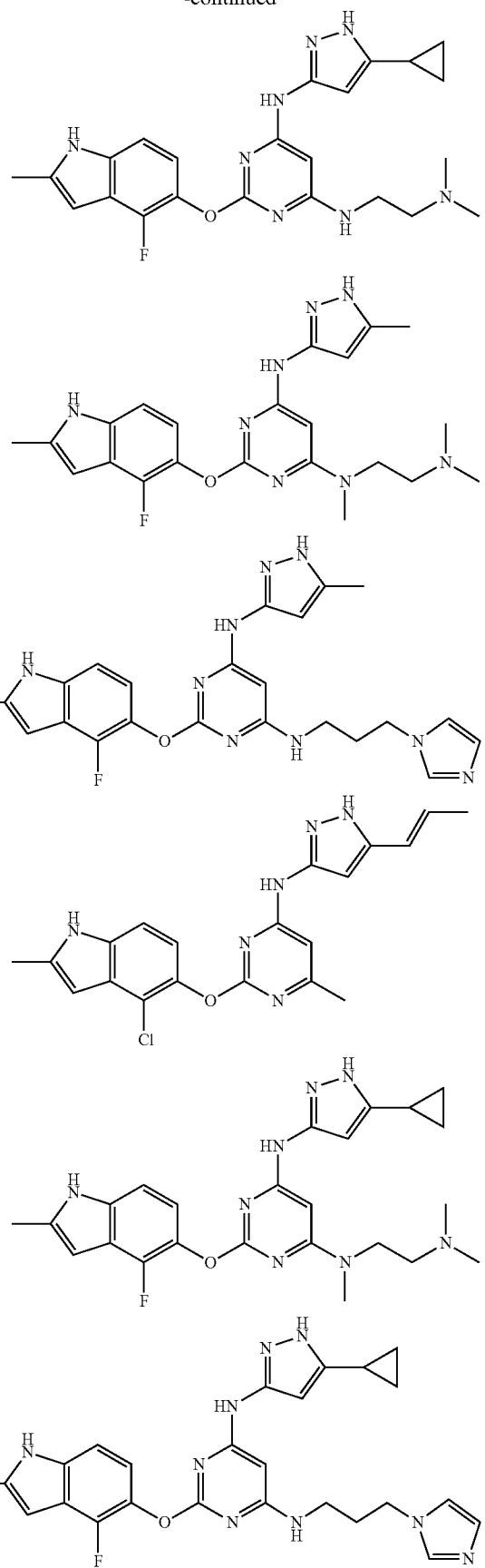

93
-continued
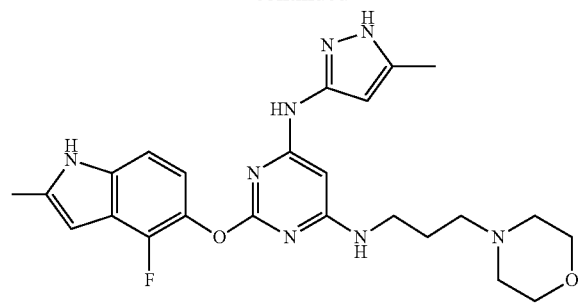
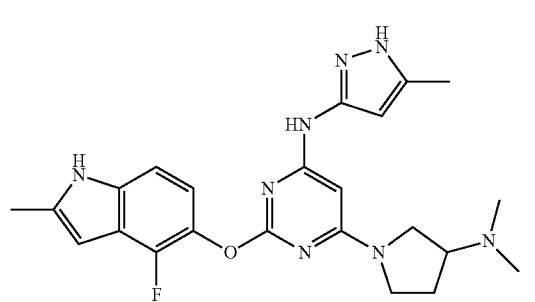
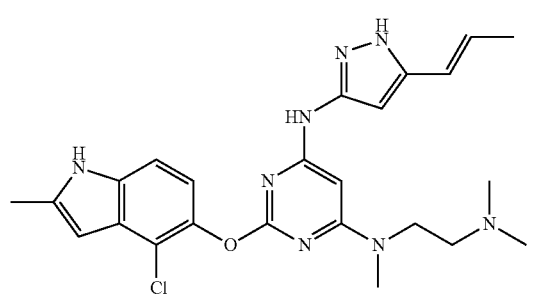
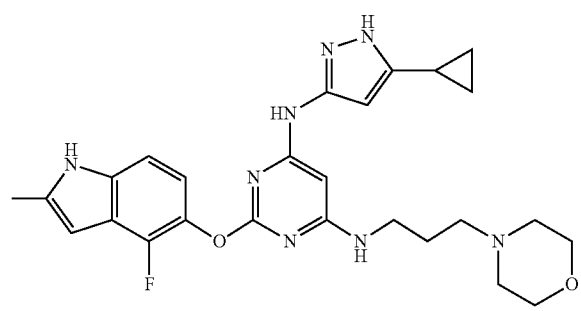
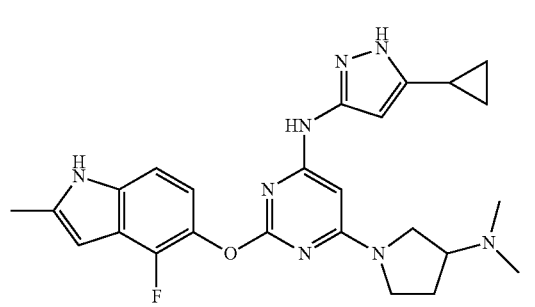
94
-continued
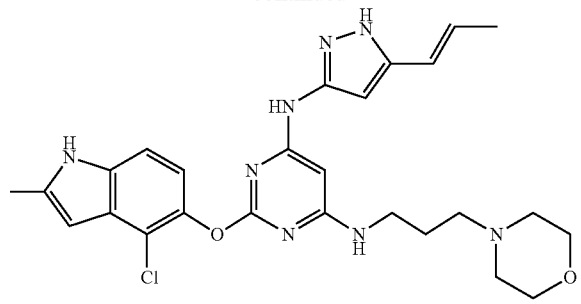
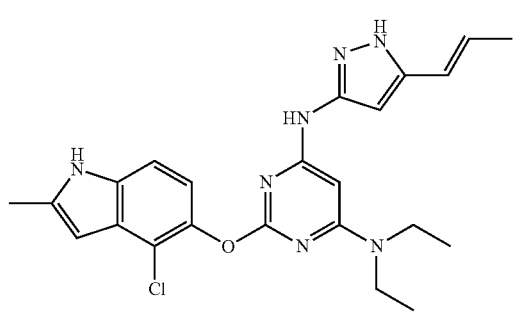
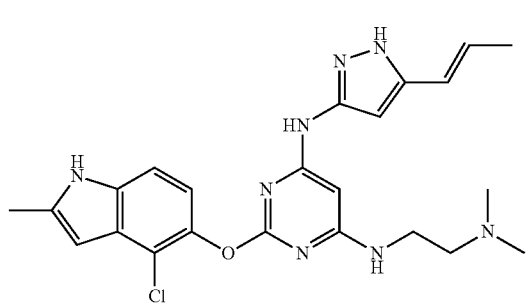
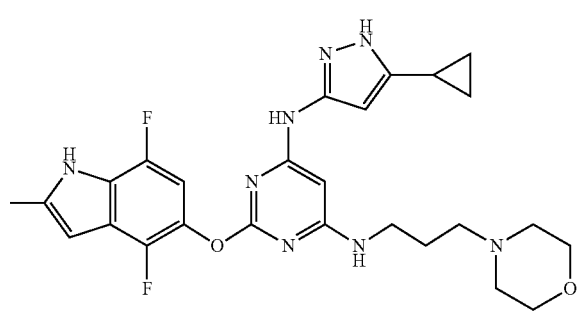
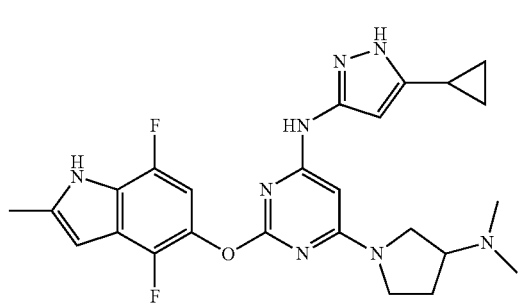

95
-continued
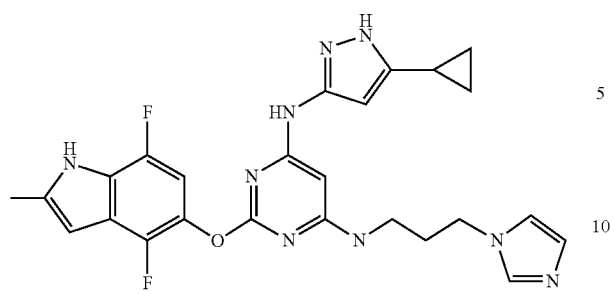
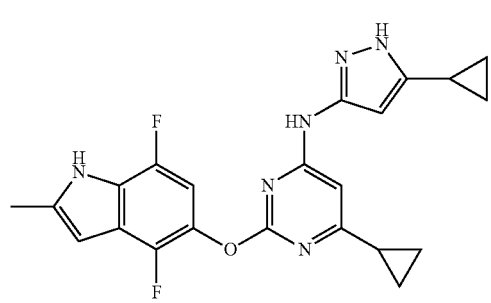
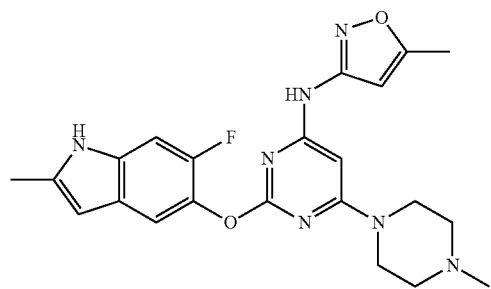
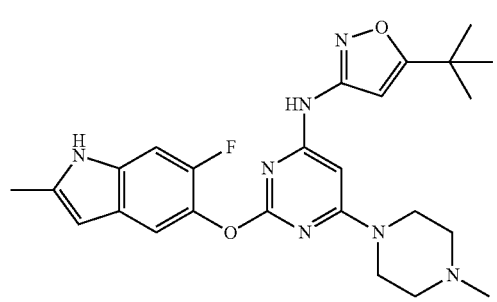
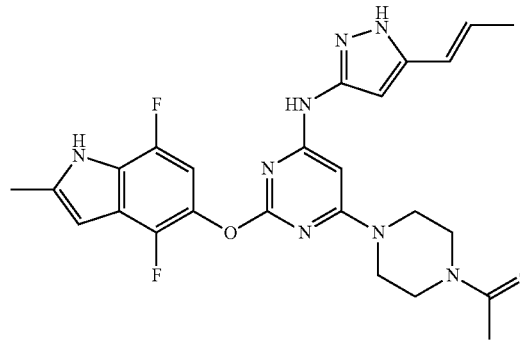
96
-continued
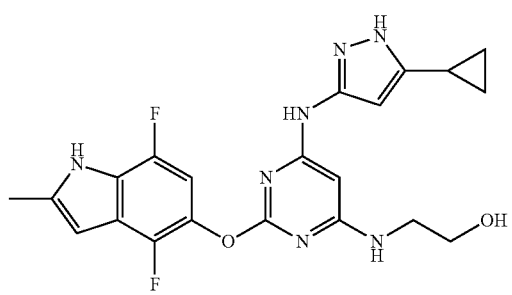
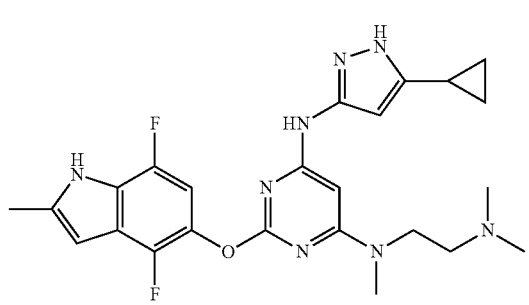
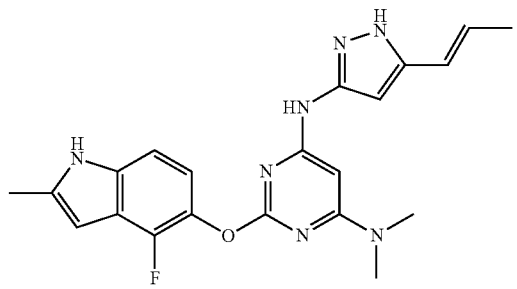
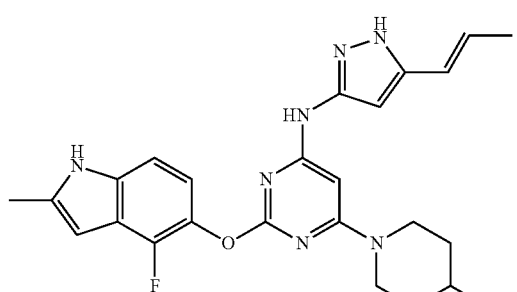
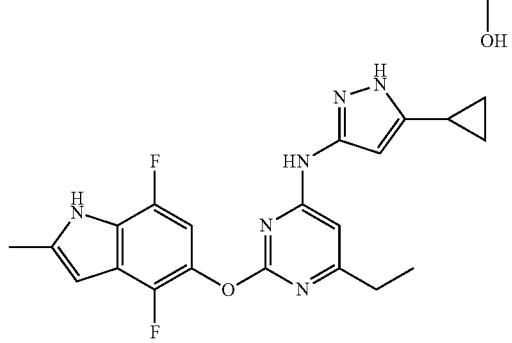

-continued
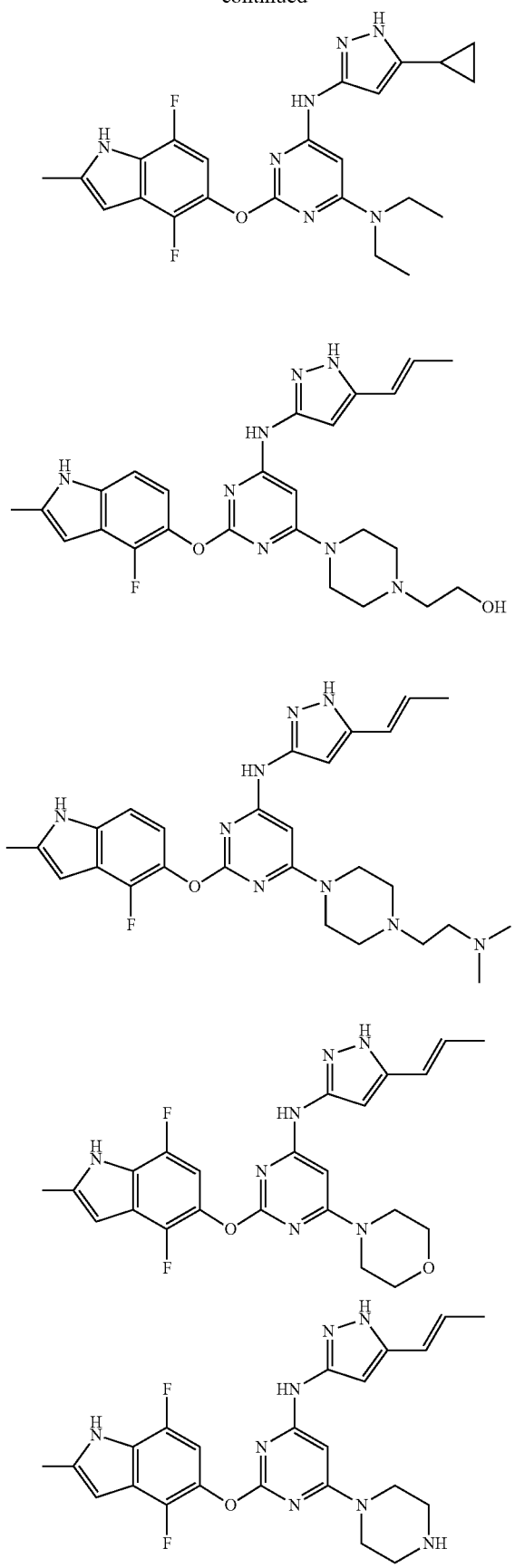
-continued
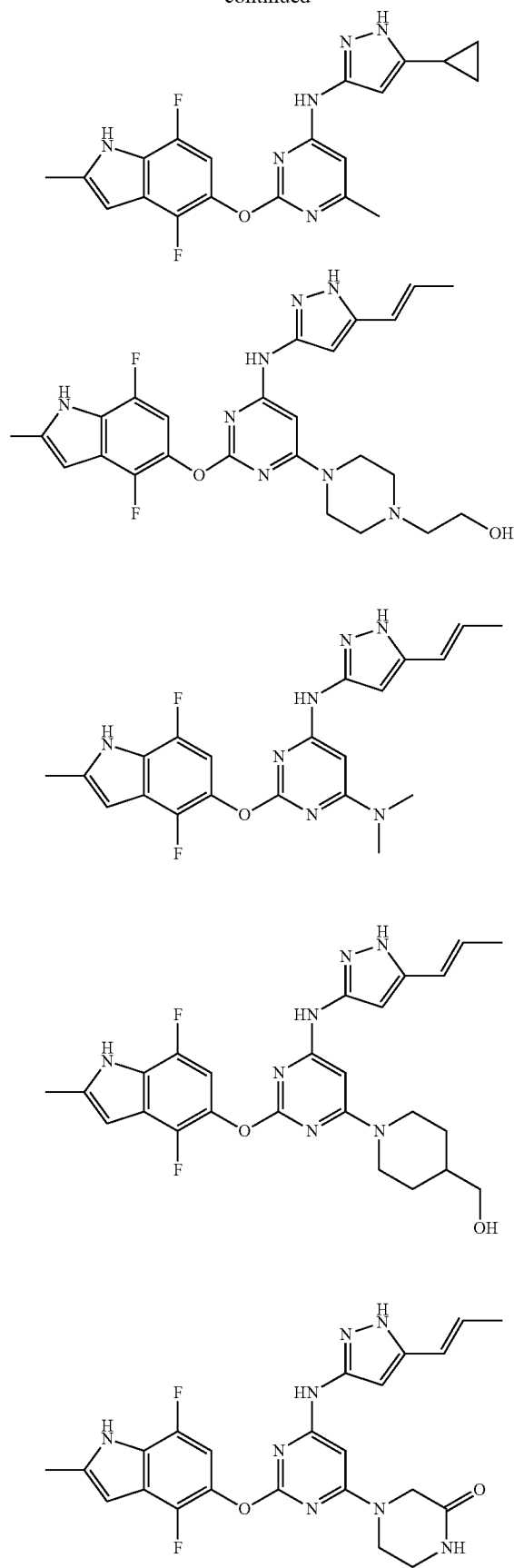

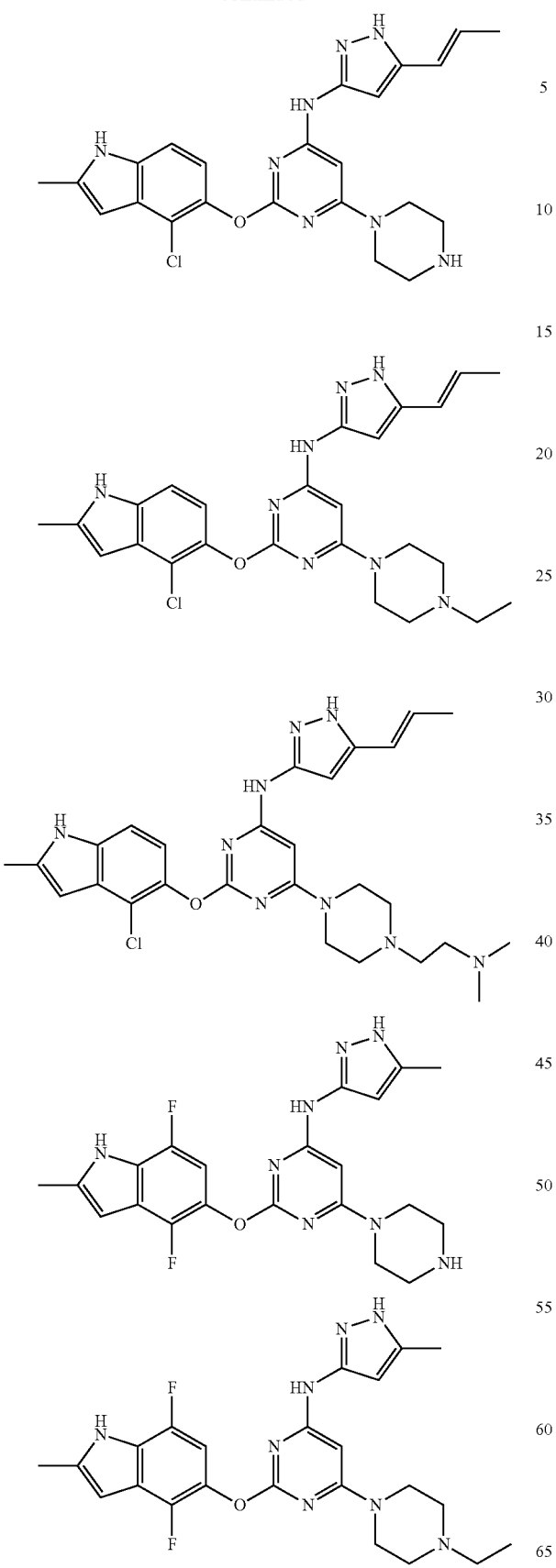
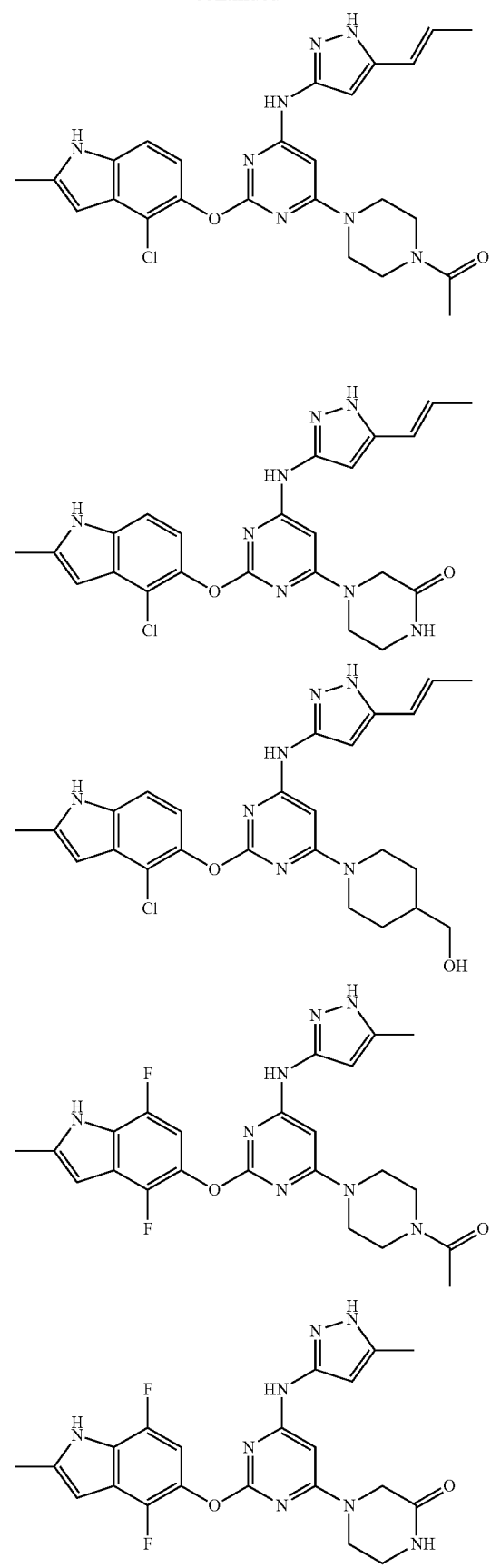

101
-continued
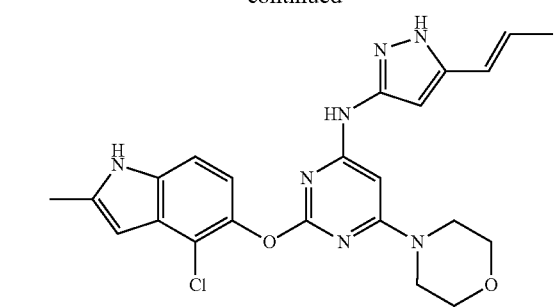
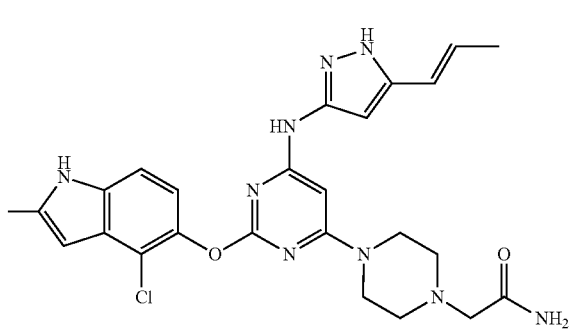
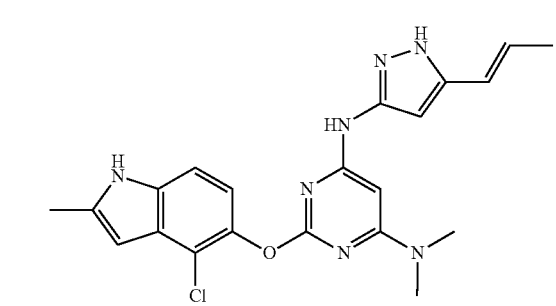
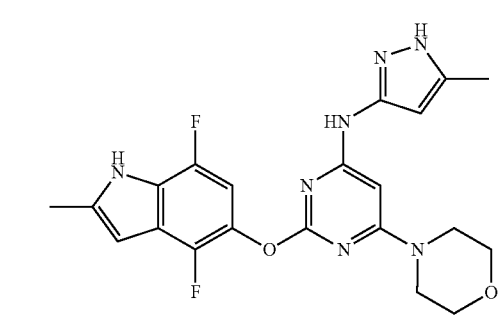
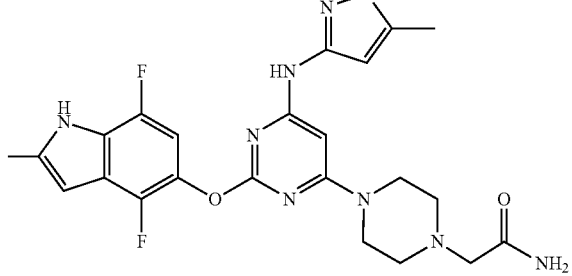
102
-continued
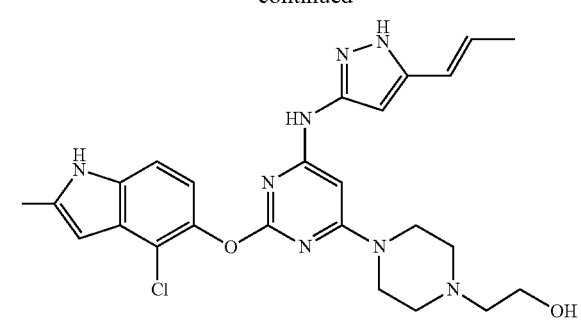
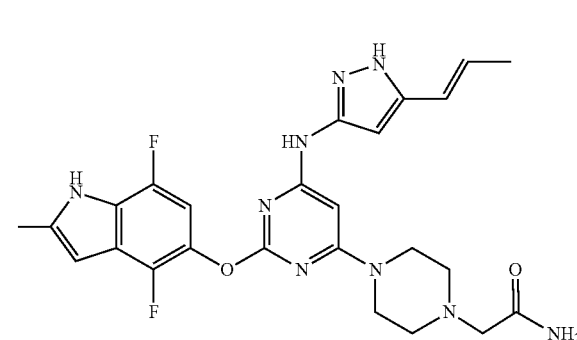
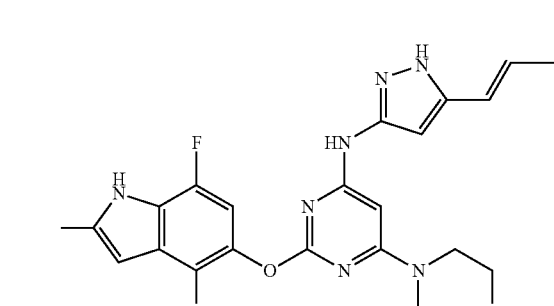
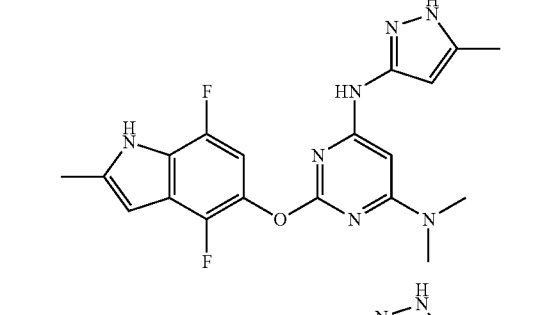
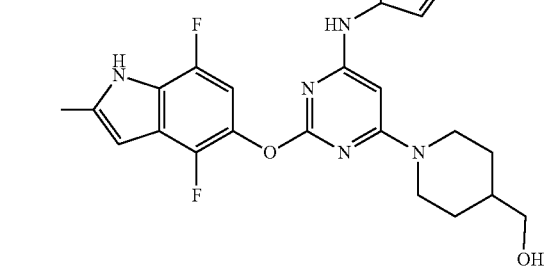

-continued
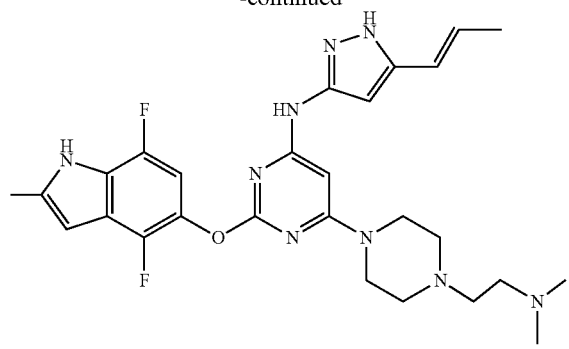
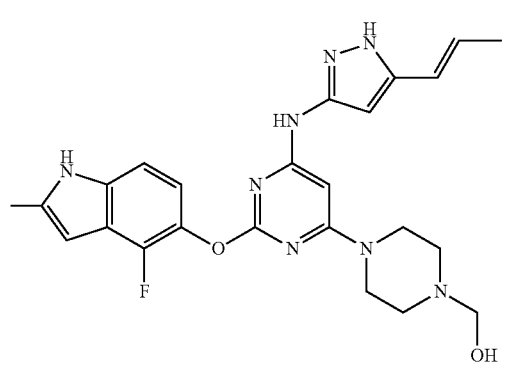
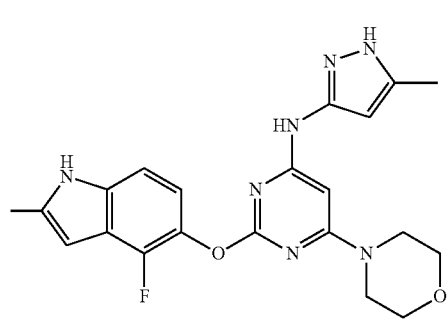
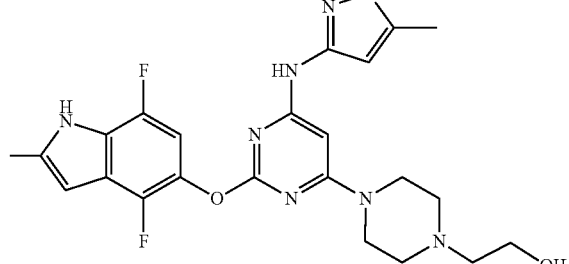
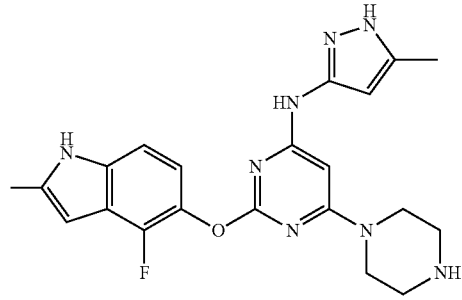
-continued
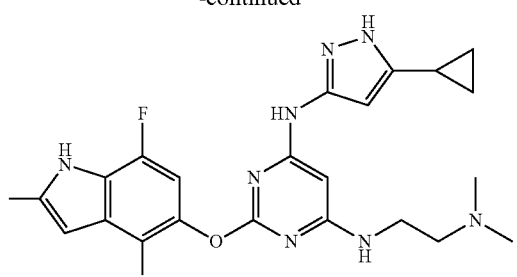
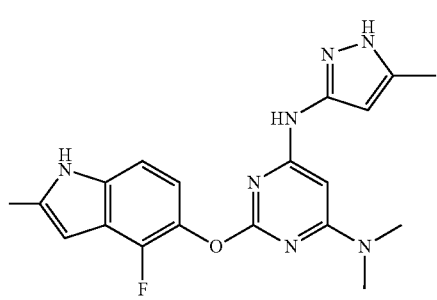
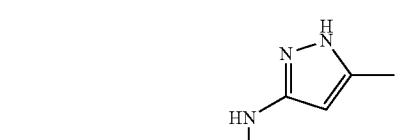
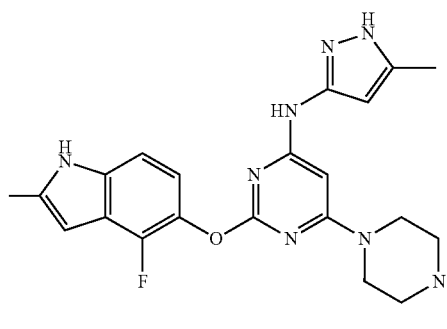
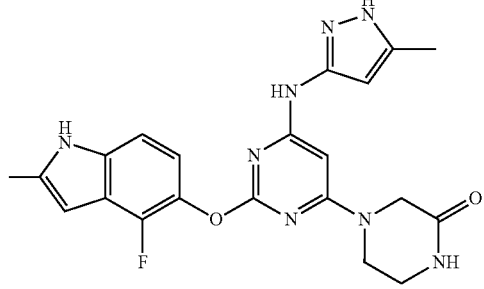

105
-continued
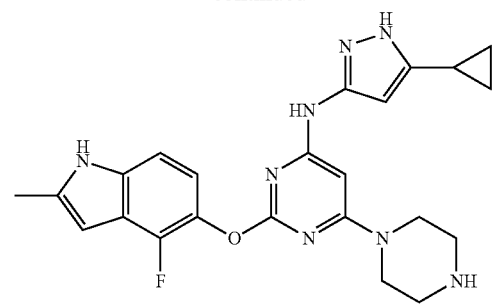
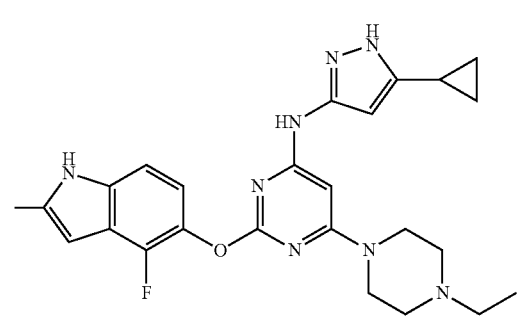
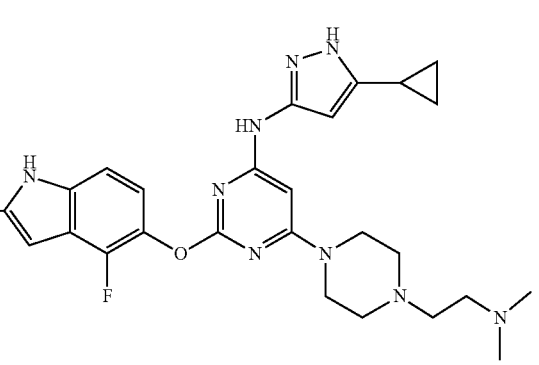
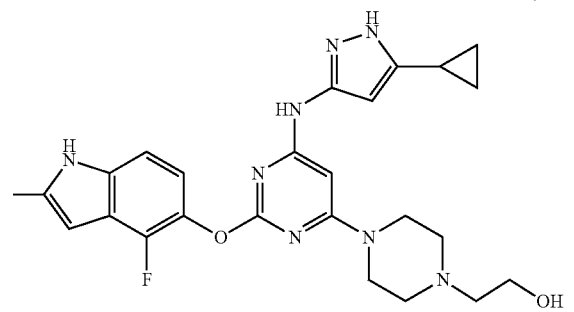
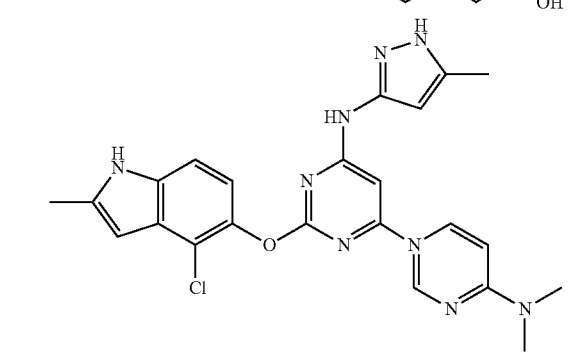
106
-continued
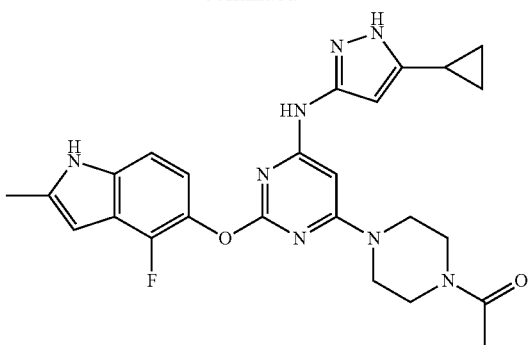
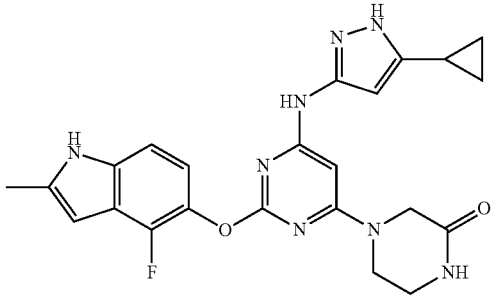
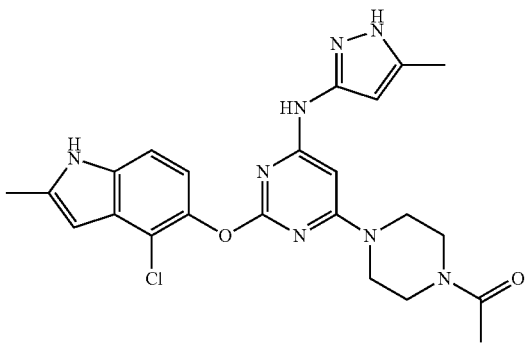
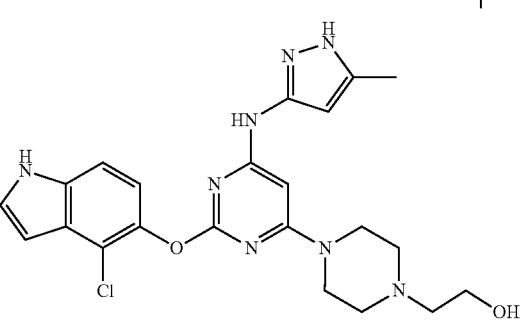
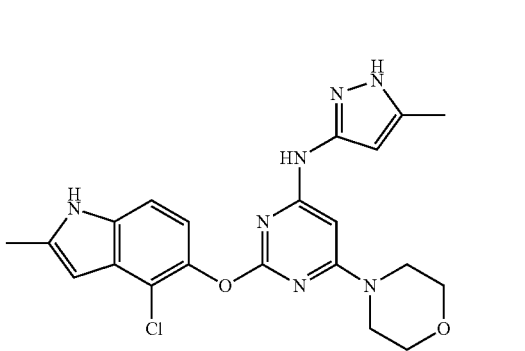

-continued
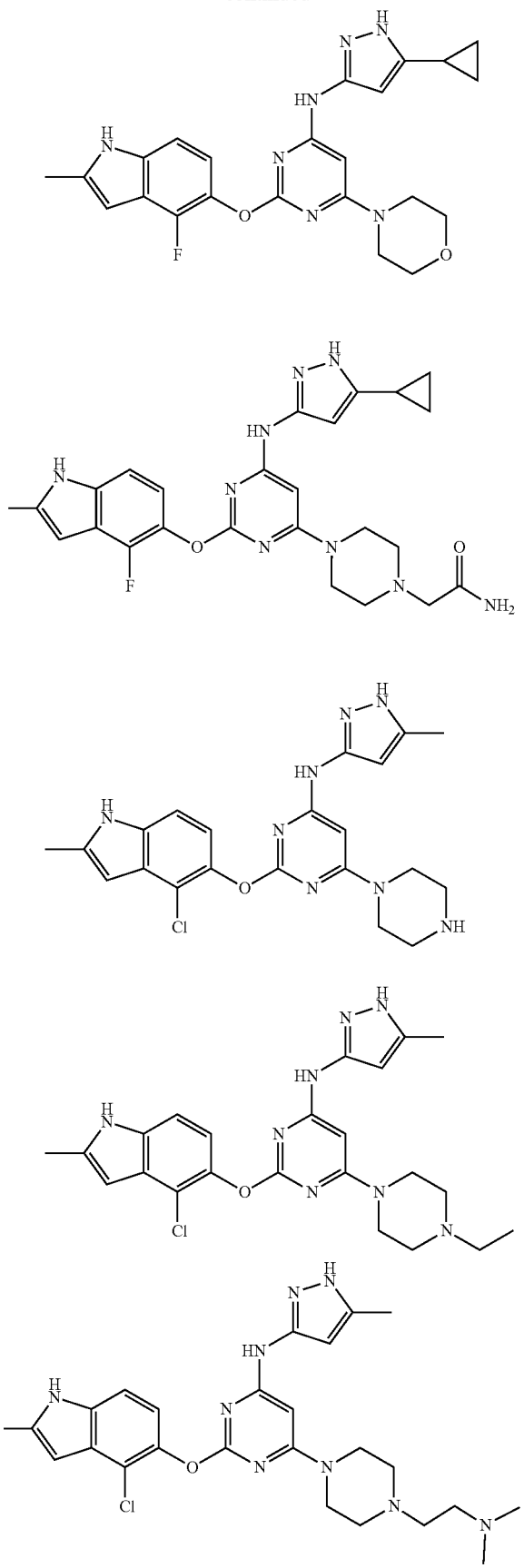
-continued
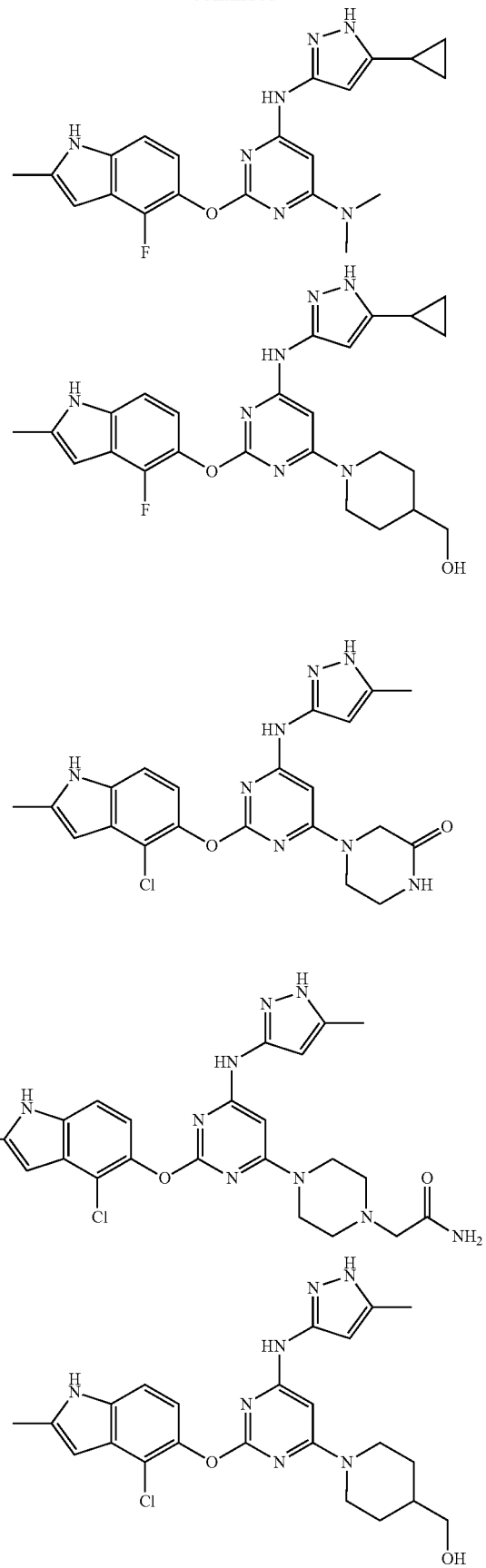

109
-continued
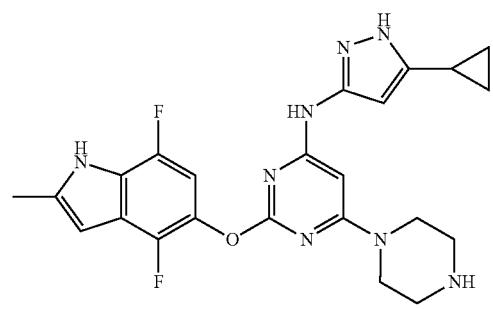
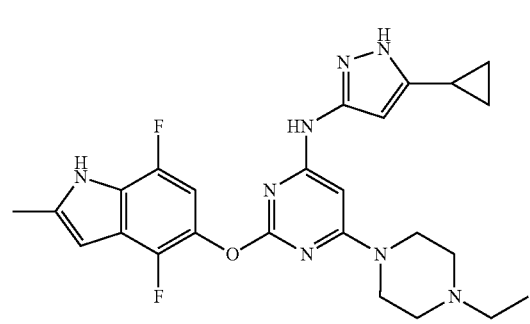
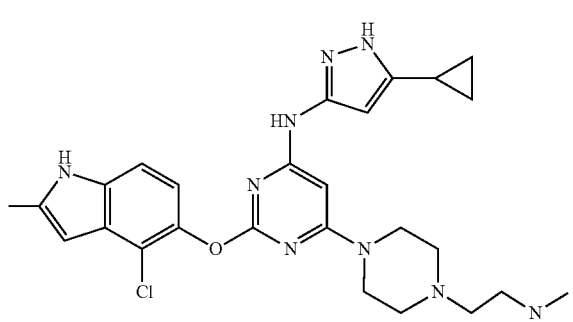
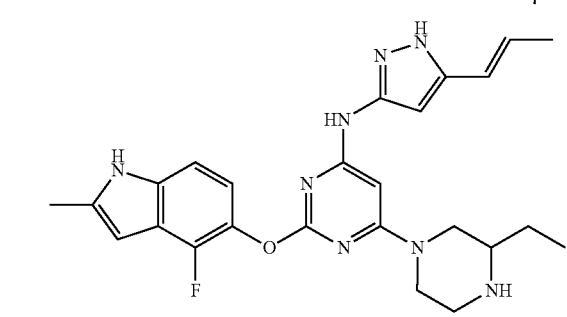
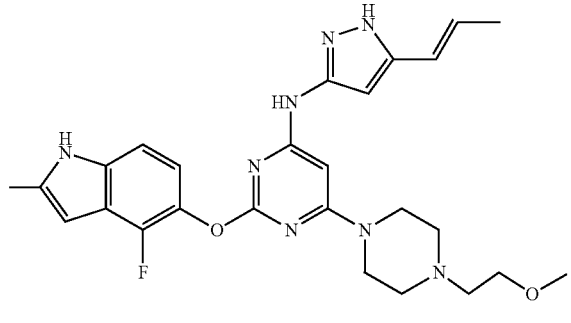
110
-continued
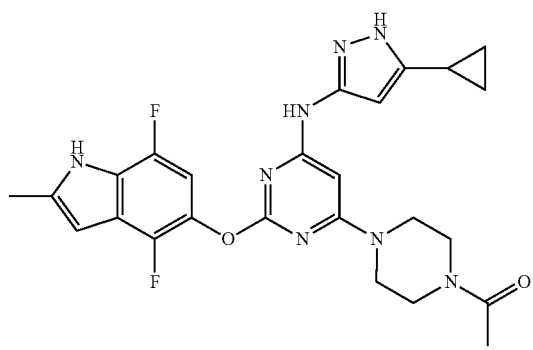
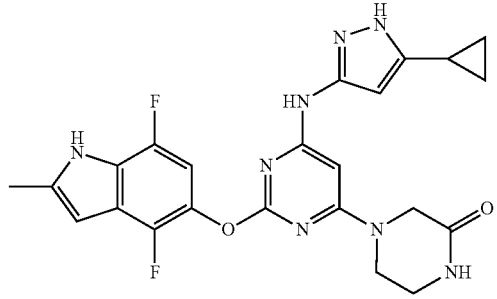
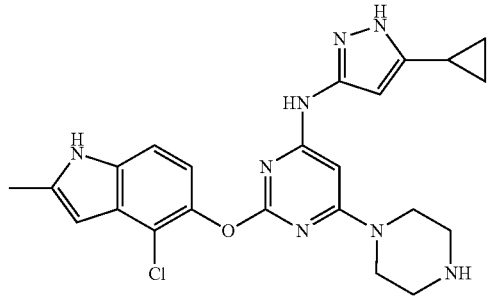
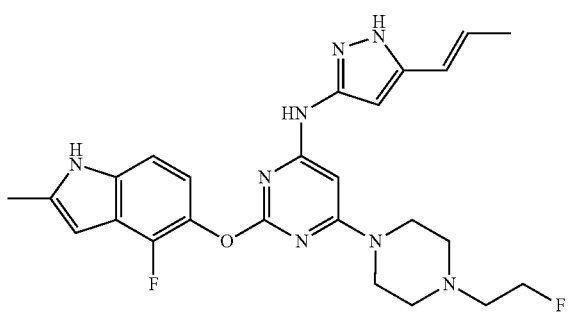
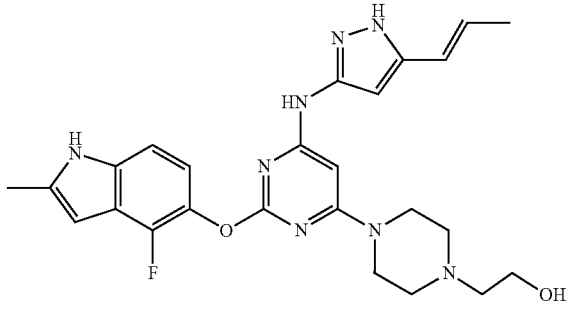

-continued
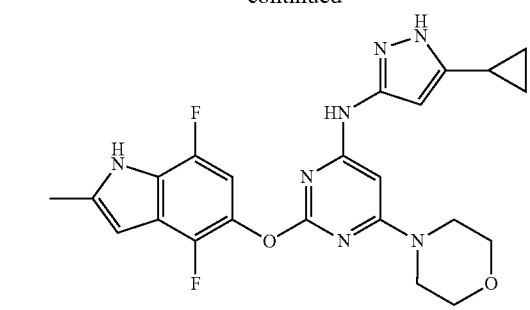
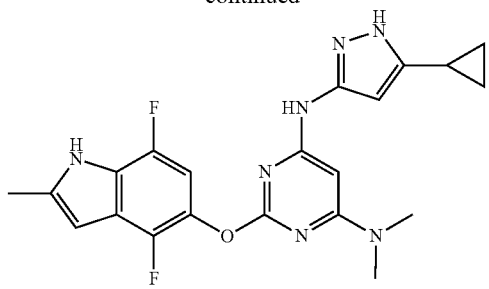
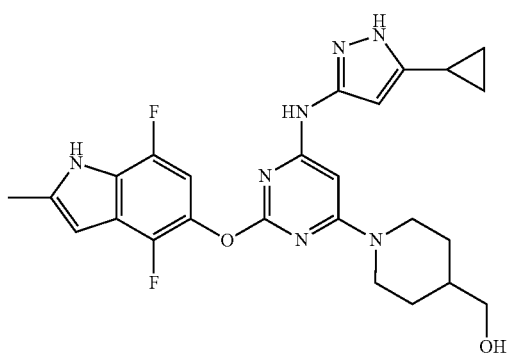
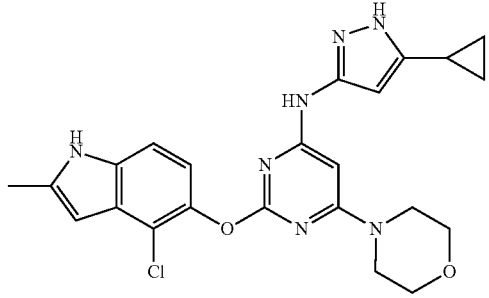
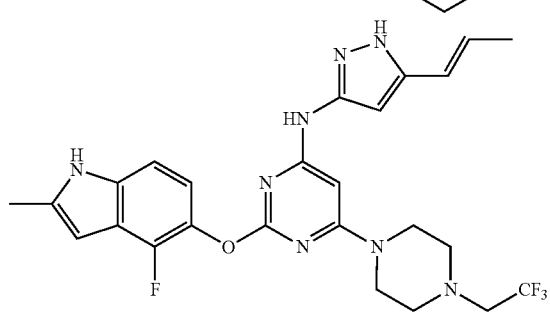
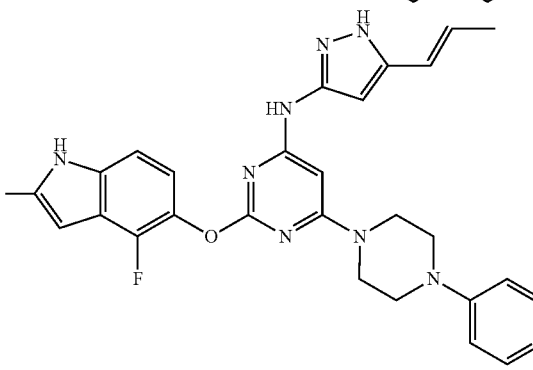

113
-continued
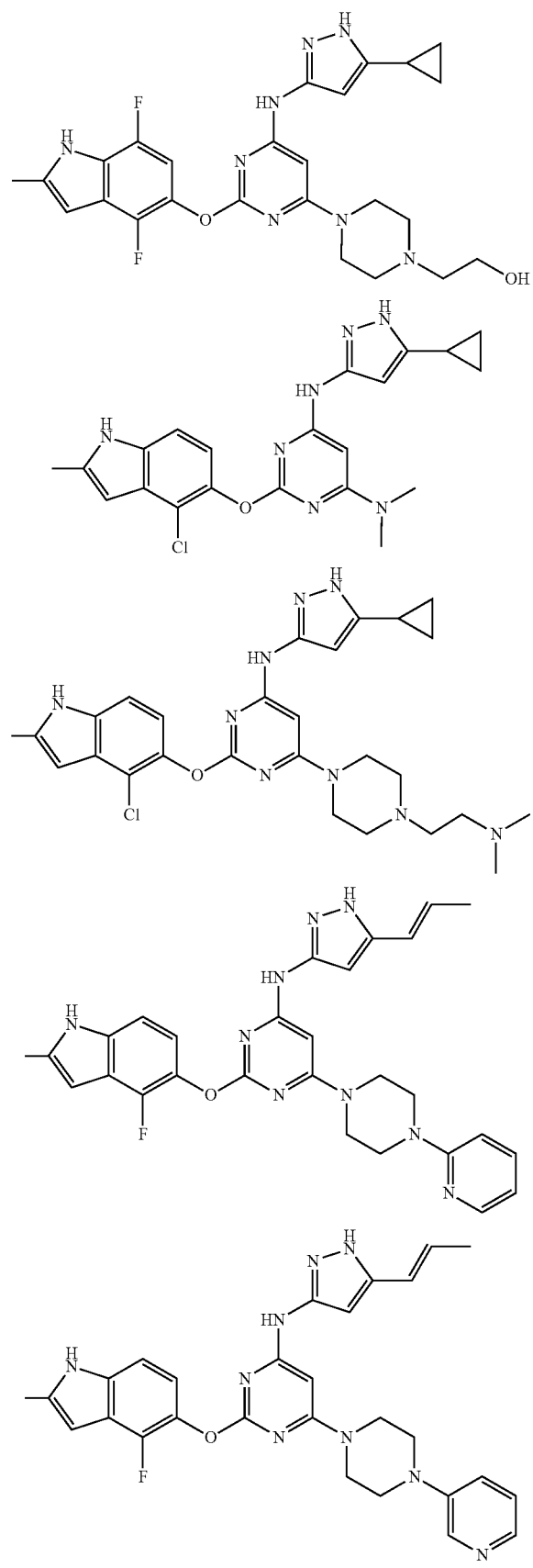
114
-continued
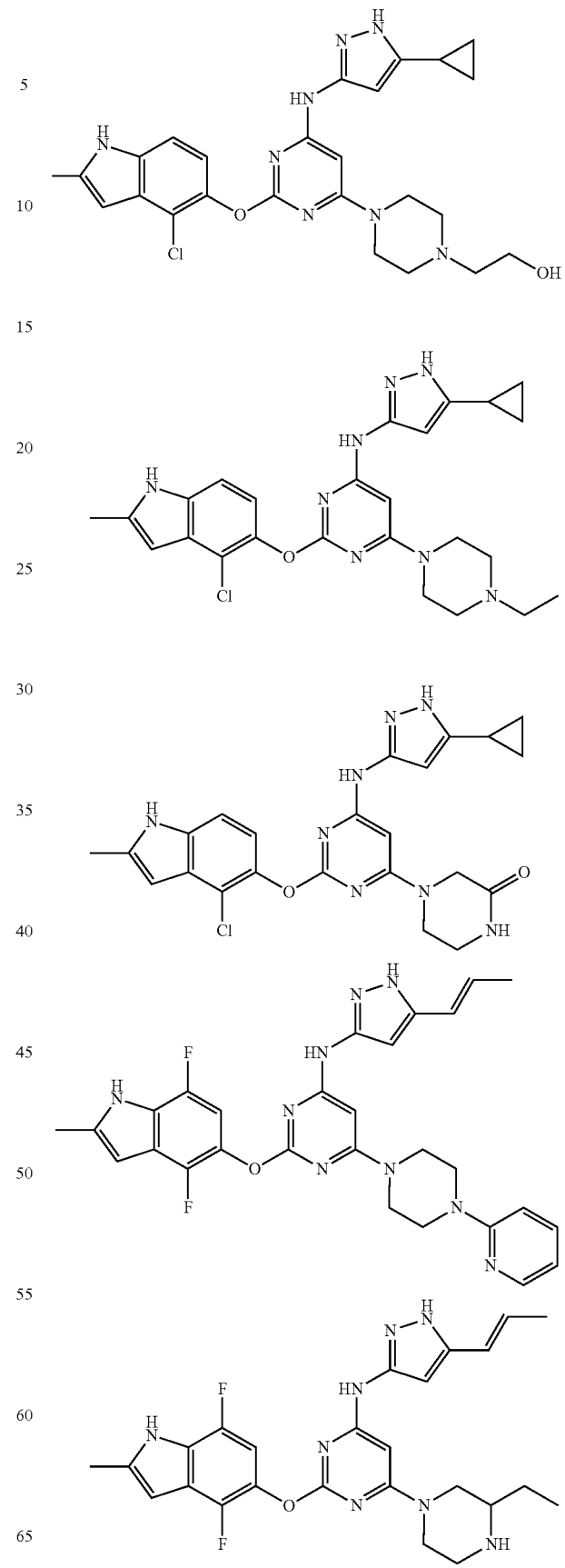

115
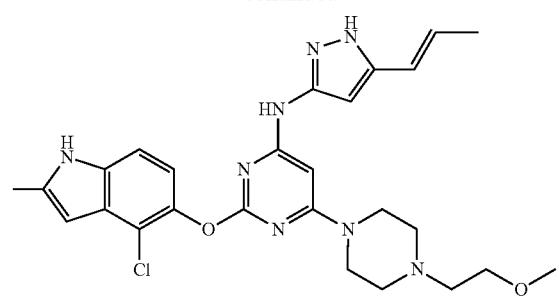
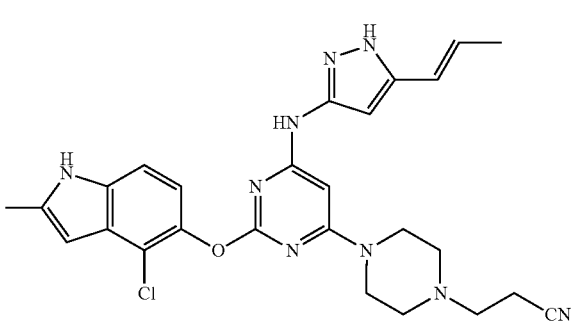
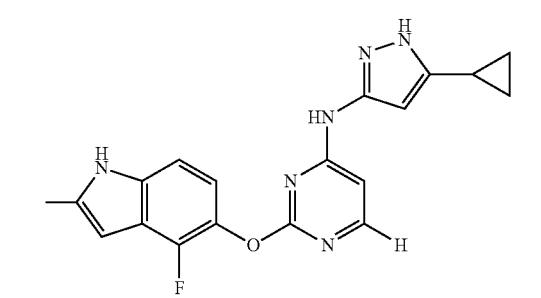
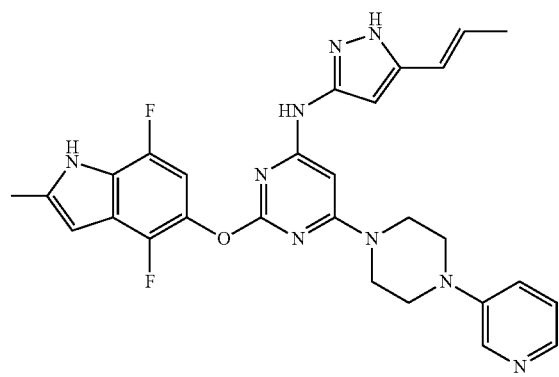
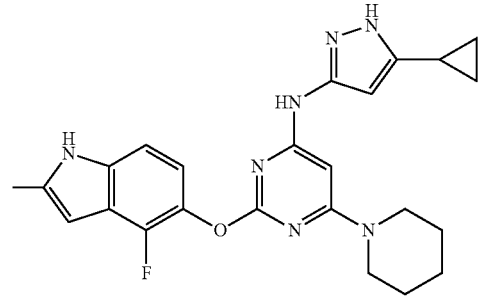
116
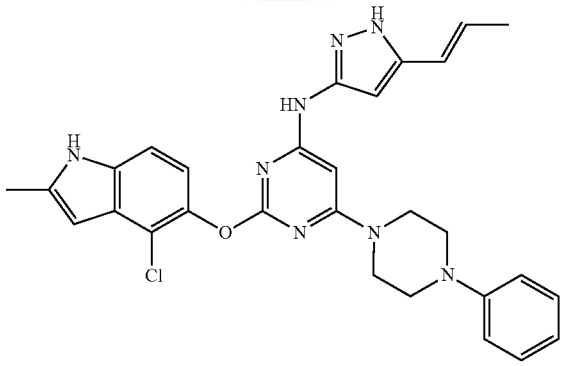
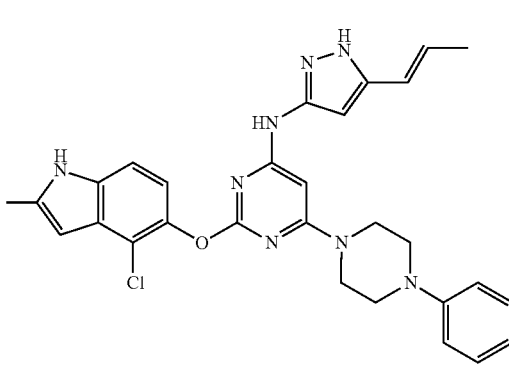
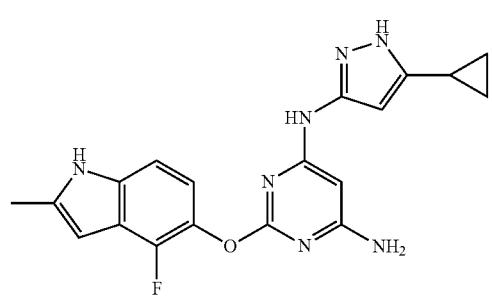
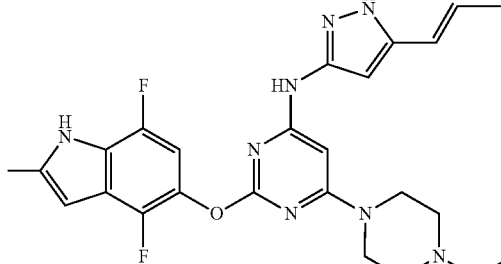
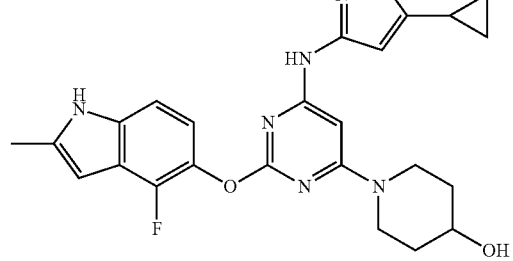

117
-continued
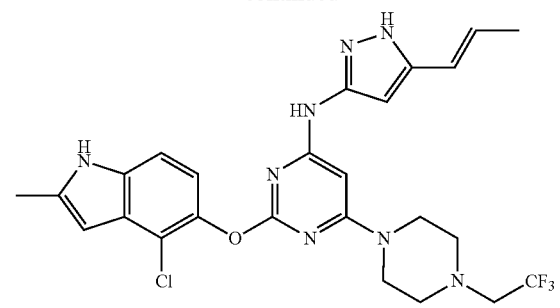
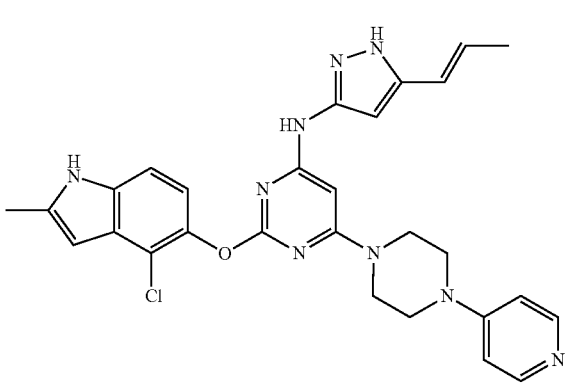
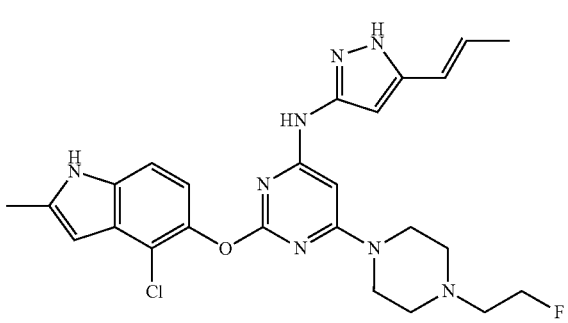
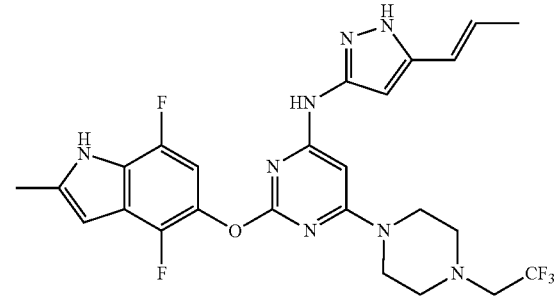
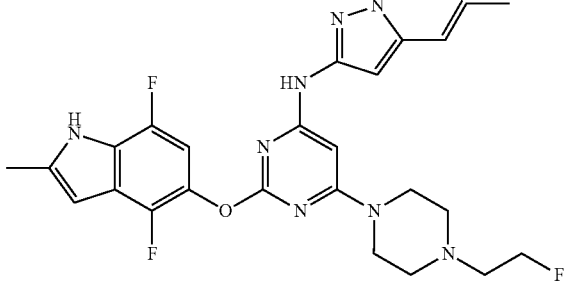
118
-continued
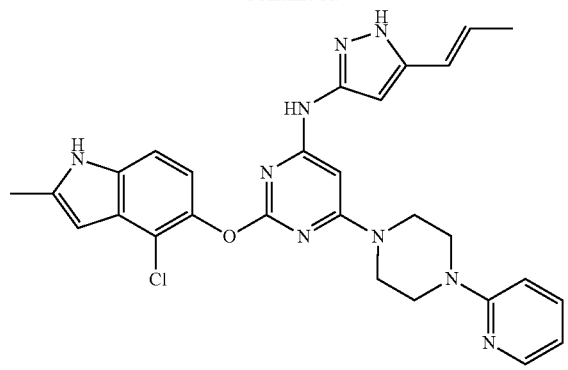
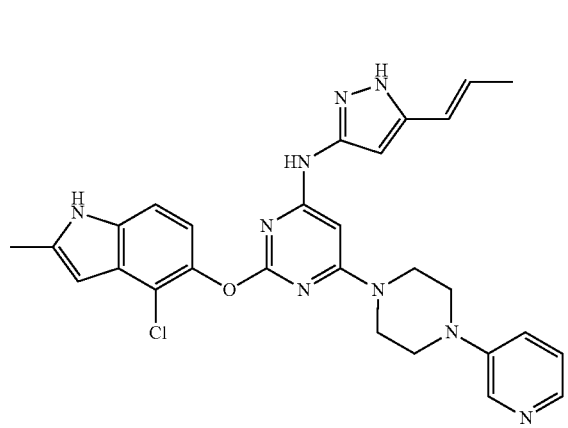
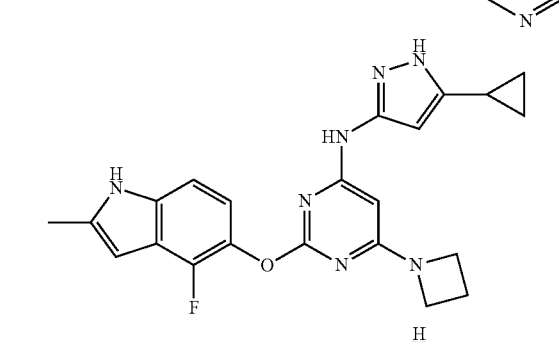
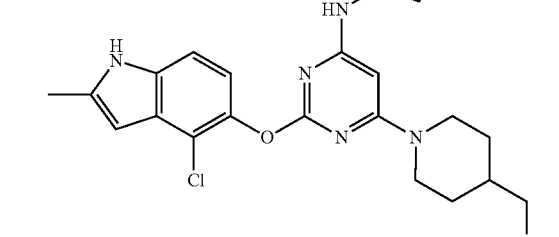
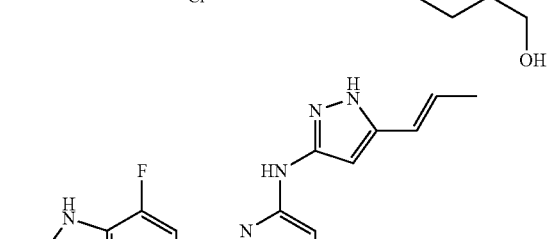
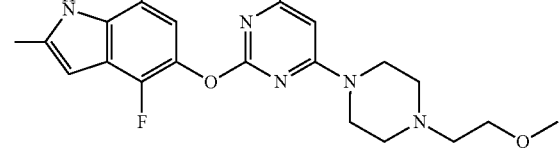

119
-continued
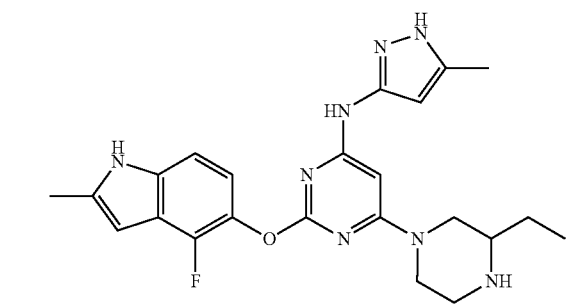
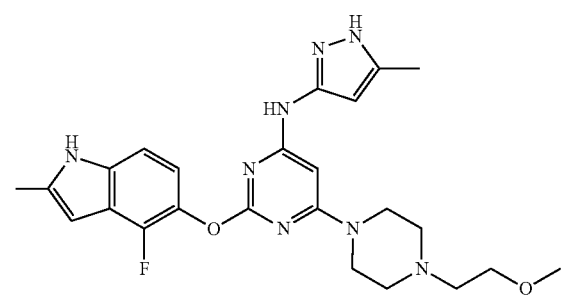
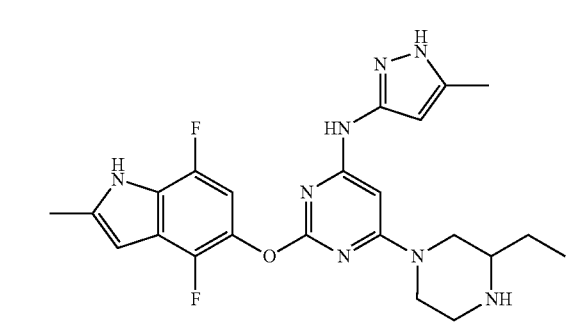
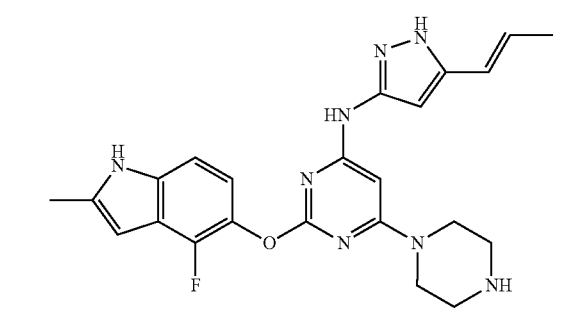
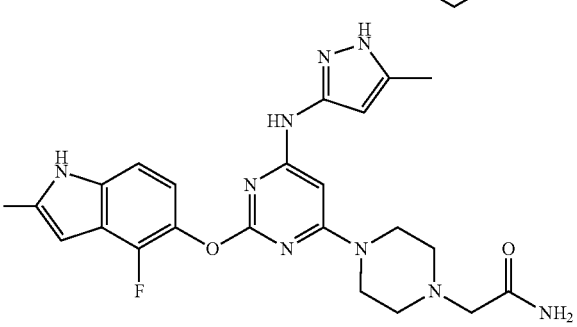
120
-continued
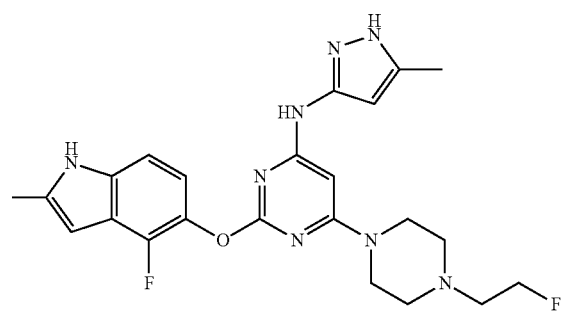
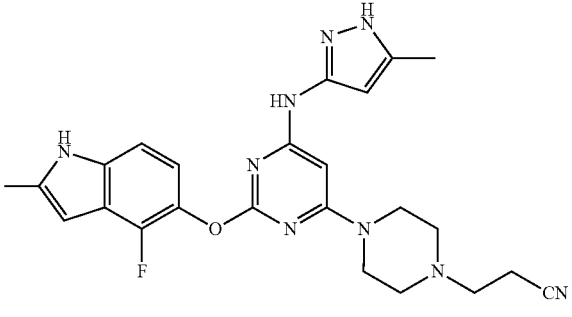
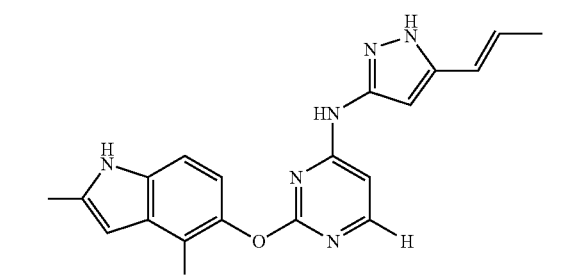
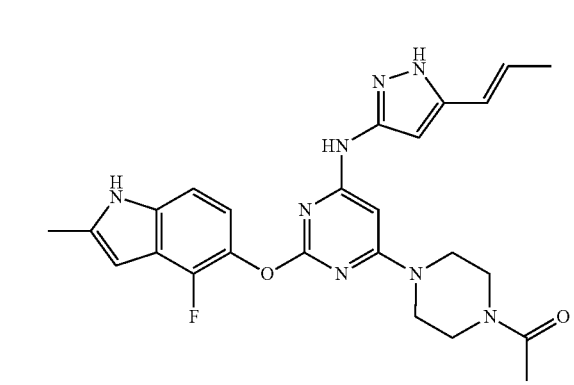
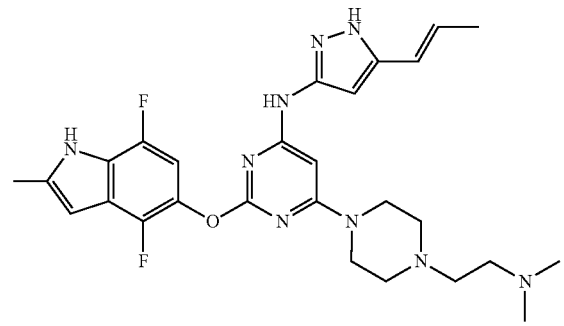

121
-continued
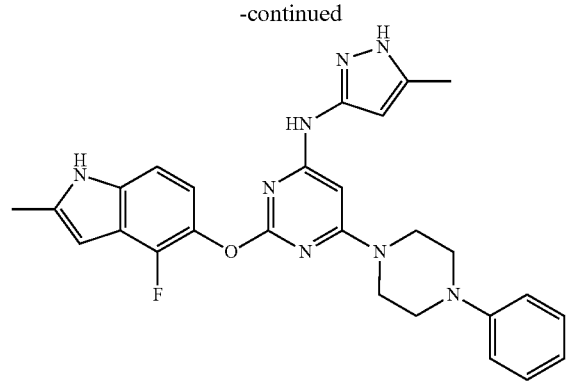
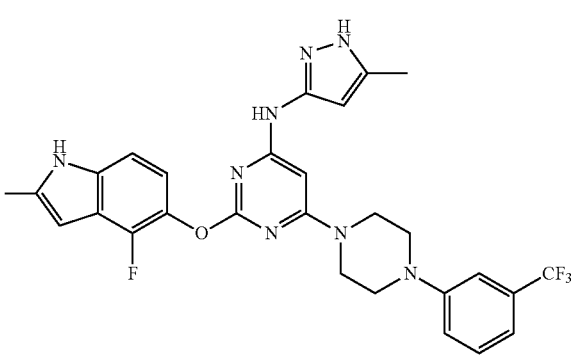
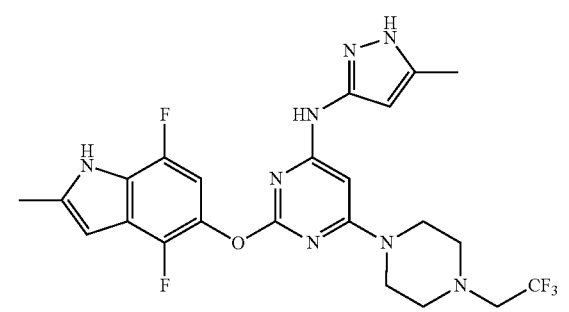
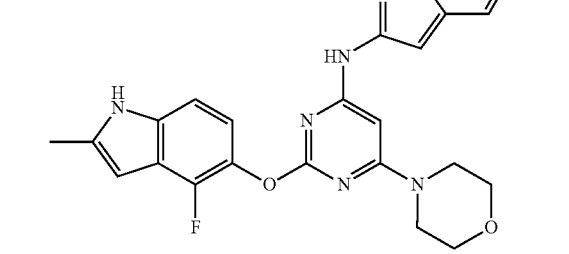
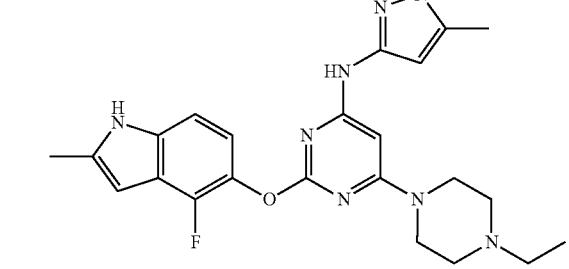
122
-continued
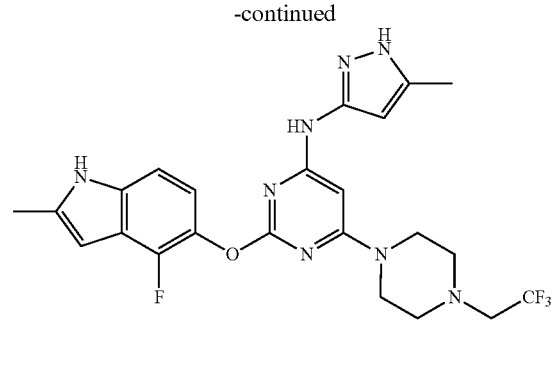
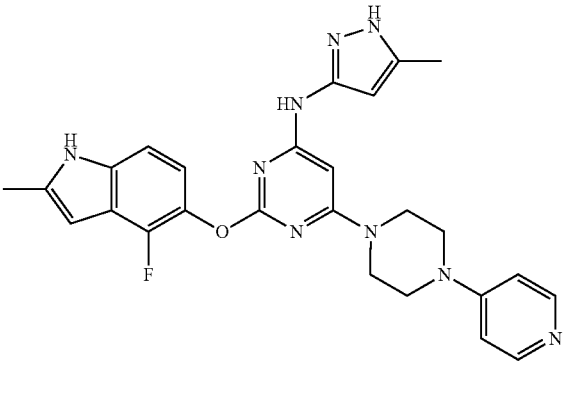
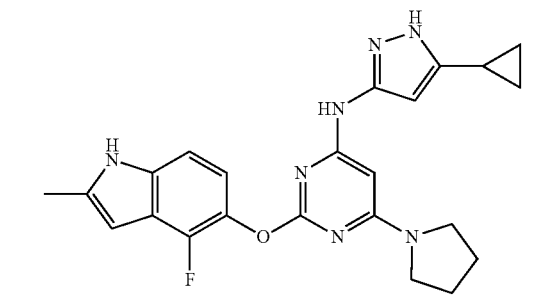
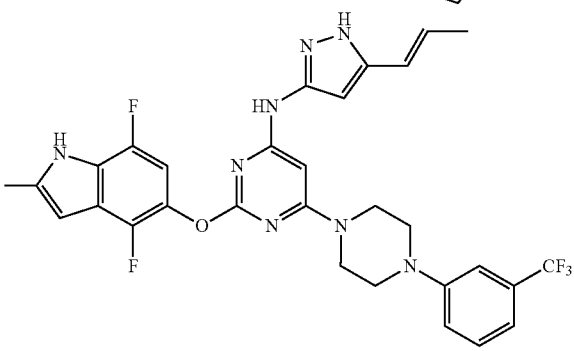
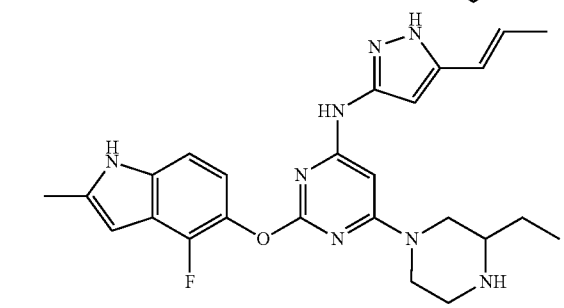

123
-continued
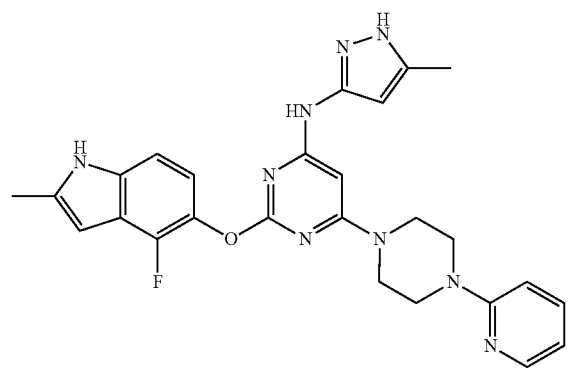
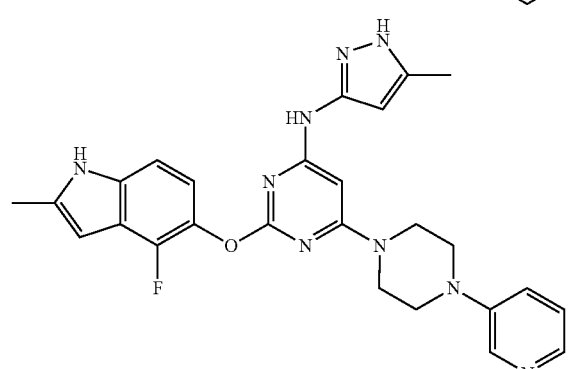
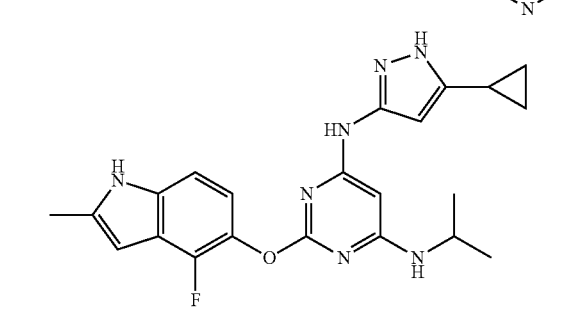
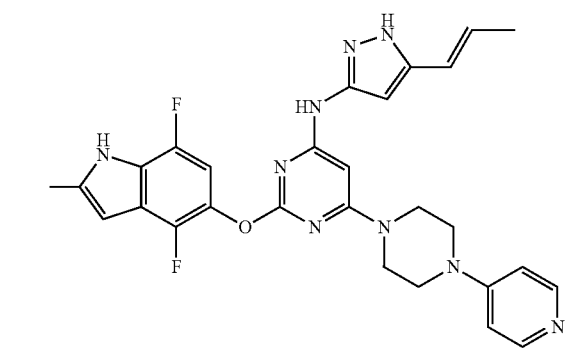
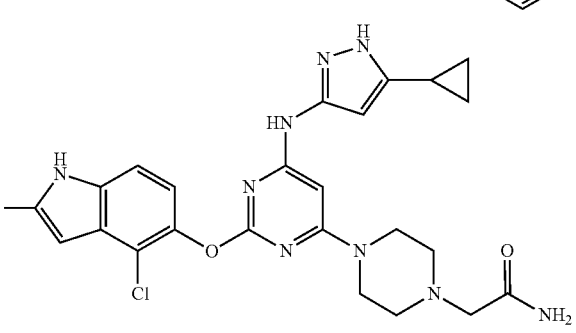
124
-continued
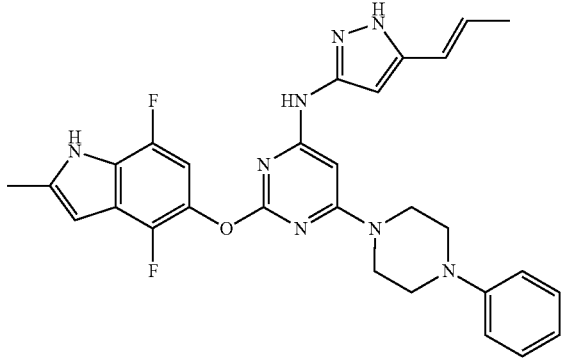
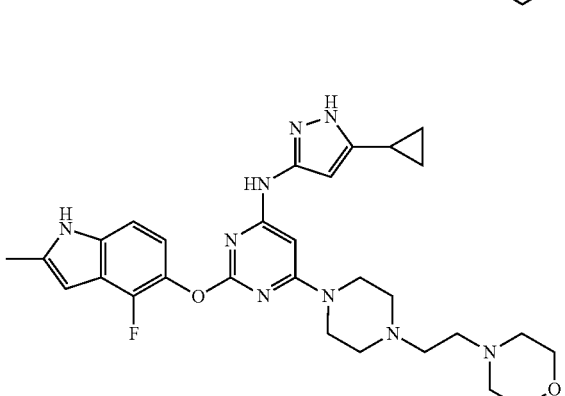
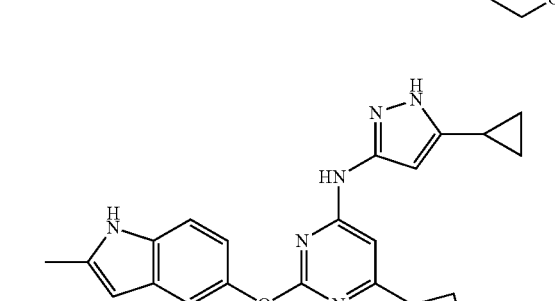
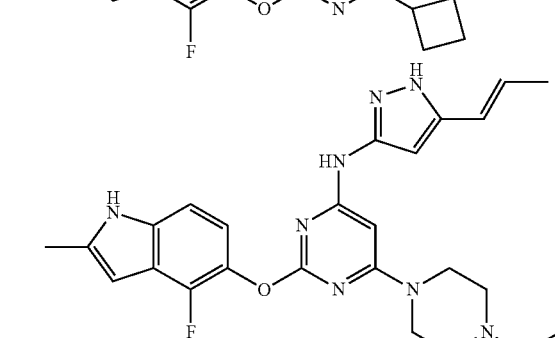
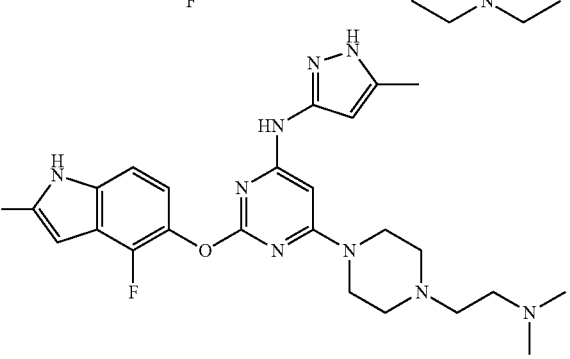

125
-continued
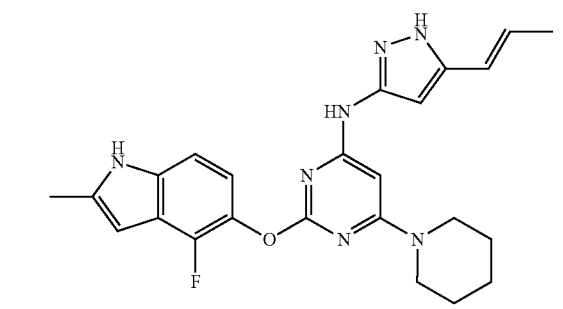
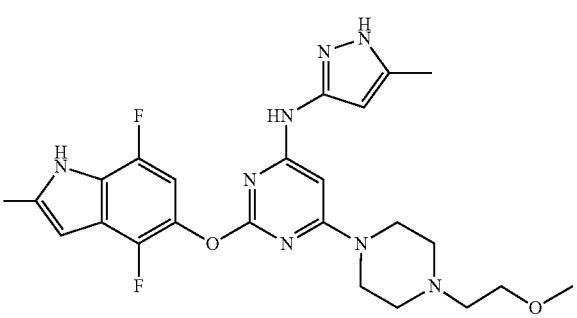
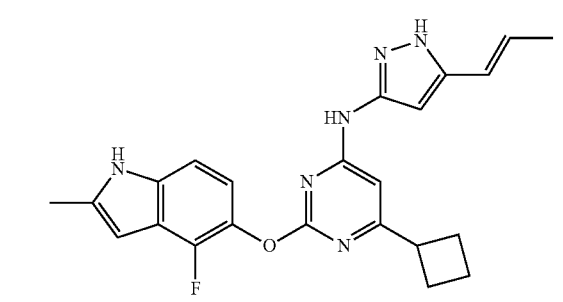
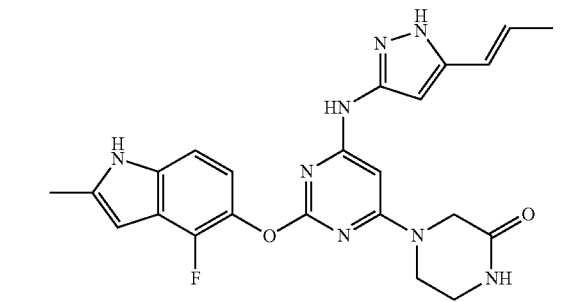
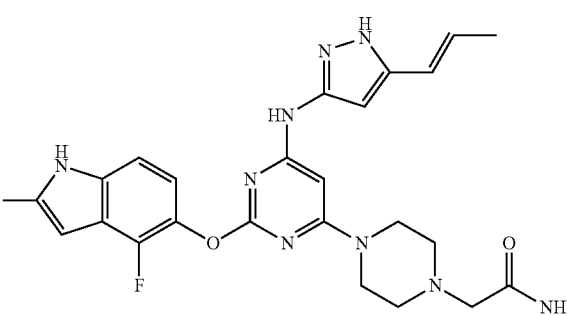
126
-continued
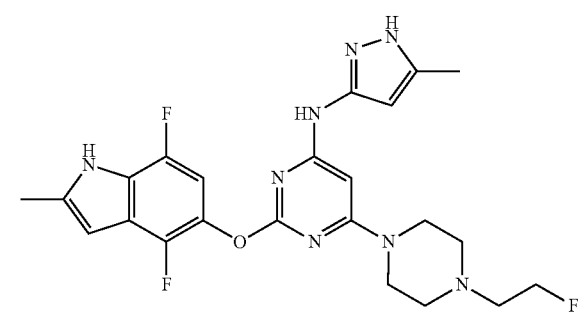
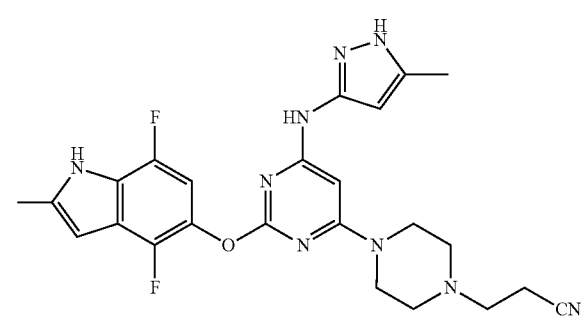
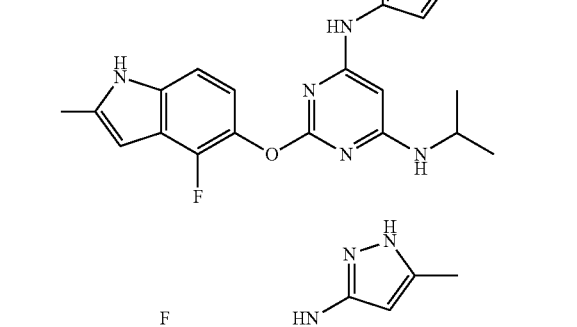
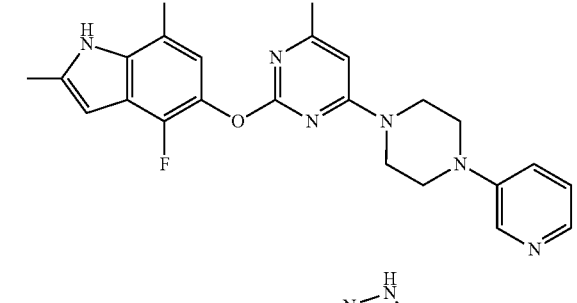
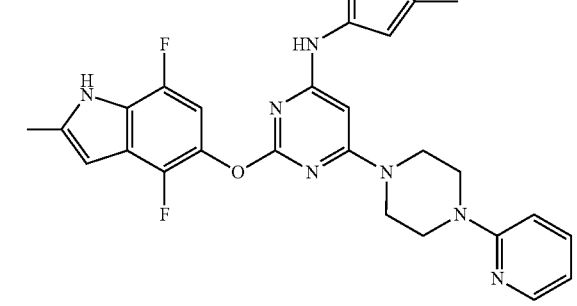

127
-continued
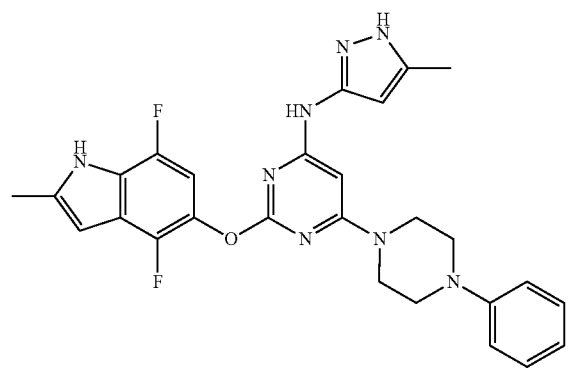
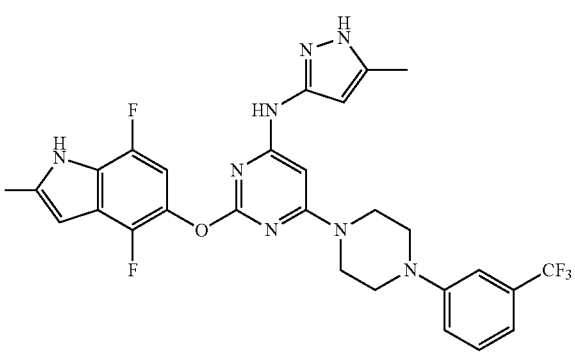
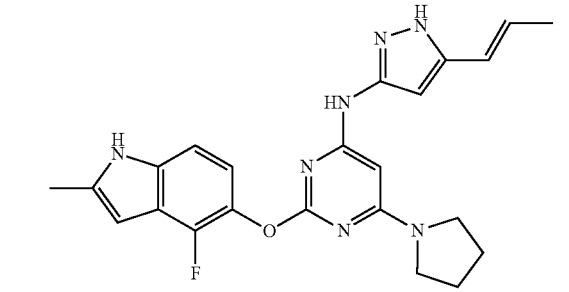
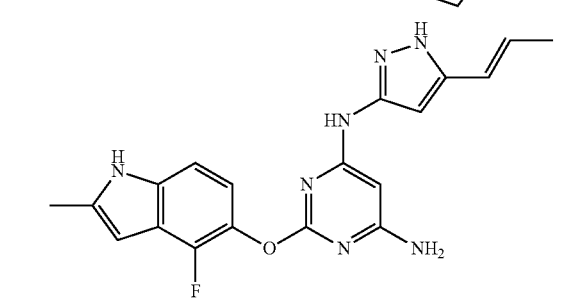
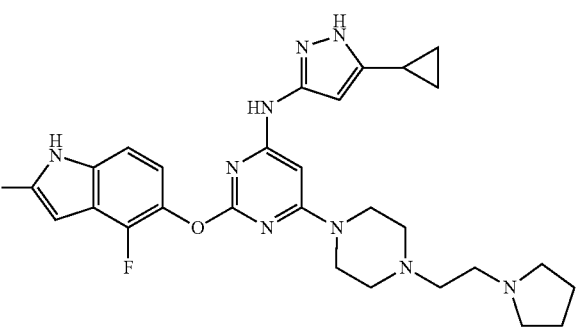
128
-continued
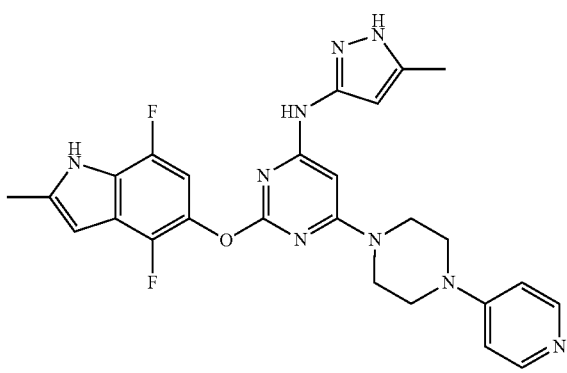
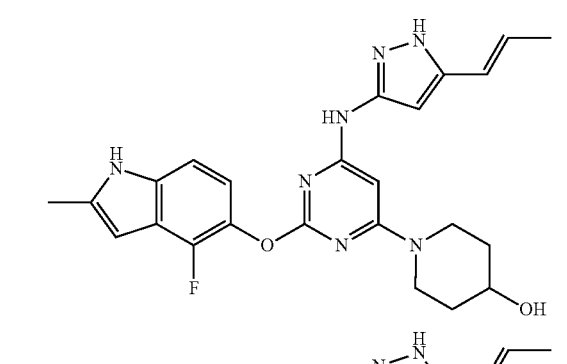
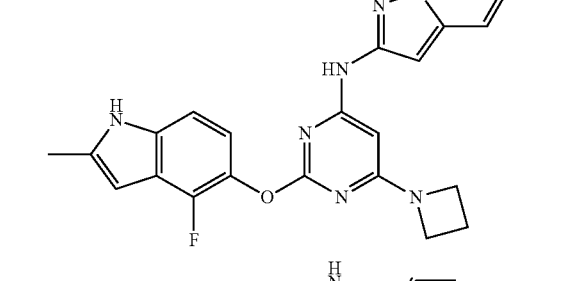
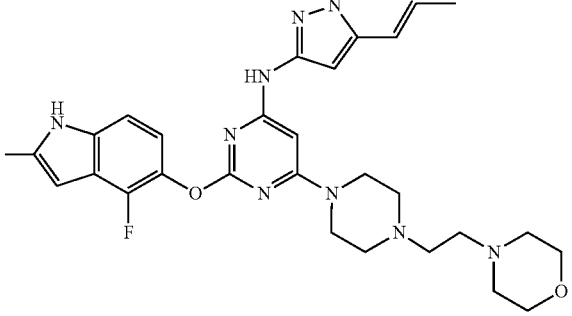
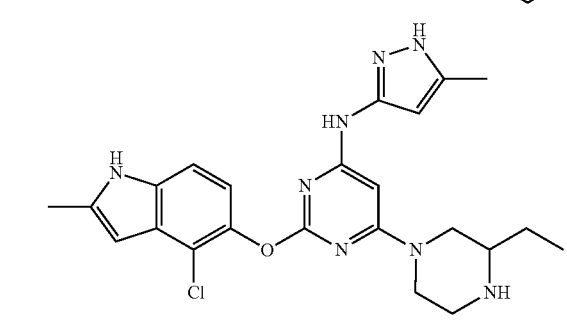

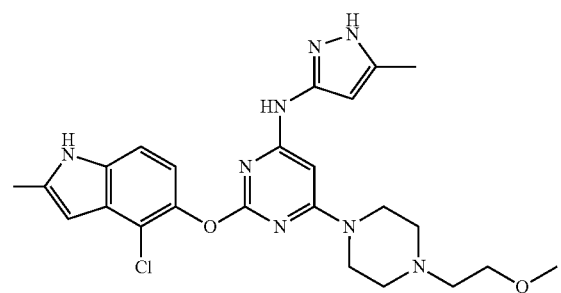
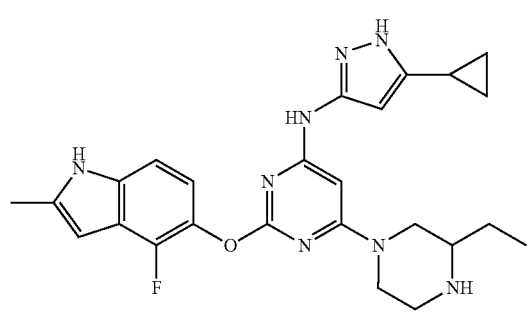
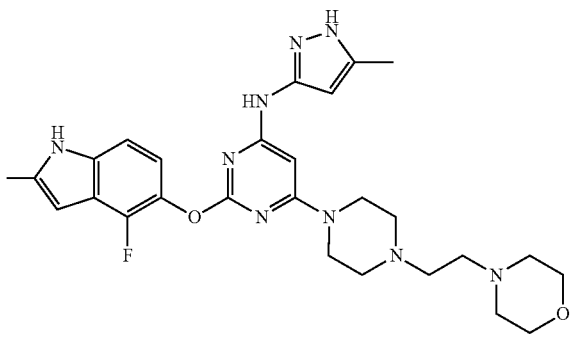
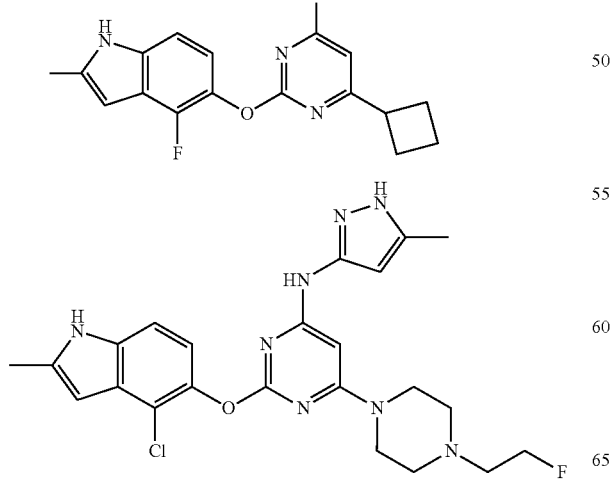
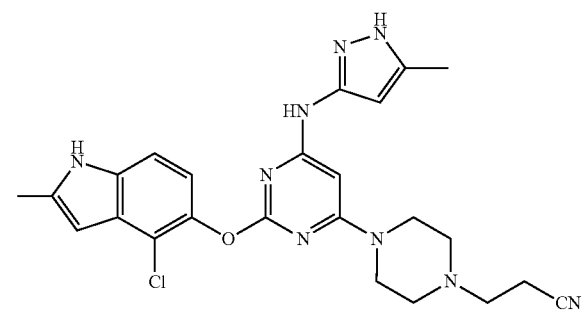
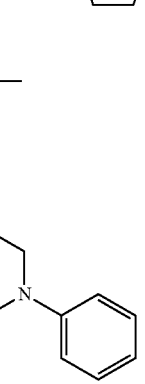

131 -continued
132 -continued
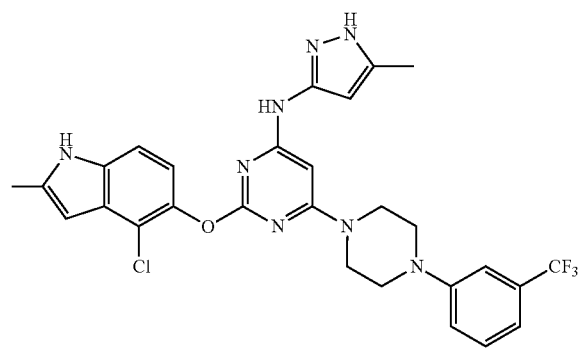
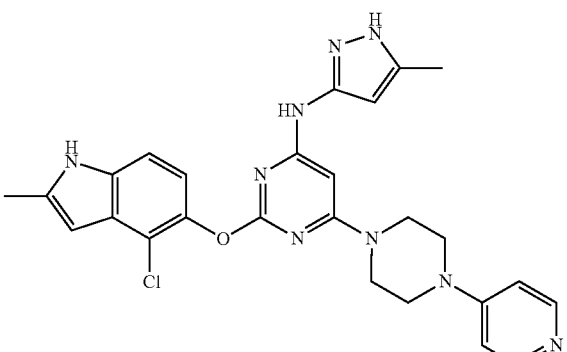

133
-continued
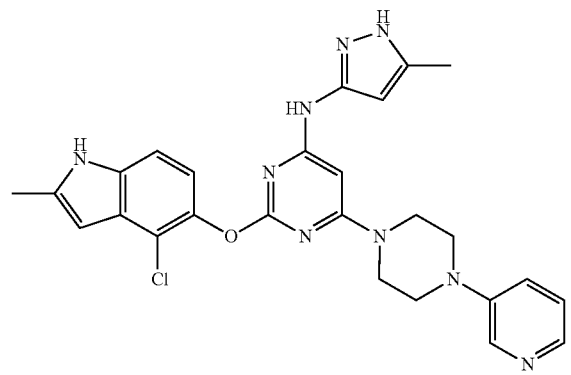
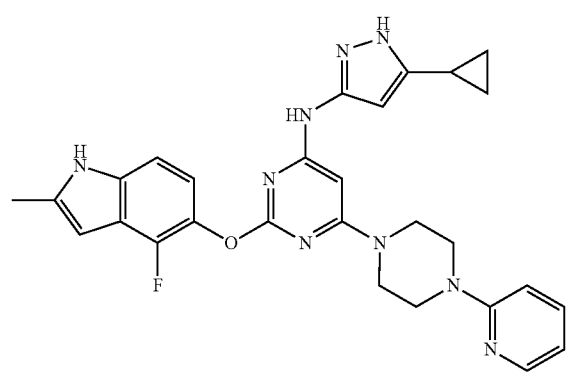
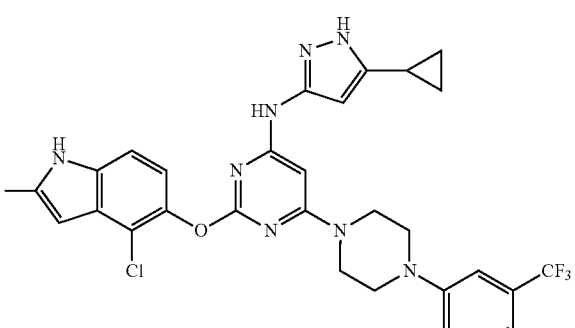
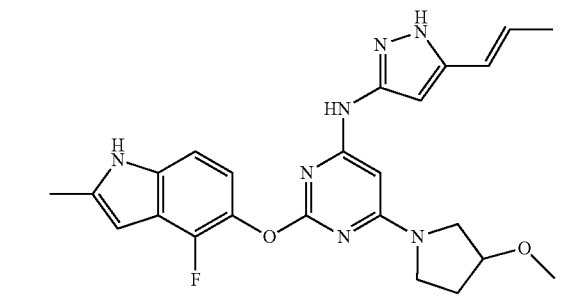
134
-continued
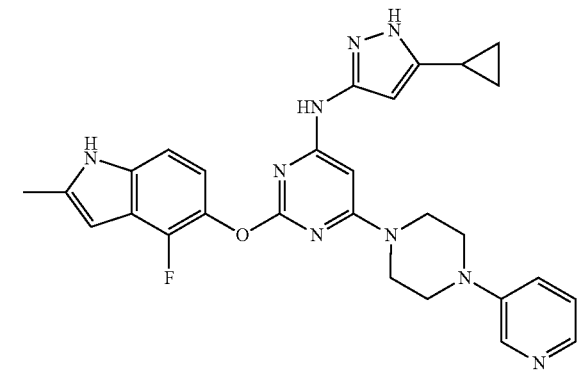
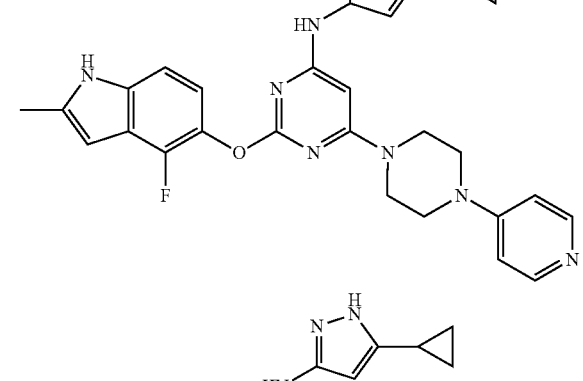
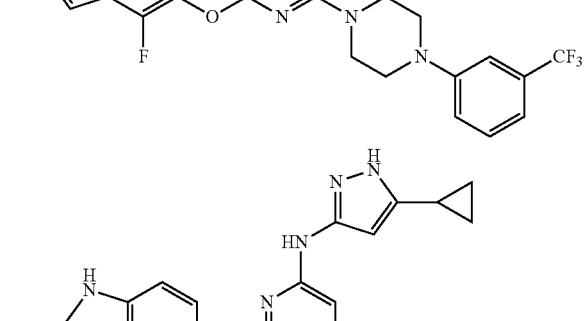
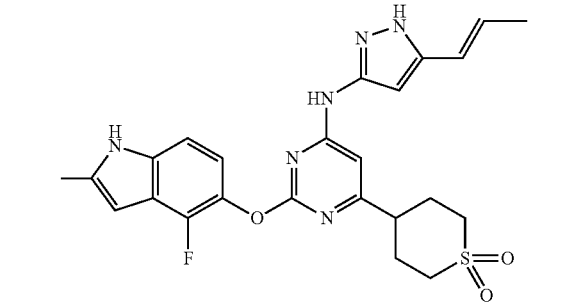

-continued
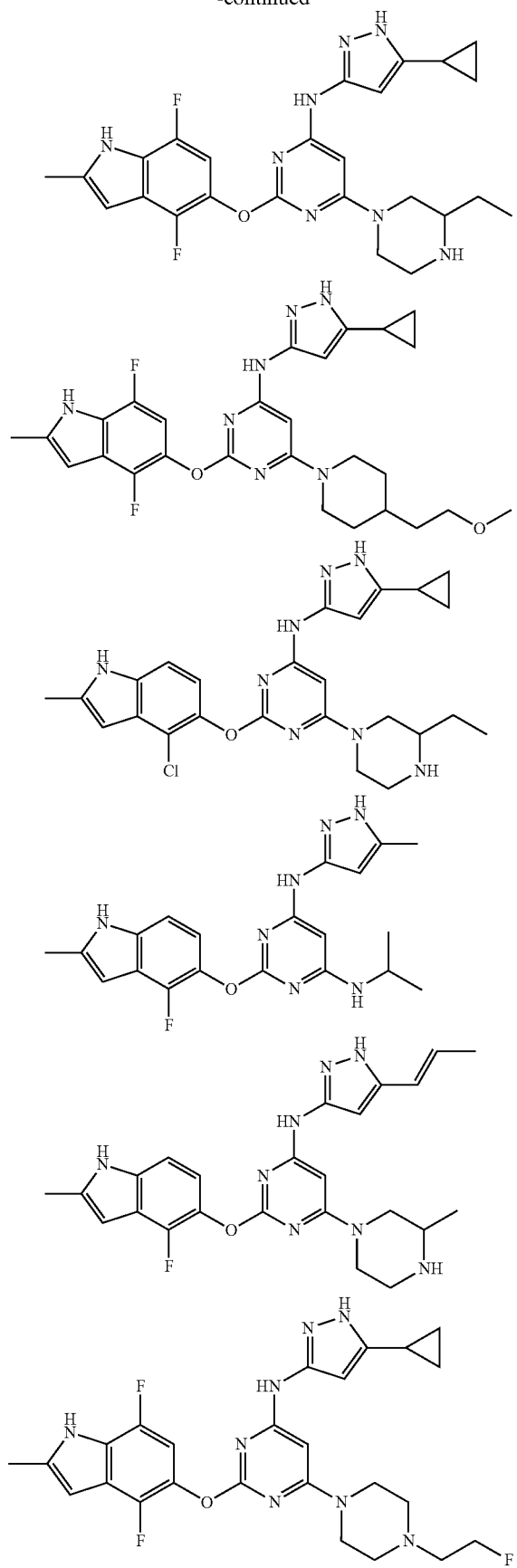
-continued
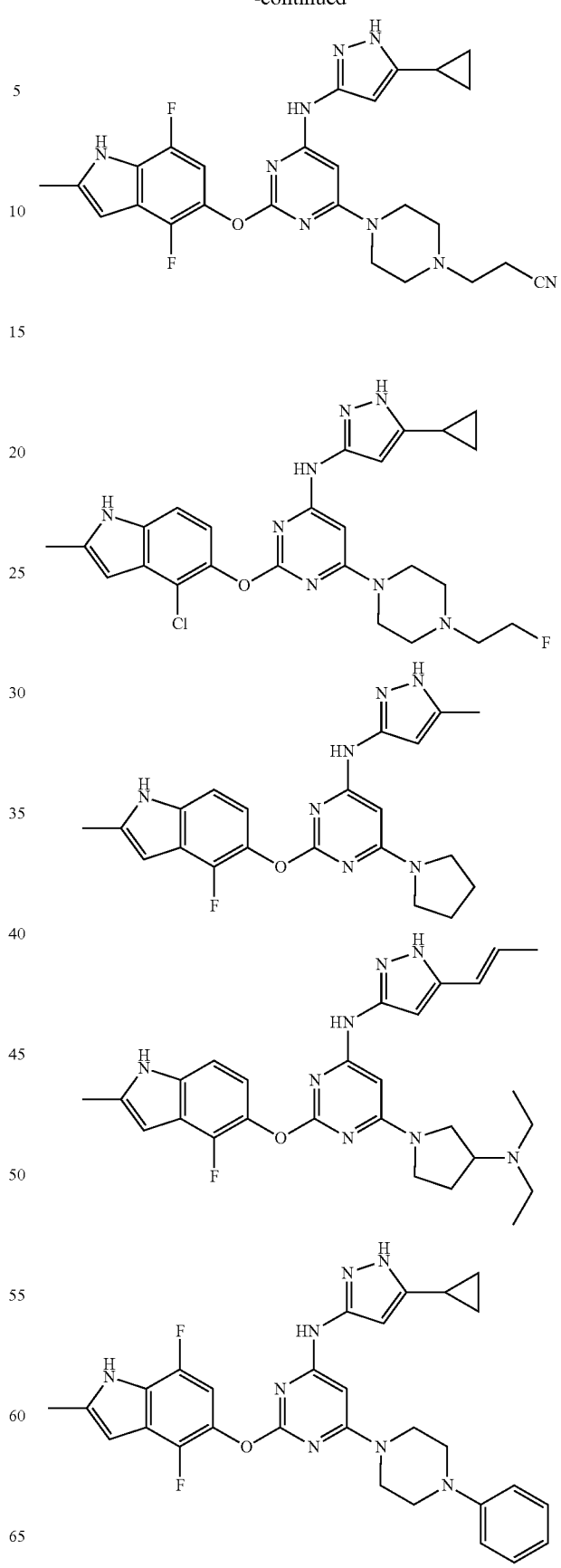

137
-continued
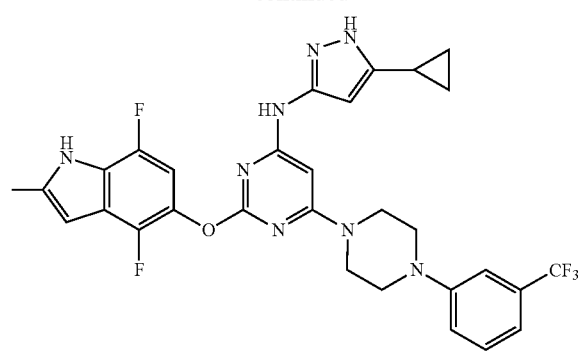
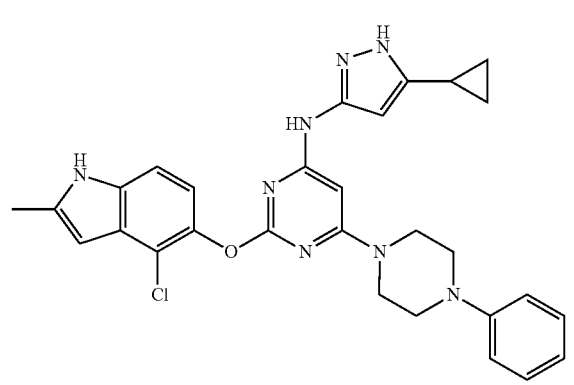
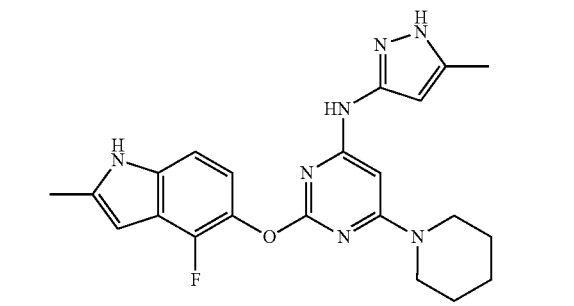
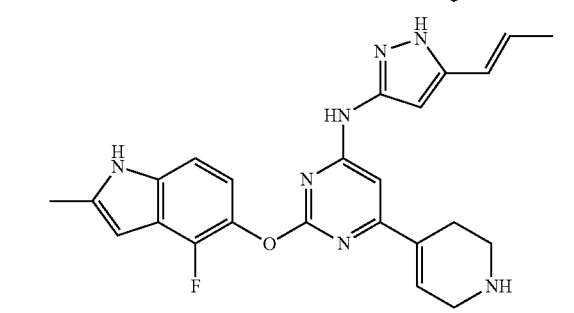
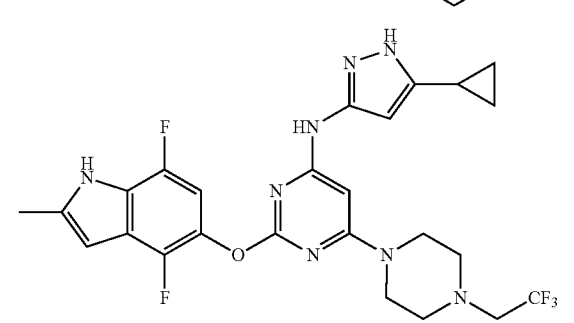
138
-continued
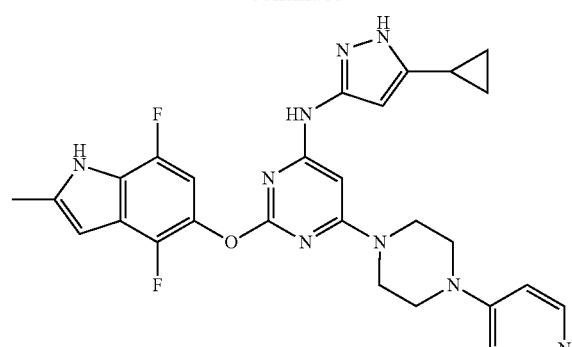
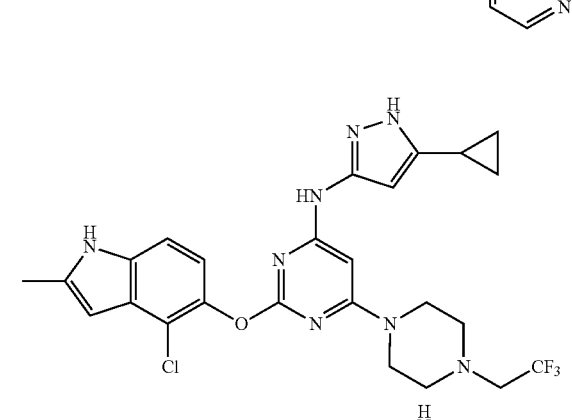
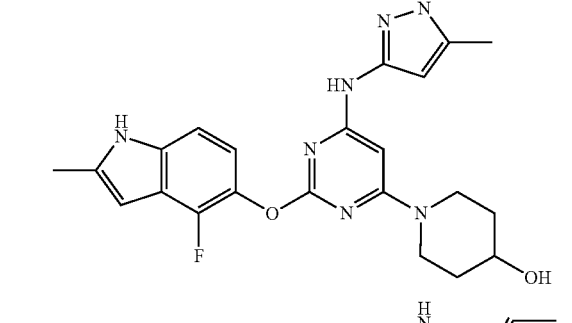
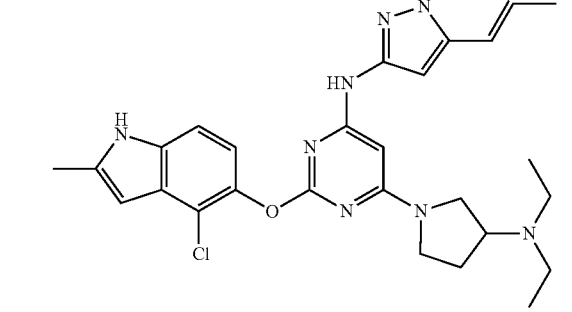
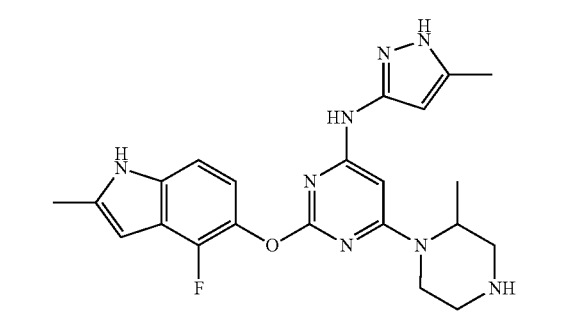

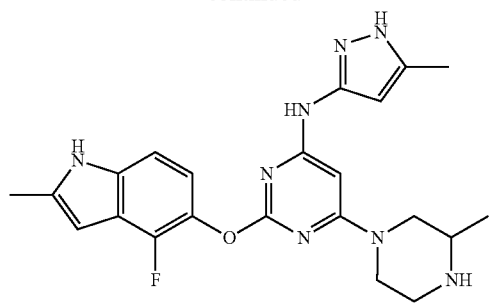
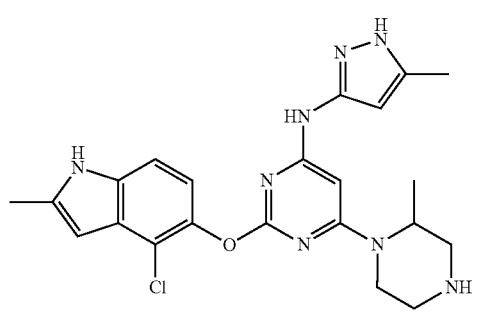
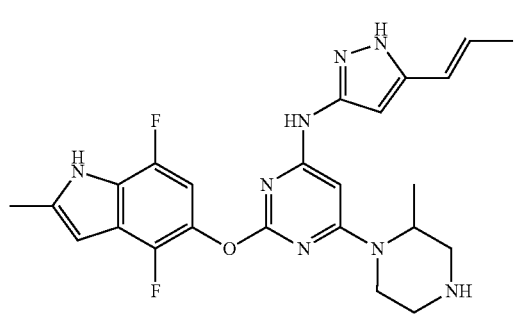
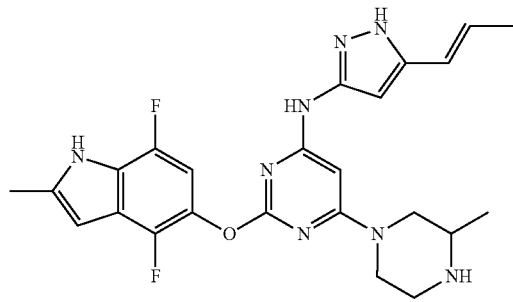
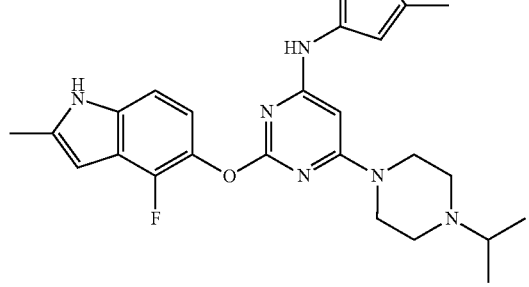
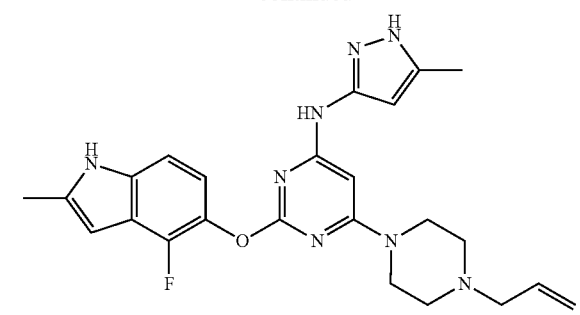
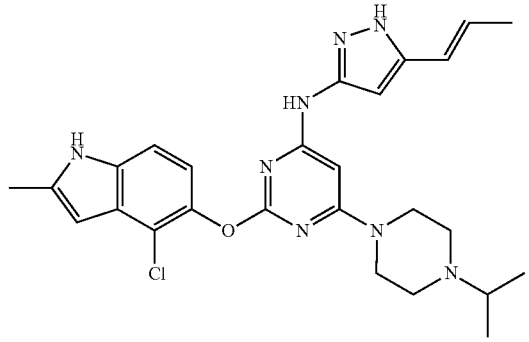
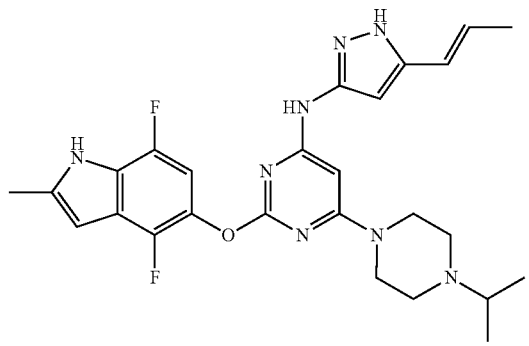
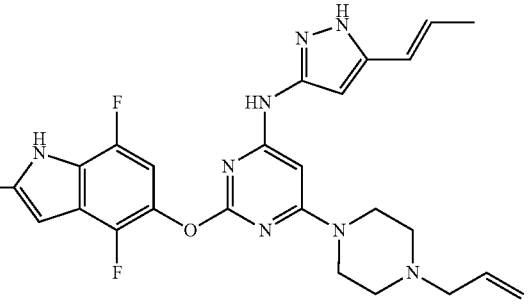
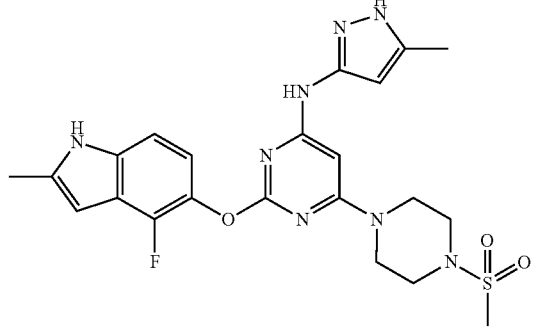

141
-continued
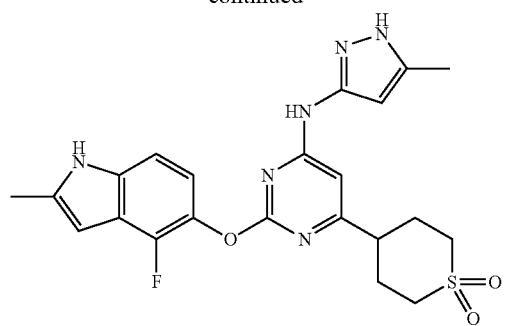
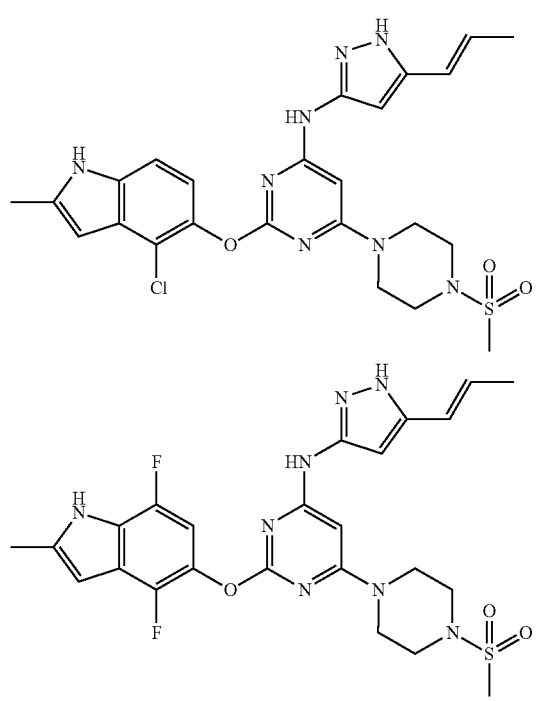
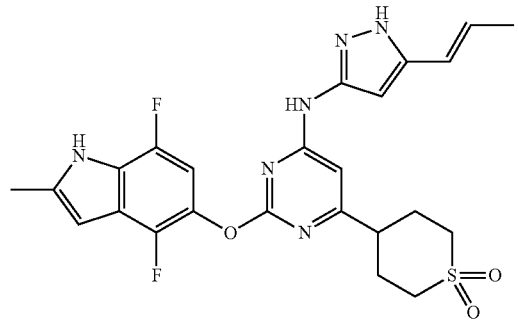
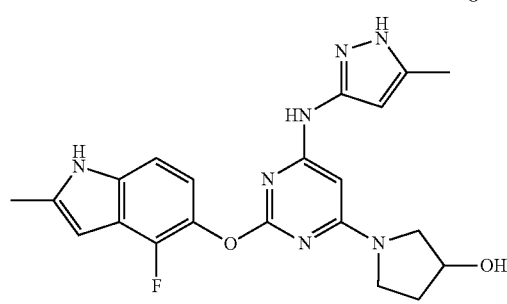
142
-continued
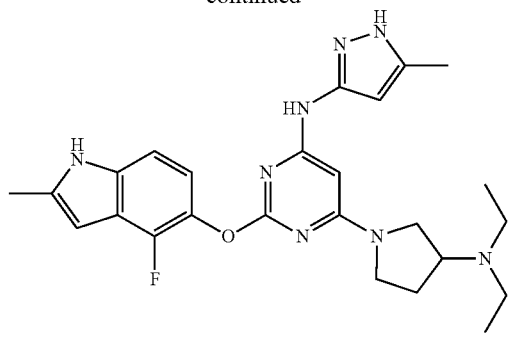
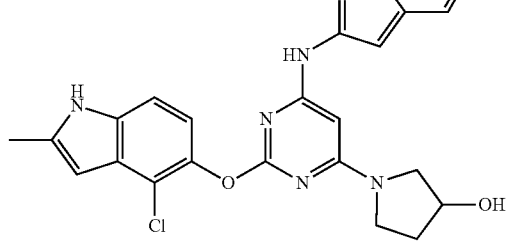
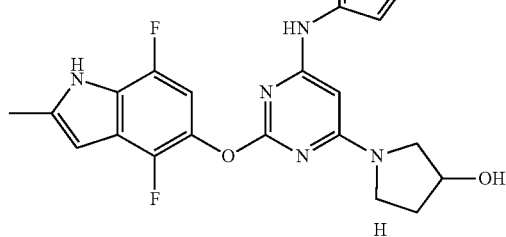
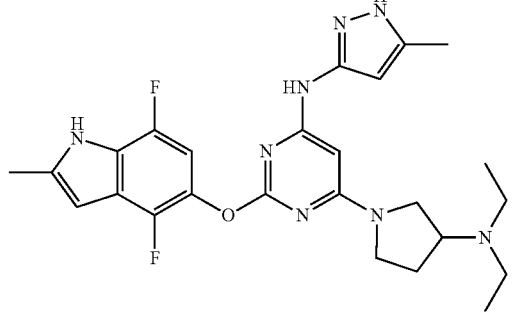
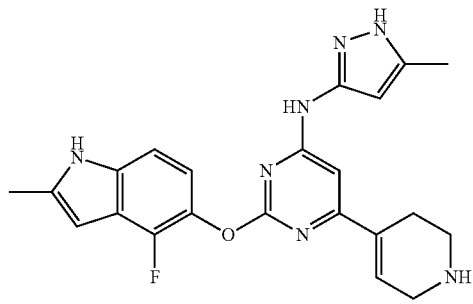

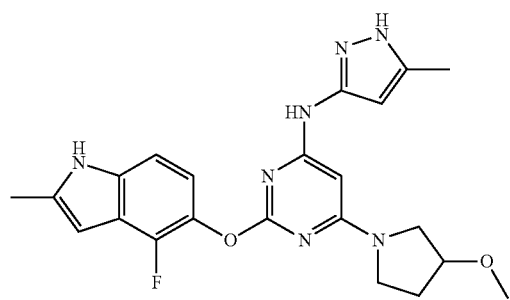
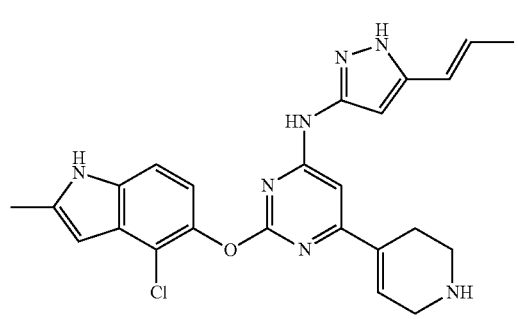
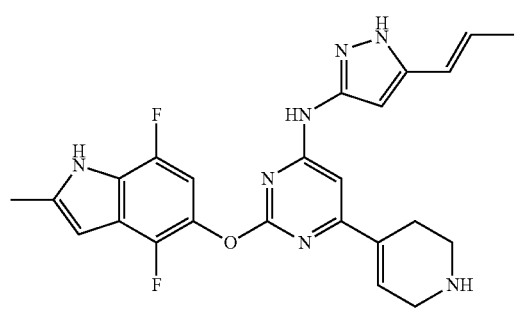
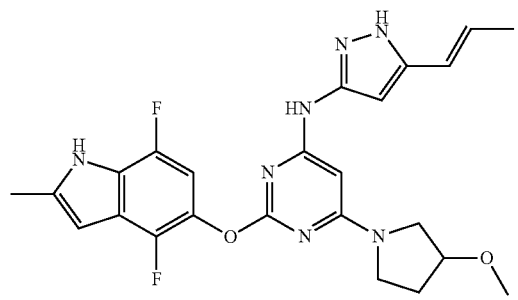
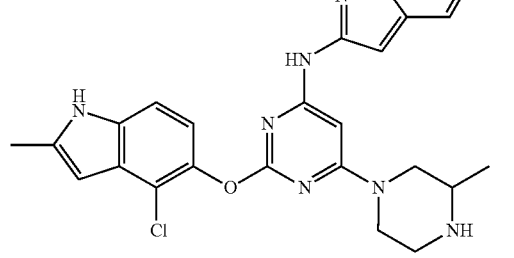
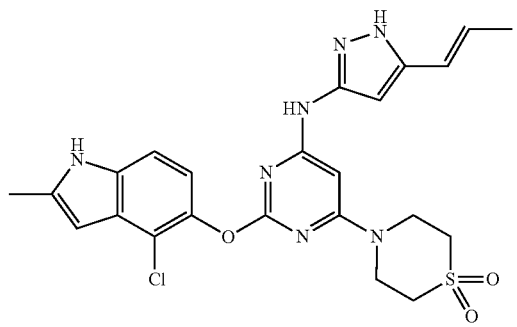
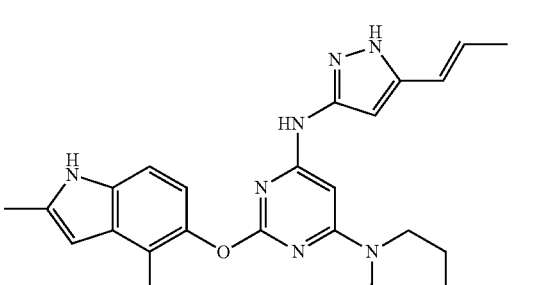
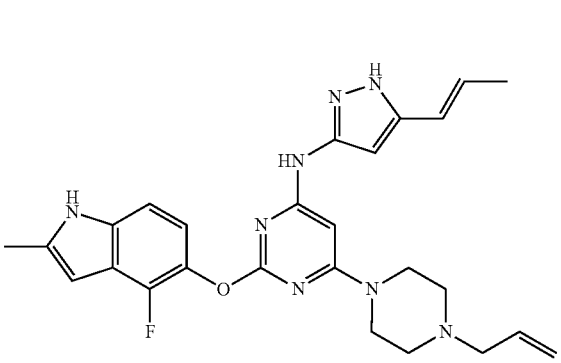
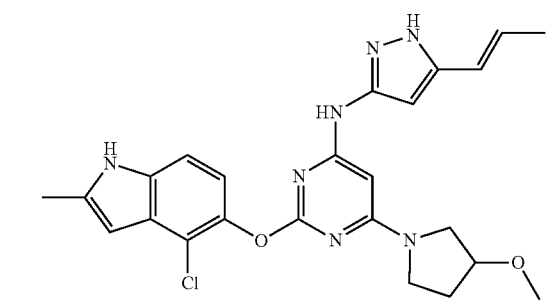
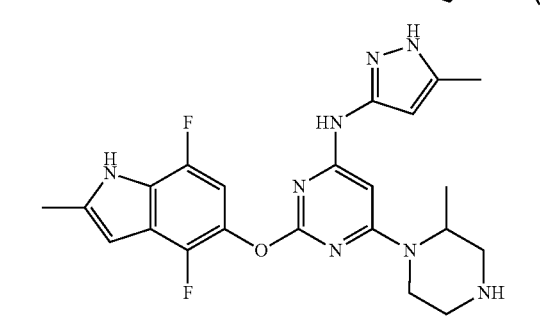

145
-continued
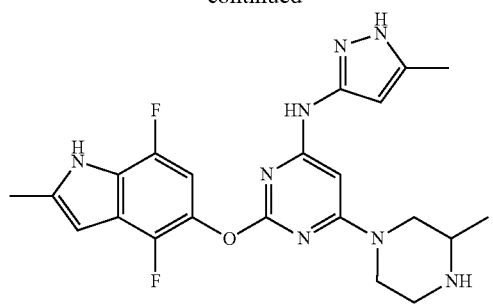
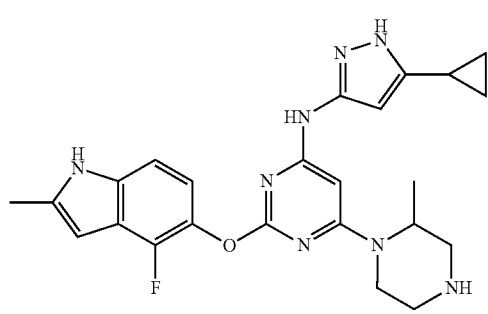
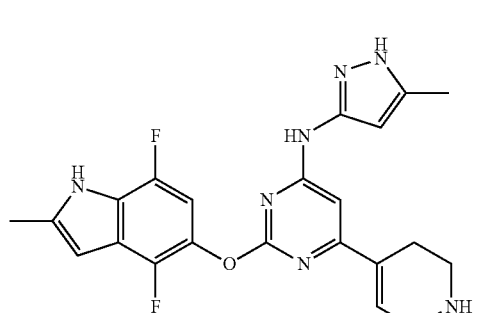
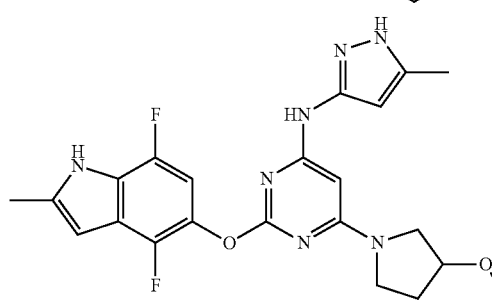
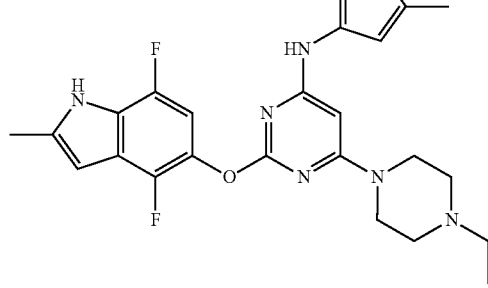
146
-continued
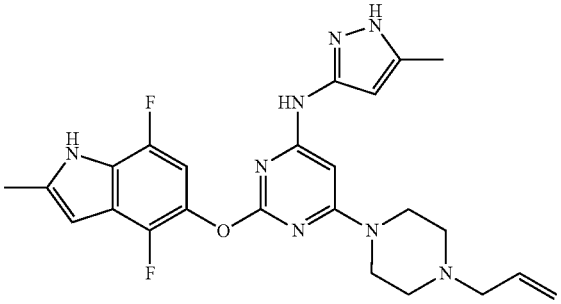
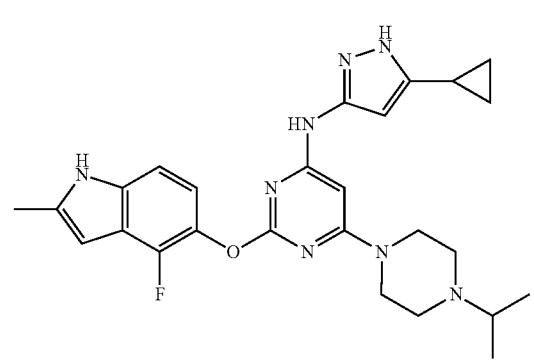
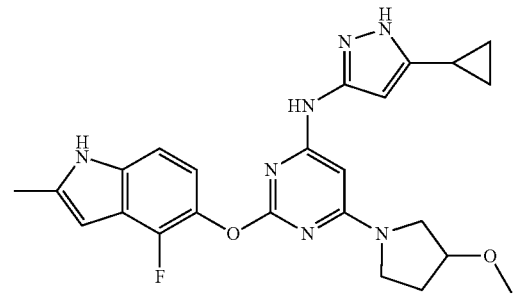
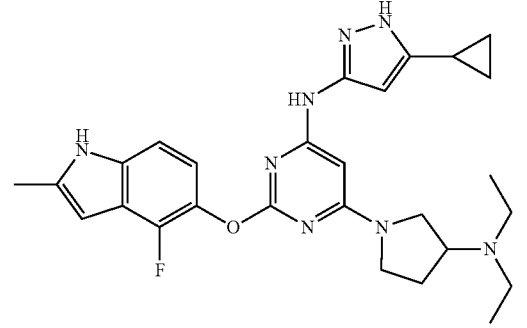
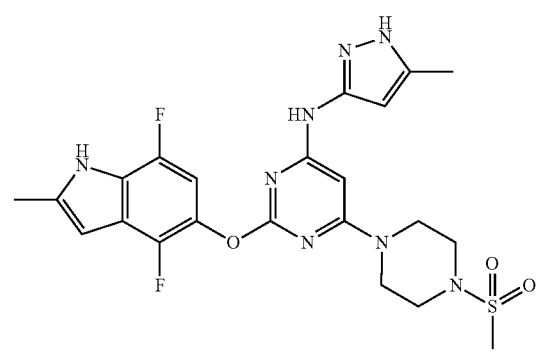

147
-continued
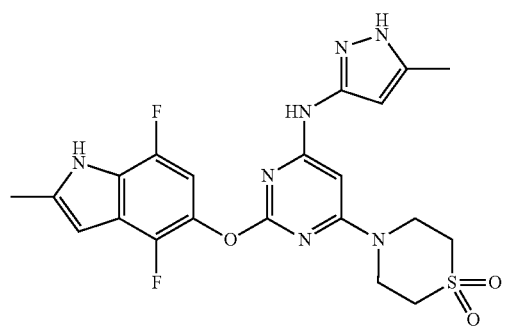
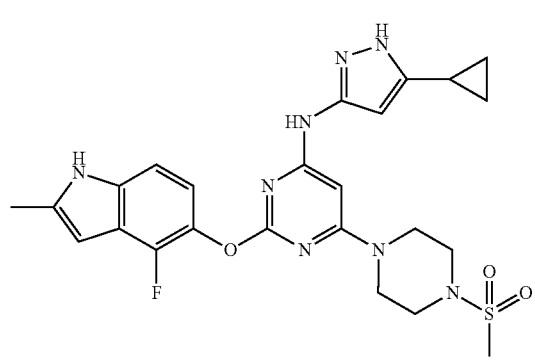
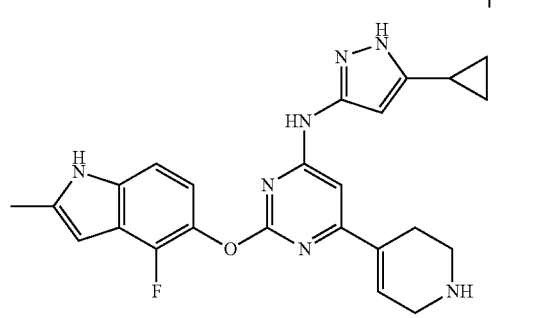
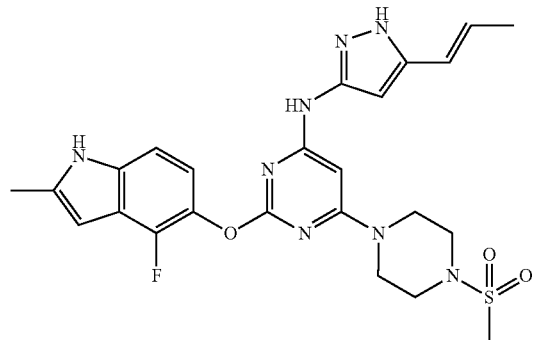
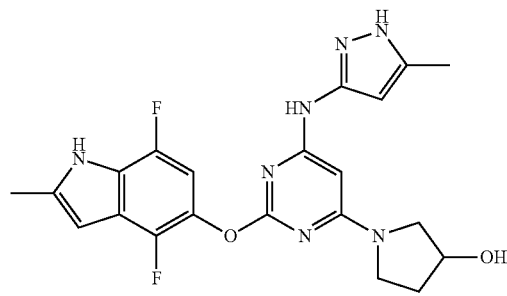
148
-continued
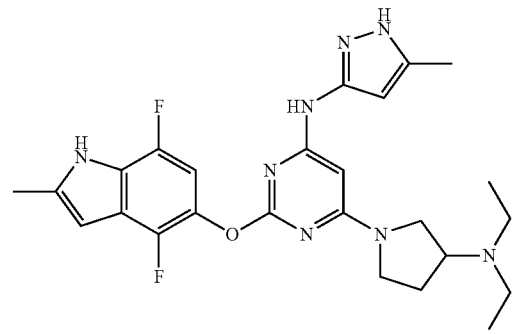
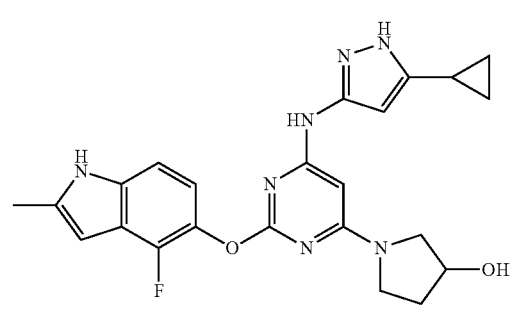
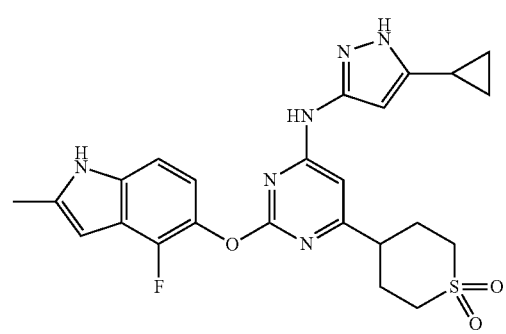
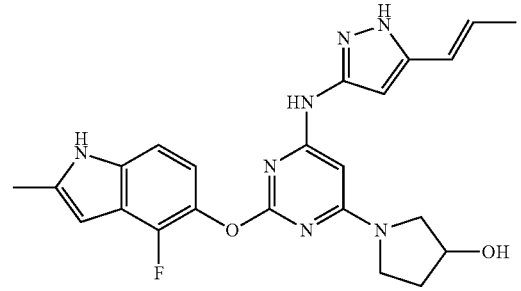
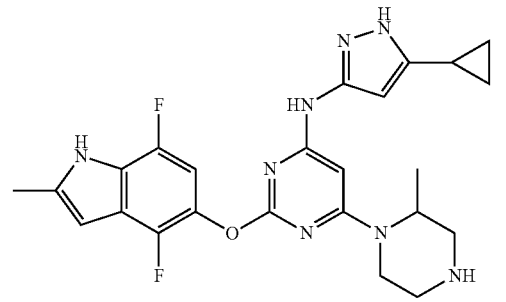

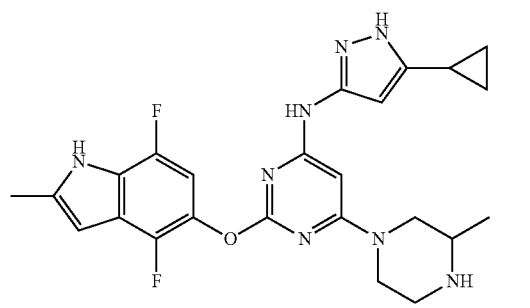
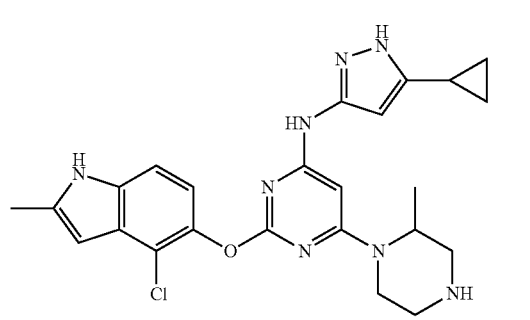
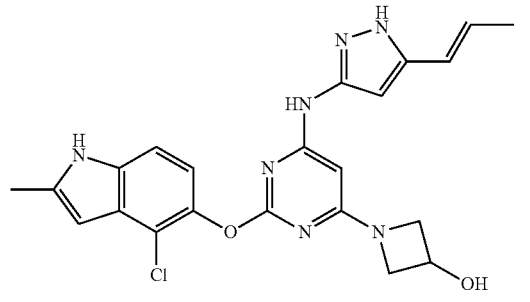
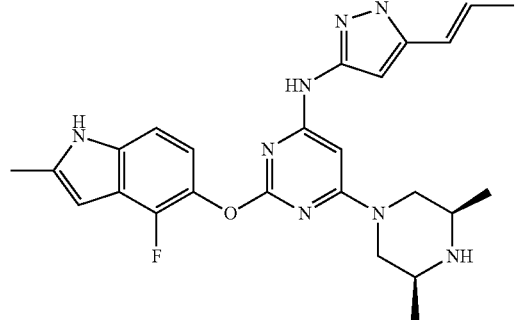
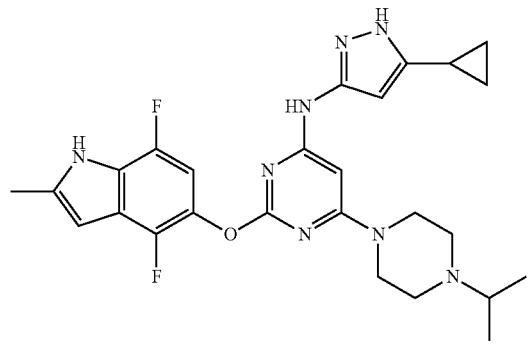
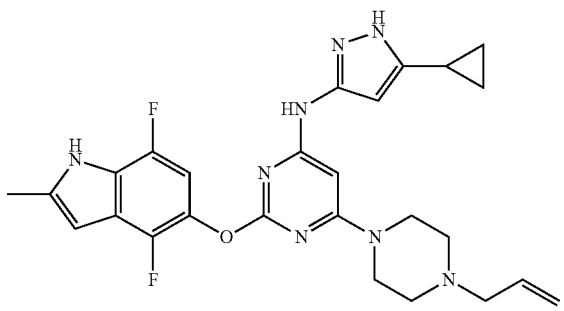
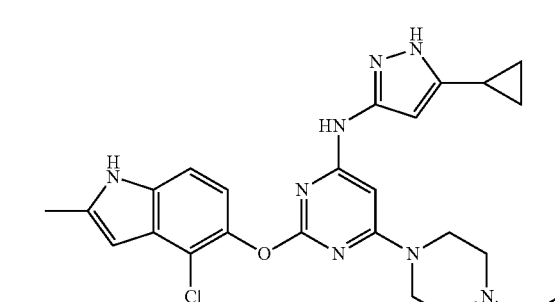
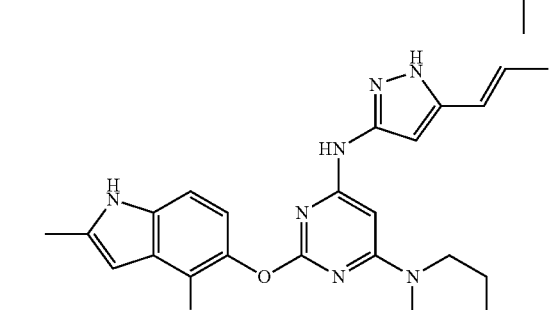
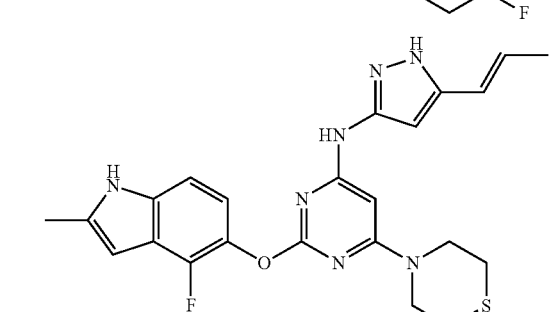
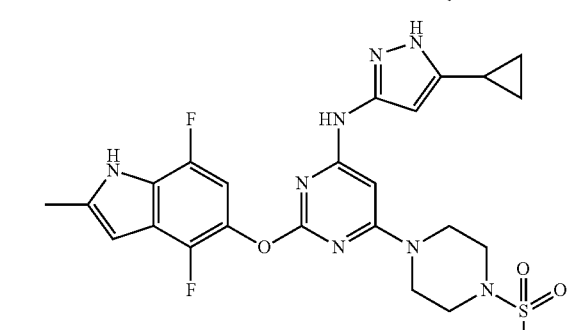

151
-continued
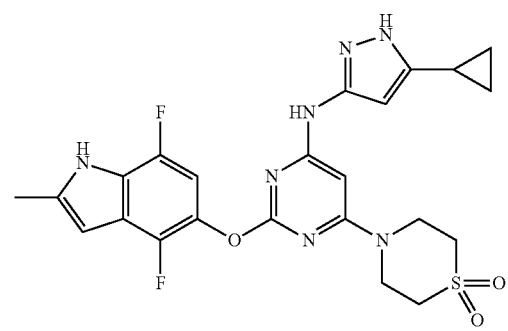
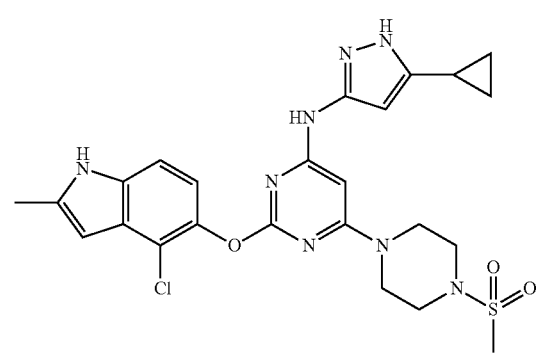
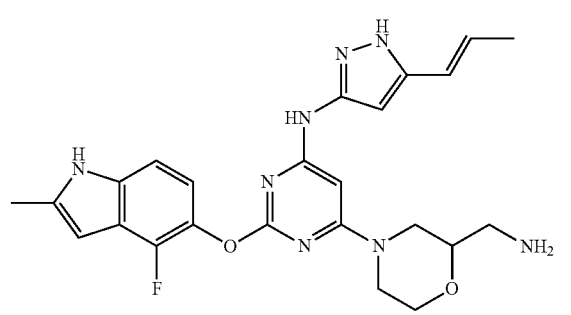
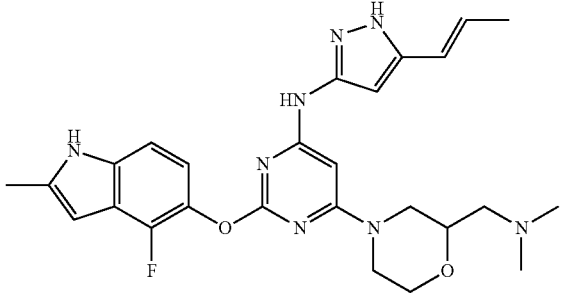
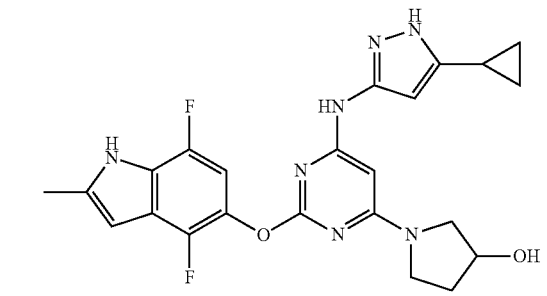
152
-continued
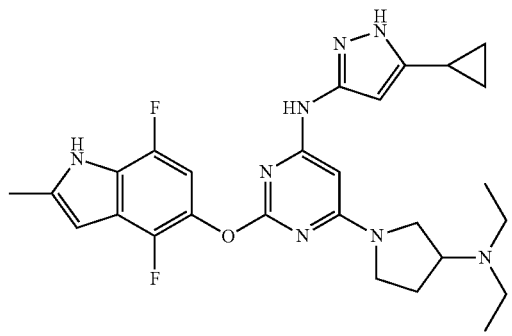
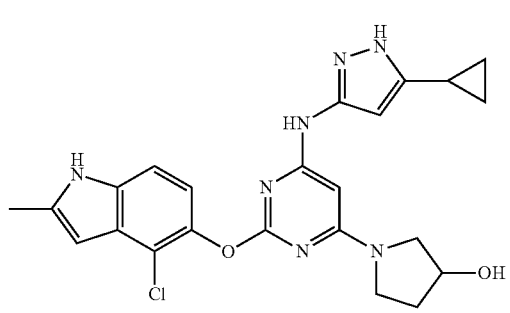
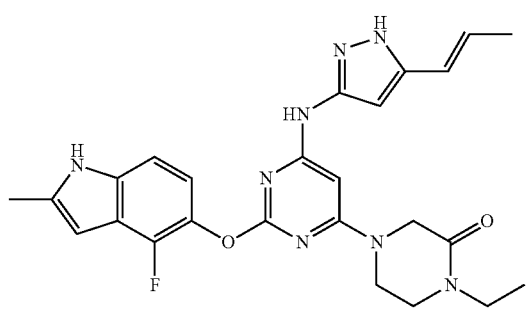
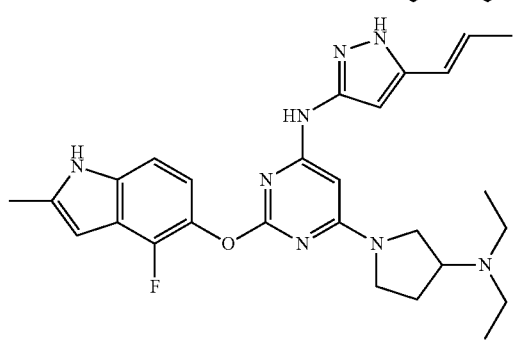
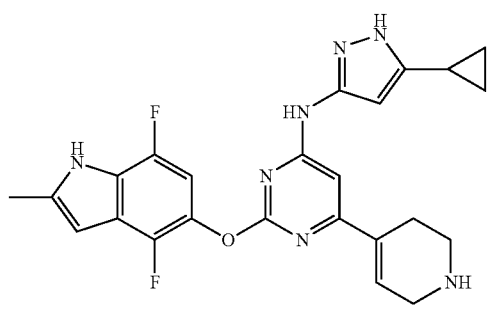

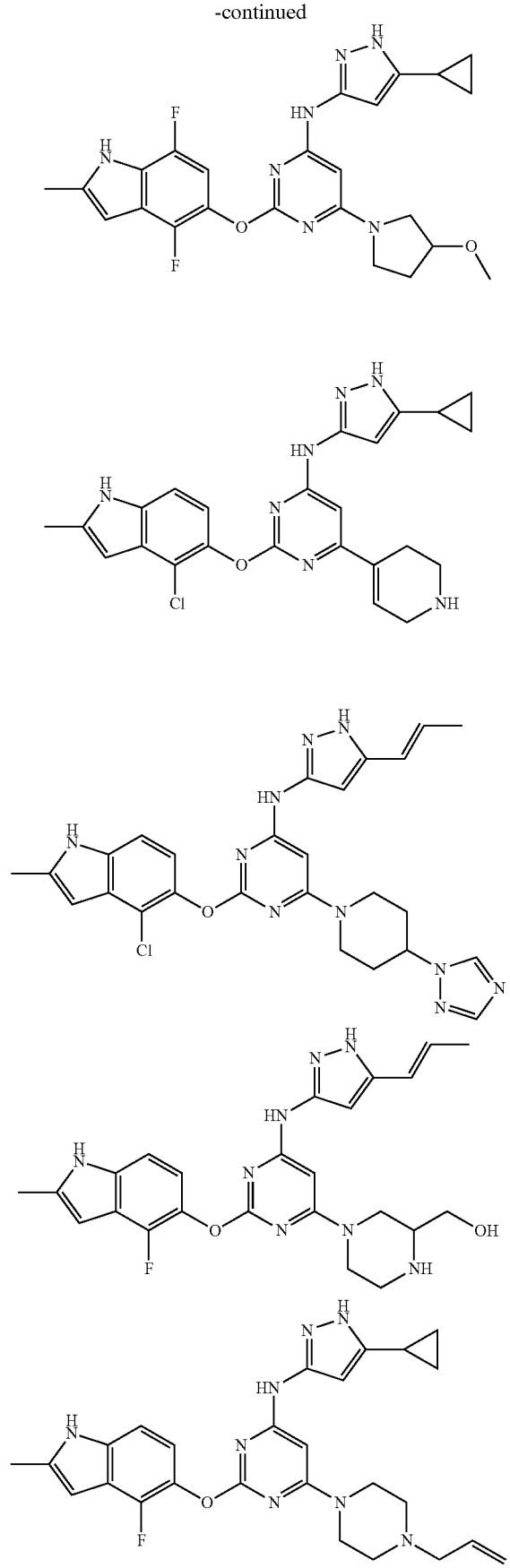
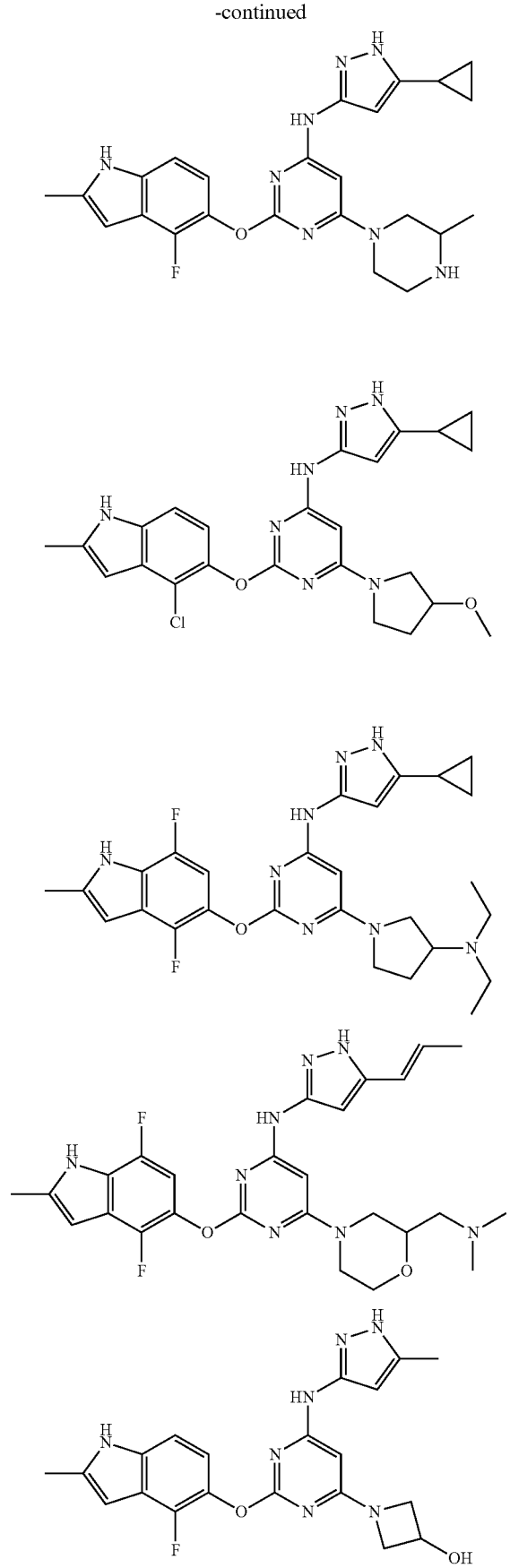

-continued
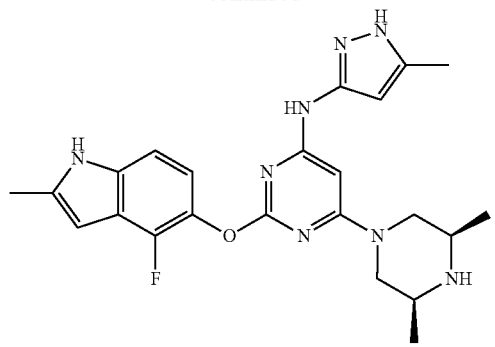
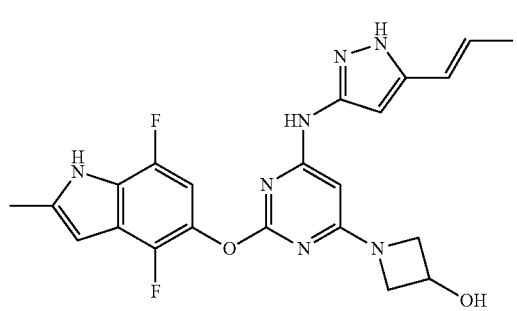
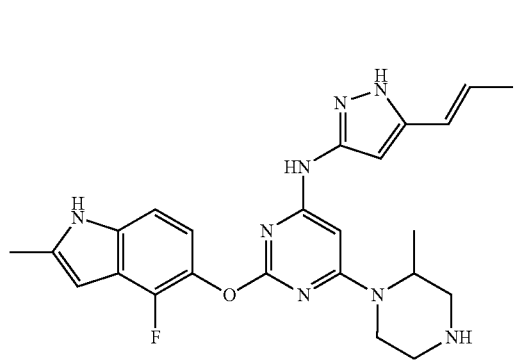
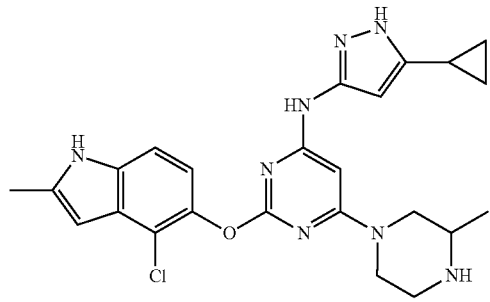
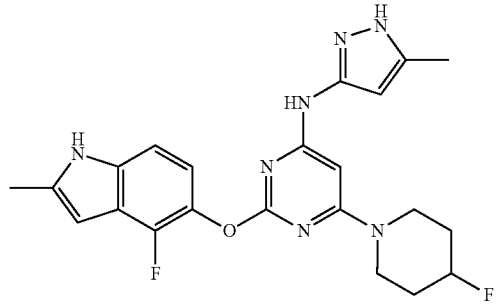
-continued
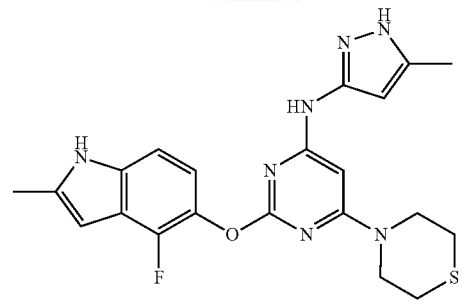
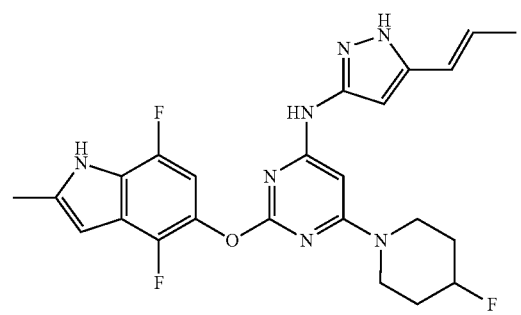
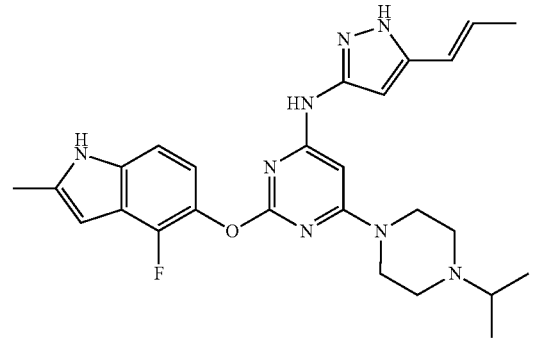
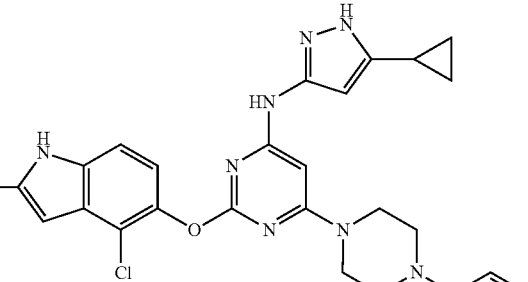
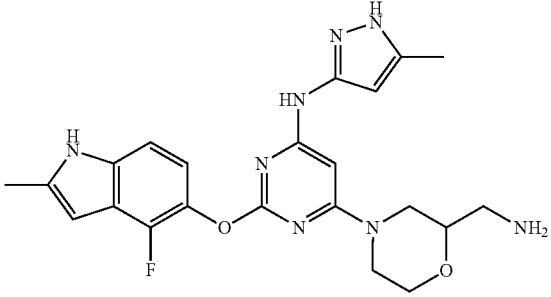

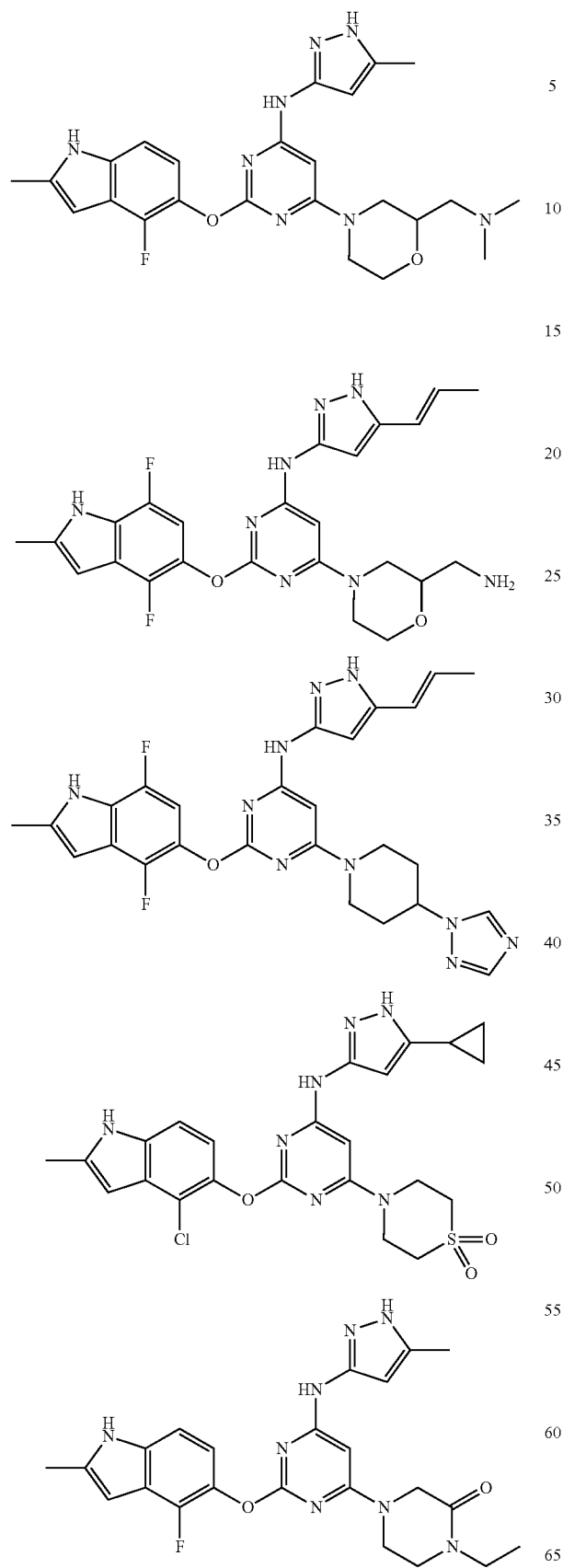
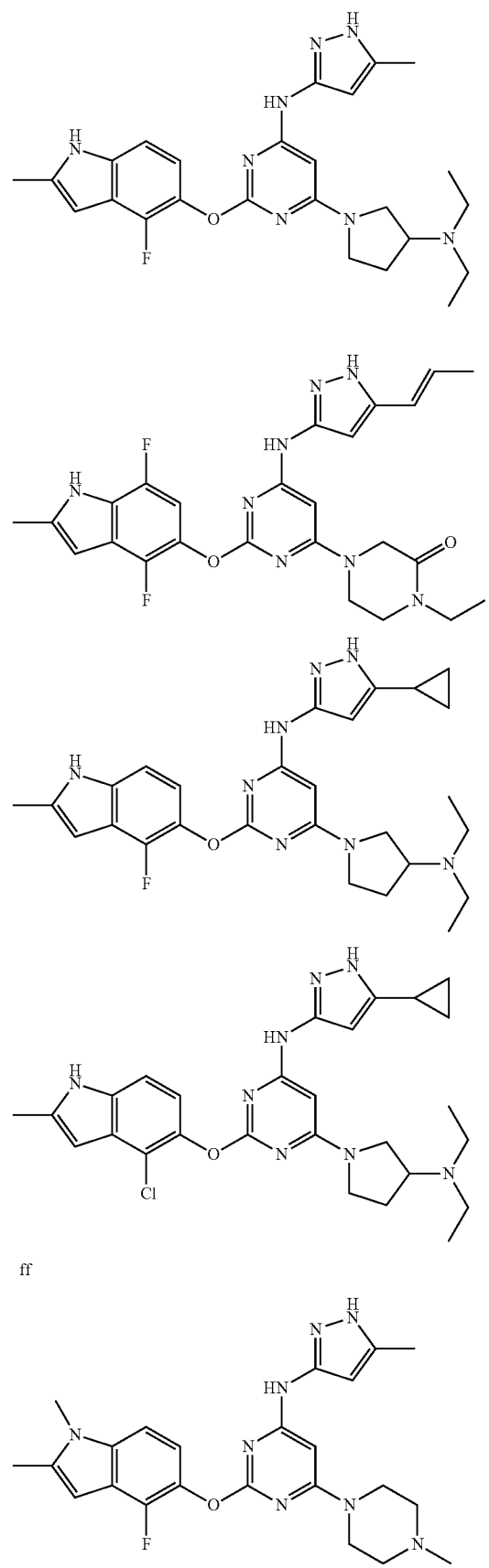

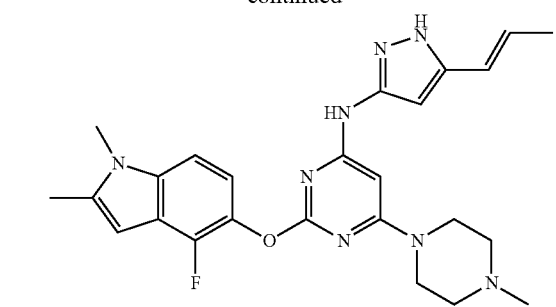
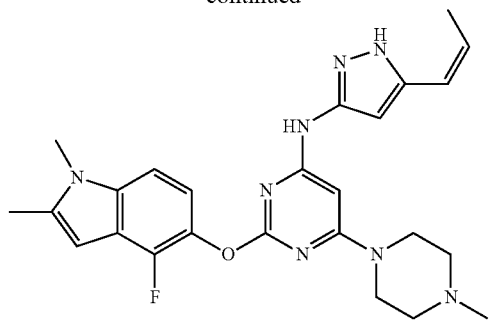
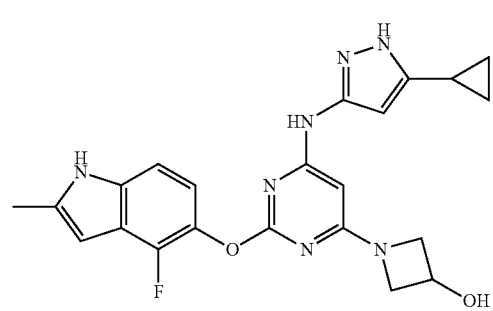
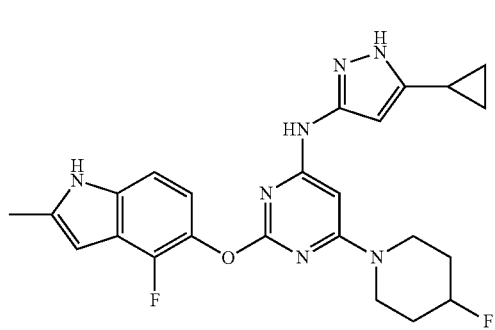
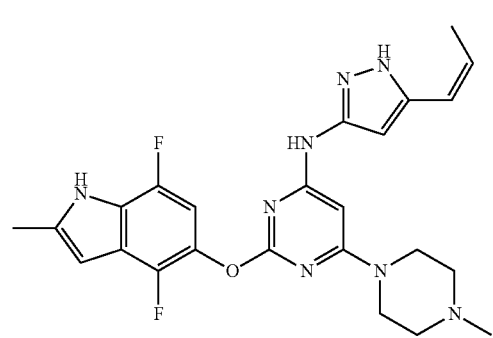
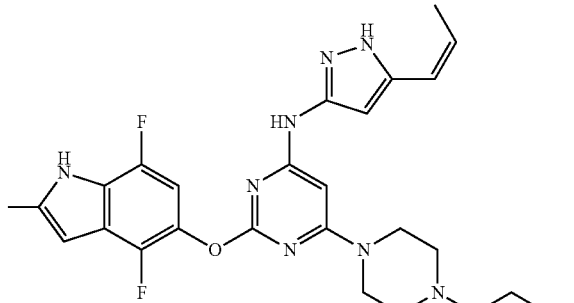
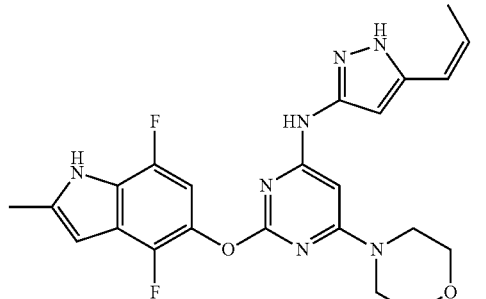
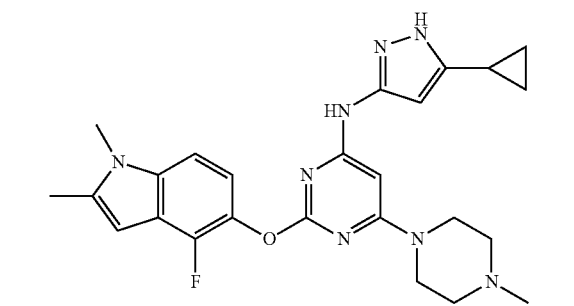
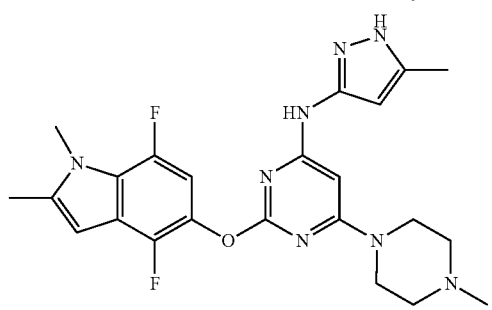

-continued
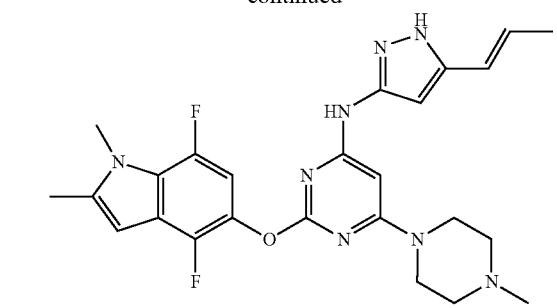
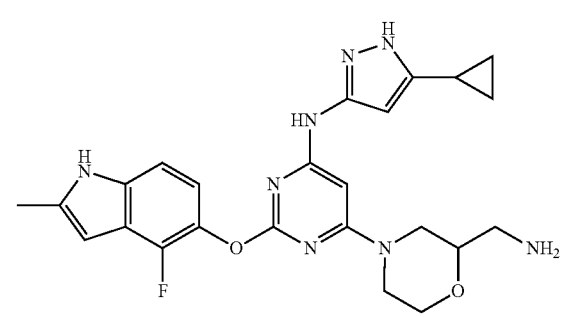
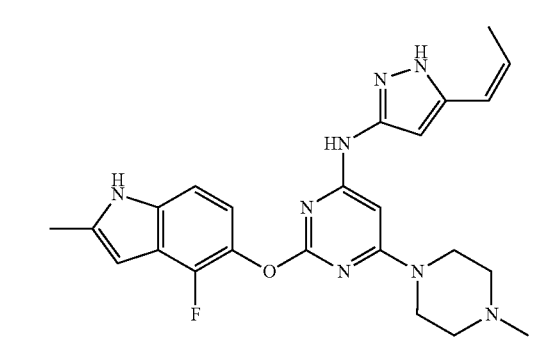
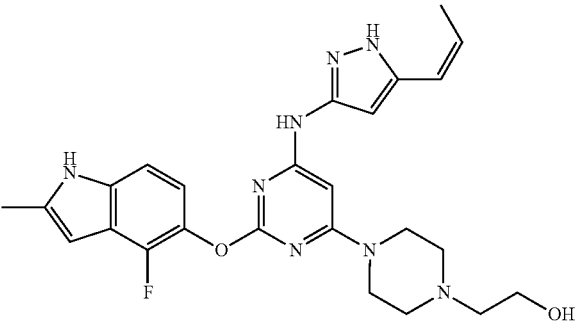
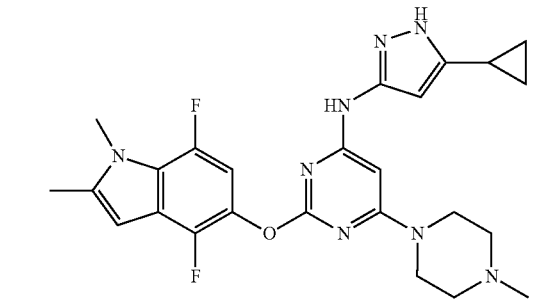
-continued
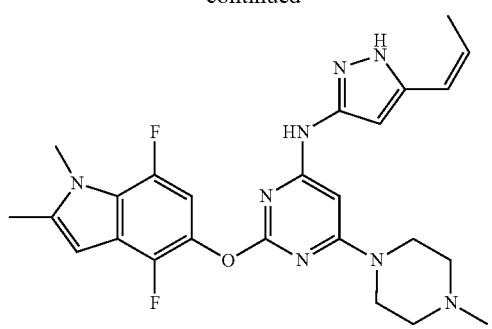
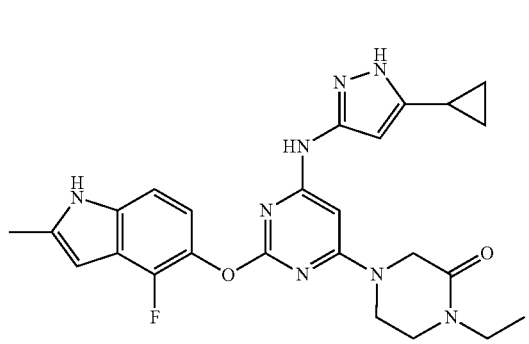
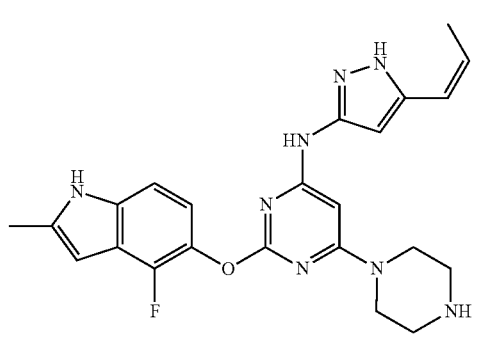
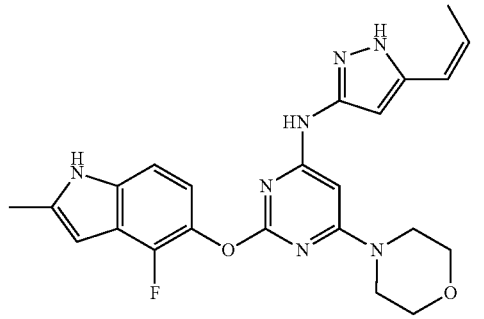
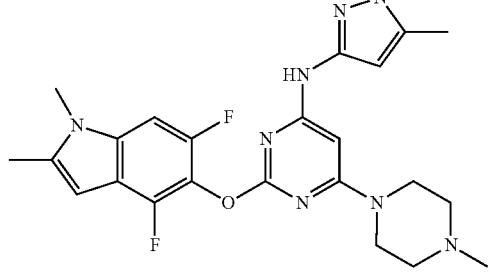

163
-continued
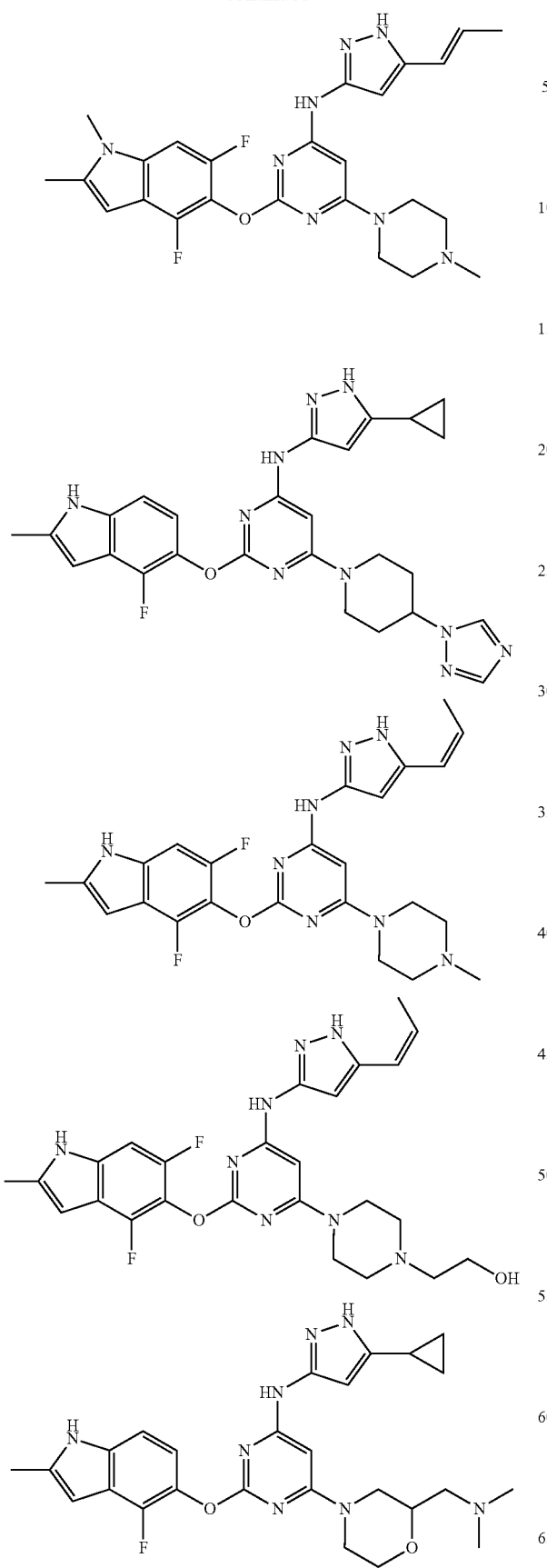
164
-continued
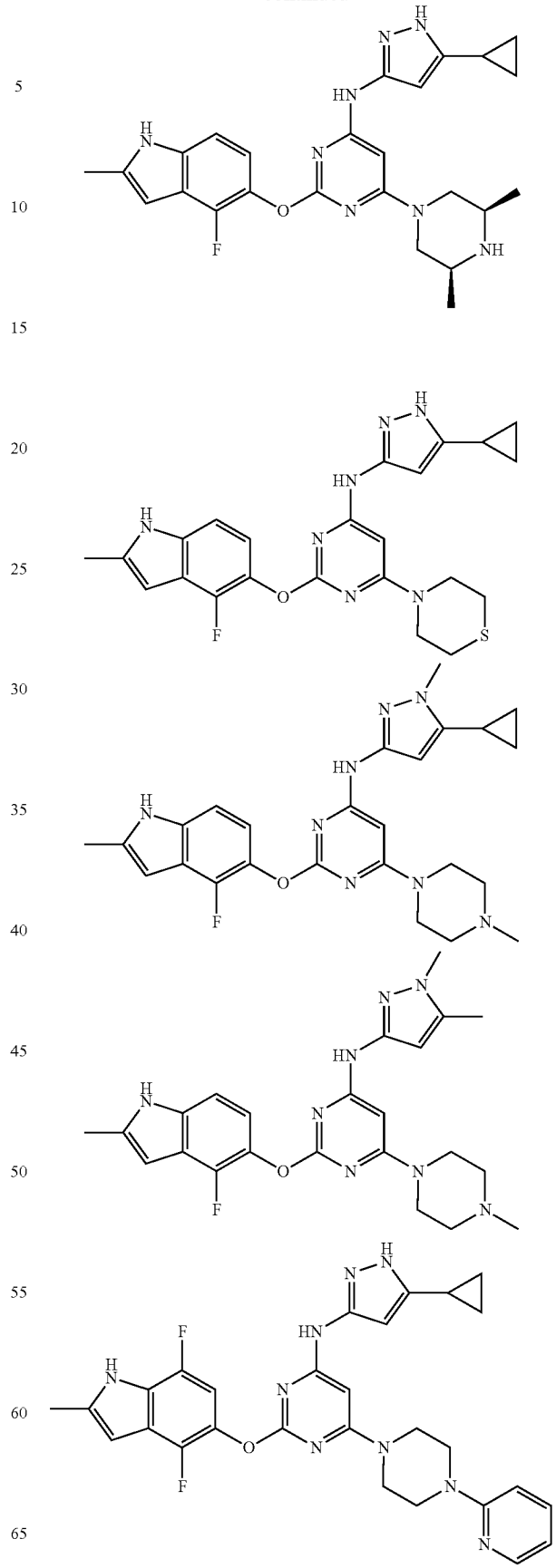

-continued
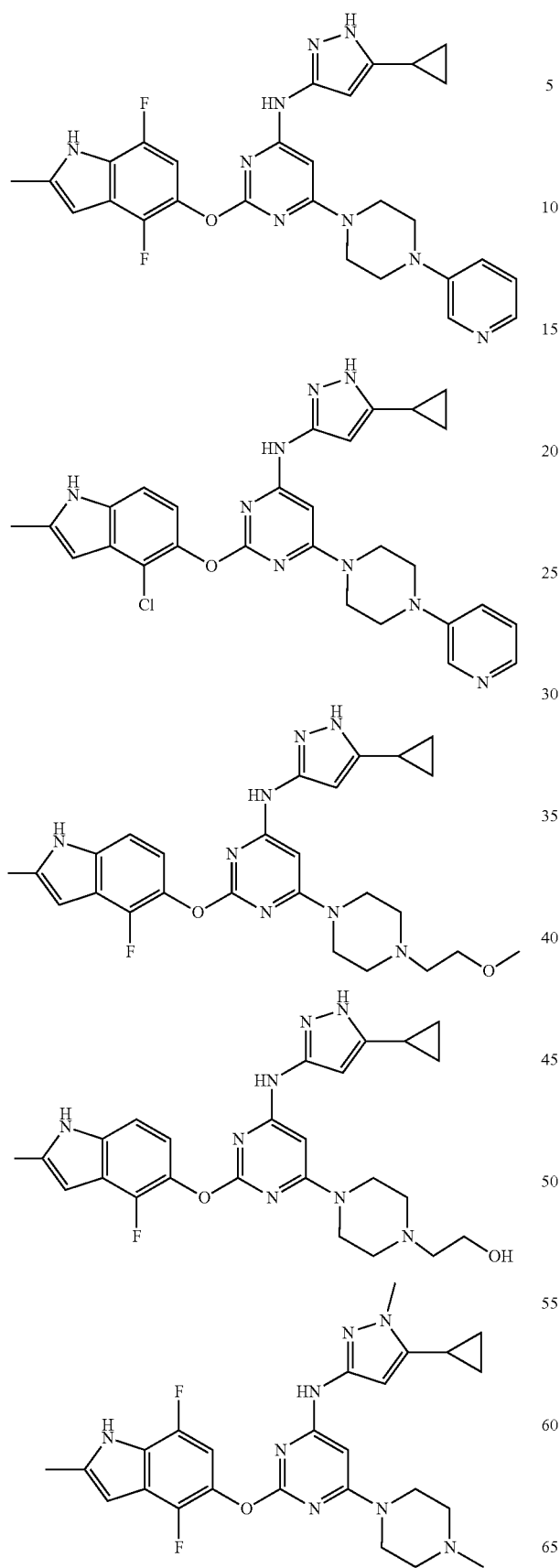
-continued
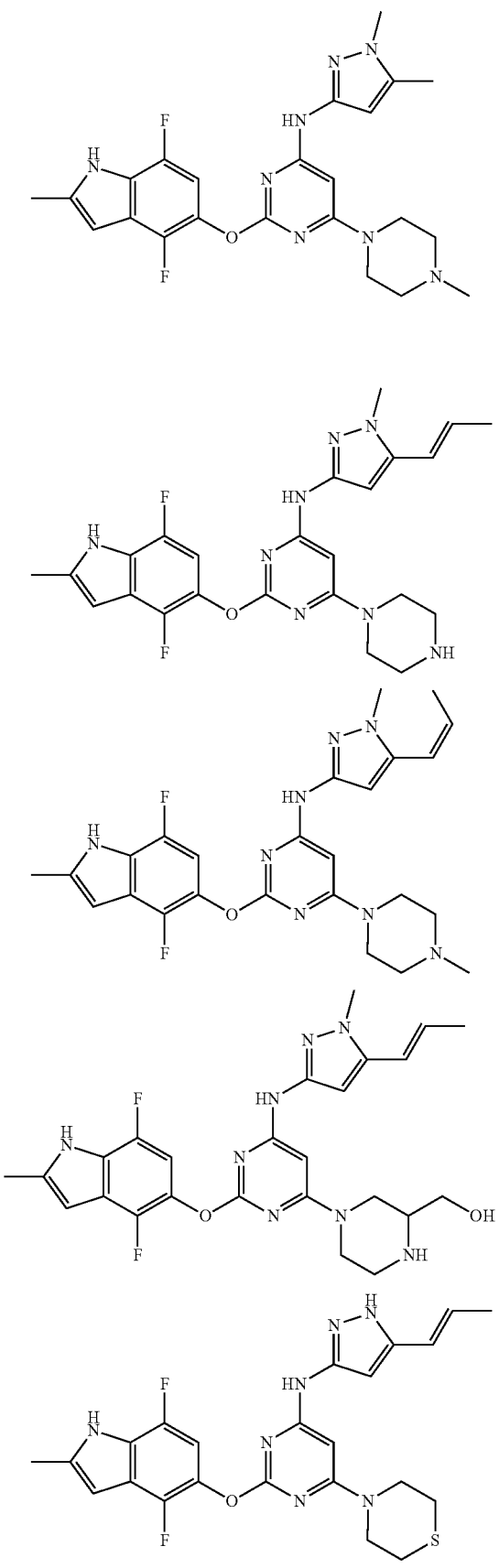

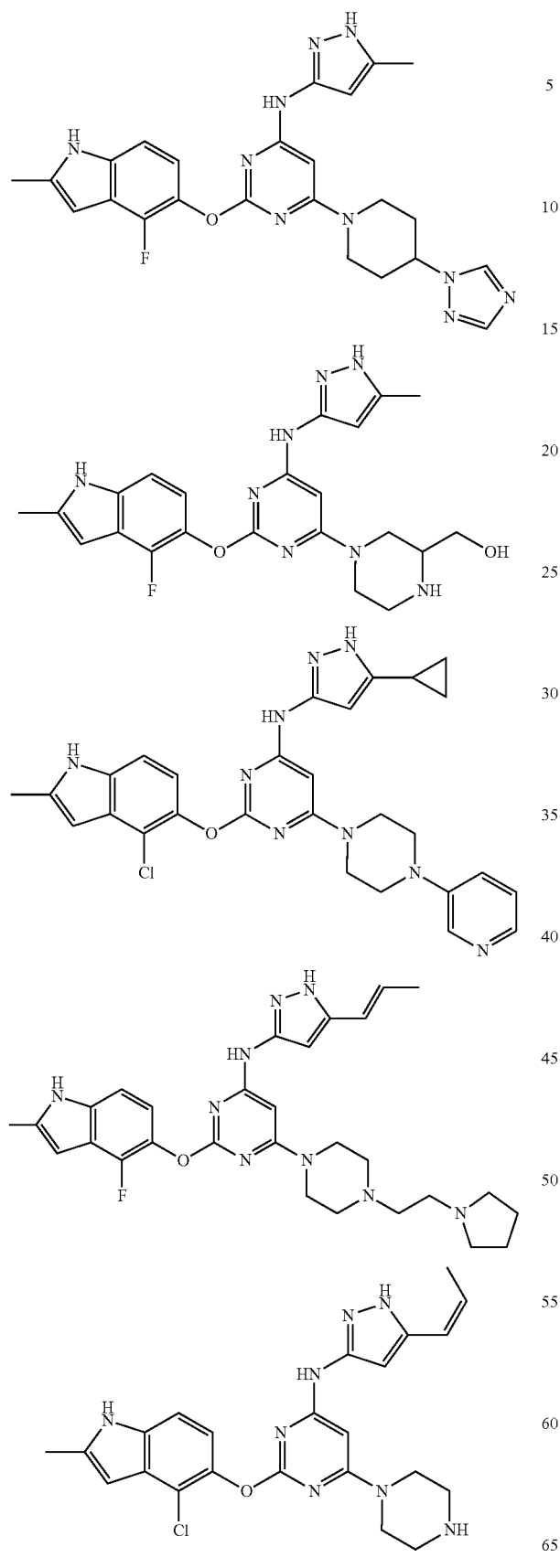
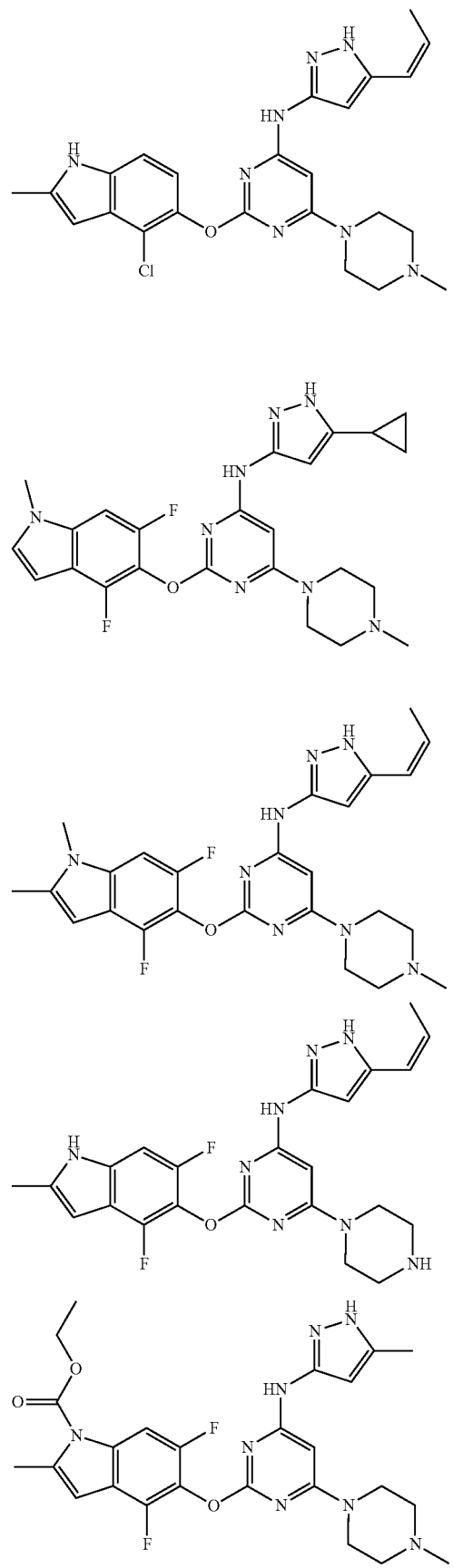

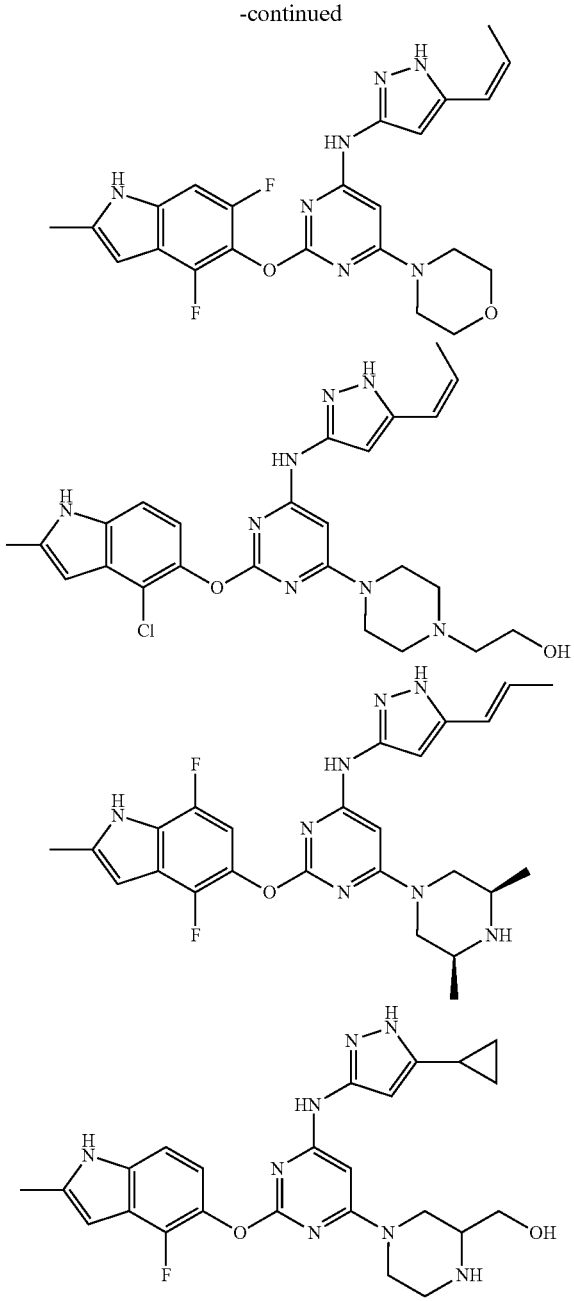

In another embodiment, a method of preparing the inventive compounds is provided. The compounds of the present invention can be generally prepared using 4,6-dichloro-2-methylsulfonylpyrimidine, or 2,4,6-trichloropyrimidine, or 4,6-dichloro-2-(methylthio)pyrimidine as a starting material. Compound (I) may contain various stereoisomers, geometric isomers, tautomeric isomers, and the like. All of possible isomers and their mixtures are included in the present invention, and the mixing ratio is not particularly limited.

The pyrimidine derivative compounds of Formula (IIa, IIb and IIc) in this invention can be synthesized from commercially available precursors using established protocols. By way of example, a synthetic route similar to that shown in any of the following Schemes may be used, together with synthetic methods known in the art of synthetic organic chemistry, or variations thereon as appreciated by those skilled in the art. Each variable in the following schemes refers to any group consistent with the description of the compounds provided herein.

In the Schemes that follow the term "reduction" refers to the process of reducing a nitro functionality to an amino functionality, or the process of transforming an ester functionality to an alcohol. The reduction of a nitro group can be carried out in a number of ways well known to those skilled in the art of organic synthesis including, but not limited to, catalytic hydrogenation, reduction with $SnCl_2$ and reduction with titanium bichloride. In the Schemes that follow, the term "hydrolyze" refers to the reaction of a substrate or reactant with water. More specifically, "hydrolyze" refers to the conversion of an ester or nitrite functionality into a carboxylic acid. This process can be catalyzed by a variety of acids or bases well known to those skilled in the art of organic synthesis.

The compounds of Formula (IIa, IIb, and IIc) may be prepared by use of known chemical reactions and procedures. The following general preparative methods are presented to aid one of skill in the art in synthesizing the inhibitors, with more detailed examples being presented in the experimental section describing the working examples.

Propenyl-pyrazol amine as defined in formula (III) is not commercially available. It can be prepared by several methods as described earlier (see, e.g., U.S. provisional application No. 61/555,738).

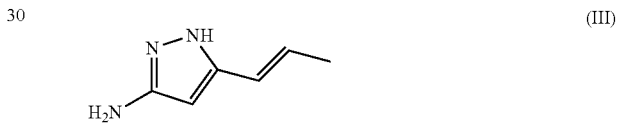

Precursors of substituted indol-5-ol as defined in formula (IV) can be purchased from suppliers, or synthesized from commercially available precursors using established protocols. (WO 2004/009542, P33-38; Journal of Medicinal Chemistry, 2006, Vol 49, No. 7, P2143-2146; Org. Lett. Vol 10, No 12, 2008, P 2369-2372; WO 00/47212, P245-250; WO 2009036055 A1, P57).

Especially, precursor 4-7-d-fluoroindol-5-ol as defined in formula (IVa) was not reported before and can be prepared with the same token.

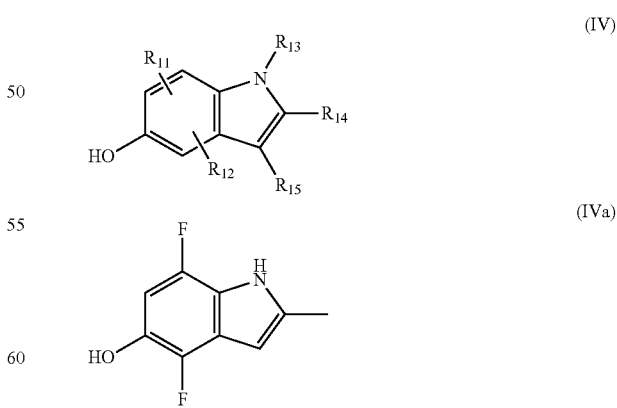

For example, as illustrated in scheme 1, precursor (IV) can be prepared from the commercially available starting materials via several steps. Also various synthetic routs can be utilized to prepare the compound.

Scheme 1
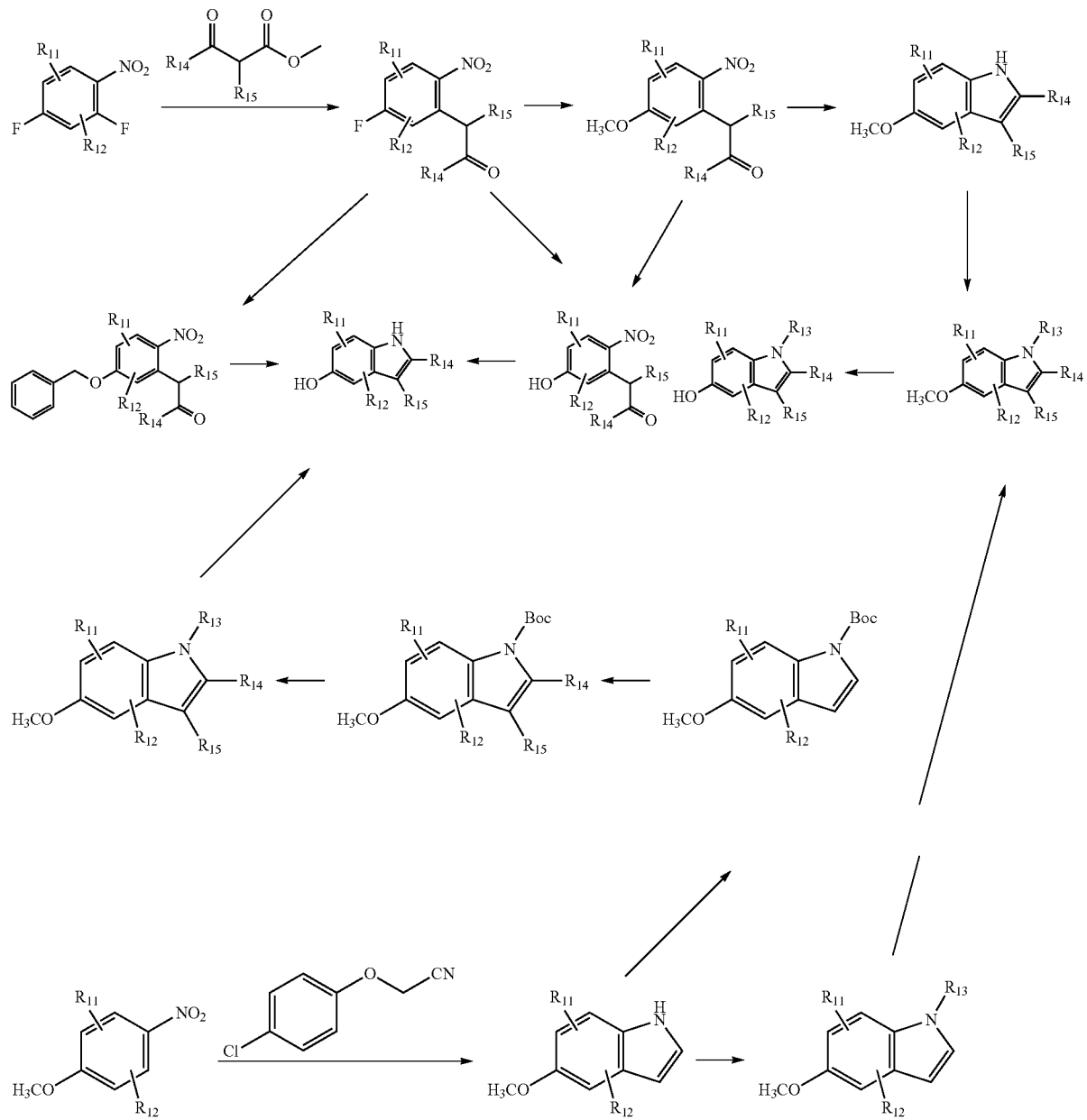
The preparation of the compounds of formula (IIa, IIb and IIc) in this invention can be carried out by methods known in the art.
-continued
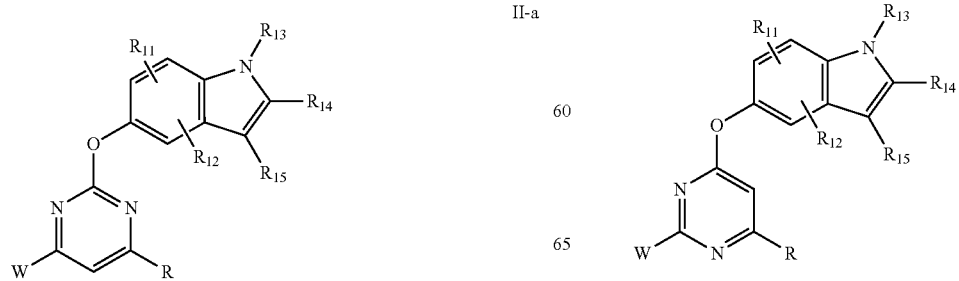

-continued

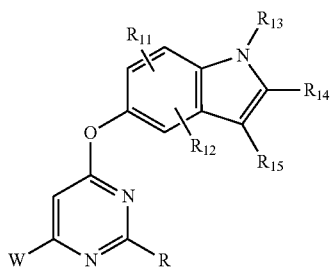

II-c

As shown in scheme 2, the pyrimidine derivative (IIa) can be synthesized by the reaction of 2,4,6-trichloropyrimidine, or 4,6-dichloro-2-(methylsulfonyl)pyrimidine, with a sequence of sustituted idole-5-ol s to give dichloropyrimidine intermediate of compound b, which can react with WH to produce the advanced monochloro intermediate of compound c. The displacement of the last chlorine by RH can be achieved by increasing the temperature, affording the final compound (IIa). The reaction can be stepwise or in one pot. Alternative sequence can also be used to make pyrimidine derivatives. With the same token, Compound IIb and IIc can also be synthesized.

Scheme 2

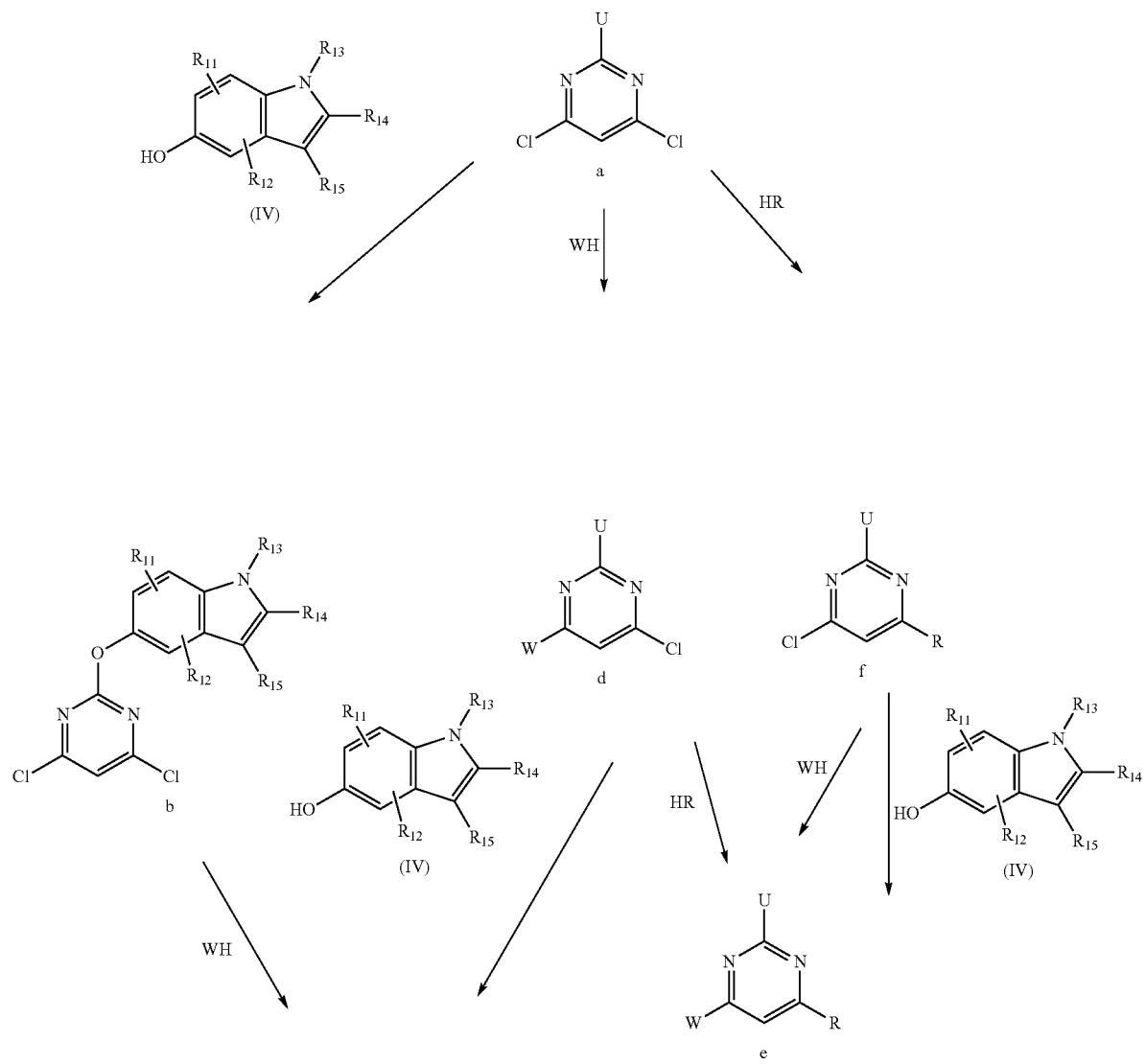

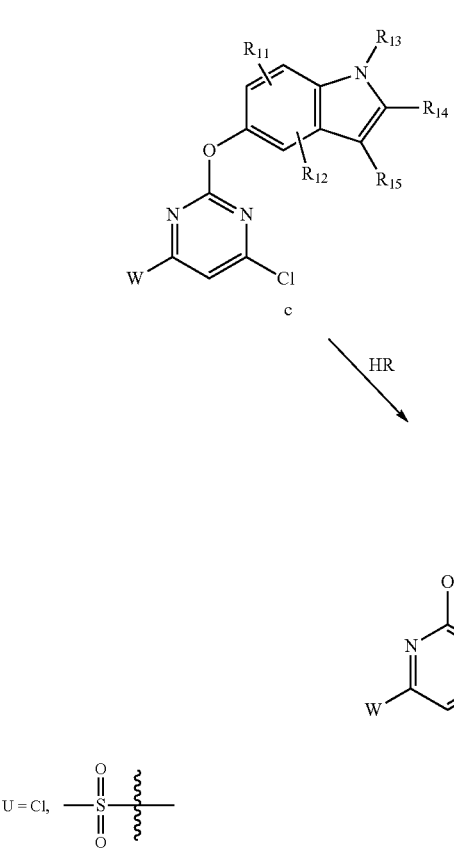

-continued

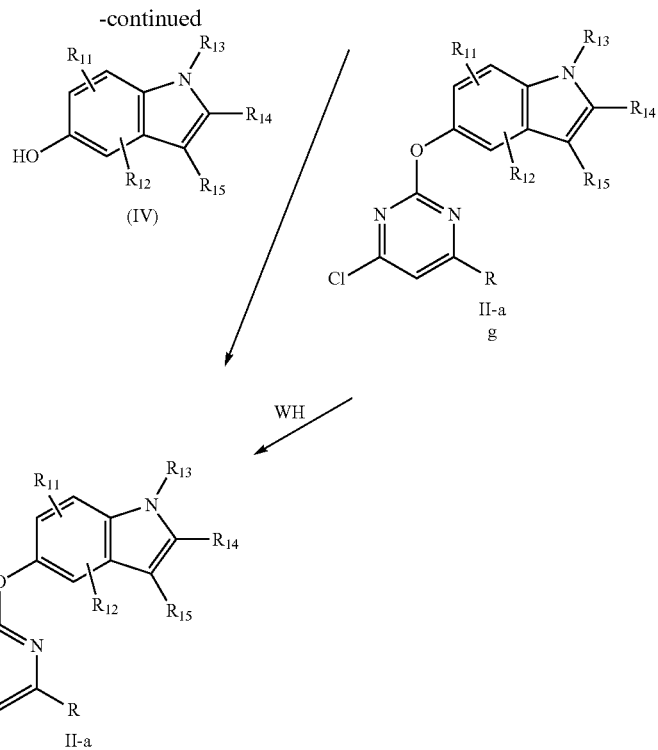

The reaction is preferably conducted in the presence of an inert solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane, heptane, ligroin and petroleum ether; aromatic hydrocarbons, such as benzene, toluene and xylene; halogenated hydrocarbons, especially aromatic and aliphatic hydrocarbons, such as methylene chloride, chloroform, carbon tetrachloride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitro compounds, which may be nitroalkanes or nitroaranes, such as nitroethane and nitrobenzene; nitriles, such as acetonitrile and isobutyronitrile; amides, which may be fatty acid amides, such as formamide, dimethylformamide, dimethylacetamide and hexamethylphosphoric triamide; and sulphoxides, such as dimethyl sulphoxide and sulpholane.

The reaction can take place over a wide range of temperatures, and the precise reaction temperature is not critical to the invention. In general, we find it convenient to carry out the reaction at a temperature of from −50° C. to 100° C.

The present invention provides compositions of matter that are formulations of one or more active drugs and a pharmaceutically-acceptable carrier. In this regard, the invention provides a composition for administration to a mammalian subject, which may include a compound of formula I, or its pharmaceutically acceptable salts.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutically acceptable compositions of this invention may be orally administered in any orally acceptable dosage form including, but not limited to, capsules, tablets, troches, elixirs, suspensions, syrups, wafers, chewing gums, aqueous suspensions or solutions.

The oral compositions may contain additional ingredients such as: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring. When the dosage unit form is a capsule, it may additionally contain a liquid carrier such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors. Materials used in preparing these various compositions should be pharmaceutically or veterinarally pure and non-toxic in the amounts used.

For the purposes of parenteral therapeutic administration, the active ingredient may be incorporated into a solution or suspension. The solutions or suspensions may also include the following components: a sterile diluents such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final fog n should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration, may then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

In accordance with the invention, there are provided compositions containing triazine derivatives and methods useful for the in vivo delivery of triazine derivatives in the form of nanoparticles, which are suitable for any of the aforesaid routes of administration.

U.S. Pat. Nos. 5,916,596, 6,506,405 and 6,537,579 teach the preparation of nanoparticles from the biocompatible polymers, such as albumin. Thus, in accordance with the present invention, there are provided methods for the formation of nanoparticles of the present invention by a solvent evaporation technique from an oil-in-water emulsion prepared under conditions of high shear forces (e.g., sonication, high pressure homogenization, or the like).

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

In accordance with the invention, the compounds of the invention may be used to treat diseases associated with cellular proliferation or hyperproliferation, such as cancers which include but are not limited to tumors of the nasal cavity, paranasal sinuses, nasopharynx, oral cavity, oropharynx, larynx, hypopharynx, salivary glands, and paragangliomas. The compounds of the invention may also be used to treat cancers of the liver and biliary tree (particularly hepatocellular carcinoma), intestinal cancers, particularly colorectal cancer, ovarian cancer, small cell and non-small cell lung cancer, breast cancer, sarcomas (including fibrosarcoma, malignant fibrous histiocytoma, embryonal rhabdomysocarcoma, leiomysosarcoma, neuro-fibrosarcoma, osteosarcoma, synovial sarcoma, liposarcoma, and alveolar soft part sarcoma), neoplasms of the central nervous systems (particularly brain cancer), and lymphomas (including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma).

The compounds and methods of the present invention, either when administered alone or in combination with other agents (e.g., chemotherapeutic agents or protein therapeutic agents described below) are also useful in treating a variety of disorders, including but not limited to, for example: stroke, cardiovascular disease, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), pleural effusions, rheumatoid arthritis, diabetic retinopathy, retinitis pigmentosa, and retinopathies, including diabetic retinopathy and retinopathy of prematurity, inflammatory diseases, restenosis, asthma, acute or adult respiratory distress syndrome (ARDS), lupus, vascular leakage, protection from ischemic or reperfusion injury such as ischemic or reperfusion injury incurred during organ transplantation, transplantation tolerance induction; ischemic or reperfusion injury following angioplasty; arthritis (such as rheumatoid arthritis, psoriatic arthritis or osteoarthritis); multiple sclerosis; inflammatory bowel disease, including ulcerative colitis and Crohn's disease; lupus (systemic lupus crythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including those where kineses such as Src-family kineses are activated or overexpressed, such as colon carcinoma and thymoma, or cancers where kinase activity facilitates tumor growth or survival; glomerulonephritis, serum sickness; uticaria; allergic diseases such as respiratory allergies (asthma, hay fever, allergic rhinitis) or skin allergies; mycosis fungoides; acute inflammatory responses (such as acute or adult respiratory distress syndrome and ischemial reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener s granulomatosis, and Behcet's disease; scleroderma; preeclampsia; thalassemia; Kaposi's sarcoma; von Hippel Lindau disease; and the like.

In accordance with the invention, the compounds of the invention may be used to treat diseases associated with undesired cellular proliferation or hyperproliferation comprising identifying the mammal afflicted with said disease or condition and administering to said afflicted mammal a composition comprising the compound of formula 1, wherein the disease or condition is associated with a kinase.

In accordance with the invention, the compounds of the invention may be used to treat diseases associated with undesired cellular proliferation or hyperproliferation comprising identifying the mammal afflicted with said disease or condition and administering to said afflicted mammal a composition comprising the compound of formula 1, wherein the disease or condition is associated with a tyrosine kinase.

In accordance with the invention, the compounds of the invention may be used to treat diseases associated with undesired cellular proliferation or hyperproliferation comprising identifying the mammal afflicted with said disease or condition and administering to said afflicted mammal a composition comprising the compound of formula 1, wherein the disease or condition is associated with the kinase that is a serine kinase or a threonine kinase.

In accordance with the invention, the compounds of the invention may be used to treat diseases associated with undesired cellular proliferation or hyperproliferation comprising identifying the mammal afflicted with said disease or condition and administering to said afflicted mammal a composition comprising the compound of formula 1, wherein the disease or condition is associated with the kinase that is a Src family kinase.

The invention also provides methods of treating a mammal afflicted with the above diseases and conditions. The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

In one aspect, the invention compounds are administered in combination with chemotherapeutic agent, an anti-inflammatory agent, antihistamines, chemotherapeutic agent, immunomodulator, therapeutic antibody or a protein kinase inhibitor, e.g., a tyrosine kinase inhibitor, to a subject in need of such treatment.

The method includes administering one or more of the inventive compounds to the afflicted mammal. The method may further include the administration of a second active agent or more active agents, such as a cytotoxic agent, including alkylating agents, tumor necrosis factors, intercalators, microtubulin inhibitors, and topoisomerase inhibitors. The second active agent may be co-administered in the same composition or in a second composition. Examples of suitable second active agents include, but are not limited to, a cytotoxic drug such as Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Oiniaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

In accordance with the invention, the compounds and compositions may be used at sub-cytotoxic levels in combination with other agents in order to achieve highly selective activity in the treatment of non-neoplastic disorders, such as heart disease, stroke and neurodegenerative diseases (Whitesell et al., Curr Cancer Drug Targets (2003), 3(5), 349-58).

The exemplary therapeutic agents that may be administered in combination with invention compounds include EGFR inhibitors, such as gefitinib, erlotinib, and cetuximab. Her2 inhibitors include canertinib, EKB-569, and GW-572016. Also included are Src inhibitors, dasatinib, as well as Casodex (bicalutamide), Tamoxifen, MEK-1 kinase inhibitors, MARK kinase inhibitors, PI3 inhibitors, and PDGF inhibitors, such as imatinib, Hsp90 inhibitors, such as 17-AAG and 17-DMAG. Also included are anti-angiogenic and antivascular agents which, by interrupting blood flow to solid tumors, render cancer cells quiescent by depriving them of nutrition. Castration, which also renders androgen dependent carcinomas non-proliferative, may also be utilized. Also included are IGF1R inhibitors, inhibitors of non-receptor and receptor tyrosine kineses, and inhibitors of integrin.

The pharmaceutical composition and method of the present invention may further combine other protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay. The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

Other therapeutic agents for the combinatory therapy include cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and for gpn39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HM:G CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one having ordinary skill in the art.

Embodiments

In embodiment (1) is presented a compound of the formula (I)

I or a pharmaceutically acceptable derivative or prodrug thereof,
or a pharmaceutically acceptable derivative or prodrug thereof, wherein;
R is selected from:
(i) hydrogen, amino, alkyl amino;
(ii) $C_1$-$C_6$ alkyl, $C_2$-$C_6$ alkenyl, $C_2$-$C_6$ alkynyl;
(iii) K—Ar.
Ar represents heteroaryl or aryl, each of which is substituted with from 0 to 4 substituents independently chosen from:
(1) halogen, hydroxy, amino, amide, cyano, —COOH, —$SO_2NH_2$, oxo, nitro and alkoxycarbonyl; and
(2) $C_1$-$C_6$ alkyl, $C_1$-$C_6$ alkoxy, $C_3$-$C_{10}$ cycloalkyl, $C_2$-$C_6$ alkenyl, $C_2$-$C_6$ alkynyl, $C_2$-$C_6$ alkanoyl, $C_1$-$C_6$ haloalkyl, $C_1$-$C_6$ haloalkoxy, mono- and di-($C_1$-$C_6$ alkyl)amino, $C_1$-$C_6$ alkylsulfonyl, mono- and di-($C_1$-$C_6$alkyl) sulfonamido and mono- and di-($C_1$-$C_6$ alkyl)aminocarbonyl; phenyl $C_0$-$C_4$ alkyl and (4- to 7-membered heterocycle) $C_0$-$C_4$ alkyl, each of which is substituted with from 0 to 4 secondary substituents independently chosen from halogen, hydroxy, cyano, oxo, imino, $C_1$-$C_4$ alkyl, $C_1$-$C_4$ alkoxy and $C_1$-$C_4$ haloalkyl.
K is selected from
a) O, S, SO, $SO_2$;
b) $(CH_2)_m$, m=0-3, —$O(CH_2)_p$, p=1-3, —$S(CH_2)_p$, p=1-3, —$N(CH_2)_p$, p=1-3, —$(CH_2)_pO$, p=1-3;
c) $NR_1$
$R_1$ represents hydrogen, alkyl, cycloalkyl, alkenyl, alkynyl, alkylthio, aryl, arylalkyl.

(iv) groups of the formula (Ia):

(Ia)

wherein:
$R_2$ represents hydrogen, $C_1$-$C_4$ alkyl, oxo;
X is CH, when $R_3$ is hydrogen; or X—$R_3$ is O; or X is N, $R_3$ represents groups of hydrogen, $C_1$-$C_6$ alkyl, $C_2$-$C_6$ alkenyl, $C_2$-$C_6$ alkynyl, $C_3$-$C_{10}$ aryl or heteroaryl, ($C_3$-$C_7$ cycloalkyl) $C_1$-$C_4$ alkyl, $C_1$-$C_6$ haloalkyl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy, mono- and di-($C_3$-$C_8$ cycloalkyl)amino $C_0$-$C_4$ alkyl, (4- to 7-membered heterocycle) $C_0$-$C_4$ alkyl, $C_1$-$C_6$ alkylsulfonyl, mono- and di-($C_1$-$C_6$ alkyl) sulfonamido, and mono- and di-($C_1$-$C_6$ alkyl)aminocarbonyl, each of which is substituted with from 0 to 4 substituents independently chosen from halogen, hydroxy, cyano, amino, —COOH and oxo.
Het is selected from any heterocycle, which is substituted with from 0 to 4 substituents independently chosen from:
(i) $C_1$-$C_6$ alkyl, $C_2$-$C_6$ alkenyl, $C_2$-$C_6$ alkynyl;
(ii) halogen, hydroxy, amino, amide, cyano, —COOH, —$SO_2NH_2$, oxo, nitro and alkoxycarbonyl,
(iii) aryl.
$R_{11}$ and $R_{12}$ are independently selected from: Hydrogen, F, Cl, Br, CN, $C_1$-$C_4$ alkyl, $C_1$-$C_6$ alkoxy.
$R_{13}$, $R_{14}$ and $R_{15}$ are independently selected from Hydrogene, $C_1$-$C_4$ alkyl, $C_2$-$C_6$ alkenyl, $C_2$-$C_6$ alkynyl, $C_3$-$C_{10}$ aryl or heteroaryl, $C_1$-$C_6$ alkoxy, $C_1$-$C_6$ alkylthio, $C_2$-$C_6$ alkanoyl, $C_1$-$C_6$ alkoxycarbonyl, $C_2$-$C_6$ alkanoyloxy.

In embodiment (2) is presented a process for making the compound of embodiment (1) or its pharmaceutically acceptable salts, hydrates, solvates, crystal forms salts and individual diastereomers thereof.

In embodiment (3) is presented a pharmaceutical composition comprising at least one compound of embodiment (1) or its pharmaceutically acceptable salts, hydrates, solvates, crystal forms salts and individual diastereomers thereof, and a pharmaceutically acceptable carrier.

In embodiment (4) is presented the composition according to embodiment (3), further comprising an additional therapeutic agent.

In embodiment (5) is presented the compound with the formula:

In embodiment (6) is presented a process for making the compound of embodiment (5) or its pharmaceutically acceptable salts, hydrates, solvates, crystal forms salts and individual diastereomers thereof.

In embodiment (7) is presented a pharmaceutical composition comprising the compound of embodiment (5) or its pharmaceutically acceptable salts, hydrates, solvates, crystal forms salts and individual diastereomers thereof, and a pharmaceutically acceptable carrier.

In embodiment (8) is presented the composition according to embodiment (7), further comprising an additional therapeutic agent.

In embodiment (9) is presented the compound with the formula:

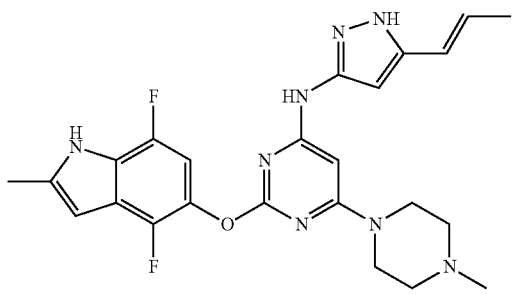

In embodiment (10) is presented a process for making the compound of embodiment (9) or its pharmaceutically acceptable salts, hydrates, solvates, crystal forms salts and individual diastereomers thereof.

In embodiment (11) is presented a pharmaceutical composition comprising the compound of embodiment (9) or its pharmaceutically acceptable salts, hydrates, solvates, crystal forms salts and individual diastereomers thereof, and a pharmaceutically acceptable carrier.

In embodiment (12) is presented the composition according to embodiment (11), further comprising an additional therapeutic agent.

In embodiment (13) is presented the compound with the formula:

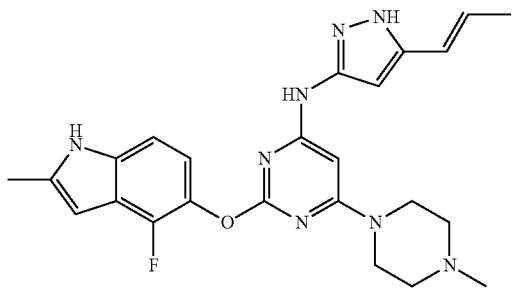

In embodiment (14) is presented a process for making the compound of embodiment (13) or its pharmaceutically acceptable salts, hydrates, solvates, crystal forms salts and individual diastereomers thereof.

In embodiment (15) is presented a pharmaceutical composition comprising the compound of embodiment (13) or its pharmaceutically acceptable salts, hydrates, solvates, crystal forms salts and individual diastereomers thereof, and a pharmaceutically acceptable carrier.

In embodiment (16) is presented the composition according to embodiment (15), further comprising an additional therapeutic agent.

In embodiment (17) is presented the compound with the formula:

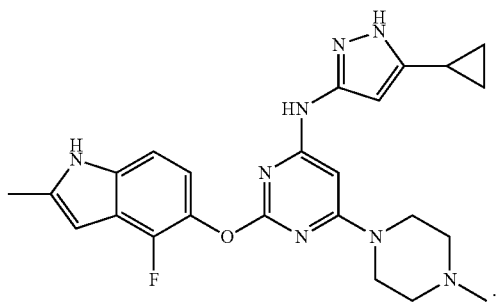

In embodiment (18) is presented a process for making the compound of embodiment (17) or its pharmaceutically acceptable salts, hydrates, solvates, crystal forms salts and individual diastereomers thereof.

In embodiment (19) is presented a pharmaceutical composition comprising the compound of embodiment (17) or its pharmaceutically acceptable salts, hydrates, solvates, crystal forms salts and individual diastereomers thereof, and a pharmaceutically acceptable carrier.

In embodiment (20) is presented the composition according to embodiment (19), further comprising an additional therapeutic agent.

In embodiment (21) is presented the compound with the formula:

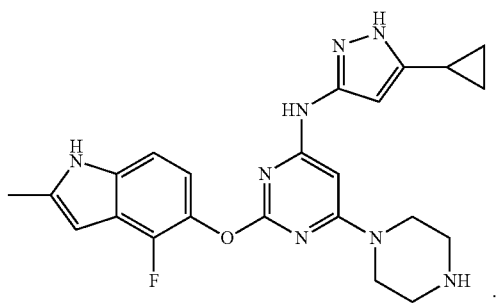 [SMILES: Cc1cc2c(F)c(Oc3nc(Nc4cc(C5CC5)[nH]n4)cc(N4CCNCC4)n3)ccc2[nH]1]

In embodiment (22) is presented a process for making the compound of embodiment (21) or its pharmaceutically acceptable salts, hydrates, solvates, crystal forms salts and individual diastereomers thereof.

In embodiment (23) is presented a pharmaceutical composition comprising the compound of embodiment (21) or its pharmaceutically acceptable salts, hydrates, solvates, crystal forms salts and individual diastereomers thereof, and a pharmaceutically acceptable carrier.

In embodiment (24) is presented the composition according to embodiment (23), further comprising an additional therapeutic agent.

In embodiment (25) is presented the compound with the formula:

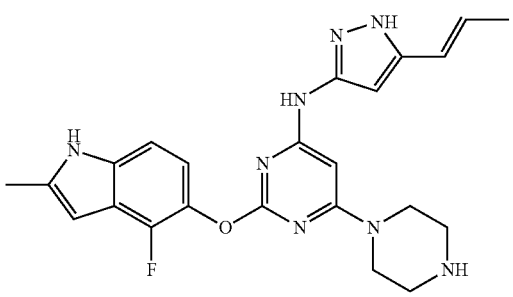

In embodiment (26) is presented a process for making the compound of embodiment (25) or its pharmaceutically acceptable salts, hydrates, solvates, crystal forms salts and individual diastereomers thereof.

In embodiment (27) is presented a pharmaceutical composition comprising the compound of embodiment (25) or its pharmaceutically acceptable salts, hydrates, solvates, crystal forms salts and individual diastereomers thereof, and a pharmaceutically acceptable carrier.

In embodiment (28) is presented the composition according to embodiment (27), further comprising an additional therapeutic agent.

In embodiment (29) is presented the compound with the formula:

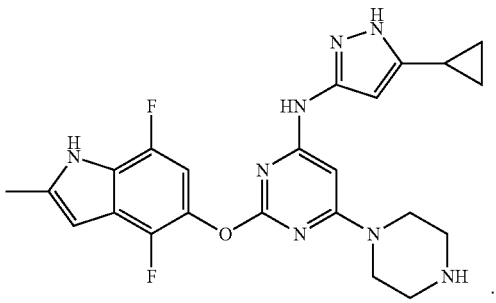 [SMILES: Cc1cc2c(F)c(Oc3nc(Nc4cc(C5CC5)[nH]n4)cc(N4CCNCC4)n3)cc(F)c2[nH]1]

In embodiment (30) is presented a process for making the compound of embodiment (29) or its pharmaceutically acceptable salts, hydrates, solvates, crystal forms salts and individual diastereomers thereof.

In embodiment (31) is presented a pharmaceutical composition comprising the compound of embodiment (29) or its pharmaceutically acceptable salts, hydrates, solvates, crystal forms salts and individual diastereomers thereof, and a pharmaceutically acceptable carrier.

In embodiment (32) is presented the composition according to embodiment (31), further comprising an additional therapeutic agent.

In embodiment (33) is presented the compound with the formula:

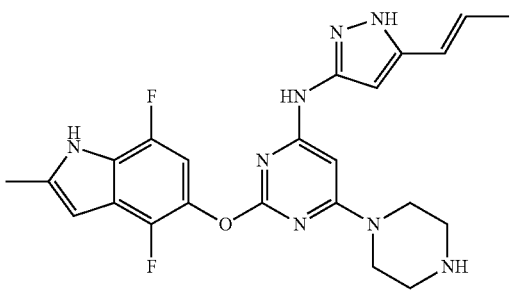

In embodiment (34) is presented a process for making the compound of embodiment (33) or its pharmaceutically acceptable salts, hydrates, solvates, crystal forms salts and individual diastereomers thereof.

In embodiment (35) is presented a pharmaceutical composition comprising the compound of embodiment (33) or its pharmaceutically acceptable salts, hydrates, solvates, crystal forms salts and individual diastereomers thereof, and a pharmaceutically acceptable carrier.

In embodiment (36) is presented the composition according to embodiment (35), further comprising an additional therapeutic agent.

In embodiment (37) is presented a method of inhibiting kinase activity, comprising contacting a kinase with the compound of any one of the embodiments (1), (5), (9), (13), (17), (21), (25), (29), or (33), whereby kinase activity is inhibited.

In embodiment (38) is presented a method of treating cancer, comprising contacting the tumor cell lines with the compound of any one of the embodiments (1), (5), (9), (13), (17), (21), (25), (29), or (33), whereby the growth activity of the tumor lines is reduced.

In embodiment (39) is presented the method of the embodiment (38), in which the concentration of the pharmaceutical composition of resulting in a 50% reduction in the net tumor increase is from 0.01. to 1.9 µM.

In embodiment (40) is presented the method of the embodiment (38), in which the tumor cell lines are those of Leukemia, non-small cell lung cancer, colon, cancer, CNS cancer, melanoma, ovarian cancer, renal cancer, prostate cancer, and breast cancer.

In embodiment (41) is presented the method of the embodiment (40), in which the Leukemia is chronic myeogenous leukemia (CML) xenograft.

In embodiment (42) is presented a use of the compound of any one of the embodiments (1), (5), (9), (13), (17), (21), (25), (29), or (33) in the treatment of cancer.

In embodiment (43) is presented a use of the compound of any one of the embodiments (1), (5), (9), (13), (17), (21), (25), (29), or (33) for the manufacture of a medicament for the treatment of cancer.

EXAMPLES

The invention further encompasses pharmaceutical compositions comprising any one or more of the compounds disclosed herein and said compounds in the form of pharmaceutically acceptable salts, hydrates, solvates, crystal forms and individual stereoisomers thereof (e.g., diastereomers, enantiomer), and as in a composition with a pharmaceutically acceptable carrier. These include, but are not limited to, wherein the inventive compounds are formulated into a composition in a neutral or salt form.

"Pharmaceutically acceptable salts" include the acid addition salts (formed with the free amino groups of the protein) which are formed with inorganic acids such as, for example, hydrochloric or phosphoric acids, or such as organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, and procaine and the like.

"Salts" are chemical combinations of two ionizable components (e.g., when dissolved in water), one acidic and the other basic with respect to one another. If in a salt form, a drug can be either the acidic or the basic component.

"Pharmaceutically acceptable salts" include any salt form of the compound wherein the salt is safe for animal ingestion (e.g., nontoxic to humans when taken orally). Exemplary such salts that can be used in accordance with the invention include, but are not limited to, 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cyclopentanepropionate, digluconate, dodecylsulfate, edetate, edisylate, estolate, esylate, ethanesulfonate, finnarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, isothionate, lactate, lactobionate, laurate, laurylsulphonate, malate, maleate, mandelate, mesylate, methanesulfonate, methylbromide, methylnitrate, methyl sulfate, mucate, naphthylate, napsylate, nicotinate, nitrate, N-methylglucamine ammonium salt, oleate, oxalate, palmitate, pamoate, pantothenate, pectinate, persulfate, phosphate, phosphateldiphosphate, picrate, pivalate, polygalacturonate, propionate, p-toluenesulfonate, saccharate, salicylate, stearate, subacetate, succinate, sulfate, sulfosaliculate, suramate, tannate, tartrate, teoclate, thiocyanate, tosylate, triethiodide, undecanoate, and valerate salts, and the like (see also S. M. Berge et al., Pharmaceutical Salts, *J. Pharm. Scis.*, 1977, 66:1-18; P. L. Gould, Salt selection for basic drugs, *Int'l J. Pharms.* 1986, 33:201-17.)

"Solvates" are compositions which, during the process of crystallization of a compound from solution, trap molecules of the solvent in the forming lattice.

"Hydrates" are solvates wherein the solvent was water.

"Crystal" forms are solid compositions wherein the molecules making up the composition are packed in a repeating lattice structure. When more than one lattice pattern is possible for compositions made up the same molecules, the different compositions are called "polymorphs."

"Diastereomers" are stereoisomers that are not related as object and mirror image, but still differ are in the arrangement in three-dimensional space about one tetrahedral, sp3-hybridized carbon.

An "enantiomer" is one of two stereoisomers that are mirror images of each other, but are non-superposable (not identical).

"Pharmaceutically acceptable carrier" is any excipient which is non-toxic and aids in a drug's function (see also, Rowe R C et al., Handbook of Pharmaceutical Excipients, 5th ed., 2006.)

The following examples are provided to further illustrate the present invention but, of course, should not be construed as in any way limiting its scope.

All experiments were performed under anhydrous conditions (i.e. dry solvents) in an atmosphere of argon, except where stated, using oven-dried apparatus and employing standard techniques in handling air-sensitive materials. Aqueous solutions of sodium bicarbonate (NaHCO3) and sodium chloride (brine) were saturated.

Analytical thin layer chromatography (TLC) was carried out on Merck Kiesel gel 60 F254 plates with visualization by ultraviolet and/or anisaldehyde, potassium permanganate or phosphomolybdic acid dips.

NMR spectra: 1H Nuclear magnetic resonance spectra were recorded at 400 MHz. Data are presented as follows: chemical shift, multiplicity (s=singlet, d=doublet, t=triplet, q=quartet, qn=quintet, dd=doublet of doublets, m=multiplet, bs=broad singlet), coupling constant (J/Hz) and integration. Coupling constants were taken and calculated directly from the spectra and are uncorrected.

Low resolution mass spectra: Electrospray (ES+) ionization was used. The protonated parent ion (M+H) or parent sodium ion (M+Na) or fragment of highest mass is quoted. Analytical gradient consisted of 10% ACN in water ramping up to 100% ACN over 5 minutes unless otherwise stated.

High performance liquid chromatography (HPLC) was use to analyze the purity of triazine derivatives. HPLC was performed on a Phenomenex Synergi Polar-RP, 4 u, 80 Å, 150×4.6 mm column using a vShimadzusystem equipped with SPD-M10A Phosphodiode Array Detector. Mobile phase A was water and mobile phase B was acetonitrile with a gradient from 20% to 80% B over 60 minutes and re-equilibrate at A/B (80:20) for 10 minutes. UV detection was at 220 and 54 nm.

Example 1

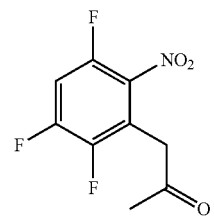

(1)

A 250 mL flask was charged with potassium tert-butoxide (5.75 g, 51.26 mmol) and tetrahydrofuran (50 m L). The resulting suspension was cooled to 5-10° C. before ethyl acetoacetate (6.67 g, 51.26 mmol) was I added. The rate of addition was controlled so that the internal temperature of the reactor did not exceed 15° C. The resulting mixture became homogeneous and was pale yellow in color. After addition was completed, the reaction mixture was cooled to 0° C. and then 2,3,4,6-tetrafluoronitrobenzene (5.00 g, 25.63 mol) in tetrabydrofuran (20 m L) was added. After addition was complete, the resulting brown reaction mixture was stirred at about 0° C. (ice batch) for 30 min. 1 N HCl were slowly added and the brown solution eventually became a clear yellow solution. The pH of the aqueous phase was pH 6. The mixture was I extracted with ethyl acetate (3×) and the combined organic extracts were washed with brine (50 mL) and concentrated in vacuo to afford orange oil.

The oil obtained above was charged into a 250 L round bottom flask and dissolved in glacial acetic acid (25 mL). Sulfuric acid (conc., 15 mL) was then added and a vigorous evolution of gas was observed in addition to a slight exotherm. Stirring was initiated and the reaction mixture was heated at 70° C. for 7 h, after which time TLC analysis indicated 100% conversion. The reaction mixture was cooled to between 15° C. to 20° C. and ethyl acetate (200 mL) was added followed by the addition of water (100 mL). Sat. NaOH solution in water was added slowly to adjust the pH-7. The mixture was extracted with ethyl acetate (3×100 mL). The combined organic extracts were washed with brine. The brown organic extracts were concentrated under reduced pressure to afford crude compound as brown oil.

The crude product was purified by column chromatography (silica gel, 0-30% ethyl acetate in hexanes) to give the desired compound 3.00 g (50% yield, 1). The other component is the isomer (minor product, 1.00 g, 16%). 1H NMR (DMSO-d6, 400 MHz) δ 8.01 (ddd, J=17.3 Hz, J=10.4 Hz, J=6.7 Hz, 1H), 4.15 (d, J=1.7 Hz, 2H), 2.24 (s, 3H).

Example 2

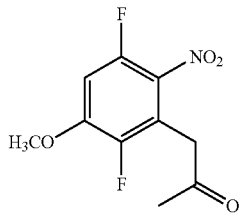

(2)

A mixture of Compound 1 (2.82 g, 12.10 mmol) and potassium carbonate (1.83 g, 13.30 mmol) in methanol (50 mL) was heated at 35° C. for 1.5 h. TLC was checked and the starting material was consumed. The reaction mixture was then cooled and concentrated in vacuo to remove most of the methanol. The residue was diluted with ethyl acetate (100 mL) and water. The mixture was neutralized with 2N HCl to PH 4~5. The mixture was extracted with ethyl acetate/hexanes (95/5, 3×100 ml). The combined organic layer was washed with brine, dried (Na2SO4) and concentrated to give yellow solids (2) 2.90 g (98% yield), which was used directly from the next step reaction without purification. 1H NMR (DMSO-d6, 400 MHz) δ 7.47 (dd, J=12.7 Hz, J=7.4 Hz, 1H), 4.07 (d, J=1.96 Hz, 2H), 3.95 (s, 3H), 2.20 (s, 3H).

Example 3

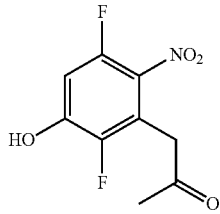

(3)

Method 1:

A mixture of 1-(25-difluoro-3-methoxy-6-nitrophenyl)-propan-2-one (Compound 2) from previous step and pyridinium chloride (5 equiv.) was stirred at 175° C. for 120 min. The reaction was cooled to room temperature, diluted I with IN HCl and ethyl acetate and filtered. The filtrate was washed with brine (2×), dried and concentrated in vacuo to give compound 3 of 1-(2-fluoro-3-hydroxy-6 nitrophenyl)-propan-2-one as a pink solid, which was used without further purification for the next step.

Method 2:

A mixture of Compound 1 (33.0 g, 141.5 mmol), NaOAc (134.8 g, 7.5 eq) and dimethylformamide (450 mL) was stirred at 65° C. for 12 h. The solvent was evaporated under reduced pressure. The crude residue was dissolved in water (800 mL) and EtOAc (200 mL). The mixture was extracted with EtOAc (2×400 mL). The organic layer was further washed with brine (1×150 mL), dried over Na₂SO₄ and concentrated to give Compound 3 (40 g). The crude residue was used in the next step without further purification.

Example 4

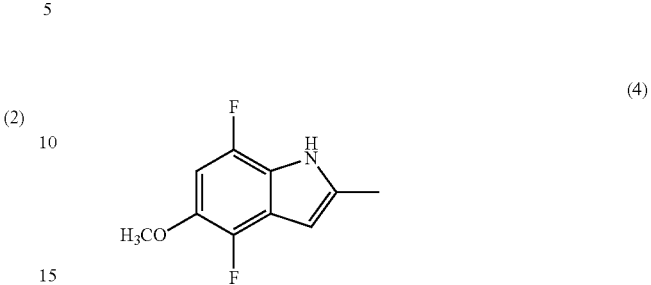

(4)

To a solution of sodium dithionite (15.91 g, 91.36 mmol) in water (150 mL) was added a solution of Compound 2 (2.80 g, 11.42 mmol) in dioxane (17 ml) drop wise at room temperature. After addition, the mixture was stirred at room temperature until TLC analysis indicated no starting material remained (overnight). Upon completion, the white solids formed was collected by filtration and washed by water (3×15 ml). the solids were dried under vacuum overnight to give the desired product 4 as white solids (820 mg, 36% yield). The compound was used directly for the next step reaction without purification. ¹H NMR (DMSO-d6, 400 MHz) 611.41 (br, 1H), 6.82 (dd, J=12.1 Hz, J=6.2 Hz, 1H), 6.17 (s, 1H), 3.77 (s, 3H), 2.34 (s, 3H); ESI-MS: calcd for (C10H9F2NO) 197. found 198 (MH⁺).

Example 5

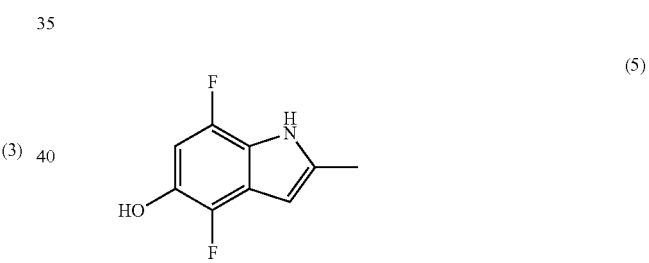

(5)

Method 1:

To a cold solution of Compound 4 (350 mg, 1.78 mmol) in dichloromethane (25 ml) was added a solution of boron tribromide (1N in DCM, 6.00 mL, 6.00 mmol) at −78° C. The mixture was slowly warmed up to room temperature and stirred about 1 h. TLC analysis indicated the completion of the reaction. The mixture was poured into ice, sat. NaHCO₃ was added. The mixture was extracted with DCM (3×). The organic was washed with brine, dried (Na₂SO₄) and concentrated to give brown solids of Compound 5 (281 mg, 86% yield) which was used directly for the next step reaction without purification. ¹H NMR (DMSO-d6, 400 MHz) δ 11.25 (s, 1H), 9.05 (s, 1H), 6.47 (dd, J=11.7 Hz, J=6.4 Hz, 1H), 6.10 (s, 1H), 2.32 (s, 3H).

Method 2:

Compound 3 (9.09 g, 39.33 mmol) was added to a round bottom flask. Water (200 mL) was added, and the yellow suspension was stirred at RT. Sodium dithionite (53 g, 304.42 mmol) was added in several portions and the reaction mixture was stirred room temperature until TLC analysis indicated no starting material remained. Upon completion, the reaction mixture was cooled to 0° C. and the tan solid product was collected by vacuum filtration. The wet product was dried under high vacuum to afford Compound 5 of 4,7-difluoro-2-methyl-1H-indol-5-ol (3.80 g) which was characterized by $^1$H NMR as in Method 1.

Example 6

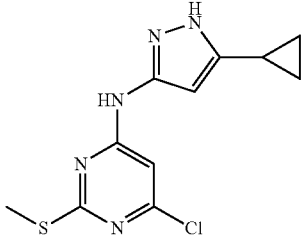

(6)

To a solution of 4,4-dichloro-2-methlysulfonyl pyrimidine (5.0 g, 25.6 mmol) in DMF (20.0 mL) was added a solution of 3-amino-5-cyclopropyl pyrazole (3.5 g, 28.2 mmol) and DIPEA (4.9 mL, 28.2 mmol) in DMF (5.0 mL) at room temperature. Sodium iodide (4.2 g, 28.2 mmol) was added and reaction was stirred overnight at 60° C. overnight. Then water was added and solid was collected by filtration. Filtrate was extracted with EtOAc twice. Combined organic solvent was dried over sodium sulfate, filtered and concentrated. Residue provide Compound 6 as light yellow solid (6.2 mg, 96%). $^1$H NMR (400 MHz, DMSO-$d_6$) δ 12.14 (bs, 1H, NH), 10.16 (bs, 1H, NH), 3.31 (s, 1H), 2.46 (s, 3H, CH$_3$), 1.88-1.84 (m, 1H, CH), 0.92-0.64 (m, 4H, Ar—H).

Example 7

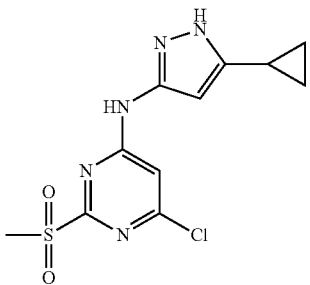

(7)

To a solution of 6-chloro-N-(5-cyclopropyl-1H-pyrazol-3-yl)-2-(methylthio)pyrimidin-4-amine (6.0 g, 23.8 mmol) in MeOH (160.0 mL) was added a solution of oxone (33.7 g, 54.8 mmol) in water (140.0 mL) in portion over 20 minute at 0° C. Reaction was stirred at this temperature for 30 minutes at room temperature overnight. Then mixture was filtered and solid was re-suspended in saturated NaHCO$_3$ in water. Mixture filtered and solid was washed with water, diethyl ether. Solid provide Compound 7 as light yellow solid (5.6 g, 75%). $^1$H NMR (400 MHz, DMSO-$d_6$) δ 12.33 (bs, 1H, NH), 10.93 (bs, 1H, NH), 3.34 (s, 3H, CH$_3$), 1.93-1.89 (m, 1H, CH), 0.96-0.68 (m, 4H, Ar—H).

Example 8

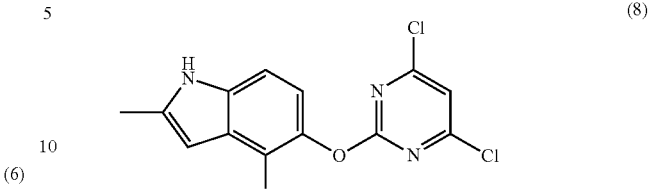

(8)

The solution of 4,6-dichloro-2-methylsulfonylpyrimidine (6.87 g, 30.27 mmol), and 2-methyl-4-fluoro-1-H-indol-5-ol (5.00 g, 30.27 mmol) in THF (100 mL) was cooled to −70° C. with dry-ice/isopropyl alcohol. A suspension of potassium t-butoxide (4.25 g, 37.84 mmole) in THF (50 mL) was added to the reaction mixture drop wise. The temperature of the mixture was controlled below −50° C. After addition, the reaction was stirred at −70° C. for 1.5 h, then warmed up to room temperature over a period of 1.5 h. The TLC was checked and both starting materials were consumed. Saturated ammonium chloride in water was added and the mixture was extracted with ethyl acetate/hexanes (80/20) three times. The combined organic was washed with brine, dried over sodium sulfate and concentrated. The crude product was a pad of silica gel eluted with 20% ethyl acetate in hexanes. The collected fraction was concentrated to give the desired product as light-yellow solids (QW660) (7.51 g, 79% yield). The solids were directly used for the next step reaction without further purification.

Example 9

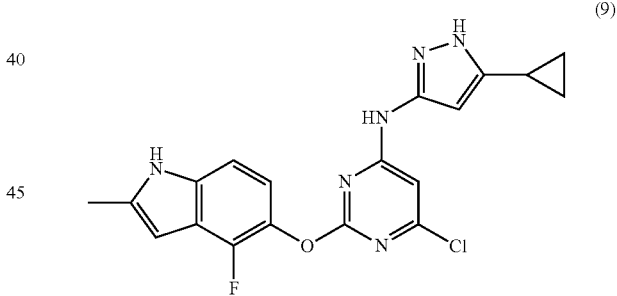

(9)

Method 1 (from 7)

To a solution of 6-chloro-N-(5-cyclopropyl-1H-pyrazol-3-yl)-2-(methylsulfonyl)pyrimidin-4-amine (0.8 g, 2.55 mmol) in tBuOH (50 mL) was added 4-fluoro-2-methyl-1H-indol-5-ol (0.46 g, 2.80 mmol) and KOtBu (0.32 g, 2.20 mmol) at room temperature. Reaction was stirred at 50° C. overnight. After cooling, reaction was diluted with DCM and washed with sat. NaHCO$_3$. Aqueous phase was extracted with DCM/isopropanol (4:1) twice. The combined organic layers were dried over anhydrous Na$_2$SO$_4$ and concentrated in vacuo. The resulting crude product was purified by Teledyne-Isco flash system by using CH$_2$Cl$_2$/MeOH, 0 to 5% of methanol in dichloromethane to provide Compound 9 as light yellow solid (0.86 g, 85%).

Method 2 (from 8):

The solution of Compound 8 (5.00 g, 16.02 mmol), added 5-cyclopropyl-1-methyl-1H-pyrazol-3-amine (3.45 g, 28.03 mmol), sodium iodide (3.60 g, 24.03 mmol) and DIPEA (4.20 ml, 24.03 mmol) in DMF (50 mL) was stirred at 65° C. for 48 hours TLC was checked and the starting material was consumed. The mixture was poured into water (500 ml) and cooled with ice. The solids were collected by filtration, washed by water and hexanes. The slides were dissolved into dichloromethane/methanol. The solution was concentrated to minimum amount of solvents. The solids were collected by filtration, washed by methanol to give a light yellow solids (9) (4.50 g, 71% yield)). $^1$H NMR (400 MHz, DMSO-d$_6$) δ 12.98 (bs, 1H, NH), 11.32 (bs, H, NH), 10.32 (bs, 1H, NH), 7.15-5.16 (m, 5H, Ar—H), 2.40 (s, 3H, CH$_3$), 1.39 (m, 1H, CH), 0.65-0.07 (m, 4H, Ar—H); ESI-MS: calcd for (C19H16ClFN6O) 398. found 399 [M+H]$^+$.

Example 10

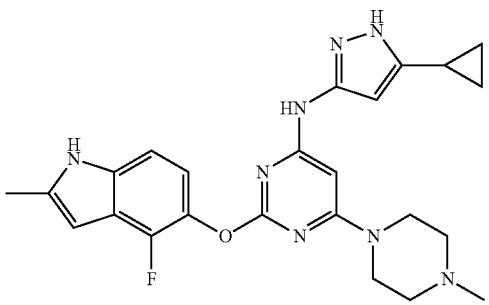

(10)

To a solution of 6-chloro-N-(5-cyclopropyl-1H-pyrazol-3-yl)-2-((4-fluoro-2-methyl-1H-indol-5-yl)oxy)pyrimidin-4-amine (100 mg, 0.25 mmol) and 1-methyl piperazine (0.70 mL, 6.25 mmol) in isopropanol (2 mL) was heated to 90° C. overnight in a sealed tube. After cooling, reaction mixture was diluted with dichloromethane and washed with saturated NaHCO$_3$. Aqueous phase was extracted with dichloromethane/isopropanol mixture (4:1). The combined organic layers were dried over anhydrous Na$_2$SO$_4$ and concentrated in vacuo. The resulting crude product was purified by Teledyne-Isco flash system by using CH$_2$Cl$_2$/MeOH, 0 to 10% of methanol in dichloromethane to provide Compound 10 as light yellow solid (63 mg, 54%). $^1$H NMR (400 MHz, DMSO-d$_6$) δ 11.73 (bs, 1H, NH), 11.21 (bs, H, NH), 9.21 (bs, 1H, NH), 7.09-6.08 (m, 4H, Ar—H), 5.25 (bs, 1H, Ar—H), 3.42 (m, 4H, 2CH$_2$), 2.39 (s, 3H, CH$_3$), 2.35 (m, 4H, 2CH$_2$), 2.20 (s, 3H, CH$_3$), 1.49 (m, 1H, CH), 0.69-0.13 (m, 4H, Ar—H); ESI-MS: calcd for (C24H27FN8O) 462. found 463 [M−H]$^+$. HPLC: retention time: 13.47 min. purity: 100%.

Example 11

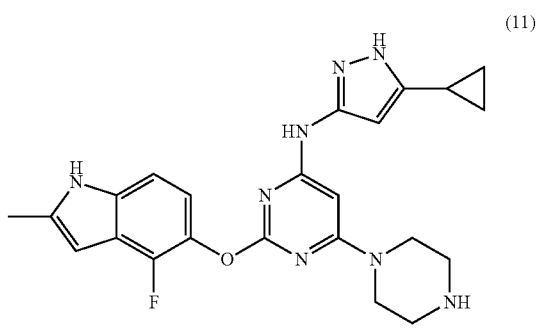 [SMILES: Cc1cc2c(F)c(Oc3nc(Nc4cc(C5CC5)[nH]n4)cc(N4CCNCC4)n3)ccc2[nH]1]

(11)

Solution of 6-chloro-N-(5-cyclopropyl-1H-pyrazol-3-yl)-2-((4-fluoro-2-methyl-1H-indol-5-yl)oxy)pyrimidin-4-amine (100 mg, 0.25 mmol) and piperazine (538 mg, 6.25 mmol) in isopropanol (2 mL) was heated to 90° C. overnight in a sealed tube. After cooling, reaction mixture was diluted with dichloromethane and washed with saturated NaHCO$_3$. Aqueous phase was extracted with dichloromethane/isopropanol mixture (4:1). The combined organic layers were dried over anhydrous Na$_2$SO$_4$ and concentrated in vacuo. The resulting crude product was purified by Teledyne-Isco flash system by using CH$_2$Cl$_2$/MeOH, 0 to 20% of methanol in dichloromethane to provide compound 11 as light yellow solid (24 mg, 22%). $^1$H NMR (400 MHz, DMSO-d$_6$) δ 11.73 (bs, 1H, NH), 11.21 (bs, H, NH), 9.19 (bs, 1H, NH), 7.09-6.01 (m, 4H, Ar—H), 5.26 (bs, 1H, Ar—H), 3.55 (bs, 1H, CH), 3.42 (m, 4H, 2CH$_2$), 2.74 (bs, 4H, 2CH$_2$), 2.39 (s, 3H, CH$_3$), 1.49 (m, 1H, CH), 0.69-0.12 (m, 4H, Ar—H); ESI-MS: calcd for (C23H25FN8O) 448. found 449 [M+H]$^+$. HPLC: retention time: 12.60 min. purity: 99%.

Examples 12-44

Following the same procedure as in example 10, the Compounds 12-44 were also prepared from Compound 9 and characterized by LC-MS.

| Example number | Compounds Structure | LC-MS (M + H)$^+$ |
|---|---|---|
| 12 | 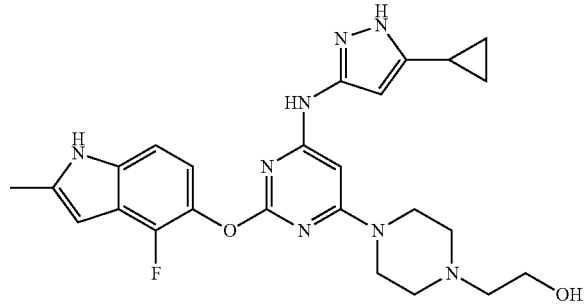 [SMILES: Cc1cc2c(F)c(Oc3nc(Nc4cc(C5CC5)[nH]n4)cc(N4CCN(CCO)CC4)n3)ccc2[nH]1] | 493 |

-continued
| Example number | Compounds Structure | LC-MS (M + H)+ |
|---|---|---|
| 13 | 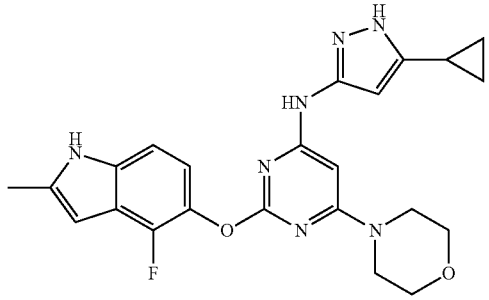 [SMILES: Cc1cc2c(F)c(Oc3nc(Nc4cc(C5CC5)[nH]n4)cc(N4CCOCC4)n3)ccc2[nH]1] | 450 |
| 14 | 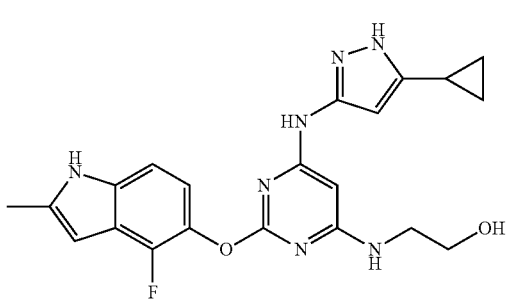 [SMILES: Cc1cc2c(F)c(Oc3nc(NCCO)cc(Nc4cc(C5CC5)[nH]n4)n3)ccc2[nH]1] | 424 |
| 15 | 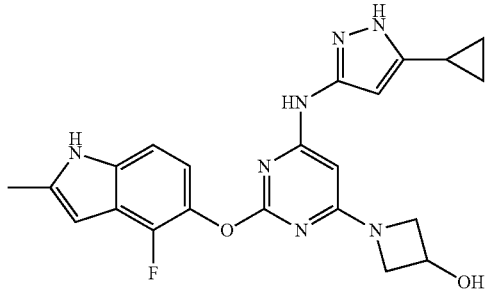 [SMILES: Cc1cc2c(F)c(Oc3nc(Nc4cc(C5CC5)[nH]n4)cc(N4CC(O)C4)n3)ccc2[nH]1] | 436 |
| 16 | 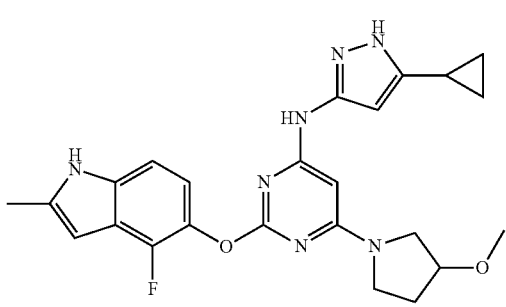 | 464 |
| 17 | 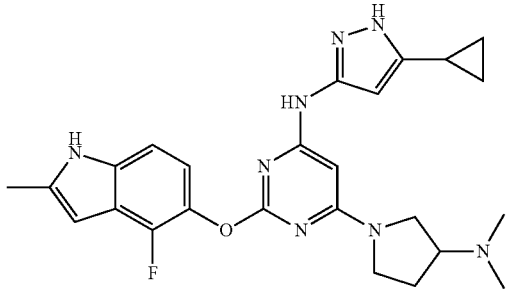 | 477 |

-continued
| Example number | Compounds Structure | LC-MS (M + H)+ |
|---|---|---|
| 18 | 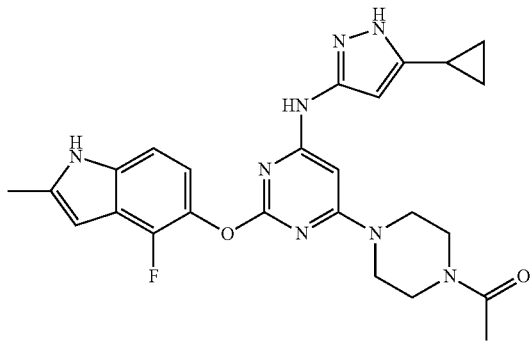 [SMILES: CC(=O)N1CCN(c2cc(Nc3cc(C4CC4)[nH]n3)nc(Oc3ccc4[nH]c(C)cc4c3F)n2)CC1] | 491 |
| 19 | 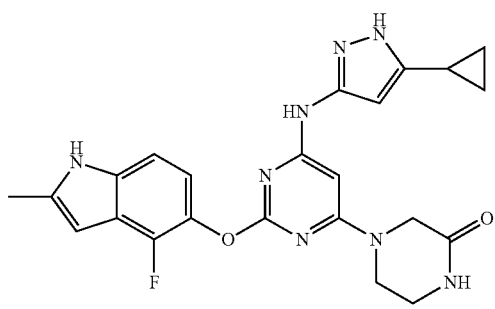 [SMILES: Cc1cc2c(F)c(Oc3nc(Nc4cc(C5CC5)[nH]n4)cc(N4CCNC(=O)C4)n3)ccc2[nH]1] | 463 |
| 20 | 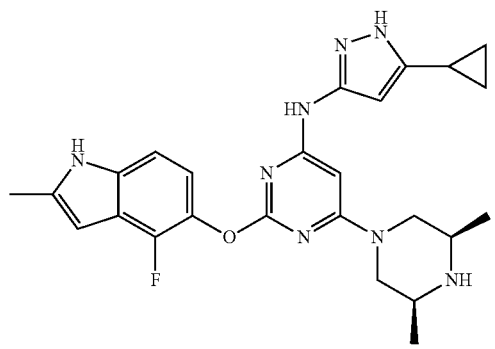 | 477 |
| 21 | 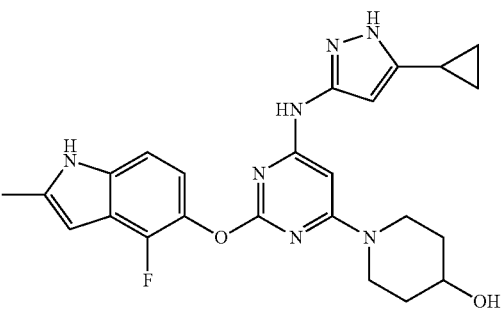 [SMILES: Cc1cc2c(F)c(Oc3nc(Nc4cc(C5CC5)[nH]n4)cc(N4CCC(O)CC4)n3)ccc2[nH]1] | 464 |

-continued
| Example number | Compounds Structure | LC-MS (M + H)+ |
|---|---|---|
| 22 | 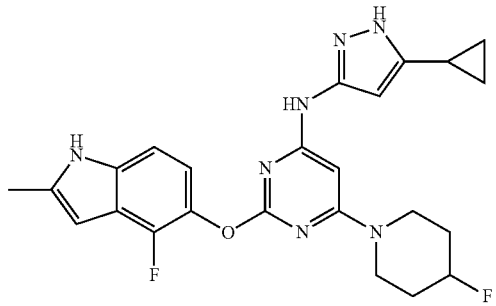 [SMILES: Cc1cc2c(F)c(Oc3nc(Nc4cc(C5CC5)[nH]n4)cc(N4CCC(F)CC4)n3)ccc2[nH]1] | 466 |
| 23 | 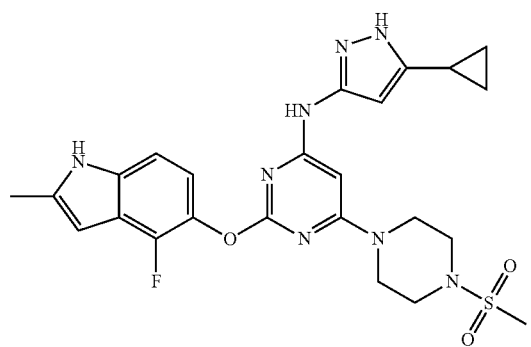 | 527 |
| 24 | 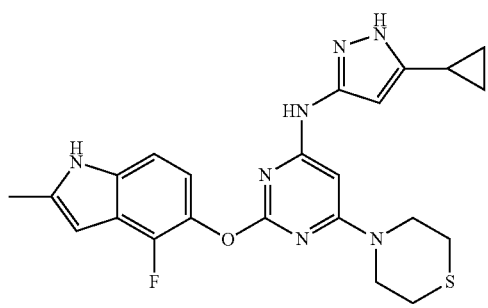 | 466 |
| 25 | 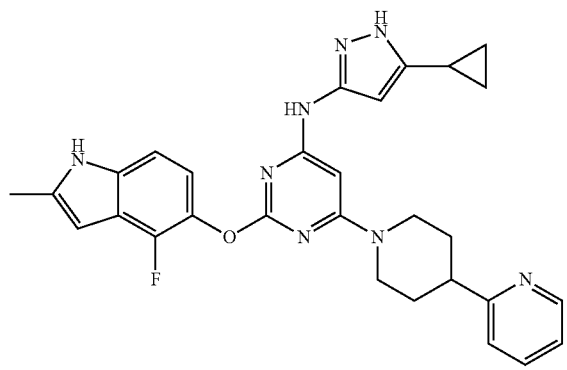 [SMILES: Cc1cc2c(F)c(Oc3nc(Nc4cc(C5CC5)[nH]n4)cc(N4CCC(c5ccccn5)CC4)n3)ccc2[nH]1] | 526 |

-continued
| Example number | Compounds Structure | LC-MS (M + H)+ |
|---|---|---|
| 26 | 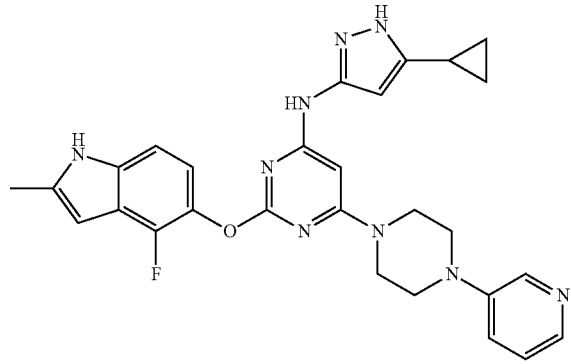 [SMILES: Cc1cc2c(F)c(Oc3nc(Nc4cc(C5CC5)[nH]n4)cc(N4CCN(c5cccnc5)CC4)n3)ccc2[nH]1] | 526 |
| 27 | 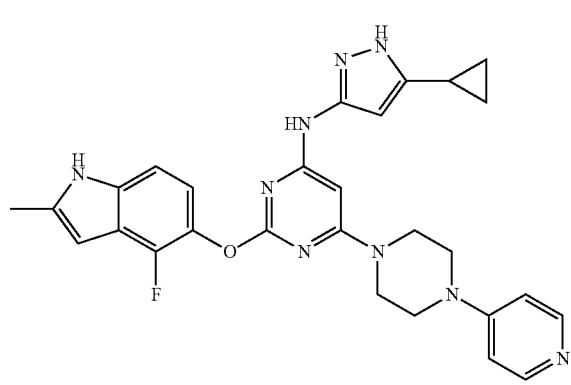 [SMILES: Cc1cc2c(F)c(Oc3nc(Nc4cc(C5CC5)[nH]n4)cc(N4CCN(c5ccncc5)CC4)n3)ccc2[nH]1] | 526 |
| 28 | 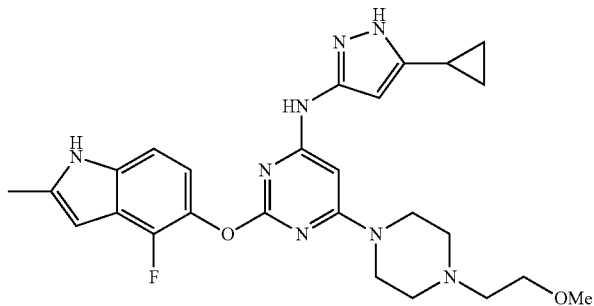 [SMILES: COCCN1CCN(c2cc(Nc3cc(C4CC4)[nH]n3)nc(Oc3ccc4[nH]c(C)cc4c3F)n2)CC1] | 507 |
| 29 | 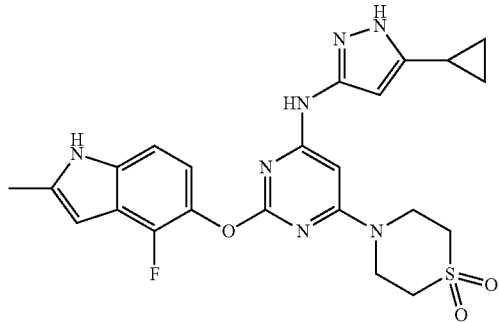 [SMILES: Cc1cc2c(F)c(Oc3nc(Nc4cc(C5CC5)[nH]n4)cc(N4CCS(=O)(=O)CC4)n3)ccc2[nH]1] | 498 |

| Example number | Compounds Structure | LC-MS (M + H)+ |
|---|---|---|
| 30 | 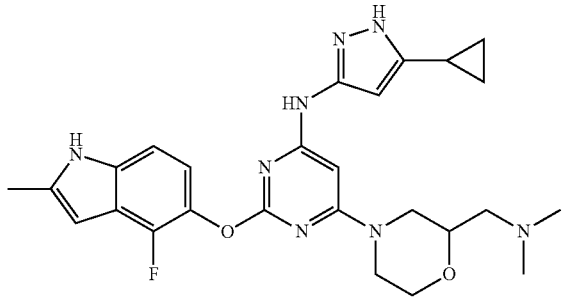 | 507 |
| 31 | 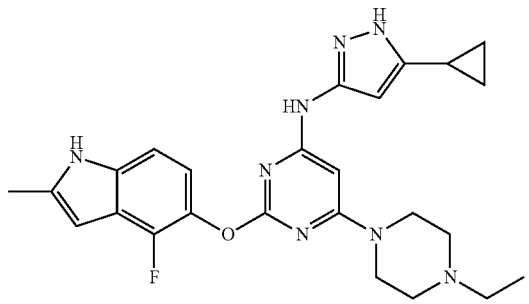 [SMILES: CCN1CCN(c2cc(Nc3cc(C4CC4)[nH]n3)nc(Oc3ccc4[nH]c(C)cc4c3F)n2)CC1] | 477 |
| 32 | 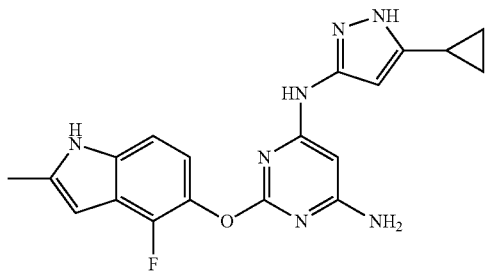 [SMILES: Cc1cc2c(F)c(Oc3nc(N)cc(Nc4cc(C5CC5)[nH]n4)n3)ccc2[nH]1] | 380 |
| 33 | 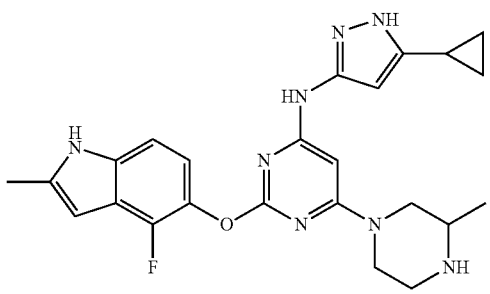 | 463 |
| 34 | 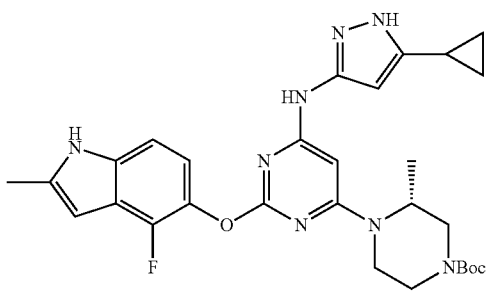 [SMILES: Cc1cc2c(F)c(Oc3nc(Nc4cc(C5CC5)[nH]n4)cc(N4CCN(C(=O)OC(C)(C)C)C[C@H]4C)n3)ccc2[nH]1] | 563 |

| Example number | Compounds Structure | LC-MS (M + H)+ |
|---|---|---|
| 35 | 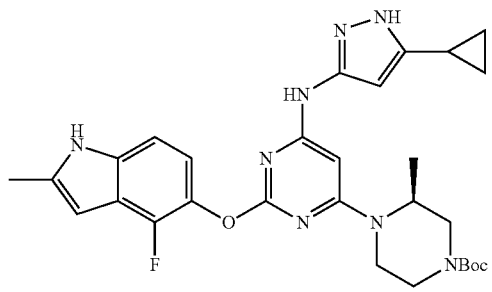 [SMILES: Cc1cc2c(F)c(Oc3nc(Nc4cc(C5CC5)[nH]n4)cc(N4CCN(C(=O)OC(C)(C)C)C[C@@H]4C)n3)ccc2[nH]1] | 563 |
| 36 | 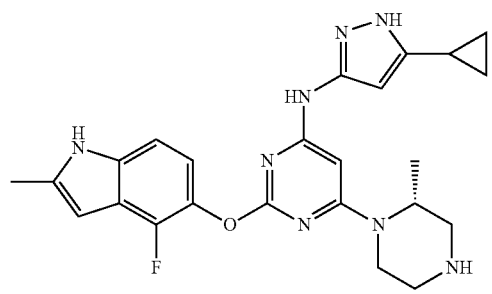 [SMILES: Cc1cc2c(F)c(Oc3nc(Nc4cc(C5CC5)[nH]n4)cc(N4CCNC[C@H]4C)n3)ccc2[nH]1] | 463 |
| 37 | 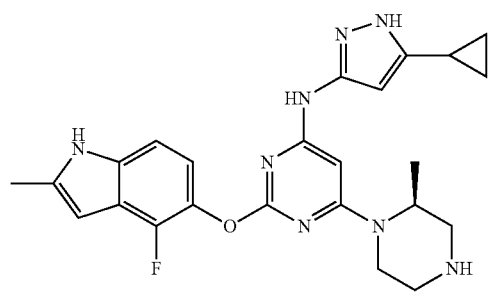 [SMILES: Cc1cc2c(F)c(Oc3nc(Nc4cc(C5CC5)[nH]n4)cc(N4CCNC[C@@H]4C)n3)ccc2[nH]1] | 463 |
| 38 | 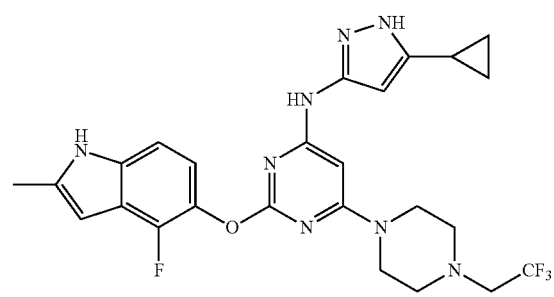 [SMILES: Cc1cc2c(F)c(Oc3nc(Nc4cc(C5CC5)[nH]n4)cc(N4CCN(CC(F)(F)F)CC4)n3)ccc2[nH]1] | 531 |

| Example number | Compounds Structure | LC-MS (M + H)+ |
|---|---|---|
| 39 | 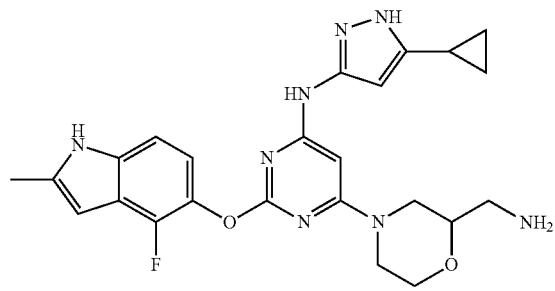 [SMILES: Cc1cc2c(F)c(Oc3nc(Nc4cc(C5CC5)[nH]n4)cc(N4CCOC(CN)C4)n3)ccc2[nH]1] | 479 |
| 40 | 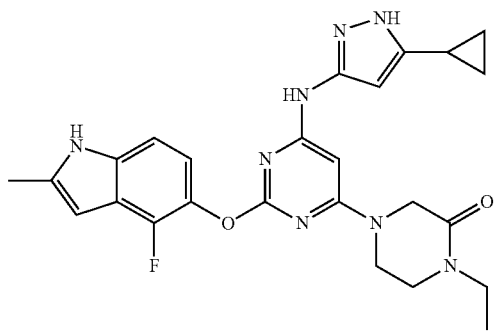 [SMILES: CCN1CCN(c2cc(Nc3cc(C4CC4)[nH]n3)nc(Oc3ccc4[nH]c(C)cc4c3F)n2)CC1=O] | 515 |
| 41 | 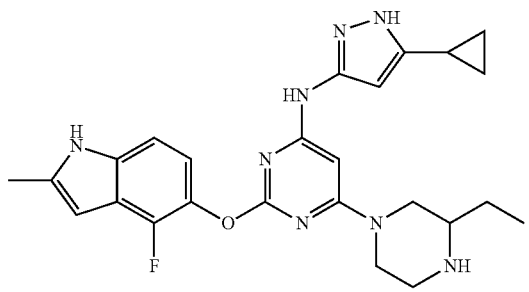 [SMILES: CCC1CN(c2cc(Nc3cc(C4CC4)[nH]n3)nc(Oc3ccc4[nH]c(C)cc4c3F)n2)CCN1] | 477 |
| 42 | 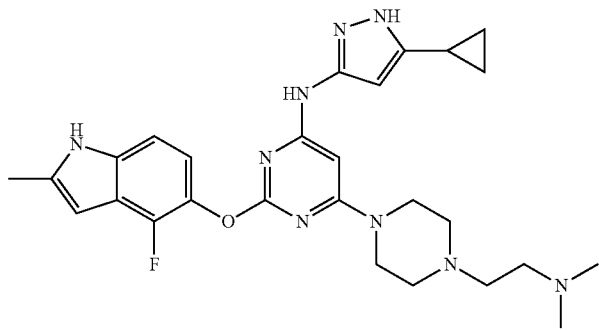 | 520 |

| Example number | Compounds Structure | LC-MS (M + H)+ |
|---|---|---|
| 43 | | 479 |
| 44 | | 478 |

Example 45

(45)

To a solution of N-(5-cyclopropyl-1H-pyrazol-3-yl)-2-((4-fluoro-2-methyl-1H-indol-5-yl)oxy)-6-(piperazin-1-yl)pyrimidin-4-amine (50 mg, 0.11 mmol) in isopropanol (1 mL) was added 1-fluoro-2-iodoethane (0.02 mL, 0.22 mmol) and K$_2$CO$_3$ (76 mg, 055 mmol) and was heated to 75° C. overnight in a sealed tube. After cooling, reaction mixture was diluted with dichloromethane and washed with saturated NaHCO$_3$. Aqueous phase was extracted with dichloromethane. The combined organic layers were dried over anhydrous Na$_2$SO$_4$ and concentrated in vacuo. The resulting crude product was purified by Teledyne-Isco flash system by using CH$_2$Cl$_2$/MeOH, 0 to 10% of methanol in dichloromethane to provide Compound 45 as light yellow solid (20 mg, 36%). $^1$H NMR (400 MHz, DMSO-d$_6$) δ 11.72 (bs, 1H, NH), 11.21 (bs, H, NH), 9.21 (bs, 1H, NH), 7.10-6.04 (m, 4H, Ar—H), 5.25 (bs, 1H, Ar—H), 4.63-2.38 (m, 15H), 1.51 (m, 1H, CH), 0.69-0.11 (m, 4H, Ar—H); ESI-MS: calcd for (C25H28F2N8O) 494. found 495 [M+H]+. HPLC: retention time: 15.02 min. purity: 86%.

Example 46

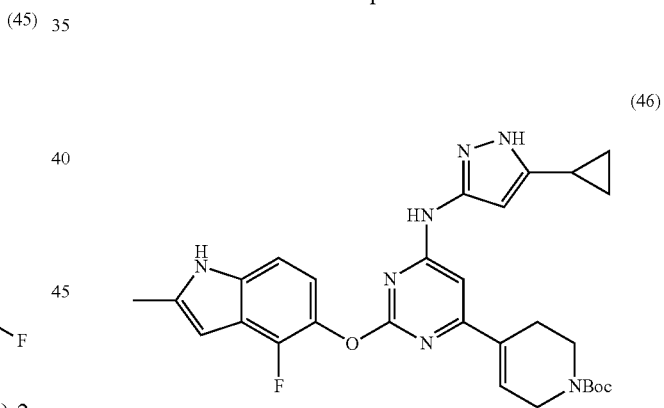

(46)

To a solution of 6-chloro-N-(5-cyclopropyl-1H-pyrazol-3-yl)-2-((4-fluoro-2-methyl-1H-indol-5-yl)oxy)pyrimidin-4-amine (0.100 g, 0.143 mmol), 1-N-boc-4-(4,4,5,5-tetramethyl-[1,3,2]dioxaborolan-2-yl)-3,6-dihydro-2H-pyridine (0.058 g, 0.188 mmol), and tetrakis(triphenylphosphine)palladium (0) (0.026 g, 0.025 mmol) in dimethoxyethane (2 mL) under argon was added aqueous 2M Na$_2$CO$_3$ (0.276 mL, 0.552 mmol). The mixtures were degassed with a stream of argon for 3 min, then it was heated to 90° C. for 24 h in a sealed tube. The cooled mixtures were quenched with 1N NaOH and extracted with dichloromethane/isopropanol (8:2). The combined organic layers were dried over anhydrous Na$_2$SO$_4$ and concentrated in vacuo. The residue was purified by flash chromatography over silica gel with CH$_2$Cl$_2$:MeOH (9:1) to give Compound 46 (0.036 g, 53%) as a light yellow solid. $^1$H NMR (400 MHz, DMSO-d): δ

11.85 (bs, 1H), 11.24 (s, 1H), 9.92 (bs, 1H), 7.10 (d, 1H, J=8.4 Hz), 6.86 (m, 1H), 6.76 (bs, 1H), 6.53 (bs, 1H), 6.18 (s, 1H), 5.25 (bs, 1H), 4.02 (m, 2H), 3.50 (m, 2H), 2.38 (bs, 5H), 1.41 (bs, 10H), 0.65 (m, 2H), −0.02 (m, 2H). MS (ESI): Calcd. for $C_{29}H_{32}FN_7O_3$: 545. found 546 (M+H).

Example 47

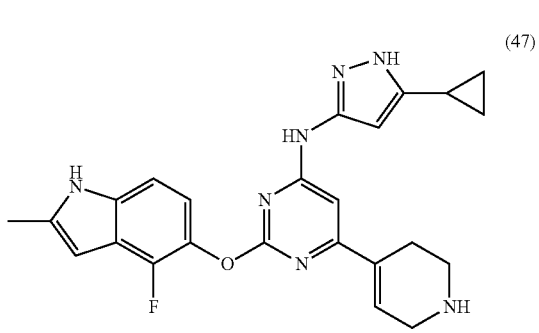 [SMILES: Cc1cc2c(F)c(Oc3nc(Nc4cc(C5CC5)[nH]n4)cc(C4=CCNCC4)n3)ccc2[nH]1]

(47)

Compound 46 (0.035 g, 0.062 mmol) was dissolved with 20% trifluoromethyl acetic acid in dichloromethane (5 mL) and stirred for 3 h. Then the mixture was neutralized with 1N aq. NaOH and extracted with dichloromethane/isopropanol (8:2) mixture. The combined organic layers were dried over anhydrous $Na_2SO_4$ and concentrated in vacuo to give Compound 47 (0.038 g, 59%) as a light yellow solid. $^1$H NMR (400 MHz, DMSO-d): δ 11.84 (bs, 1H), 11.23 (s, 1H), 9.84 (bs, 1H), 7.09 (d, 1H, J=8.4 Hz), 6.86 (m, 1H), 6.80 (bs, 1H), 6.51 (bs, 1H), 6.18 (s, 1H), 5.27 (bs, 1H), 3.37 (m, 2H), 2.87 (m, 2H), 2.38 (s, 3H), 2.24 (m, 2H), 1.44 (m, 1H), 1.22 (m, 1H), 1.02 (d, 1H, J=6.0 Hz), 0.65 (m, 2H), 0.01 (m, 2H). MS (ESI): Calcd. for $C_{24}H_{24}FN_7O$: 445. found 446 (M+H).

Example 48

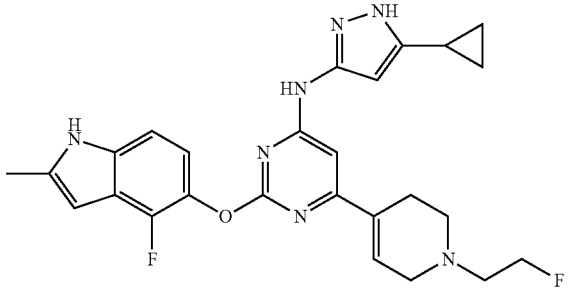

(48)

N-(5-cyclopropyl-1H-pyrazol-3-yl)-2-((4-fluoro-2-methyl-1H-indol-5-yl)oxy)-6-(1,2,3,6-tetrahydropyridin-4-yl)pyrimidin-4-amine (0.040 g, 0.090 mmol), 1-bromo-2-fluoroethane (0.031 g, 0.180 mmol), and $K_2CO_3$ (0.062 g, 0.449 mmol) dissolved with THF/$CH_3CN$ (4 mL/4 mL) solvent mixtures. The sealed tube was stirred 20 h at 75° C. and after cooling the solvent was removed to minimum. The crude was partitioned between DCM/isopropanol (8:2) and water. The organic layers were washed with saturated $NaHCO_3$, dried over anhydrous $Na_2SO_4$, and concentrated in vacuo. The residue was purified by flash chromatography over silica gel with $CH_2Cl_2$:MeOH (9:1) to give Compound 48 (0.036 g, 83%) as a light yellow solid. $^1$H NMR (400 MHz, DMSO-d): δ 11.83 (bs, 1H), 11.24 (s, 1H), 9.87 (bs, 1H), 7.10 (d, 1H, J=8.4 Hz), 6.86 (m, 1H), 6.75 (bs, 1H), 6.18 (s, 1H), 5.24 (bs, 1H), 4.63 (m, 1H), 4.53 (m, 1H), 3.46 (m, 1H), 3.40 (m, 1H), 3.21 (m, 2H), 2.78 (m, 1H), 2.71 (m, 3H), 2.37 (m, 5H), 1.43 (m, 1H), 0.65 (m, 2H), −0.03 (m, 2H). MS (ESI): Calcd. for C26H27F2N7O: 491. found 492 (M+H).

Example 49

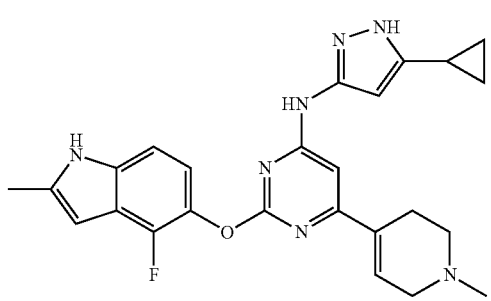

(49)

To a solution of N-(5-cyclopropyl-1H-pyrazol-3-yl)-2-((4-fluoro-2-methyl-1H-indol-5-yl)oxy)-6-(1,2,3,6-tetrahydropyridin-4-yl)pyrimidin-4-amine (0.025 g, 0.056 mmol) in tetrahydrofuran (10 mL) was added formaldehyde (37% in water, 0.911 g, 0.112 mmol) and stirred for 10 min. Then followed by the addition of sodium triacetoxyborohydride (0.024 g, 0.112 mmol) and continued to for 20 h. The mixtures were quenched with saturated $NaHCO_3$ and extracted with dichloromethane/isopropanol (8:2) mixtures. The combined organic layers were dried over anhydrous $Na_2SO_4$ and concentrated in vacuo. The residue was purified by flash chromatography over silica gel with $CH_2Cl_2$:MeOH (8:2) to give Compound 50 (0.025 g, 96%) as a light yellow solid. $^1$H NMR (400 MHz, DMSO-d): δ 11.82 (bs, 1H), 11.23 (s, 1H), 9.85 (bs, 1H), 7.09 (d, 1H, J=8.4 Hz), 6.84 (m, 1H), 6.75 (m, 1H), 6.18 (s, 1H), 5.23 (m, 1H), 4.06 (m, 1H), 3.15 (m, 3H), 3.05 (m, 2H), 2.55 (m 2H), 2.37 (m, 5H), 2.27 (s, 3H). MS (ESI): Calcd. for $C_{25}H_{26}FN_7O$: 459. found 460 (M+H).

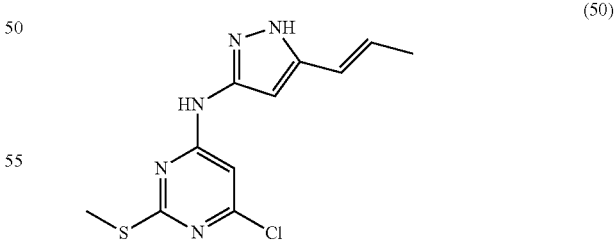

(50)

Example 50

To a suspension of 4,6-dichloro-2-methylsulfanyl-pyrimidin (390 m g, 2.00 mmol) in DMF (3.0 mL) was added a solution of (E)-5-(prop-1-en-1-yl)-1H-pyrazol-3-amine (271 mg, 2.20 mmol) and DIPEA (0.42 mL, 2.40 mmol) in DMF (2.0 mL) at room temperature, followed by addition of sodium iodide (330 mg, 2.20 mmol). After addition, the mixture was stirred at 50° C. for overnight. TLC was checked and the starting material was consumed. The mixture was poured in to water (~50 mL) and the solids were collected by filtration, washed with water, hexane. The desired product (50) was obtained as yellow solids after drying in vacuum line (286 mg, 51% yield). The product was used directly for the next step reaction without purification.

Example 51

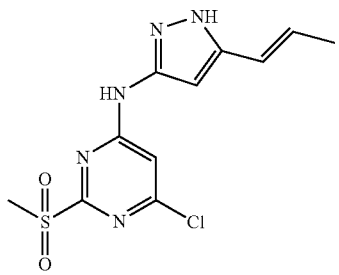

(51)

To a cold solution of Compound 50 (280 m g, 1.00 mmol) in methanol (6 mL) was added a suspension of oxane (1500 mg, 2.44 mmol) at 0° C. After addition, the mixture was stirred at 0° C. for 0.5 hours, then room temperature for 1 hour. TLC was checked and the starting material was consumed. Water was added to the reaction mixture. The mixture was extracted with ethyl acetate three times. The combined organic was washed with brine, dried over sodium sulfate and concentrated. The crude product was purified on column (0-5% methanol in DCM). The collected fraction was concentrated to give the desired product as off-white solids (51) (30 mg, 9.5% yield). $^1$H NMR (400 MHz, DMSO-$d_6$) δ 12.55 (br, 1H), 10.98 (br, 1H), 8.00-6.00 (m, 4H), 3.38 (s, 3H), 1.90 (br, 3H); ESI-MS: calcd for (C11H12C1N5O2S) 313. found 314 (MH$^+$).

Example 52

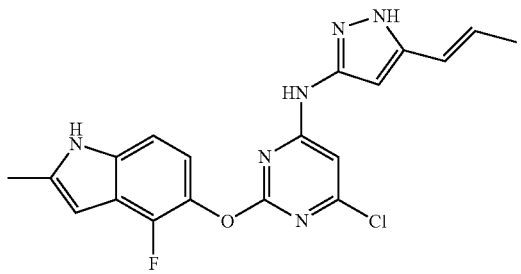

(52)

Method 1:
To a suspension of 6-chloro-N-(5propenyl-1H-pyrazol-3-yl)-2-(methylsulfonyl)pyrimidin-4-amine (51) (200 m g, 0.63 mmol) and 2-methyl-4-fluoro-1-H-indol-5-ol (110 mg, 0.67 mmol) in t-BuOH (15.0 mL) was added t-BuOK (79 mg, 0.70 mmol) at room temperature. After addition, the mixture was stirred at 55° C. for 16 hours. TLC was checked and the starting material was consumed. Water was added to the reaction mixture. The mixture was extracted with dichloromethane/isopropyl alcohol (90/10) three times. The combined organic was washed with brine, dried over sodium sulfate and concentrated. The crude product was purified on column (0-10% methanol in DCM). The collected fraction was concentrated to give the desired product as pink solids (52) (163 mg, 64% yield). $^1$H NMR (400 MHz, DMSO-$d_6$) δ 12.15 (br, 1H), 11.35 (br, 1H), 10.35 (br, 1H), 7.14 (d, J=8.8 Hz, 1H), 6.90 (t, J=8.0 Hz, 1H), 6.40 (br, 1H), 6.22 (s, 1H), 5.70-5.10 (m, 3H), 2.40 (s, 3H), 1.78 (br, 3H); ESI-MS: calcd for (C19H16C1FN6O) 398. found 399 (MH$^+$).

Method 2:
The solution of Compound 8 (5.00 g, 16.02 mmol), (E)-5-(prop-1-en-1-yl)-1H-pyrazol-3-amine (3.45 g, 28.03 mmol), sodium iodide (3.60 g, 24.03 mmol) and DIPEA (4.20 ml, 24.03 mmol) in DMF (50 mL) was stirred at 65° C. for 48 hours TLC was checked and the starting material was consumed. The mixture was poured into water (500 ml) and cooled with ice. The solids were collected by filtration, washed by water and hexanes. The slides were dissolved into dichloromethane/methanol. The solution was concentrated to minimum amount of solvents. The solids were collected by filtration, washed by methanol to give yellow solids (52) (3.88 g, 61% yield)). The mothe liquid was recovered. $^1$H NMR (400 MHz, DMSO-$d_6$). $^1$H NMR (400 MHz, DMSO-$d_6$) δ 12.15 (br, 1H), 11.35 (br, 1H), 10.35 (br, 1H), 7.14 (d, J=8.8 Hz, 1H), 6.90 (t, J=8.0 Hz, 1H), 6.40 (br, 1H), 6.22 (s, 1H), 5.70-5.10 (m, 3H), 2.40 (s, 3H), 1.78 (br, 3H); ESI-MS: calcd for (C19H16C1FN6O) 398. found 399 (MH$^+$).

Example 53

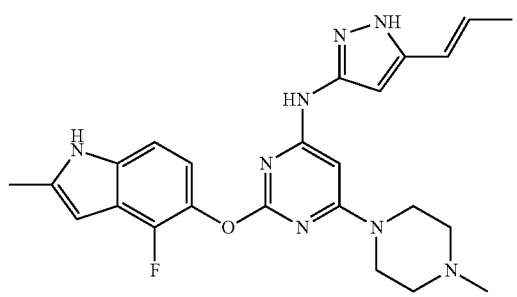

(53)

The solution of Compound 52 (1.50 g, 3.76 mmol), 1-methylpiperazine (2.83 g, 28.21 mmol) and DIPEA (1.64 ml, 9.40 mmol) in isopropyl alcohol (20.0 mL) and acetonitrile (5.0 mL) was stirred at 85° C. for 2 days. TLC was checked and the starting material was consumed. The reaction mixture was concentrated and water was added. The mixture was extracted with DCM/isopropal (10/1) three times. The combined organic was washed with, sodium bicarbonate, brine, dried over sodium sulfate and concentrated. The crude product was purified by crystallization from MeOH (~10 mL). The light-yellow solids were collected by filtration, washed with cold MeOH (1×) to give Compound 53 (1.10 g, 63% yield). $^1$H NMR (400 MHz, DMSO-$d_6$) δ 11.80 (br, 1H), 11.19 (br, 1H), 9.30 (br, 1H), 7.03 (d, J=8.8 Hz, 1H), 6.78 (t, J=8.0 Hz, 1H), 6.14 (s, 1H), 5.80-5.60 (m, 2H), 5.47 (s, 1H), 5.20 (br, 1H), 3.40 (br, 4H), 2.43 (3H, obs with solvent peak), 2.34 (s, 3H), 2.27 (br, 4H), 1.65 (d, J=6.0 Hz, 3H); ESI-MS: calcd for ($C_{24}H_{27}FN_8O$) 462. found 463 (MH$^+$).

Examples 54-73

Following the same procedure as in example 53, the Compounds 54-73 were also prepared from Compound 52 and characterized by LC-MS.

| Example number | Compounds Structure | LC-MS (M + H)$^+$ |
|---|---|---|
| 54 | | 507 |
| 55 | | 527 |
| 56 | | 491 |
| 57 | | 498 |

| Example number | Compounds Structure | LC-MS (M + H)+ |
|---|---|---|
| 58 | | 478 |
| 59 | | 464 |
| 60 | | 464 |
| 61 | | 450 |
| 62 | | 505 |

-continued
| Example number | Compounds Structure | LC-MS (M + H)+ |
|---|---|---|
| 63 | 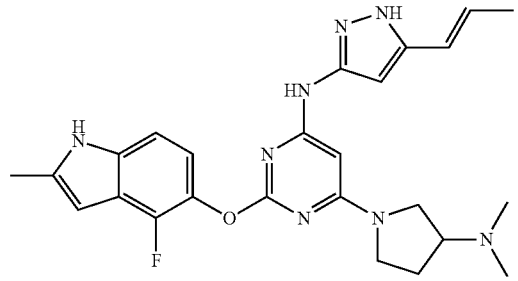 [SMILES: C/C=C/c1cc(Nc2cc(N3CCC(N(C)C)C3)nc(Oc3ccc4[nH]c(C)cc4c3F)n2)n[nH]1] | 477 |
| 64 | 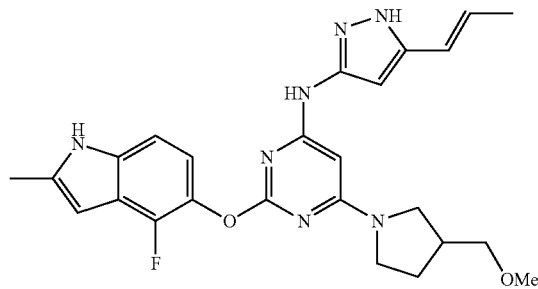 [SMILES: C/C=C/c1cc(Nc2cc(N3CCC(COC)C3)nc(Oc3ccc4[nH]c(C)cc4c3F)n2)n[nH]1] | 478 |
| 65 | 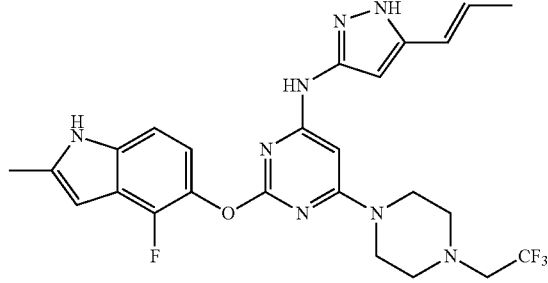 [SMILES: C/C=C/c1cc(Nc2cc(N3CCN(CC(F)(F)F)CC3)nc(Oc3ccc4[nH]c(C)cc4c3F)n2)n[nH]1] | 531 |
| 66 | 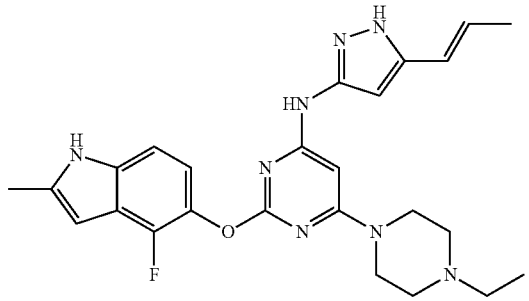 [SMILES: C/C=C/c1cc(Nc2cc(N3CCN(CC)CC3)nc(Oc3ccc4[nH]c(C)cc4c3F)n2)n[nH]1] | 493 |
| 67 | 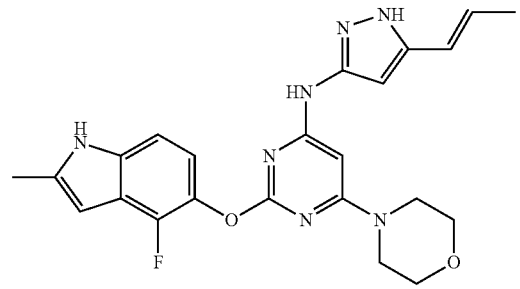 [SMILES: C/C=C/c1cc(Nc2cc(N3CCOCC3)nc(Oc3ccc4[nH]c(C)cc4c3F)n2)n[nH]1] | 450 |

-continued
| Example number | Compounds Structure | LC-MS (M + H)+ |
|---|---|---|
| 68 | 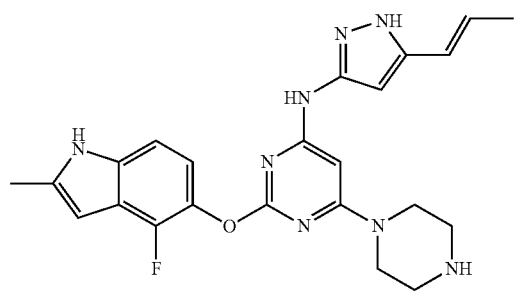 [SMILES: C/C=C/c1cc(Nc2cc(N3CCNCC3)nc(Oc3ccc4[nH]c(C)cc4c3F)n2)n[nH]1] | 449 |
| 69 | 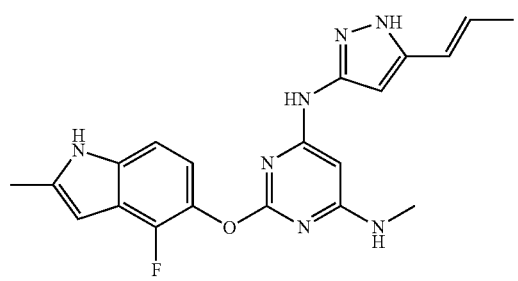 [SMILES: C/C=C/c1cc(Nc2cc(NC)nc(Oc3ccc4[nH]c(C)cc4c3F)n2)n[nH]1] | 394 |
| 70 | 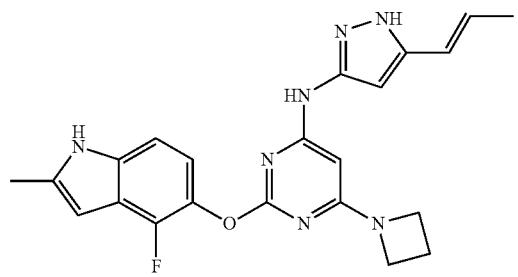 [SMILES: C/C=C/c1cc(Nc2cc(N3CCC3)nc(Oc3ccc4[nH]c(C)cc4c3F)n2)n[nH]1] | 420 |
| 71 | 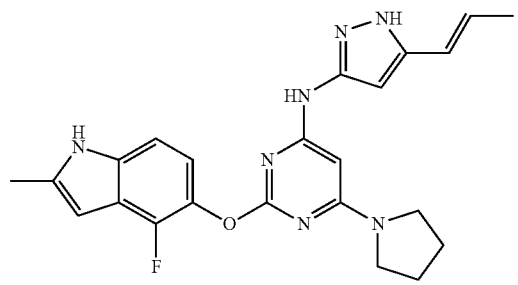 [SMILES: C/C=C/c1cc(Nc2cc(N3CCCC3)nc(Oc3ccc4[nH]c(C)cc4c3F)n2)n[nH]1] | 434 |
| 72 | 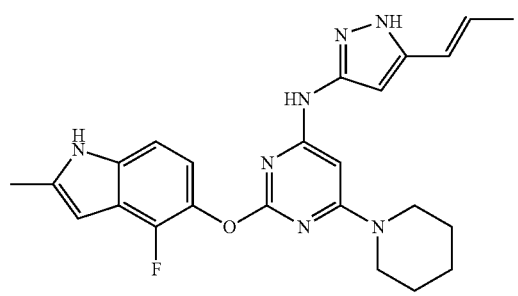 [SMILES: C/C=C/c1cc(Nc2cc(N3CCCCC3)nc(Oc3ccc4[nH]c(C)cc4c3F)n2)n[nH]1] | 448 |

| Example number | Compounds Structure | LC-MS (M + H)+ |
|---|---|---|
| 73 | | 408 |

Preparation and Characterization of Compound 68

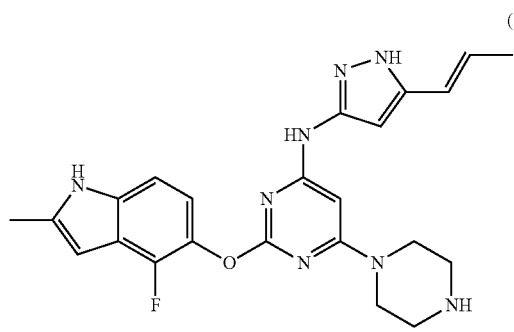
(68)

The solution of 52 (500 m g, 1.25 mmol), piperazine (540 mg, 6.27 mmol) in iso-propyl alcohol (12.0 mL) and acetonitrile (5.0 mL) was stirred at 85° C. for 3 days. TLC was checked and the starting material was consumed. Dilute sodium bicarbonate was added and the mixture was extracted with DCM three times. The combined organic was washed with brine, dried over sodium sulfate and concentrated. The crude product was purified on column (5-20% methanol in DCM). The collected fraction was concentrated to give the desired 68 as off-white solids (350 mg, 62%). $^1$H NMR (400 MHz, DMSO-d$_6$) δ 11.90 (br, 1H), 11.24 (br, 1H), 9.30 (br, 1H), 7.03 (d, J=8.8 Hz, 1H), 6.78 (t, J=8.0 Hz, 1H6.14 (s, 1H), 5.80-5.00 (m, 4H), 3.40 (m, 4H), 2.71 (m, 4H), 2.39 (s, 3H), 1.68 (d, J=6.8 Hz, 3H); ESI-MS: calcd for (C23H25FN80) 448. found 449 (MH$^+$).

Example 74

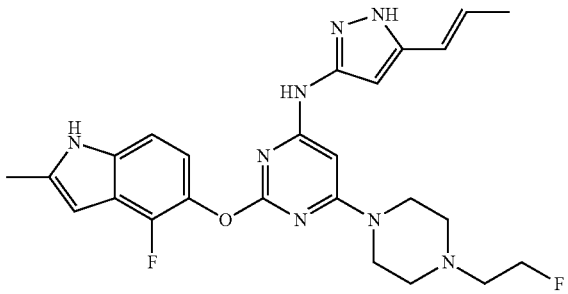
(74)

The solution of Compound 68 (50 m g, 0.11 mmol), 1-fluoro-2-iodoethane (40.72 mg, 0.23 mmol) and potassium carbonate (77 mg, 0.56 mmol) in Acetonitrile/THF (3.0 mL/3.0 mL) was stirred at 75° C. for 3 days. TLC was checked and the starting material was consumed. The solvents were removed and water was added. The mixture was extracted with DCM/isopropal (9/1) three times. The combined organic was washed with brine, dried over sodium sulfate and concentrated. The crude product was purified on column (0-10% methanol in DCM). The collected fraction was concentrated to give the desired product as off-white solids (74) (25 mg, 45% yield). $^1$H NMR (400 MHz, DMSO-d$_6$) δ 11.80 (br, 1H), 11.24 (br, 1H), 9.30 (br, 1H), 7.09 (d, J=8.8 Hz, 1H), 6.83 (t, J=8.0 Hz, 1H), 6.19 (s, 1H), 5.80-5.00 (m, 4H), 4.49 (m, 2H), 3.40 (br, 4H), 2.69 (m, 2H), 2.38 (m, 4H), 1.68 (d, J=6.8 Hz, 3H), 1.10 (s, 3H); ESI-MS: calcd for (C25H28F2N80) 494. found 495 (MO.

Example 75

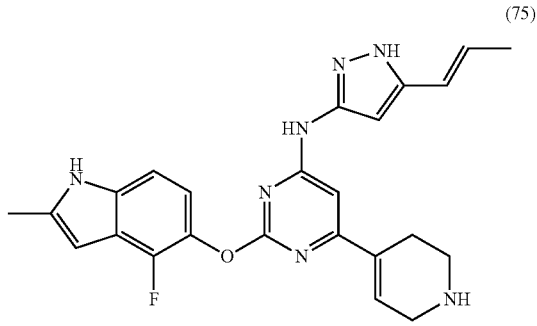 [SMILES: C/C=C/c1cc(Nc2cc(C3=CCNCC3)nc(Oc3ccc4[nH]c(C)cc4c3F)n2)n[nH]1]
(75)

To a solution of (E)-6-chloro-2-((4-fluoro-2-methyl-1H-indol-5-yl)oxy)-N-(5-(prop-1-en-1-yl)-1H-pyrazol-3-yl)pyrimidin-4-amine (0.075 g, 0.188 mmol), 1-N-boc-4-(4,4,5,5-tetramethyl-[1,3,2]dioxaborolan-2-yl)-3,6-dihydro-2H-pyridine (0.093 g, 0.301 mmol), and tetrakis(triphenylphosphine)palladium (0) (0.019 g, 0.019 mmol) in dimethoxyethane (4 mL) under argon was added aqueous 2M Na$_2$CO$_3$ (0.206 mL, 0.414 mmol). The mixtures were degassed with a stream of argon for 3 min then it was heated to 90° C. for 24 h in a sealed tube. The cooled mixtures were quenched with 1N NaOH and extracted with dichloromethane/isopropanol (8:2). The combined organic layers were dried over anhydrous Na$_2$SO$_4$ and concentrated in vacuo. The residue was then dissolved with 20% trifluoromethyl acetic acid in dichloromethane (5 mL) and stirred for 3 h. The reaction was neutralized with 1N aq. NaOH and extracted with dichloromethane/isopropanol (8:2) mixture. The combined organic layers were dried over anhydrous Na₂SO₄ and concentrated in vacuo to give Compound 75 (0.036 g, 44%) as a yellow solid. ¹H NMR (400 MHz, DMSO-d): δ 12.02 (bs, 1H), 11.29 (s, 1H), 9.98 (bs, 1H), 7.11 (d, 1H, J=8.4 Hz), 6.87 (m, 1H), 6.83 (bs, 1H), 6.52 (bs, 1H), 6.20 (s, 1H), 5.66 (m, 1H), 5.56 (bs, 1H), 5.25 (m, 1H), 3.50 (s, 1H), 3.43 (m, 2H), 2.92 (m, 2H), 2.41 (s, 3H), 2.28 (m, 2H), 1.69 (dd, 3H, J=5.2, 1.2 Hz). MS (ESI): Calcd. for C₂₄H₂₄FN₇O: 445. found 446 (M+H).

Example 76

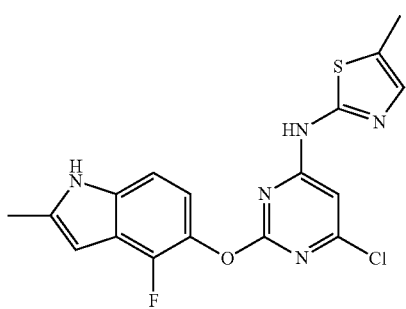
(76)

The solution of 5-((4,6-dichloropyrimidin-2-yl)oxy)-4-fluoro-2-methyl-1H-indole (0.5 g, 1.60 mmol), 5-methylthiazol-2-amine (0.22 g, 1.92 mmol), sodium iodide (0.29 g, 1.92 mmol) and DIPEA (0.39 mL, 1.92 mmol) in DMF (16.0 mL) was stirred at 70° C. overnight. The mixture was slowly added to the ice-water (10.0 mL). The mixture was cooled by ice bath and the solids were collected by filtration, washed with water and hexanes to provide Compound 76 as pale white solid (0.59 g, 95%). ¹H NMR (400 MHz, DMSO-d₆) δ 11.34 (bs, 1H), 9.81 (bs, H), 8.70 (bs, 1H), 7.22 (m, 1H), 7.14 (m, 1H), 6.97 (m, 1H), 6.25 (m, 1H), 2.40 (s, 3H), 2.02 (s, 3H); ESI-MS: calcd for (C17H13C1FN5OS) 389. found 390 [M−H]⁺.

Example 77

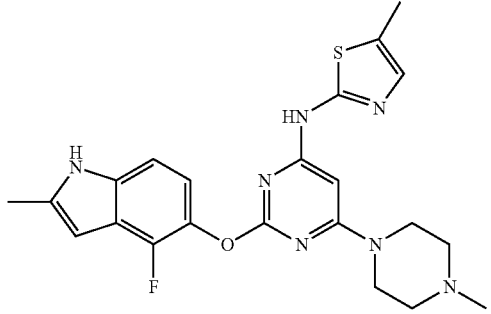
(77)

A mixture of N-(6-chloro-2-((4-fluoro-2-methyl-1H-indol-5-yl)oxy)pyrimidin-4-yl)-5-methylthiazol-2-amine (0.1 g, 0.26 mmol), 1-methyl piperazine (32 mg, 1.25 mmol), Pd(OAc)₂ (8.2 mg, 0.036 mmol) and K₂CO₃ (0.57 g, 4.10 mmol) in THF (1.5 mL) and DMF (1.0 mL) were heated in the microwave for 1.5 h at 60° C. The reaction mixture was cooled down and water was added. The resulting mixture was extracted with EtOAc and the combined extracts were washed with brine, dried over anhydrous Na₂SO₄ and then concentrated under reduced pressure. The resulting crude product was purified by Teledyne-Isco flash system by using CH₂Cl₂/MeOH, 0 to 20% of methanol in dichloromethane to provide Compound 77 as off brown solid (20 mg, 17%); ¹H NMR (400 MHz, DMSO-d₆) δ 11.27 (bs, 1H), 9.48 (bs, H), 7.35 (bs, 1H), 7.15-7.00 (m, 2H), 6.85 (m, 1H), 6.22 (m, 1H), 3.45 (m, 4H), 2.41 (s, 3H), 2.32 (m, 4H), 2.18 (s, 3H), 1.95 (s, 3H); MS (ESI): Calcd. for C22H24FN7OS: 453. found 454 (M−H)⁺.

Example 78

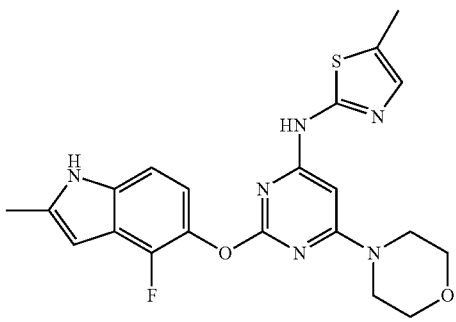
(78)

Following the same procedure as in Example 77, the Compound 78 was also prepared from Compound 76 and characterized by LC-MS 441 (M−H)⁺.

Example 79

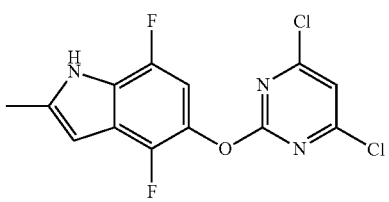
(79)

The solution of 4,6-dichloro-2-methylsulfonylpyrimidine (3.72 g, 16.38 mmol), and 2-methyl-4,7-di-fluoro-1-H-indol-5-ol (3.00 g, 16.38 mmol) in THF (100 mL) was cooled to −78° C. with dry-ice/acetone. A suspension of potassium t-butoxide (2.30 g, 20.47 mmole) in THF (50 mL) was added to the reaction mixture drop wise. The temperature of the mixture was controlled below −50° C. After addition, the reaction was stirred at −78° C. for 1 h, then warmed up to room temperature over a period of 1 h. The TLC was checked and both starting materials were consumed. Saturated ammonium chloride in water was added and the mixture was extracted with ethyl acetate/hexanes (80/20) three times. The combined organic was washed with brine, dried over sodium sulfate and concentrated. The crude product was a pad of silica gel eluted with 15% ethyl acetate in hexanes. The collected fraction was concentrated to give the desired product as light-yellow solids (79) (4.20 g, 78% yield). The solids were directly used for the next step reaction without further purification.

Example 80

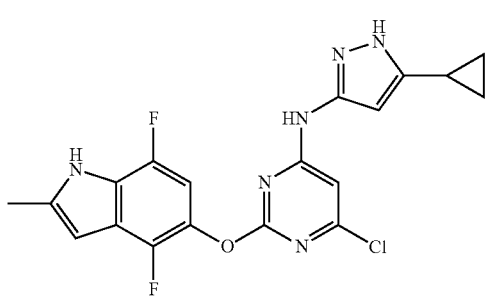

(80)

To a solution of 6-chloro-N-(5-cyclopropyl-1H-pyrazol-3-yl)-2-(methylsulfonyl)pyrimidin-4-amine (0.7 g, 2.23 mmol) in tBuOH (50 mL) was added 4,7-difluoro-2-methyl-1H-indol-5-ol (0.45 g, 2.45 mmol) and KOtBu (0.28 g, 2.45 mmol) at room temperature. Reaction was stirred at 50° C. for two days. After cooling, reaction was diluted with DCM and washed with sat. NaHCO$_3$. Aqueous phase was extracted with DCM/isopropanol (4:1) twice. The combined organic layers were dried over anhydrous Na$_2$SO$_4$ and concentrated in vacuo. The resulting crude product was purified by Teledyne-Isco flash system by using CH$_2$Cl$_2$/MeOH, 0 to 5% of methanol in dichloromethane to provide Compound 80 as light yellow solid (0.49 g, 53%).

Compound 80 can also be prepared by reaction of Compound 79 with 3-cyclopropyl-1H-pyrazol-5-amine with the same procedure as described in experiment 53 (Method 2).

Example 81

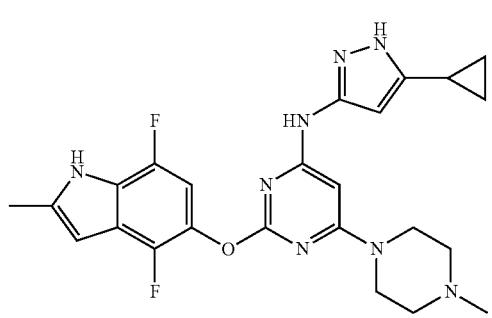

(81)

To a solution of 6-chloro-N-(5-cyclopropyl-1H-pyrazol-3-yl)-2-((4,7-difluoro-2-methyl-1H-indol-5-yl)oxy)pyrimidin-4-amine (80 mg, 0.20 mmol) and 1-methyl piperazine (0.56 mL, 5.00 mmol) in isopropanol (1 mL) was heated to 90° C. overnight in a sealed tube. After cooling, reaction mixture was diluted with dichloromethane and washed with saturated NaHCO$_3$. Aqueous phase was extracted with dichloromethane/isopropanol mixture (4:1). The combined organic layers were dried over anhydrous Na$_2$SO$_4$ and concentrated in vacuo. The resulting crude product was purified by Teledyne-Isco flash system by using CH$_2$Cl$_2$/MeOH, 0 to 10% of methanol in dichloromethane to provide Compound 81 (also referred to herein as "NTW-3475") as light yellow solid (33 mg, 36%). $^1$H NMR (400 MHz, DMSO-d$_6$) δ 11.76 (bs, 1H, NH), 11.70 (bs, H, NH), 9.26 (bs, 1H, NH), 6.86-5.97 (m, 3H, Ar—H), 5.26 (bs, 1H, Ar—H), 3.43 (m, 4H, 2CH$_2$), 2.40 (s, 3H, CH$_3$), 2.35 (m, 4H, 2CH$_2$), 2.20 (s, 3H, CH$_3$), 1.49 (in, 1H, CH), 0.71-0.09 (m, 4H, Ar—H); ESI-MS: calcd for (C24H26F2N8O) 480. found 481 [M–H]$^+$. HPLC: retention time: 14.84 min. purity: 100%.

Examples 82-85

Following the same procedure as in example 81, the Compounds 82-85 were also prepared from Compound 80 and characterized by LC-MS.

| Example number | Compounds Structure | LC-MS (M + H)$^+$ |
|---|---|---|
| 82 | 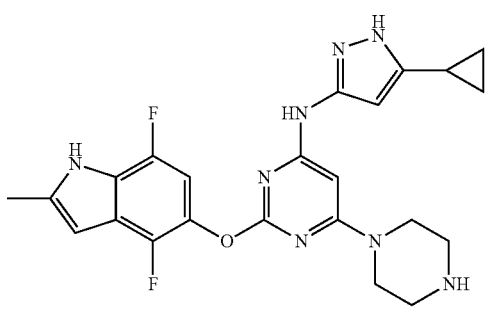 [SMILES: Cc1cc2c(F)c(Oc3nc(Nc4cc(C5CC5)[nH]n4)cc(N4CCNCC4)n3)cc(F)c2[nH]1] | 467 |

| Example number | Compounds Structure | LC-MS (M + H)+ |
|---|---|---|
| 83 | 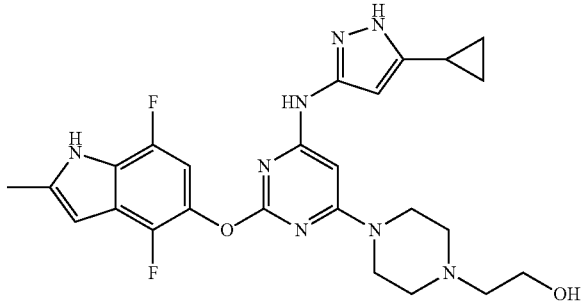 [SMILES: Cc1cc2c(F)c(Oc3nc(Nc4cc(C5CC5)[nH]n4)cc(N4CCN(CCO)CC4)n3)cc(F)c2[nH]1] | 511 |
| 84 | 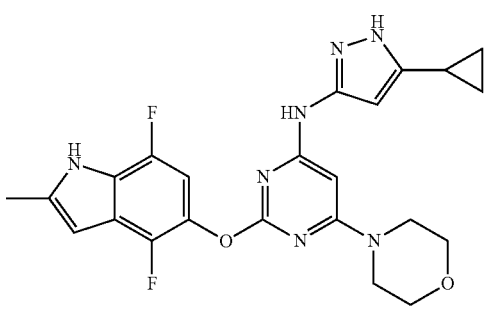 [SMILES: Cc1cc2c(F)c(Oc3nc(Nc4cc(C5CC5)[nH]n4)cc(N4CCOCC4)n3)cc(F)c2[nH]1] | 468 |
| 85 | 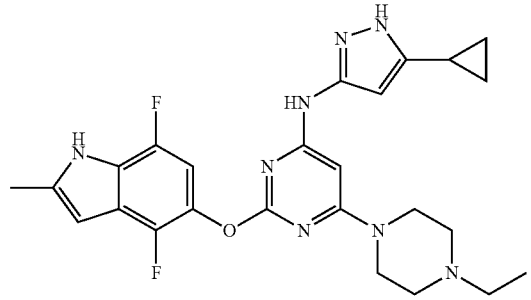 | 495 |

Preparation and Characterization of Compound 82

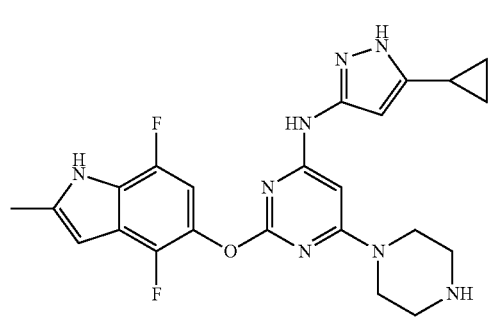

(82)

Solution of 6-chloro-N-(5-cyclopropyl-1H-pyrazol-3-yl)-2-((4,7-difluoro-2-methyl-1H-indol-5-yl)oxy)pyrimidin-4-amine (Compound 80) (80 mg, 0.20 mmol) and piperazine (431 mg, 5.00 mmol) in isopropanol (1 mL) was heated to 90° C. overnight in a sealed tube. After cooling, reaction mixture was diluted with dichloromethane and washed with saturated NaHCO$_3$. Aqueous phase was extracted with dichloromethane/isopropanol mixture (4:1). The combined organic layers were dried over anhydrous Na$_2$SO$_4$ and concentrated in vacuo. The resulting crude product was purified by Teledyne-Isco flash system by using CH$_2$Cl$_2$/MeOH, 0 to 20% of methanol in dichloromethane to provide compound 82 as light yellow solid (46 mg, 51%). $^1$H NMR (400 MHz, DMSO-d$_6$) δ 11.75 (bs, 1H, NH), 11.68 (bs, H, NH), 9.24 (bs, 1H, NH), 6.85-5.99 (m, 3H, Ar—H), 5.26 (bs, 1H, Ar—H), 3.37 (m, 4H, 2CH$_2$), 2.75 (m, 4H, 2CH$_2$), 2.40 (s, 3H, CH$_3$), 1.49 (m, 1H, CH), 0.70-0.10 (m, 4H, Ar—H); ESI-MS: calcd for (C23H24F2N8O) 466. found 467 [M+H]$^+$. HPLC: retention time: 13.91 min. purity: 100%.

Example 86

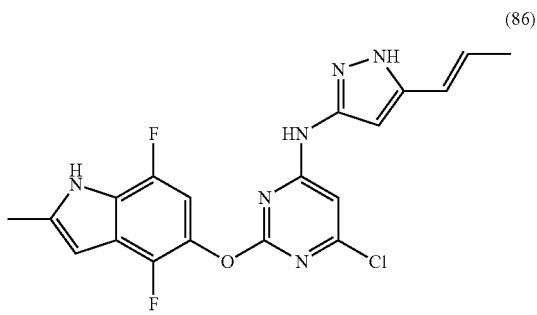 [SMILES: C/C=C/c1cc(Nc2cc(Cl)nc(Oc3cc(F)c4[nH]c(C)cc4c3F)n2)n[nH]1]

(86)

The solution of Compound 79 (4.20 g, 12.72 mmol), (E)-5-(prop-1-en-1-yl)-1H-pyrazol-3-amine (2.82 g, 22.90 mmol), sodium iodide (2.86 g, 19.08 mmol) and DIPEA (3.33 ml, 19.08 mmol) in DMF (35 mL) was stirred at 65° C. for 48 hours TLC was checked and the starting material was consumed. The mixture was cooled with ice and the solids were collected by filtration, washed by water and hexanes. The slides were dissolved into dichloromethane/methanol. The solution was concentrated to minimum amount of solvents. The solids were collected by filtration, washed by methanol to give yellow solids (1.90 g). The mothe liquid was purified by column. The desired parts were collected, concentrated and filtered to give light-yellow solids (0.82 g). The combined solids (86) were used for the next step reactions (2.72 g, 51%) $^1$H NMR (400 MHz, DMSO-d$_6$) δ 12.15 (br, 1H), 11.80 (br, 1H), 10.40 (br, 1H), 6.95 (dd, J=10.8 Hz, J=5.6 Hz, 1H), 6.40 (br, 1H), 6.22 (s, 1H), 5.70-5.10 (m, 3H), 2.40 (s, 3H), 1.78 (br, 3H); ESI-MS: calcd for (C19H15C1F2N6O) 416. found 417 (MH$^+$).

Alternatively, Compound 86 can also be prepared from the reaction of 6-chloro-N-(5propenyl-1H-pyrazol-3-yl)-2-(methylsulfonyl)pyrimidin-4-amine and 2-methyl-4,7-difluoro-1-H-indol-5-ol with the same protocol as described earlier.

Example 87

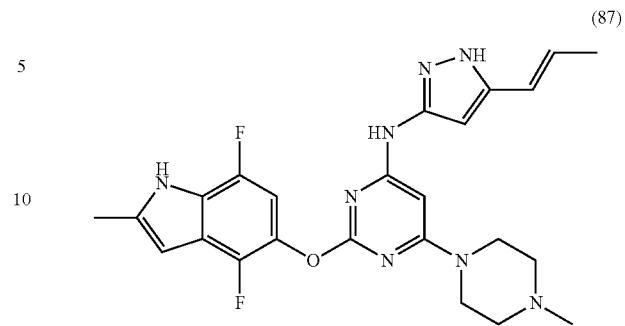

(87)

The solution of 86 (45 m g, 0.11 mmol), 1-methyl piperazine (270 mg, 2.70 mmol) and DIPEA (0.10 ml, 0.54 mmol) in isopropyl alcohol (3.0 mL) and acetonitrile (1.0 mL) was stirred at 85° C. for 3 days. TLC was checked and the starting material was consumed. Dilute sodium bicarbonate was added and the mixture was extracted with DCM three times. The combined organic was washed with brine, dried over sodium sulfate and concentrated. The crude product was purified on column (0-15% methanol in DCM). The collected fraction was concentrated to give the desired product as off-white solids (Compound 87, also referred to herein as "NTW-3456") (33 mg, 66% yield). $^1$H NMR (400 MHz, DMSO-d$_6$) δ 11.90 (br, 1H), 11.71 (br, 1H), 9.30 (br, 1H), 6.85 (dd, J=10.8 Hz, J=5.6 Hz, 1H), 6.29 (s, 1H), 5.80-5.00 (m, 4H), 3.40 (br, 4H), 2.40 (m, 7H), 2.18 (s, 3H), 1.68 (d, J=6.8 Hz, 3H); ESI-MS: calcd for (C24H26F2N8O) 480. found 481 (MH$^+$).

Examples 88-99

Following the same procedure as in example 87, the Compounds 88-99 were also prepared from Compound 86 and characterized by LC-MS.

| Example number | Compounds Structure | LC-MS (M + H)$^+$ |
|---|---|---|
| 88 | ![structure] | 511 |
| 89 | ![structure] | 468 |

-continued
| Example number | Compounds Structure | LC-MS (M + H)+ |
|---|---|---|
| 90 | 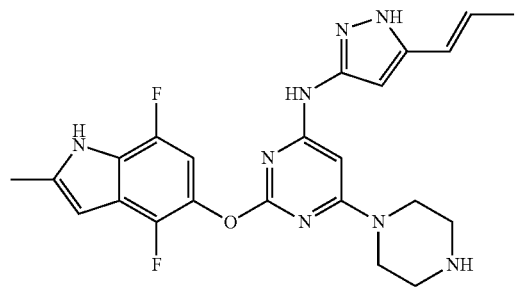 [SMILES: C/C=C/c1cc(Nc2cc(N3CCNCC3)nc(Oc3cc(F)c4[nH]c(C)cc4c3F)n2)n[nH]1] | 467 |
| 91 | 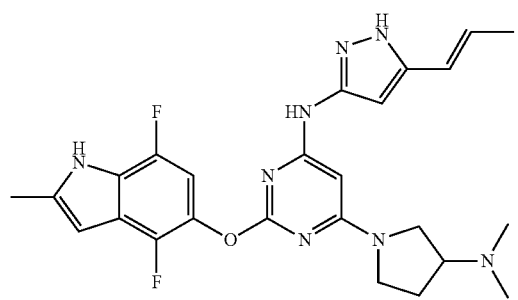 [SMILES: C/C=C/c1cc(Nc2cc(N3CCC(N(C)C)C3)nc(Oc3cc(F)c4[nH]c(C)cc4c3F)n2)n[nH]1] | 495 |
| 92 | 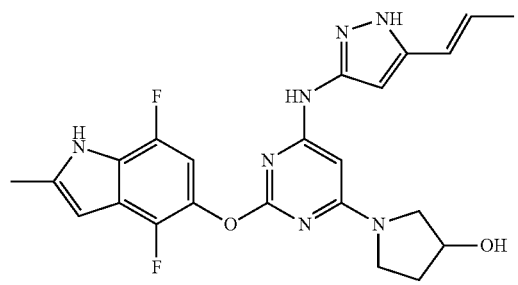 [SMILES: C/C=C/c1cc(Nc2cc(N3CCC(O)C3)nc(Oc3cc(F)c4[nH]c(C)cc4c3F)n2)n[nH]1] | 468 |
| 93 | 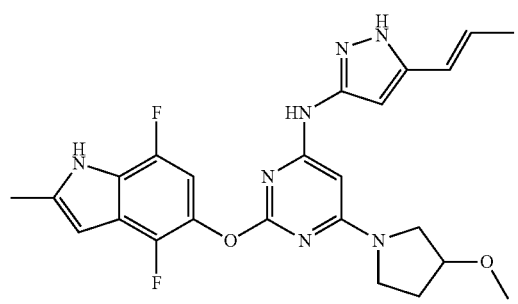 [SMILES: C/C=C/c1cc(Nc2cc(N3CCC(OC)C3)nc(Oc3cc(F)c4[nH]c(C)cc4c3F)n2)n[nH]1] | 482 |
| 94 | 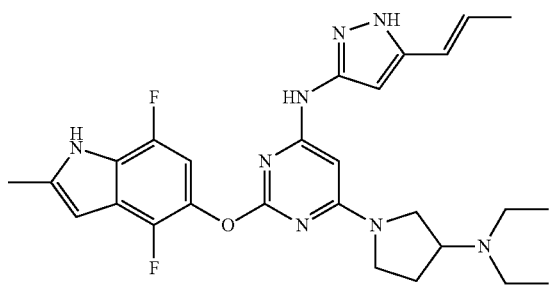 [SMILES: C/C=C/c1cc(Nc2cc(N3CCC(N(CC)CC)C3)nc(Oc3cc(F)c4[nH]c(C)cc4c3F)n2)n[nH]1] | 523 |

| Example number | Compounds Structure | LC-MS (M + H)+ |
|---|---|---|
| 95 | 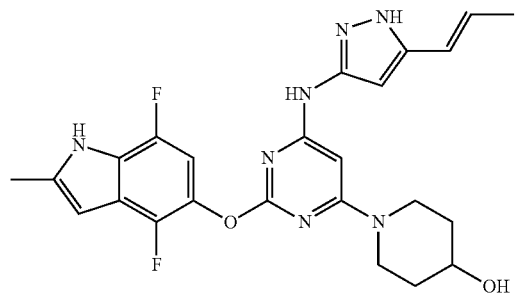 [SMILES: C/C=C/c1cc(Nc2cc(N3CCC(O)CC3)nc(Oc3cc(F)c4[nH]c(C)cc4c3F)n2)n[nH]1] | 482 |
| 96 | 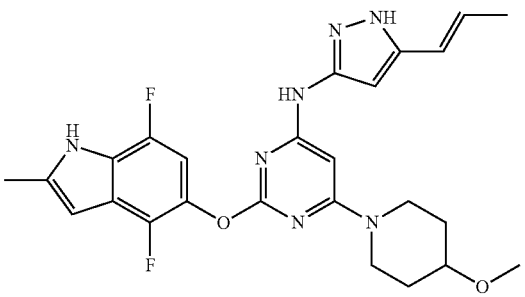 | 496 |
| 97 | 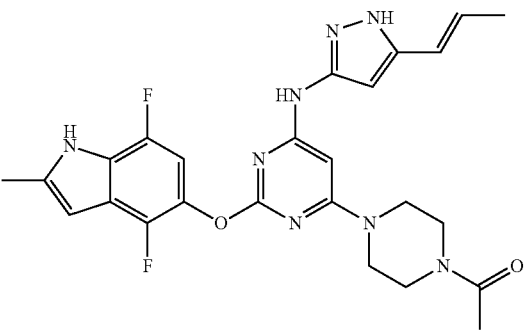 [SMILES: C/C=C/c1cc(Nc2cc(N3CCN(C(C)=O)CC3)nc(Oc3cc(F)c4[nH]c(C)cc4c3F)n2)n[nH]1] | 509 |
| 98 | 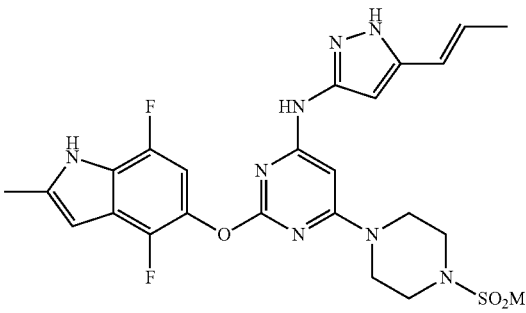 | 545 |

| Example number | Compounds Structure | LC-MS (M + H)+ |
|---|---|---|
| 99 | | 495 |

Preparation and Characterization of Compound 90

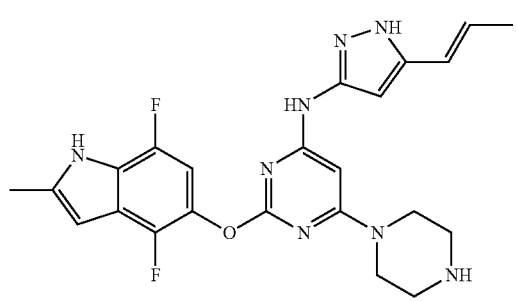

(90)

The solution of 86 (45 m g, 0.11 mmol), piperazine (232 mg, 2.70 mmol) and DIPEA (0.10 ml, 0.54 mmol) in isopropyl alcohol (3.0 mL) and acetonitrile (1.0 mL) was stirred at 85° C. for 3 days. TLC was checked and the starting material was consumed. Dilute sodium bicarbonate was added and the mixture was extracted with DCM three times. The combined organic layer was washed with brine, dried over sodium sulfate and concentrated. The crude product was purified on column (0-20% methanol in DCM). The collected fraction was concentrated to give the desired product as off-white solids (90) (21 mg, 43%). $^1$H NMR (400 MHz, DMSO-d$_6$) δ 11.90 (br, 1H), 11.67 (br, 1H), 9.30 (br, 1H), 6.79 (dd, J=10.8 Hz, J=5.6 Hz, 1H), 6.25 (s, 1H), 5.80-5.00 (m, 4H), 3.59 (m, 4H), 2.80 (m, 4H), 2.34 (s, 3H), 1.68 (d, J=6.8 Hz, 3H); ESI-MS: calcd for (C23H24F2N80) 466. found 467 (MH+).

Example 100

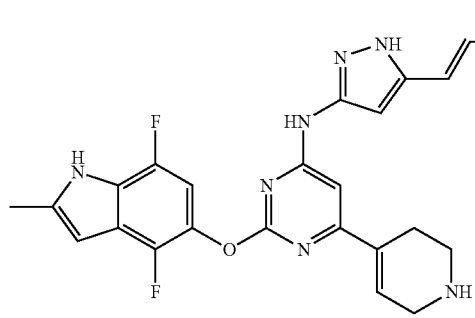

(100)

To a solution of (E)-6-chloro-2-((4,7-difluoro-2-methyl-1H-indol-5-yl)oxy)-N-(5-(prop-1-en-1-yl)-1H-pyrazol-3-yl)pyrimidin-4-amine (0.075 g, 0.179 mmol), 1-N-boc-4-(4,4,5,5-tetramethyl-[1,3,2]dioxaborolan-2-yl)-3,6-dihydro-2H-pyridine (0.089 g, 0.287 mmol), and tetrakis(triphenylphosphine)palladium (0) (0.018 g, 0.018 mmol) in dimethoxylethane (4 mL) under argon was added aqueous 2M Na$_2$CO$_3$ (0.197 mL, 0.396 mmol). The mixtures were degassed with a stream of argon for 3 min then it was heated to 90° C. for 24 h in a sealed tube. The cooled mixtures were quenched with 1N NaOH and extracted with dichloromethane/isopropanol (8:2). The combined organic layers were dried over anhydrous Na$_2$SO$_4$ and concentrated in vacuo. The residue was then dissolved with 20% trifluoromethyl acetic acid in dichloromethane (5 mL) and stirred for 3 h. The reaction was neutralized with 1N aq. NaOH and extracted with dichloromethane/isopropanol (8:2) mixture. The combined organic layers were dried over anhydrous Na$_2$SO$_4$ and concentrated in vacuo to give Compound 100 (0.041 g, 49%) as a yellow solid. $^1$H NMR (400 MHz, DMSO-d): δ 12.08 (bs, 1H), 11.77 (s, 1H), 10.04 (bs, 1H), 6.89 (q, 1H, J=5.6 Hz), 6.84 (m, 1H), 6.52 (bs, 1H), 6.32 (s, 1H), 5.70 (m, 1H), 5.59 (bs, 1H), 5.26 (m, 1H), 3.49 (s, 1H), 3.45 (m, 2H), 2.94 (m, 2H), 2.42 (s, 3H), 2.30 (m, 2H), 1.71 (dd, 3H, J=5.2, 1.2 Hz). MS (ESI): Calcd. for C$_{24}$H$_{23}$F$_2$N$_7$O: 463. found 464 (M+H).

Example 101

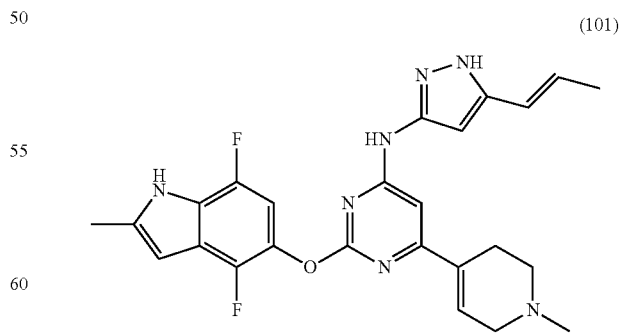

(101)

To a solution of (E)-2-((4,7-difluoro-2-methyl-1H-indol-5-yl)oxy)-N-(5-(prop-1-en-1-yl)-1H-pyrazol-3-yl)-6-(1,2,3,6-tetrahydropyridin-4-yl)pyrimidin-4-amine (0.022 g, 0.048 mmol) in tetrahydrofuran (10 mL) was added formaldehyde (37% in water, 0.012 g, 0.142 mmol) and stirred for 10 min. Then followed by the addition of sodium triacetoxyborohydride (0.030 g, 0.142 mmol) and continued to for 20 h. The mixtures were quenched with saturated NaHCO₃ and extracted with dichloromethane/isopropanol (8:2) mixtures. The combined organic layers were dried over anhydrous Na₂SO₄ and concentrated in vacuo. The residue was purified by flash chromatography over silica gel with CH₂Cl₂:MeOH (8:2) to give Compound 101 (0.020 g, 87%) as a light yellow solid. ¹H NMR (400 MHz, DMSO-d): δ 12.08 (bs, 1H), 11.77 (s, 1H), 10.03 (bs, 1H), 7.09 (m, 1H), 6.79 (m, 1H), 6.52 (m, 1H), 6.32 (s, 1H), 5.67 (m, 1H), 5.57 (m, 1H), 5.24 (m, 1H), 3.06 (m, 2H), 2.56 (m, 2H), 2.42 (s, 3H), 2.40 (m, 2H0, 2.28 (s, 3H), 1.71 (dd, 3H, J=6.8, 1.2 Hz). MS (ESI): Calcd. for C$_{25}$H$_{25}$F$_2$N$_7$O: 477. found 478 (M+H).

Example 102

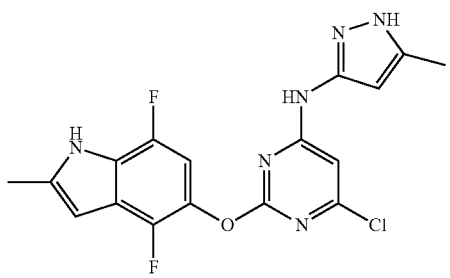

(102)

To a suspension of 6-chloro-N-(5-methyl-1H-pyrazol-3-yl)-2-(methylsulfonyl)pyrimidin-4-amine (700 m g, 2.43 mmol) and 2-methyl-4,7-di-fluoro-1-H-indol-5-ol (499 mg, 2.72 mmol) in t-BuOH (50.0 mL) was added t-BuOK (33 mg, 2.92 mmol) at room temperature. After addition, the mixture was stirred at 55° C. for 16 hours. TLC was checked and the starting material was consumed. Water was added to the reaction mixture. The mixture was extracted with dichloromethane/isopropyl alcohol (90/10) three times. The combined organic was washed with brine, dried over sodium sulfate and concentrated. The crude product was purified on column (0-10% methanol in DCM). The collected fraction was concentrated to give the desired product as pink solids (102) (435 mg, 46% yield). ¹H NMR (400 MHz, DMSO-d₆) δ 11.80 (br, 1H), 11.77 (br, 1H), 10.30 (br, 1H), 6.95 (dd, J=10.8 Hz, J=5.6 Hz, 1H), 6.40 (br, 1H), 6.32 (s, 1H), 5.25 (br, 1H), 2.40 (s, 3H), 1.78 (s, 3H); ESI-MS: calcd for (C17H13C1F2N6O) 390. found 391 (MH⁺).

Example 103

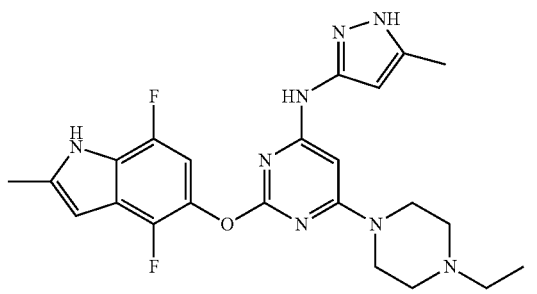

(103)

The solution of Compound 102 (50 in g, 0.13 mmol), 1-ethyl piperazine (365 mg, 3.20 mmol) and DIPEA (0.11 ml, 0.64 mmol) in isopropyl alcohol (2.5 mL) was stirred at 85° C. for 3 days. TLC was checked and the starting material was consumed. Dilute sodium bicarbonate was added and the mixture was extracted with DCM three times. The combined organic was washed with brine, dried over sodium sulfate and concentrated. The crude product was purified on column (0-15% methanol in DCM). The collected fraction was concentrated to give the desired product as off-white solids (103) (45 mg, 75% yield). ¹H NMR (400 MHz, DMSO-d₆) δ 11.65 (br, 2H), 9.20 (br, 1H), 6.82 (dd, J=10.8 Hz, J=5.6 Hz, 1H), 6.27 (s, 1H), 6.07 (br, 1H), 5.35 (s, 1H), 3.40 (br, 4H), 2.31 (m, 9H), 1.95 (s, 3H), 1.00 (t, J=7.2 Hz, 3H); ESI-MS: calcd for (C23H26F2N8O) 468. found 469 (MH⁺.

Examples 104-109

Following the same procedure as in example 103, the Compounds 104-109 were also prepared from Compound 102 and characterized by LC-MS.

| Example number | Compounds Structure | LC-MS (M + H)⁺ |
|---|---|---|
| 104 | 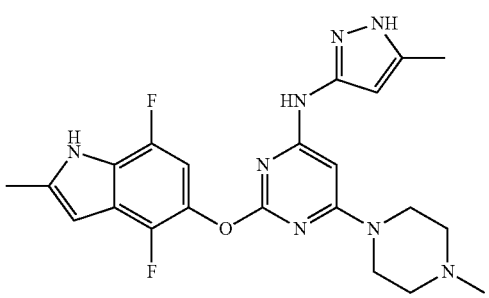 | 455 |

-continued

| Example number | Compounds Structure | LC-MS (M + H)+ |
|---|---|---|
| 105 | | 485 |
| 106 | | 441 |
| 107 | | 442 |
| 108 | | 455 |
| 109 | | 458 |

Example 110

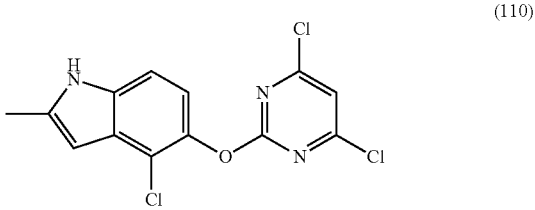

The solution of 4,6-dichloro-2-methylsulfonylpyrimidine (938 mg, 4.13 mmol), and 2-methyl-4-chloro-1-H-indol-5-ol (750 mg, 4.13 mmol) in THF (20 mL) was cooled to −78° C. with dry-ice/acetone. A suspension of potassium t-butoxide (510 mg, 4.54 mmol) in THF (10 mL) was added to the reaction mixture drop wise. The temperature of the mixture was controlled below −50° C. After addition, the reaction was stirred at −78° C. for 1 h, then warmed up to room temperature over a period of 1.5 h. The TLC was checked and both starting materials were consumed. Saturated ammonium chloride in water was added and the mixture was extracted with ethyl acetate/hexanes (95/5) three times. The combined organic was washed with brine, dried over sodium sulfate and concentrated. The crude product was a pad of silica gel eluted with 20% ethyl acetate in hexanes. The collected fraction was concentrated to give the desired product as light-yellow solids (110) (900 mg, 66% yield). The solids were directly used for the next step reaction without further purification. $^1$H NMR (400 MHz, DMSO-d$_6$) δ 11.42 (s, 1H), 7.75 (s, 1H), 7.30 (d, J=8.4 Hz, 1H), 7.00 (d, J 8.4 Hz, 1H), 6.21 (s, 1H), 2.41 (s, 3H); ESI-MS: calcd for (C13H8C13N3O) 326. found 327 (MH$^+$).

Example 111

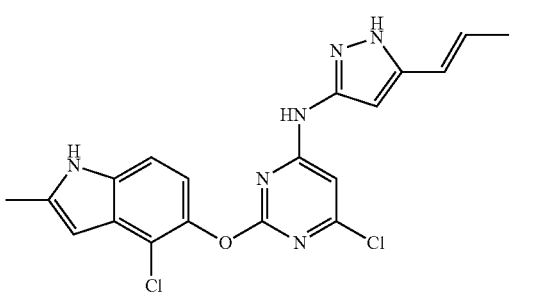

The solution of 5-((4,6-dichloropyrimidin-2-yl)oxy)-4-chloro-2-methyl-1H-indole (0.85 g, 2.59 mmol), (E)-5-(prop-1-en-1-yl)-1H-pyrazol-3-amine (0.48 g, 3.89 mmol), sodium iodide (0.58 g, 3.89 mmol) and DIPEA (0.68 mL, 3.89 mmol) in DMF (10.0 mL) was stirred at 70° C. for 2 days. The mixture was slowly added to the water (200.0 mL). The mixture was cooled by ice bath and the solids were collected by filtration, washed by water and hexanes. The solid was dissolved in CH$_2$Cl$_2$/MeOH and concentrated. Resulting crude was purified by Teledyne-Isco flash system by using CH$_2$Cl$_2$/MeOH, 0 to 5% of methanol in dichloromethane to provide Compound 111 as light yellow solid (0.75 g, 70%). $^1$H NMR (400 MHz, DMSO-d$_6$) δ 12.13 (bs, 1H, NH), 11.42 (bs, H, Nil), 10.38 (bs, 1H, NH), 7.32-5.17 (m, 7H, 5Ar—H, 2CH), 2.44 (s, 3H, CH$_3$), 1.71 (d, 3H, CH$_3$); ESI-MS: calcd for (C19H16C12N6O) 415. found 416 [M+H]$^+$.

Example 112

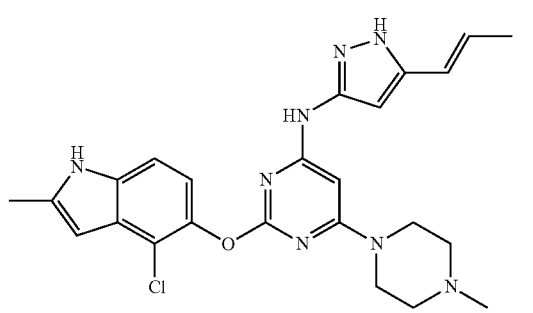

Solution of (E)-6-chloro-2-((4-chloro-2-methyl-1H-indol-5-yl)oxy)-N-(5-(prop-1-en-1-yl)-1H-pyrazol-3-yl)pyrimidin-4-amine (50 mg, 0.12 mmol) and 1-methyl piperazine (0.067 mL, 0.60 mmol) in isopropanol (1.0 mL) was heated to 85° C. overnight. After cooling, reaction mixture was diluted with dichloromethane and washed with water. Aqueous phase was extracted with dichloromethane. The combined organic layers were dried over anhydrous Na$_2$SO$_4$ and concentrated. The resulting crude product was purified by Teledyne-Isco flash system by using CH$_2$Cl$_2$/MeOH, 0 to 10% of methanol in dichloromethane to provide Compound 112 as white solid (25 mg, 43%). $^1$H NMR (400 MHz, DMSO-d$_6$) δ 11.88 (bs, 1H, NH), 11.31 (bs, H, NH), 9.32 (bs, 1H, NH), 7.27-5.34 (m, 7H, 5Ar—H, 2CH), 3.44 (m, 4H, 2CH$_2$), 2.43-2.35 (m, 7H, 2CH$_2$CH$_3$), 2.21 (s, 3H, CH$_3$), 1.71 (d, 3H, CH$_3$); ESI-MS: calcd for (C24H27C1N8O) 478. found 479 [M+H]$^+$. HPLC: retention time: 15.70 min. purity: 92%.

Examples 113-116

Following the same procedure as in example 112, the Compounds 113-116 were also prepared from Compound 111 and characterized by LC-MS.

| Example number | Compound Structure | LC-MS (M + H)+ |
|---|---|---|
| 113 | 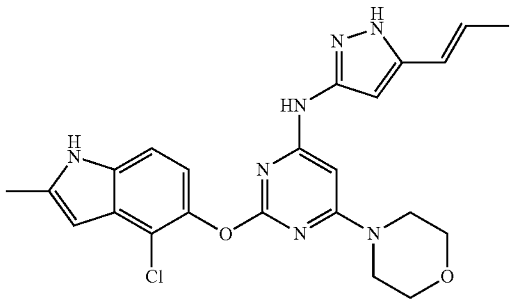 [SMILES: C/C=C/c1cc(Nc2cc(N3CCOCC3)nc(Oc3ccc4[nH]c(C)cc4c3Cl)n2)n[nH]1] | 466 |
| 114 | 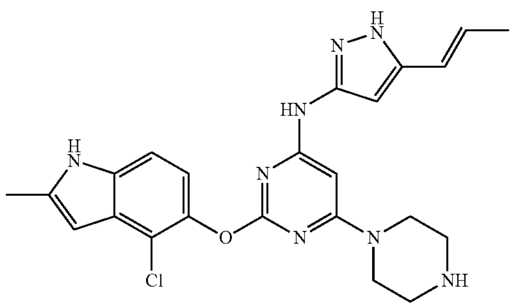 [SMILES: C/C=C/c1cc(Nc2cc(N3CCNCC3)nc(Oc3ccc4[nH]c(C)cc4c3Cl)n2)n[nH]1] | 465 |
| 115 | 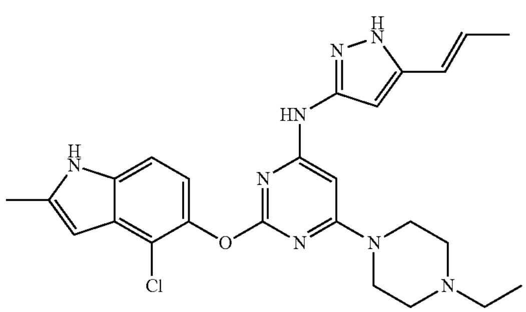 [SMILES: C/C=C/c1cc(Nc2cc(N3CCN(CC)CC3)nc(Oc3ccc4[nH]c(C)cc4c3Cl)n2)n[nH]1] | 494 |
| 116 | 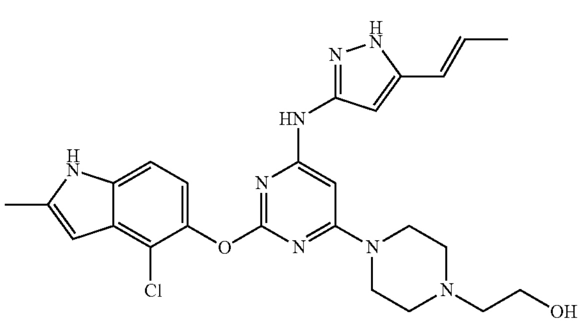 [SMILES: C/C=C/c1cc(Nc2cc(N3CCN(CCO)CC3)nc(Oc3ccc4[nH]c(C)cc4c3Cl)n2)n[nH]1] | 510 |

Example 117

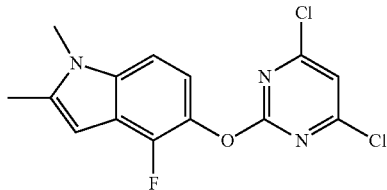

(117)

To a cold (0° C.) suspension of sodium hydride (60%, 1.54 g, 38.5 mmol) in DMF (20 mL) was added slowly a solution of 5-((4,6-dichloropyrimidin-2-yl)oxy)-4-fluoro-2-methyl-1H-indole (Compound 8, 6.00 g, 19.2 mmol) and idomethan (5.46 g, 38.5 mmol) in DMF (28 mL). The reaction mixture was stirred at 0° C. for 2 hours. TLC was checked and the starting material was consumed. The mixture was poured to cold water portion wise and the container was put to ice bath. The white solids were collected by filtration, washed with water and trinuated with hexanes. After further drying on vacuum line, 6.03 g white solids (117) were obtained (96% yield) No further purification was conducted. $^1$H NMR (400 MHz, DMSO-do) δ 7.76 (s, 1H), 7.26 (d, J=8.8 Hz, 1H), 7.03 (t, J=8.0 Hz, 1H) 6.34 (s, 1H), 3.69 (s, 3H), 2.41 (s, 3H); ESI-MS: calcd for (C14H10C12FN3O) 325. found 326 (MH$^+$).

Example 118

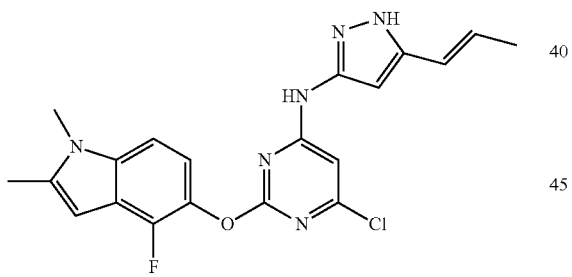

(118)

The solution of 5-((4,6-dichloropyrimidin-2-yl)oxy)-4-fluoro-1,2-dimethyl-1H-indole (Compound 117, 2.68 g, 8.22 mmol), (E)-5-(prop-1-en-1-yl)-1H-pyrazol-3-amine (1.77 g, 14.38 mmol), sodium iodide (1.85 g, 12.33 mmol) and DIPEA (2.15 ml, 12.33 mmol) in DMF (80 mL) was stirred at 65° C. for 24 hours TLC was checked and the starting material was consumed. The mixture was poured into water (500 mL) and cooled with ice. The solids were collected by filtration, washed by water and hexanes. The slides were dissolved into dichloromethane/methanol. The solution was concentrated to minimum amount of solvents. The solids were collected by filtration, washed by methanol to give yellow solids (118) (2.27 g, 67% yield)). The mothe liquid was recovered. $^1$H NMR (400 MHz, DMSO-d$_6$). $^1$H NMR (400 MHz, DMSO-d$_6$) δ 12.15 (br, 1H), 10.35 (br, 1H), 7.14 (m, 1H), 6.90 (m, 1H), 6.40 (br, 1H), 6.22 (s, 1H), 5.70-5.10 (m, 3H), 3.80 (br, 3H) 2.40 (s, 3H), 1.78 (br, 3H); ESI-MS: calcd for (C20H18C1FN6O) 412. found 413 (MH$^+$).

Example 119

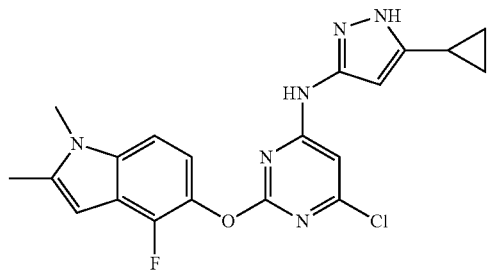

(119)

With same procedure as described in example 120, under the same condition, the reaction of compound 119 and 3-cyclopropylpyrozole-5-amine generated Compound 119. $^1$H NMR (400 MHz, DMSO-d$_6$). NMR (400 MHz, DMSO-d$_6$) δ 12.15 (br, 1H), 10.35 (br, 1H), 7.14 (m, 1H), 7.00 (m, 1H), 6.50 (br, 1H), 6.22 (s, 1H), 5.00 (br, 1H), 3.80 (s, 3H) 2.40 (s, 3H), 1.50 (br, 1H), 1.20 (br, 2H), 0.80 (br, 2H); ESI-MS: calcd for (C20H18C1FN6O) 412. found 413 (MH$^+$).

Example 120

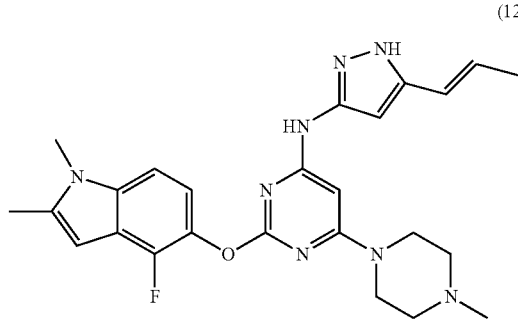

(120)

The solution of Compound 118 (150 mg, 0.36 mmol), 1-methylpiperazine (181 mg, 1.81 mmol) and DIPEA (0.13 ml, 0.73 mmol) in DMSO (3.5 mL) was stirred at 75° C. for 3 days. TLC was checked and the starting material was consumed. The reaction mixture was poured into dilute sodium bicarbonate in water (~1%) and cooled with ice bath. The solids were collected by filtration, washed by water and hexanes to give light-brown solids 161 mg. The crude product was trinuated with MeOH, filtered and washed by MeOH to give Compound 120 as light-yellow solids (82 mg, 47% yield). $^1$H NMR (400 MHz, DMSO-d$_6$) δ 11.92 (br, 1H), 9.31 (br, 1H), 7.20 (d, J=8.8 Hz, 1H), 6.92 (t, J=8.0 Hz, 1H), 6.28 (s, 1H), 5.80-5.60 (m, 4H), 3.70 (s, 3H), 3.42 (br, 4H), 2.42 (s, 3H), 2.34 (m, 4H), 2.19 (s, 3H), 1.67 (d, J=6.0 Hz, 3H); ESI-MS: calcd for (C25H29FN8O) 476. found 477 (MO.

Example 121

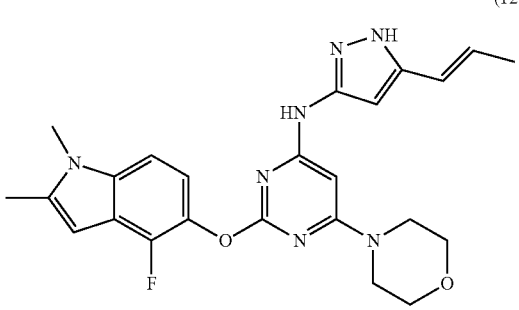

(121)

From Compound 118, with the same procedure as described in example 120, Compound 121 was prepared. $^1$H NMR (400 MHz, DMSO-$d_6$) δ 11.92 (br, 1H), 9.38 (br, 1H), 7.23 (d, J=8.8 Hz, 1H), 6.92 (t, J=8.0 Hz, 1H), 6.28 (s, 1H), 5.80-5.60 (m, 4H), 3.70 (s, 3H), 3.60 (br, 4H), 3.40 (m, 4H), 2.42 (s, 3H), 1.67 (d, J=6.0 Hz, 3H); ESI-MS: calcd for (C24H26FN7O2) 463. found 464 (MH$^+$).

Example 122

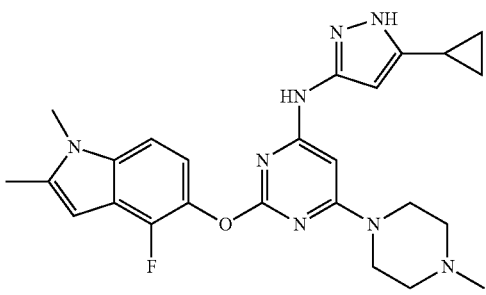

(122)

From Compound 119, with the same procedure as described in example 120, Compound 122 was prepared. $^1$H NMR (400 MHz, DMSO-$d_6$) δ 11.92 (br, 1H), 9.31 (br, 1H), 7.30 (d, J=8.8 Hz, 1H), 6.92 (t, J=8.0 Hz, 1H), 6.28 (s, 1H), 6.00 (br, 1H), 5.15 (br, 1H), 3.78 (s, 3H), 3.70 (br, 4H), 2.80 (m, 4H), 2.57-2.42 (s,s, 6H), 1.80 (br, 1H), 0.85 (br, 2H), 0.00 (br, 2H); ESI-MS: calcd for (C25H29FN8O) 476. found 477 (MH$^+$).

Example 123

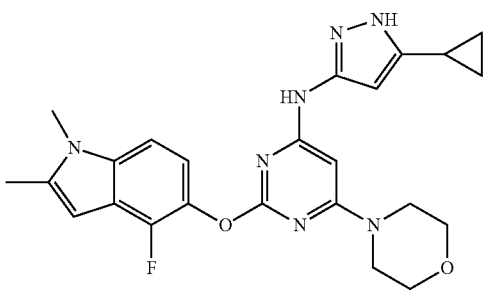

(123)

From Compound 119, with the same procedure as described in example 120, Compound 123 was prepared. $^1$H NMR (400 MHz, DMSO-$d_6$) δ 11.92 (br, 1H), 9.31 (br, 1H), 7.22 (d, J=8.8 Hz, 1H), 6.92 (t, J=8.0 Hz, 1H), 6.27 (s, 1H), 5.90 (br, 1H), 5.15 (br, 1H), 3.68 (s, 3H), 3.60 (br, 4H), 3.40 (m, 4H), 2.39 (s, 3H), 1.60 (br, 1H), 0.85 (br, 2H), 0.00 (br, 2H); ESI-MS: calcd for C24H26FN7O2) 463. found 464 (MH$^+$).

Example 124

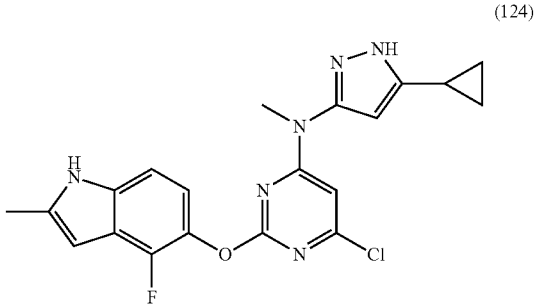 [SMILES: Cc1cc2c(F)c(Oc3nc(Cl)cc(N(C)c4cc(C5CC5)[nH]n4)n3)ccc2[nH]1]

(124)

To a solution of 5-((4,6-dichloropyrimidin-2-yl)oxy)-4-fluoro-2-methyl-1H-indole (0.109 g, 0.349 mmol), 5-cyclopropyl-N-methyl-1H-pyrazol-3-amine (0.088 g, 0.641 mmol), and diisopropylethylamine (0.124 g, 0.961 mmol) in anhydrous dimethylformamide (9 mL) under argon atmosphere was added sodium iodide (0.106 g, 0.705 mmol). The mixtures were heated to 85° C. overnight (16 h). After cooling, the solvent was removed by vacuum and then redissolved in dichloromethane/isopropanol (8:2) mixtures (50 mL) and washed with saturated NaHCO$_3$. The combined organic layers were dried over anhydrous Na$_2$SO$_4$ and concentrated in vacuo. The residue was purified by flash chromatography over silica gel with CH$_2$Cl$_2$:MeOH (95:5) to give Compound 124 (0.110 g, 77%) as a light yellow solid. $^1$H NMR (400 MHz, DMSO-d): δ 12.37 (bs, 1H), 11.27 (s, 1H), 7.93 (s, 2H), 7.09 (d, 1H, J=8.4 Hz), 6.89 (m, 1H), 6.68 (s, 1H), 6.21 (s, 1H), 5.77 (bs, 1H), 3.24 (s, 3H), 2.37 (s, 3H), 1.67 (m, 1H), 0.83 (m, 2H), 0.51 (m, 2H). MS (ESI): Calcd. for C$_{20}$H$_{18}$ClFN$_6$O: 412. found 413 (M+H).

Example 125

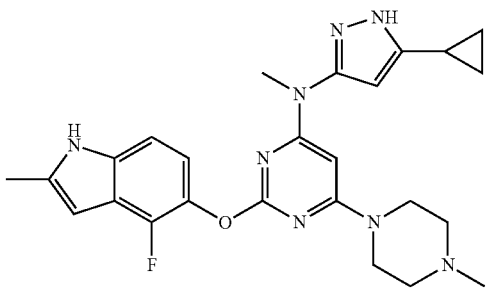

(125)

To a solution of 6-chloro-N-(5-cyclopropyl-1H-pyrazol-3-yl)-2-((4-fluoro-2-methyl-1H-indol-5-yl)oxy)-N-methyl-pyrimidin-4-amine (0.105 g, 0.255 mmol), 1-methylpiperazine (0.102 g, 1.021 mmol), and DIPEA (0.099 g, 0.765 mmol) in isopropanol (1.0 mL) was heated to 80° C. for 2 days in a sealed tube. The cooled mixtures were extracted with dichloromethane/isopropanol (8:2) and washed with saturated NaHCO$_3$. The combined organic layers were dried over anhydrous Na$_2$SO$_4$ and concentrated in vacuo. The residue was purified by flash chromatography over silica gel with CH$_2$Cl$_2$:MeOH (95:5) to give Compound 125 (0.083 g, 68%) as an off-white solid. $^1$H NMR (400 MHz, DMSO-d): δ 11.62 (s, 1H), 10.81 (s, 1H), 6.70 (d, 1H, J=8.4 Hz), 6.47 (m, 1H), 5.81 (s, 1H), 5.49 9s, 1H), 5.25 9s, 1H), 3.04 (m, 4H), 2.84 (s, 3H), 2.00 (s, 3H), 1.93 (m, 4H), 1.81 (s, 3H), 1.16 (m, 1H), 0.38 (m, 2H), 0.006 (m, 2H). MS (ESI): Calcd. for C$_{25}$H$_{29}$FN$_8$O: 476. found 478 (M+H).

Example 126

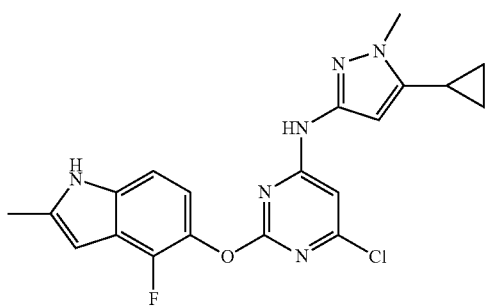

(126)

To a solution of 5-((4,6-dichloropyrimidin-2-yl)oxy)-4-fluoro-2-methyl-1H-indole (0.109 g, 0.349 mmol), 5-cyclopropyl-1-methyl-1H-pyrazol-3-amine (0.088 g, 0.641 mmol), and diisopropylethylamine (0.124 g, 0.961 mmol) in anhydrous dimethylformamide (9 mL) under argon atmosphere was added sodium iodide (0.106 g, 0.705 mmol). The mixtures were heated to 85° C. overnight (16 h). After cooling, the solvent was removed by vacuum and then redissolved in dichloromethane/isopropanol (8:2) mixtures (50 mL) and washed with sat. NaHCO$_3$. The combined organic layers were dried over anhydrous Na$_2$SO$_4$ and concentrated in vacuo. The residue was purified by flash chromatography over silica gel with CH$_2$Cl$_2$:MeOH (9:1) to give Compound 126 (0.255 g, 97%) as an off-white solid. $^1$H NMR (400 MHz, DMSO-d): δ 11.32 (s, 1H), 10.31 (bs, 1H), 7.12 (d, 1H, J=8.4 Hz), 6.89 (m, 1H), 6.48 (bs, 1H), 6.20 (s, 1H), 5.13 (bs, 1H), 3.59 (bs, 3H), 2.39 (s, 3H), 1.53 (m, 1H), 0.61 (m, 2H), −0.26 (m, 2H). MS (ESI): Calcd. for C$_{20}$H$_{18}$ClFN$_6$O: 412. found 413 (M+H).

Example 127

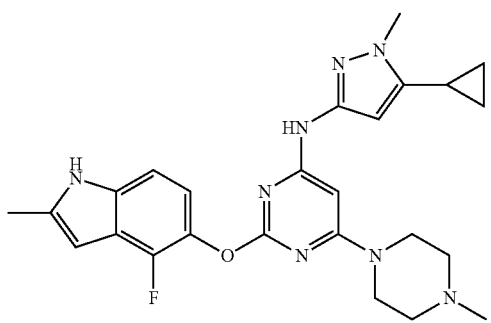

(127)

To a solution of 6-chloro-N-(5-cyclopropyl-1-methyl-1H-pyrazol-3-yl)-2-(4-fluoro-2-methyl-1H-indol-5-yl)oxy)pyrimidin-4-amine (0.100 g, 0.242 mmol), 1-methylpiperazine (0.097 g, 0.969 mmol), and DIPEA (0.094 g, 0.727 mmol) in isopropanol (1.0 mL) was heated to 80° C. for 2 days in a sealed tube. The cooled mixtures were extracted with dichloromethane/isopropanol (8:2) and washed with saturated NaHCO$_3$. The combined organic layers were dried over anhydrous Na$_2$SO$_4$ and concentrated in vacuo. The residue was purified by flash chromatography over silica gel with CH$_2$Cl$_2$:MeOH (95:5) to give Compound 127 (0.106 g, 92%) as a light yellow solid. $^1$H NMR (400 MHz, DMSO-d): δ 11.32 (s, 1H), 9.35 (s, 1H), 7.18 (d, 1H, J=8.4 Hz), 6.93 (m, 1H), 6.28 (s, 1H), 5.98 (bs, 1H), 5.27 (s, 1H), 3.68 (s, 1H), 3.52 (m, 4H), 3.26 (dd, 3H, J=5.2, 0.4 Hz), 2.49 (s, 3H), 2.44 (m, 4H0, 2.30 (s, 3H), 1.64 (m, 1H), 0.72 (m, 2H), 0.00 (m, 2H). MS (ESI): Calcd. for C$_{25}$H$_{29}$FN$_8$O: 476. found 478 (M+H).

Example 128

This example tests the inhibitory properties of representative compounds of the invention in c-Src kinase, Aurora-A kinase, Flt3 kinase, Ret kinase and TrkA Kinase assays (see, Daniele Fancelli et al, J. Med. Chem., 2006, 49 (24), pp 7247-7251). The KinaseProfiler™ Service Assay Protocols (Millipore) was used to test the kinase inhibiting activity of novel compounds from this invention. To do this, the buffer composition was as: 20 mM MOPS, 1 mM EDTA, 0.01% Brij-35, 5% Glycerol, 0.1% β-mercaptoethanol, 1 mg/mL BSA. Test compounds were initially dissolved in DMSO at the desired concentration, then serially diluted to the kinase assay buffer. In a final reaction volume of 25 Aurora-A(h) (5-10 mU) is incubated with 8 mM MOPS pH 7.0, 0.2 mM EDTA, 200 µM LRRASLG (Kemptide), 10 mM MgAcetate and [γ$^{33}$P-ATP]. The reaction was initiated by the addition of the MgATP mix. After incubation for 40 minute at room temperature, the reaction was stopped by addition of 5 µL of a 3% phosphoric acid solution. 10 µL of the reaction was then spotted onto a P30 filtermat and washed three times for 5 minutes in 50 mM phosphoric acid and once in methanol prior to drying and scintillation counting. Wells containing substrate but no kinase and wells containing a phosphopeptide control were used to set 0% and 100% phosphorylation value, respectively.

The Kinase Hotspot$^{SM}$ kinase assay was also used to test the compounds for IC50 or % inhibitions (Reaction Biology Corp.). Inhibitory IC50 values were determined by titration of compound at the optimal kinase concentration (Kinase EC50).

Table 1 shows representative data for the inhibition of abl kinase, Aurora-A kinase, c-Src kinase, Flt3 kinase, KDR kinase and Ret Kinase by the compounds of this invention at a concentration of 1 µM.

TABLE 1

| The compound of Example No. | % Inhibition @1 µM | | | | |
|---|---|---|---|---|---|
| | Abl | Auroro-A | cSrc | Flt3 | KDR | Ret |
| 10 | 112 | 99 | 100 | 100 | 95 | 101 |
| 11 | 111 | 100 | 101 | 100 | 96 | 101 |
| 12 | 112 | 100 | 100 | 100 | 96 | 101 |
| 13 | 112 | 100 | 100 | 101 | 96 | 100 |
| 15 | 108 | 101 | 99 | 100 | 91 | 101 |
| 16 | 103 | 101 | 100 | 98 | 92 | 101 |
| 17 | 108 | 100 | 98 | 100 | 93 | 98 |

TABLE 1-continued

| The compound of Example No. | % Inhibition @1 μM | | | | | |
|---|---|---|---|---|---|---|
| | Abl | Auroro-A | cSrc | Flt3 | KDR | Ret |
| 18 | 107 | 100 | 99 | 100 | 93 | 97 |
| 19 | 108 | 100 | 99 | 99 | 93 | 100 |
| 20 | 107 | 99 | 99 | 100 | 93 | 100 |
| 21 | 107 | 100 | 98 | 101 | 87 | 100 |
| 22 | 108 | 101 | 100 | 100 | 92 | 101 |
| 23 | 108 | 101 | 100 | 100 | 93 | 100 |
| 25 | 108 | 101 | 100 | 100 | 93 | 101 |
| 26 | 109 | 101 | 100 | 100 | 93 | 101 |
| 27 | 108 | 101 | 99 | 100 | 92 | 101 |
| 28 | 108 | 101 | 96 | 100 | 89 | 101 |
| 30 | 110 | 100 | 99 | 100 | 94 | 101 |
| 31 | 115 | 101 | 104 | 101 | 91 | 102 |
| 38 | 108 | 80 | 98 | 98 | 95 | 101 |
| 39 | 110 | 98 | 97 | 98 | 95 | 101 |
| 40 | 110 | 100 | 99 | 98 | 95 | 101 |
| 41 | 108 | 87 | 97 | 99 | 94 | 101 |
| 42 | 110 | 93 | 101 | 100 | 96 | 102 |
| 43 | 111 | 87 | 101 | 99 | 95 | 102 |
| 44 | 94 | 97 | 102 | 100 | 90 | 100 |
| 45 | 107 | 99 | 107 | 101 | 95 | 102 |
| 53 | 109 | 97 | 98 | 99 | 95 | 98 |
| 54 | 108 | 85 | 99 | 99 | 96 | 100 |
| 55 | 110 | 101 | 101 | 99 | 96 | 101 |
| 56 | 111 | 99 | 100 | 99 | 96 | 101 |
| 57 | 111 | 96 | 99 | 100 | 95 | 102 |
| 58 | 112 | 90 | 101 | 99 | 96 | 102 |
| 59 | 112 | 94 | 100 | 99 | 96 | 102 |
| 60 | 111 | 97 | 101 | 99 | 95 | 102 |
| 61 | 112 | 95 | 100 | 100 | 97 | 102 |
| 62 | 111 | 102 | 101 | 99 | 96 | 102 |
| 67 | 112 | 99 | 99 | 100 | 91 | 100 |
| 68 | 107 | 99 | 96 | 100 | 92 | 99 |
| 74 | 111 | 99 | 100 | 100 | 96 | 102 |
| 81 | 110 | 99 | 99 | 101 | 96 | 99 |
| 82 | 106 | 100 | 100 | 100 | 95 | 100 |
| 83 | 110 | 100 | 99 | 99 | 96 | 101 |
| 84 | 103 | 98 | 100 | 100 | 93 | 100 |
| 87 | 112 | 99 | 95 | 100 | 95 | 83 |
| 88 | 113 | 100 | 100 | 100 | 96 | 99 |
| 89 | 112 | 100 | 100 | 100 | 96 | 99 |
| 90 | 112 | 100 | 101 | 100 | 95 | 99 |
| 92 | 111 | 100 | 100 | 100 | 96 | 102 |
| 93 | 111 | 102 | 101 | 100 | 95 | 102 |
| 94 | 111 | 100 | 100 | 99 | 96 | 102 |
| 95 | 110 | 100 | 100 | 100 | 96 | 101 |
| 96 | 110 | 98 | 101 | 99 | 95 | 102 |
| 98 | 111 | 98 | 100 | 100 | 96 | 102 |
| 99 | 113 | 101 | 103 | 102 | 91 | 102 |
| 103 | 113 | 97 | 96 | 99 | 91 | 101 |
| 105 | 112 | 98 | 96 | 99 | 91 | 101 |
| 106 | 109 | 97 | 98 | 99 | 95 | 98 |
| 107 | 111 | 95 | 96 | 98 | 90 | 99 |
| 112 | 113 | 100 | 104 | 102 | 91 | 102 |
| 120 | 115 | 101 | 104 | 101 | 91 | 101 |
| 121 | 116 | 91 | 104 | 102 | 92 | 102 |
| 122 | 109 | 101 | 104 | 102 | 91 | 101 |
| 123 | 114 | 100 | 104 | 101 | 88 | 102 |

These results demonstrate that numerous embodiments of the invention with have excellent kinase inhibitory properties for a wide range of kinases.

Example 129

The embodiment of the invention disclosed in Example 81 (Compound 81) (also referred to herein as compound "NTW-3475") demonstrated strong inhibition of all the kinases in Example 128 and was chosen for further testing.

The NCI-60 DTP Human Tumor Cell Line Panel was used to further evaluate the biochemistry of NTW-3475 (see Shoemaker: *The NCI60 human tumour cell line anticancer drug screen*, Nature Reviews Cancer 6, 813-823 (1 Oct. 2006)).

The effect of NTW-3475 on kinase activity was tested for a wide range of kinases and is shown in Table 2:

TABLE 2

| Kinase | Km NTW-3475@ 0.1 μM |
|---|---|
| Abl(h) | −9 |
| Abl(m) | −2 |
| Abl (H396P) (h) | −3 |
| Abl (M351T)(h) | −2 |
| Abl (Q252H) (h) | −2 |
| Abl(T315I)(h) | −2 |
| Abl(Y253F)(h) | −2 |
| ACK1 (h) | 4 |
| ALK(h) | 17 |
| ALK4(h) | 28 |
| Arg(h) | −3 |
| AMPKα1(h) | 17 |
| AMPKα2(h) | 5 |
| Arg(m) | −2 |
| ARK5(h) | 2 |
| ASK1(h) | 112 |
| Aurora-A(h) | 7 |
| Aurora-B(h) | 1 |
| Aurora-C(h) | 21 |
| Axl(h) | 34 |
| Blk(h) | 9 |
| Blk(m) | 14 |
| Bmx(h) | 1 |
| BRK(h) | 33 |
| BrSK1(h) | 53 |
| BrSK2(h) | 44 |
| BTK(h) | 37 |
| BTK(R28H)(h) | 103 |
| CaMKI(h) | 90 |
| CaMKIIβ(h) | 99 |
| CaMKIIγ(h) | 87 |
| CaMKIδ(h) | 87 |
| CaMKIIδ(h) | 98 |
| CaMKIV(h) | 106 |
| CDK1/cyclinB(h) | 81 |
| CDK2/cyclinA(h) | 97 |
| CDK2/cyclinE(h) | 89 |
| CDK3/cyclinE(h) | 59 |
| CDK5/p25(h) | 60 |
| CDK5/p35(h) | 77 |
| CDK6/cyclinD3(h) | 65 |
| CDK7/cyclinH/MAT1 (h) | 44 |
| CDK9/cyclin T1(h) | 52 |
| CHK1(h) | 113 |
| CHK2(h) | 95 |
| CHK2(I157T)(h) | 112 |
| CHK2(R145W)(h) | 91 |
| CKIγ1(h) | 96 |
| CKIγ2(h) | 134 |
| CKIγ3 (h) | 117 |
| CKIδ(h) | 91 |
| CK1(y) | 100 |
| CK2(h) | 85 |
| CK2α2(h) | 115 |
| CLK2(h) | 90 |
| CLK3(h) | 87 |
| cKit(h) | 84 |
| cKit(D816V)(h) | 63 |
| cKit(D816H)(h) | 9 |
| cKit(V560G)(h) | 3 |
| cKit(V654A)(h) | 32 |
| CSK(h) | 75 |
| c-RAF(h) | 94 |
| cSRC(h) | 2 |
| DAPK1(h) | 88 |
| DAPK2(h) | 106 |
| DCAMKL2(h) | 87 |
| DDR2(h) | 9 |
| DMPK(h) | 102 |
| DRAK1(h) | 51 |
| DYRK2(h) | 96 |
| eEF-2K(h) | 86 |
| EGFR(h) | 108 |
| EGFR(L858R)(h) | 72 |

TABLE 2-continued

| Kinase | Km NTW-3475@ 0.1 μM |
|---|---|
| EGFR(L861Q)(h) | 52 |
| EGFR(T790M)(h) | 61 |
| EGFR(T790M,L858R)(h) | 17 |
| EphA1(h) | 12 |
| EphA2(h) | −1 |
| EphA3(h) | 22 |
| EphA4(h) | 23 |
| EphA5(h) | 122 |
| EphA7(h) | 54 |
| EphA8(h) | 16 |
| EphB2(h) | 21 |
| EphB1(h) | −1 |
| EphB3(h) | 99 |
| EphB4(h) | 14 |
| ErbB4(h) | 90 |
| FAK(h) | 78 |
| Fer(h) | 69 |
| Fes(h) | 32 |
| FGFR1(h) | −1 |
| FGFR1(V561M)(h) | −4 |
| FGFR2(h) | 0 |
| FGFR2(N549H)(h) | −1 |
| FGFR3(h) | 0 |
| FGFR4(h) | 19 |
| Fgr(h) | 2 |
| Flt1(h) | 11 |
| Flt3(D835Y)(h) | 0 |
| Flt3(h) | 1 |
| Flt4(h) | 0 |
| Fms(h) | 8 |
| Fms(Y969C)(h) | 4 |
| Fyn(h) | 1 |
| GCK(h) | 13 |
| GRK5(h) | 100 |
| GRK6(h) | 69 |
| GRK7(h) | 97 |
| GSK3α(h) | 96 |
| GSK3β(h) | 106 |
| Haspin(h) | 96 |
| Hck(h) | 18 |
| Hck(h) activated | 12 |
| HIPK1(h) | 91 |
| HIPK2(h) | 101 |
| HIPK3(h) | 88 |
| IGF-1R(h) | 5 |
| IGF-1R(h), activated | 18 |
| IKKα(h) | 102 |
| IKKβ(h) | 109 |
| IR(h) | 30 |
| IR(h), activated | 13 |
| IRR(h) | 6 |
| IRAK1(h) | 96 |
| IRAK4(h) | 67 |
| Itk(h) | 29 |
| JAK2(h) | 8 |
| JAK3(h) | 3 |
| JNK1α1(h) | 92 |
| JNK2α2(h) | 107 |
| JNK3(h) | 111 |
| KDR(h) | 14 |
| Lck(h) | −8 |
| Lck(h) activated | −1 |
| LIMK1(h) | 15 |
| LKB1(h) | 98 |
| LOK(h) | 20 |
| Lyn(h) | 5 |
| Lyn(m) | 1 |
| MAPK1(h) | 128 |
| MAPK2(h) | 105 |
| MAPK2(m) | 101 |
| MAPKAP-K2(h) | 105 |
| MAPKAP-K3(h) | 103 |
| MEK1(h) | 63 |
| MARK1(h) | 28 |
| MELK(h) | 40 |
| Mer(h) | 2 |
| Met(h) | 11 |
| Met(D1246H)(h) | 18 |
| Met(D1246N)(h) | 20 |
| Met(M1268T)(h) | 22 |
| Met(Y1248C)(h) | 20 |
| Met(Y1248D)(h) | 21 |
| Met(Y1248H)(h) | 16 |
| MINK(h) | 75 |
| MKK4(m) | 100 |
| MKK6(h) | 113 |
| MKK7β(h) | 97 |
| MLCK(h) | 110 |
| MLK1(h) | 7 |
| Mnk2(h) | 92 |
| MRCKα(h) | 102 |
| MRCKβ(h) | 108 |
| MSK1(h) | 104 |
| MSK2(h) | 90 |
| MSSK1(h) | 110 |
| MST1(h) | 24 |
| MST2(h) | 79 |
| MST3(h) | 9 |
| mTOR(h) | 115 |
| mTOR/FKBP12(h) | 63 |
| MuSK(h) | 48 |
| NEK2(h) | 101 |
| NEK3(h) | 82 |
| NEK6(h) | 90 |
| NEK7(h) | 98 |
| NEK11(h) | 102 |
| NLK(h) | 96 |
| p70S6K(h) | 84 |
| PAK2(h) | 65 |
| PAK4(h) | 70 |
| PAK5(h) | 29 |
| PAK6(h) | 85 |
| PAR-1Bα(h) | 15 |
| PASK(h) | 91 |
| PEK(h) | 103 |
| PDGFRα(h) | 67 |
| PDGFRα(D842V)(h) | 17 |
| PDGFRα(V561D)(h) | 8 |
| PDGFRβ(h) | 89 |
| PDK1(h) | 103 |
| PhKγ2(h) | 77 |
| Pim-1(h) | 114 |
| Pim-2(h) | 96 |
| Pim-3(h) | 99 |
| PKA(h) | 111 |
| PKBα(h) | 109 |
| PKBβ(h) | 97 |
| PKBγ(h) | 106 |
| PKCα(h) | 95 |
| PKCβ1(h) | 92 |
| PKCβII(h) | 109 |
| PKCγ(h) | 102 |
| PKCδ(h) | 90 |
| PKC□(h) | 99 |
| PKC□(h) | 101 |
| PKC□(h) | 105 |
| PKCμ(h) | 95 |
| PKC□(h) | 109 |
| PKCζ(h) | 109 |
| PKD2(h) | 94 |
| PKG1α(h) | 100 |
| PKGIβ(h) | 111 |
| Plk1(h) | 107 |
| Plk3(h) | 95 |
| PRAK(h) | 100 |
| PRK2(h) | 30 |
| PrKX(h) | 68 |
| PTK5(h) | 17 |
| Pyk2(h) | 59 |
| Ret(h) | −1 |
| Ret (V804L)(h) | −4 |
| Ret(V804M)(h) | 0 |
| RIPK2(h) | 90 |
| ROCK-I(h) | 93 |
| ROCK-II(h) | 58 |
| ROCK-II(r) | 42 |

TABLE 2-continued

| Kinase | Km NTW-3475@ 0.1 μM |
|---|---|
| Ron(h) | 34 |
| Ros(h) | 46 |
| Rse(h) | 55 |
| Rsk1(h) | 84 |
| Rsk1(r) | 69 |
| Rsk2(h) | 65 |
| Rsk3(h) | 25 |
| Rsk4(h) | 66 |
| SAPK2a(h) | 79 |
| SAPK2a(T106M)(h) | 95 |
| SAPK2b(h) | 103 |
| SAPK3(h) | 115 |
| SAPK4(h) | 91 |
| SGK(h) | 107 |
| SGK2(h) | 107 |
| SGK3(h) | 102 |
| SIK(h) | 33 |
| Snk(h) | 97 |
| Src(1-530)(h) | −2 |
| Src(T341M)(h) | 1 |
| SRPK1(h) | 96 |
| SRPK2(h) | 99 |
| STK33(h) | 101 |
| Syk(h) | 84 |
| TAK1(h) | 65 |
| TAO1(h) | 65 |
| TAO2(h) | 6 |
| TAO3(h) | 16 |
| TBK1(h) | 28 |
| Tec(h) activated | 52 |
| TGFBR1(h) | 44 |
| Tie2 (h) | 0 |
| Tie2(R849W)(h) | 6 |
| Tie2(Y897S)(h) | 3 |
| TLK2(h) | 5 |
| TrkA(h) | 2 |
| TrkB(h) | 1 |
| TSSK1(h) | 86 |
| TSSK2(h) | 84 |
| Txk(h) | 20 |
| ULK2(h) | 46 |
| ULK3(h) | 11 |
| WNK2(h) | 99 |
| WNK3(h) | 86 |
| VRK2(h) | 99 |
| Yes(h) | 0 |
| ZAP-70(h) | 110 |
| ZIPK(h) | 104 |

NTW-3475 showed strong kinase inhibition for a wide range of kinases (Table 2 and FIGS. 1-2), including mutant kinases wherein the mutations thought to be critical for their transformation of the cancer cells they isolated from were tested and, in particular, mutant abl kinases for which no inhibitors were known (FIG. 2).

Example 130

NTW-3475 was also tested for its antiproliferative potential using cell lines from the NCI 60 cancer cell line panel.

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Additional four, 10-fold or ½ A log serial dilutions are made to provide a total of five drug concentrations plus control. Aliquots of 100 μl of these different drug dilutions are added to the appropriate microtiter wells already containing 100 μl of medium, resulting in the required final drug concentrations.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

$[(Ti-Tz)/(C-Tz)] \times 100$ for concentrations for which $Ti >/= Tz$ $[(Ti-Tz)/Tz] \times 100$ for concentrations for which $Ti < Tz$.

Three dose response parameters are calculated for each experimental agent. Growth inhibition of 50% (GI50) is calculated from $[(Ti-Tz)/(C-Tz)] \times 100 = 50$, which is the drug concentration resulting in a 50% reduction in the net protein increase (as measured by SRB staining) in control cells during the drug incubation.

As shown in FIG. 3 NTW-3475 demonstrated strong antiproliferative activity (shown by % of control) in at least 13 of the 16 cell lines studied. This antiproliferative effect was seen a range of cell lines including cell lines from Chronic Myelogenous Leukemia, Acute Myelogenous Leukemia, Thyroid, Endometrial, Gastric, Breast and Pancreatic Carcinomas.

Example 131

This example assesses NTW-3475's anti-tumor activity using a SCID mouse xenograft models for leukemias and nude mouse xenograft models of endometrial, pancreatic and thyroid carcinomas. NTW-3475 combination therapy was also studied in murine xenografts.

The objective of the first study was to evaluate antitumor activities of the novel multiple-kinase inhibitor NTW-3475 against human MV411 human acute myelogenous leukemia (AML) xenograft model in female SCID mice.

Four or six animals were randomly assigned to each study group. Each animal was injected subcutaneously in the left and right flank area with 0.1 ml of 1.0×10$^8$ MV411 cells per mL.

Each test or control animal was placed on a 5-day on, two-day off for two cycles of vehicle negative control or 25, 50 mg/kg of NTW-3475. Tumor growth was measured with a digital hand held caliper twice weekly (once tumor emerges) prior to the first dosing and then two to three times weekly until euthanized. Animals were weighed prior to tumor cell injection, prior to dosing, two to three times weekly with tumor growth measurements, and prior to euthanasia.

Figure 4:
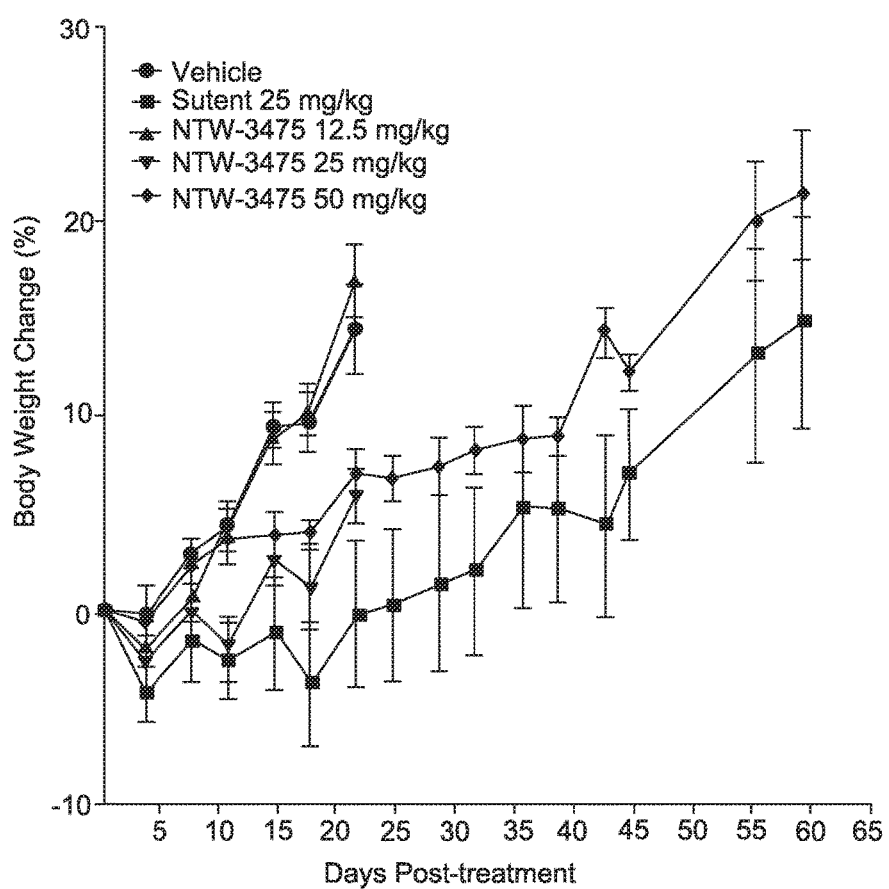
FIG. 4 depicts the animal's body weight change in a xenograft study of the treatment of Acute Myleogenous Leukemia (AML) with NTW-3475 (body weight change is a marker for overall toxicity.)
Figure 5:
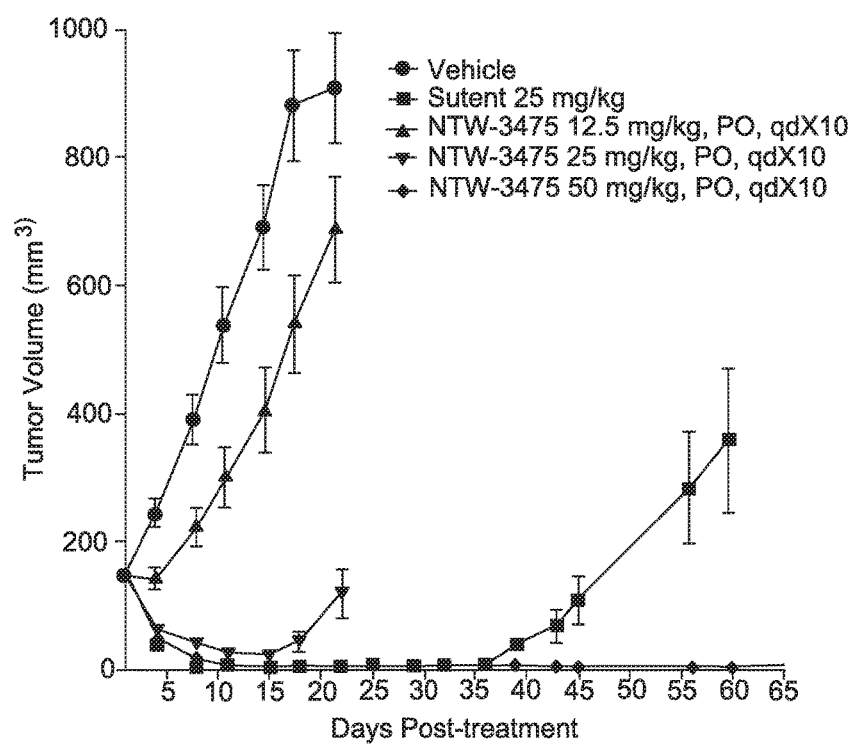
FIG. 5 depicts the tumor volume curve for NTW-3475 in the AML study, showing anti-tumor activity.
Figure 6:
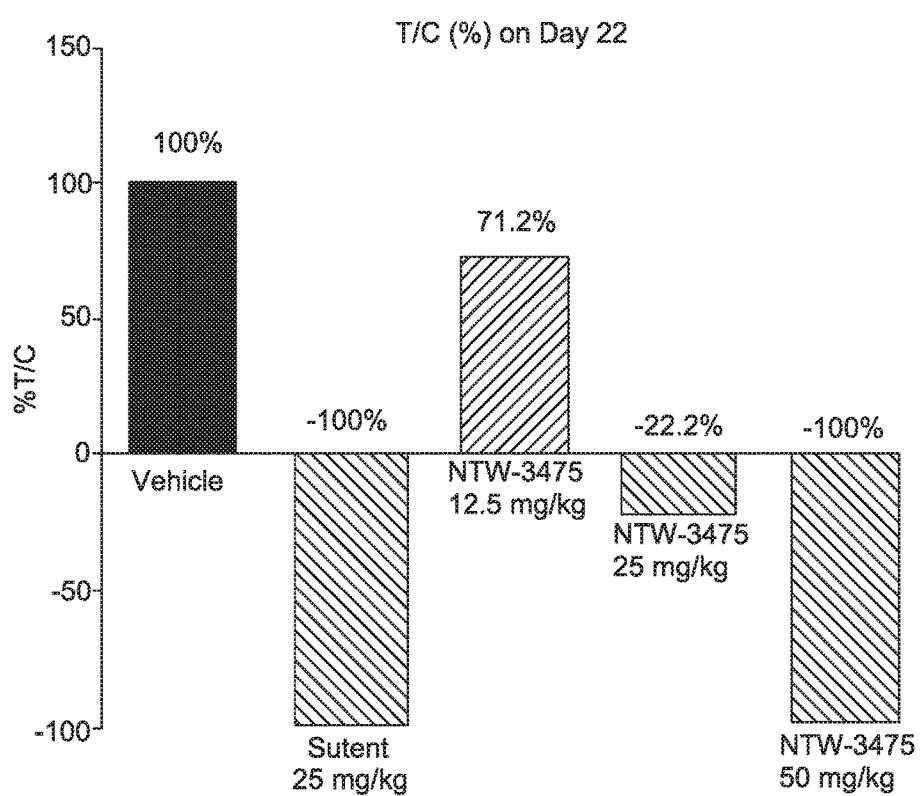
FIG. 6 depicts the relative antitumor activity of NTW-3475 in terms of the volume of tumor in animals treated with NTW-3475/volume of the AML tumor given only negative control agents.

The results are shown in FIGS. 4 (tumor weight over time), 5 (tumor volume over time), and 6 (T/C at day 22). The results indicate that NTW-3475 has a strong anti-tumor effect against AML with minimal body weight lost.

The objective of the second study was to evaluate anti-tumor activities of novel multiple-kinase inhibitor NTW-3475 in human K562 chronic myelogenous leukemia (CML) xenograft model in female SCID mice.

Four to six animals were randomly assigned to study groups. Each animal was weighed, and then injected subcutaneously in the left and right flank area with 0.1 ml of 8.0×10$^7$ K562 cells per mL.

Figure 7:
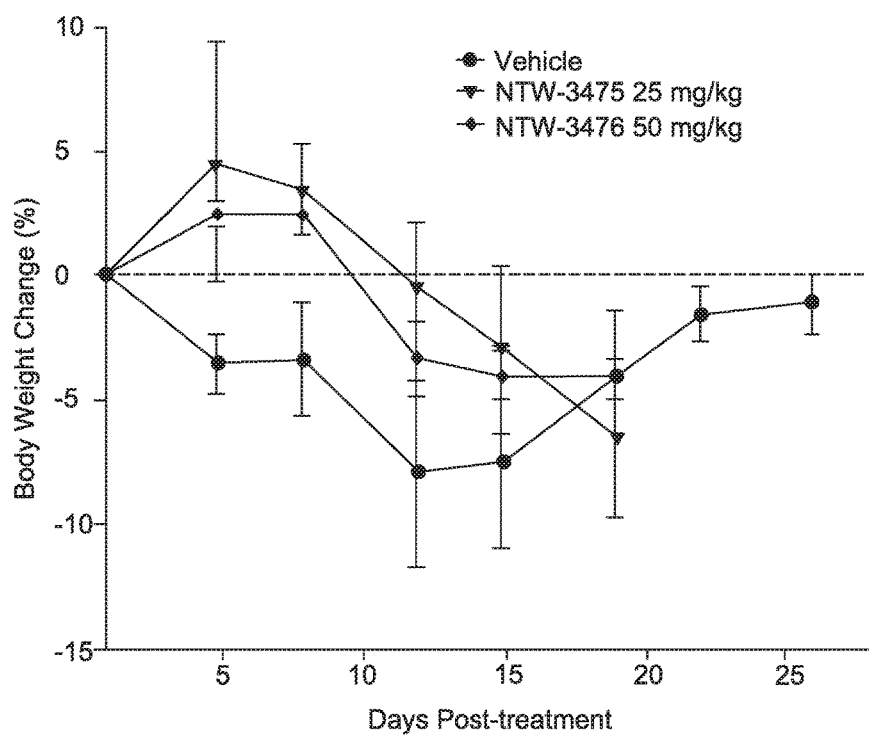
FIG. 7 depicts the animals' body weight change in the xenograft study of the utility of NTW-3475 in treating Chronic Myelogenous Leukemia (CML).
Figure 8:
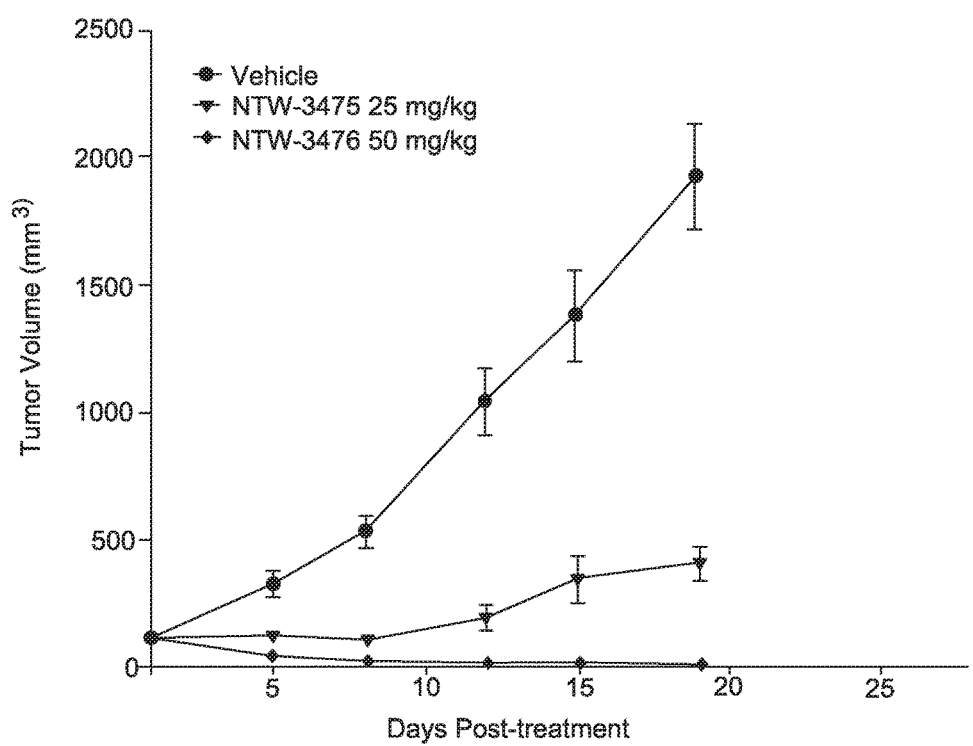
FIG. 8 depicts the tumor volume curve versus (v.) time for NTW-3475 treated and control mice in a xenograft study of Pancreatic Carcinoma.

Each test or control animal was on a 5-day on, two-day off for two cycles treatment schedule. Tumor growth was measured with a digital hand held caliper twice weekly (once tumor emerges) prior to the first dosing and then two to three times weekly until euthanized. Animals were weighed prior to tumor cell injection, prior to dosing, two to three times weekly with tumor growth measurements, and prior to euthanasia. The results are shown in FIGS. 7 and 8. The results show that NTW-3475 has a strong anti-tumor effect against CML in this model system.

The objective of the third study was to evaluate antitumor activities of novel multiple-kinase inhibitor NTW-3475 in human MIAPaCa-2 pancreatic carcinoma xenograft in athymic nude-Faxn1 mice.

Four animals were randomly assigned to study groups. Each animal was weighed, and then injected subcutaneously in the left and right flank area with 0.1 ml of 5.0×10$^7$ MIAPaCa-2 cells per mL.

Figure 9:
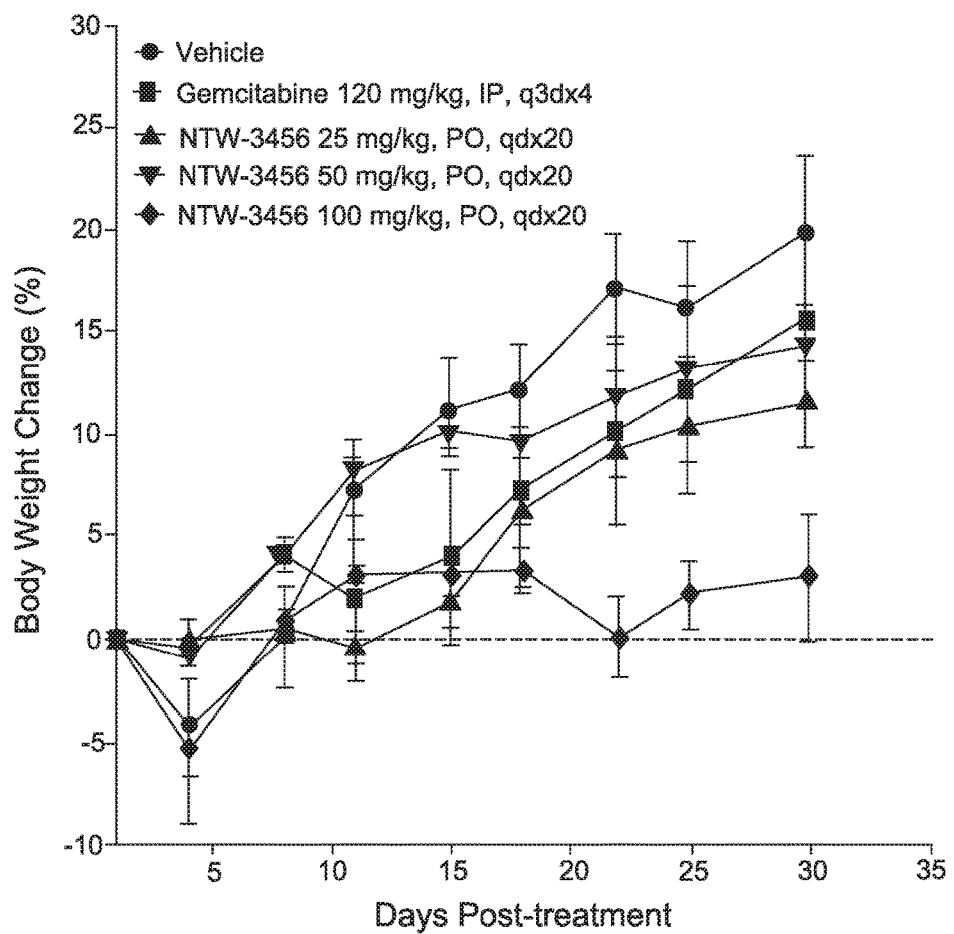
FIG. 9 depicts animals' body weight change in the xenograft with NTW-3475 (a marker for overall toxicity).
Figure 10:
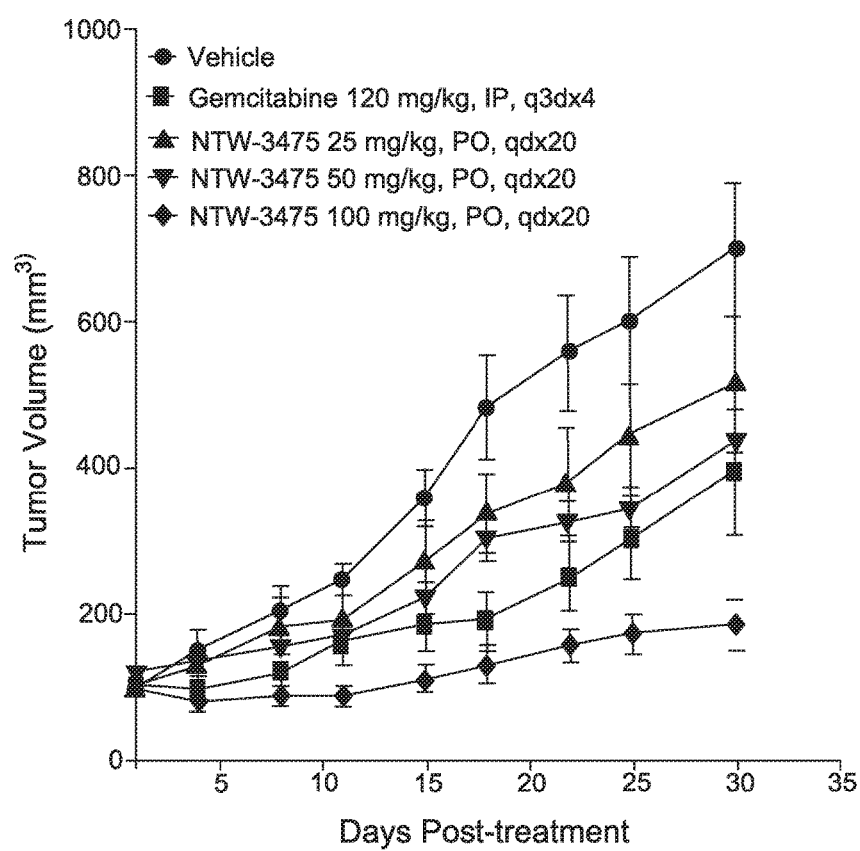
FIG. 10 depicts the relative antiproliferative activity of NTW-3475 in terms of volume of tumor in animals treated with NTW-3475/volume of tumor with NTW-3475 or a control agent.
Figure 11:
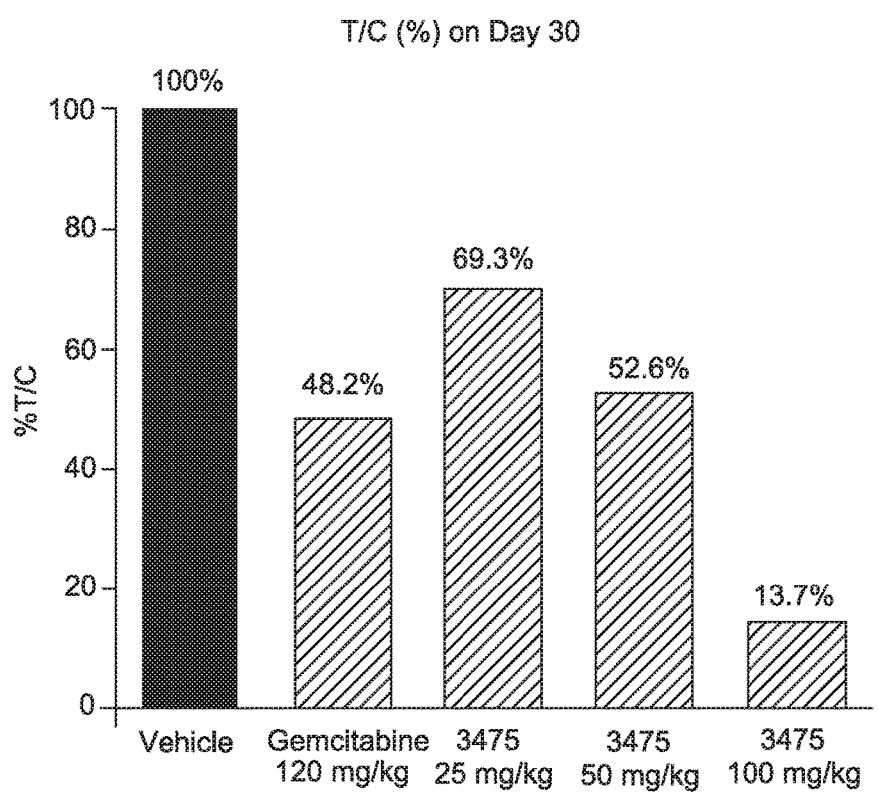
FIG. 11 depicts the relative antiproliferative activity of NTW-3475 in terms of volume of tumors in animals treated with NTW-3475/volume of tumor in animals with a control agent.

Each test or control animal was on a 5-day on, two-day off for two cycles treatment schedule with negative control vehicle, positive control Abraxane at 20 mg/kg or 25, 50 mg/kg of NTW-3475. Tumor growth was measured with a digital hand held caliper twice weekly (once tumor emerges) prior to the first dosing and then two to three times weekly until euthanized. The results are shown in FIGS. 9, 10 and 11 which indicate that NTW-3475 has a strong anti-tumor effect against pancreatic carcinoma cells in this model system.

Figure 12:
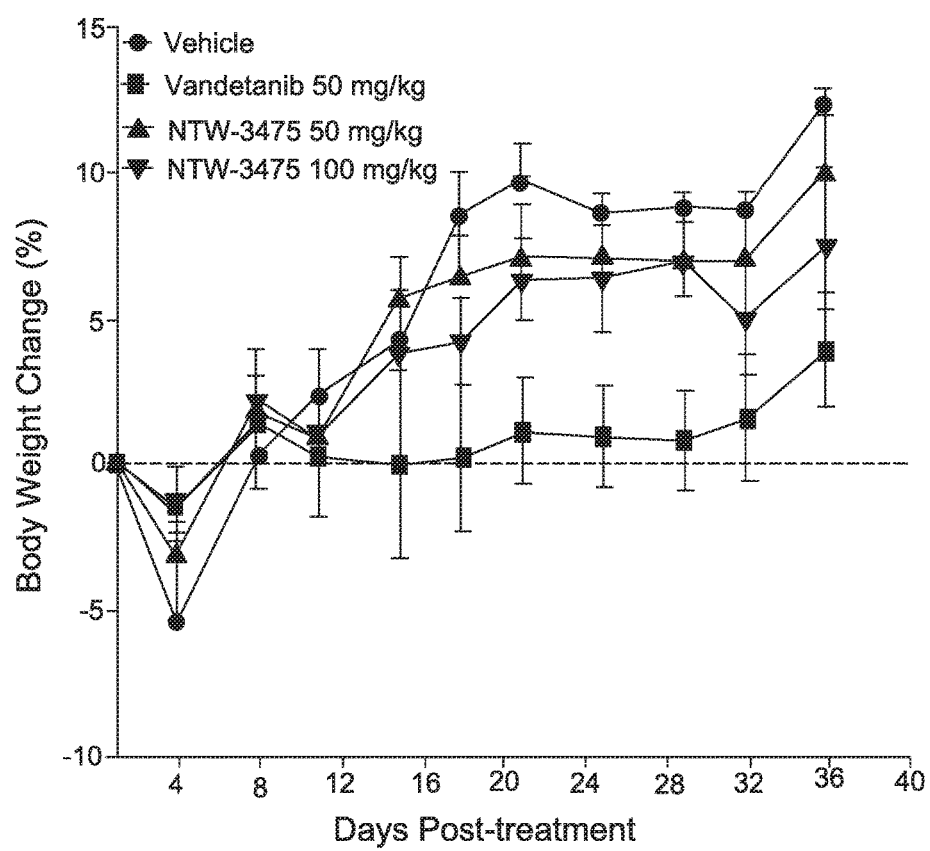
FIG. 12 depicts the weight curve for NTW-3475, in a study of its use in thyroid carcinoma.
Figure 13:
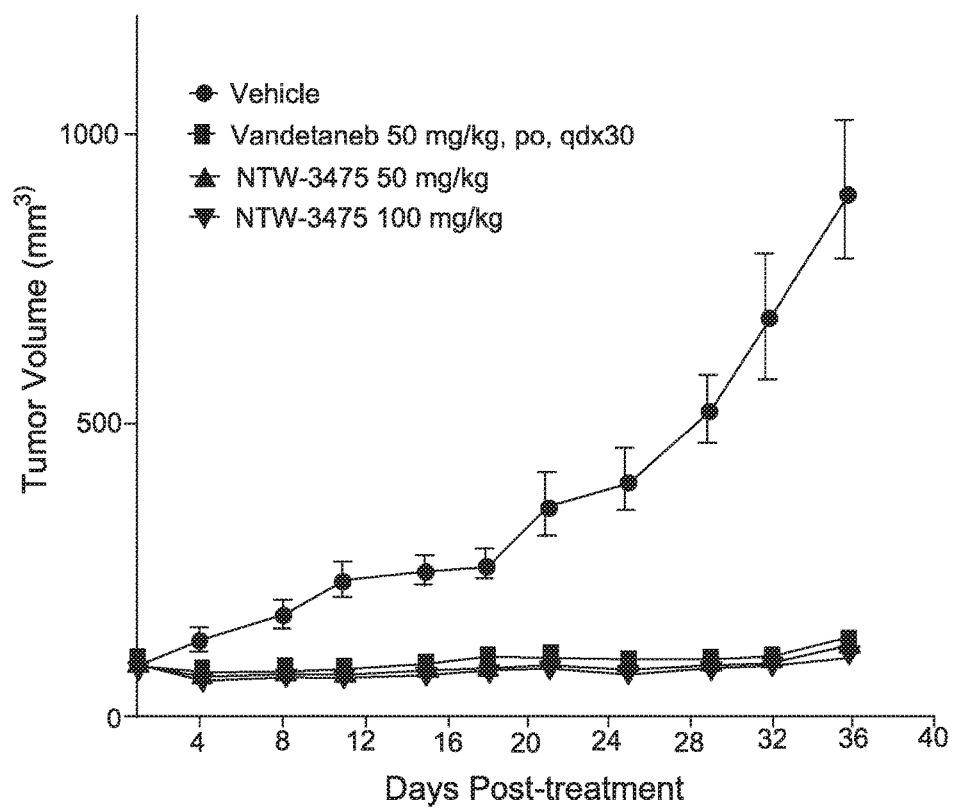
FIG. 13 depicts the tumor volume v. time curve for NTW-3475 treated thyroid cancer xenograft model.

NTW-3475 was similarly tested and shown to have an anti-tumor effect in TT human Thyroid carcinoma xenograft (FIGS. 12 and 13).

Figure 14:
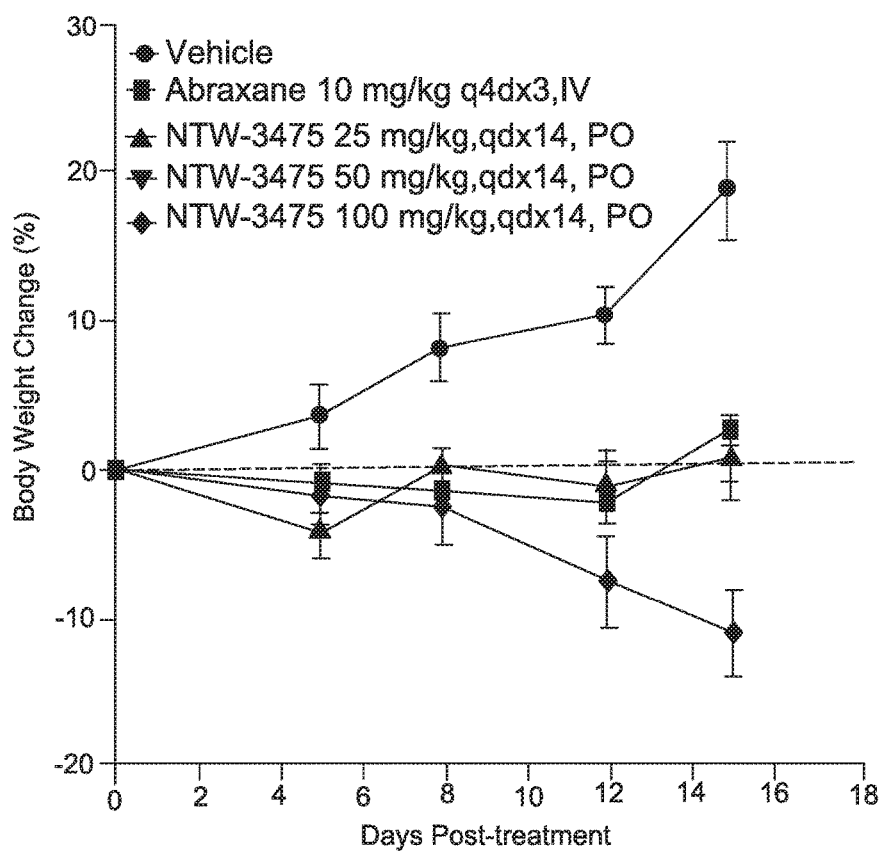
FIG. 14 depicts animals' weight while undergoing treatment with NTW-3475 alone or in combination with nanoparticulate albumin bound paclitaxel (Abraxane®) in a study of Endometrial carcinoma using a xenograft model.
Figure 15:
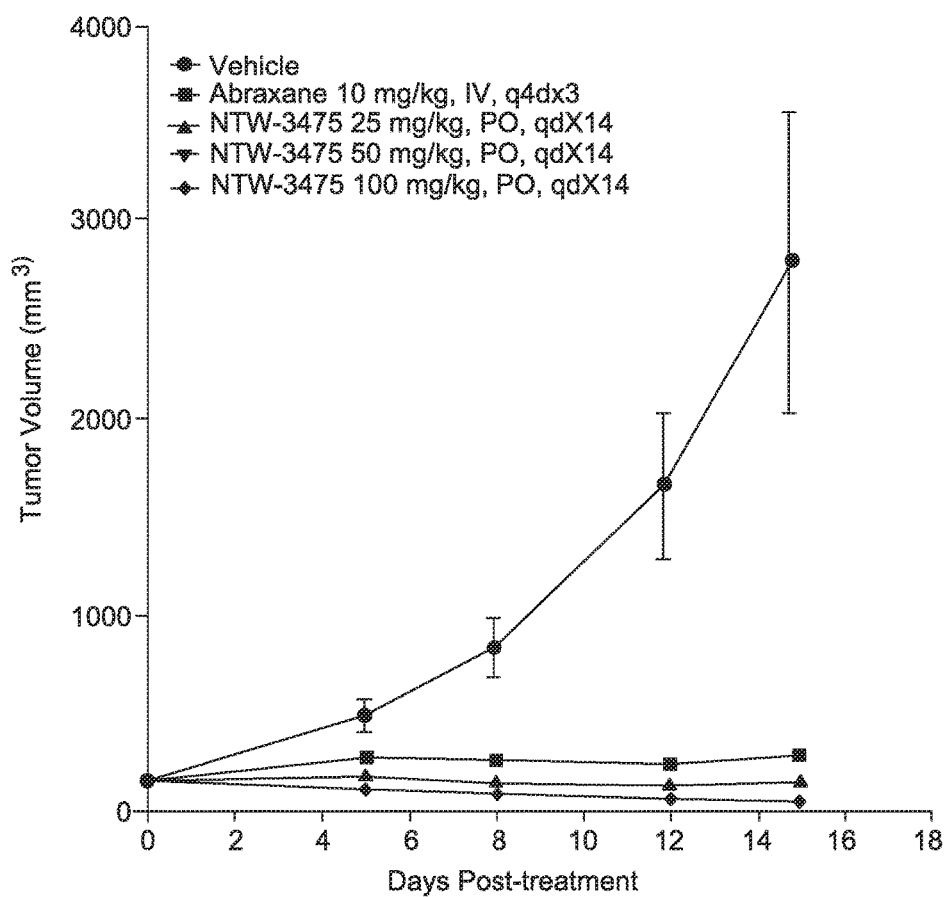
FIG. 15 depicts the tumor volume curves for NTW-3475 with or without Abraxane® in that study of Endometrial carcinoma.
Figure 16:
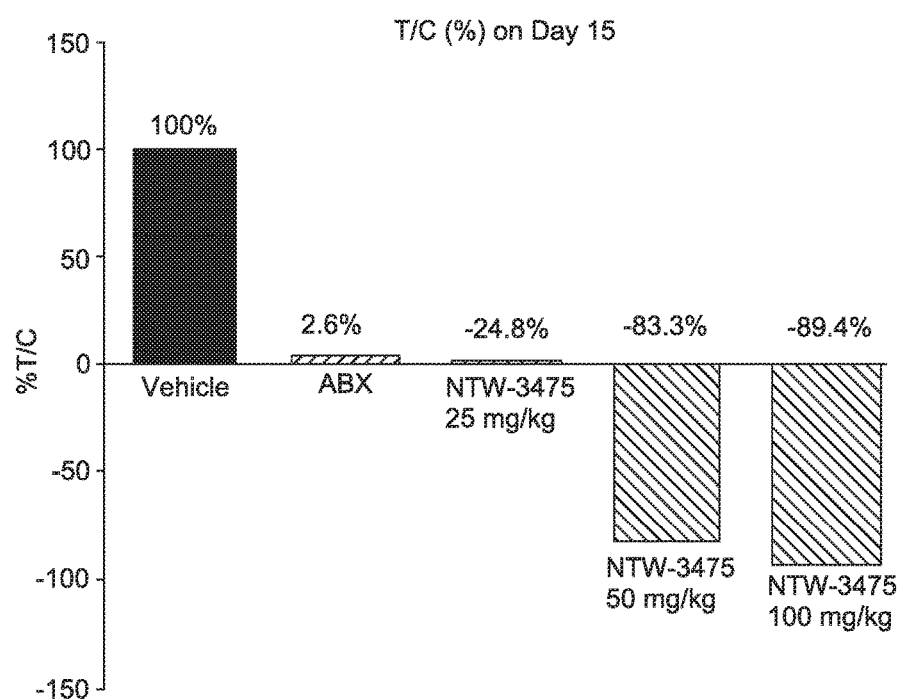
FIG. 16 depicts the relative antiproliferative activity of NTW-3475 and Abraxane®) in terms of volume of tumor in animals treated/volume of tumor in mice given a control agent from that study of Endometrial carcinoma model.

NTW-3475 was similarly tested and shown to have an anti-tumor effect in AN3 human endometrial carcinoma xenograft (FIGS. 14, 15, and 16).

Figure 17:
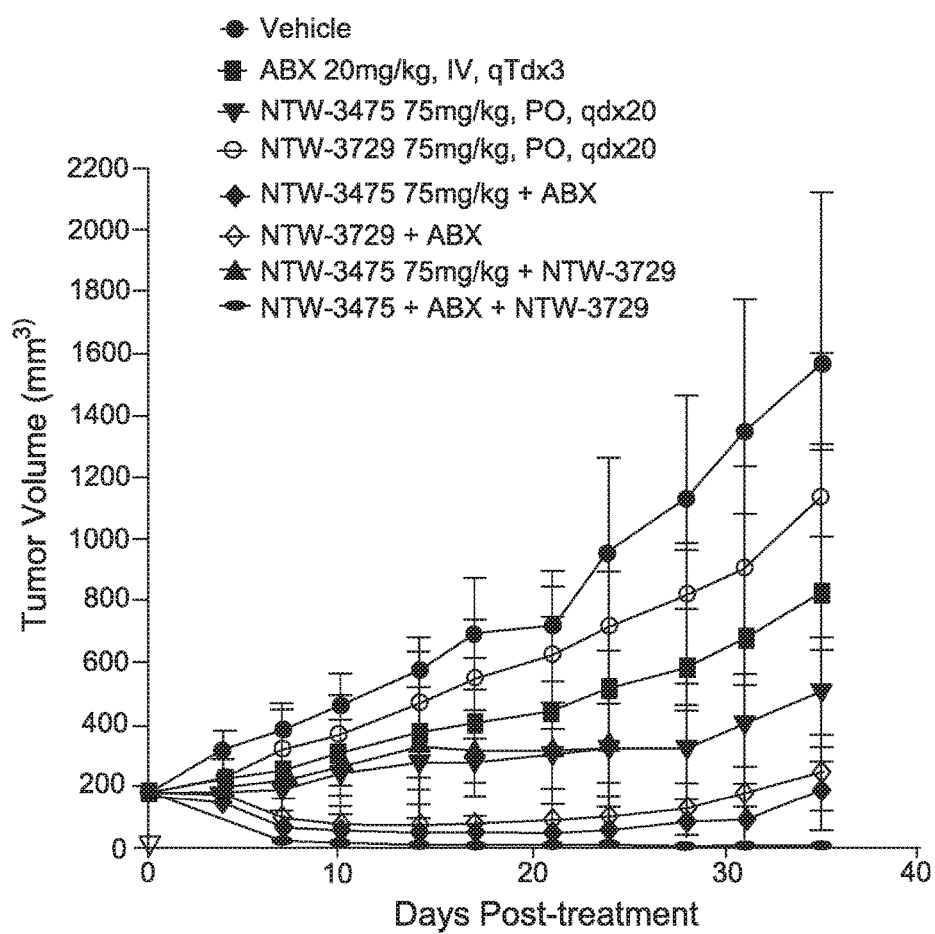
FIG. 17 depicts the tumor volume curve for NTW-3475 and the nanoparticulate, albumin bound paclitaxel, Abraxane®, for Pancreatic Carcinoma using a xenograft model.
Figure 18:
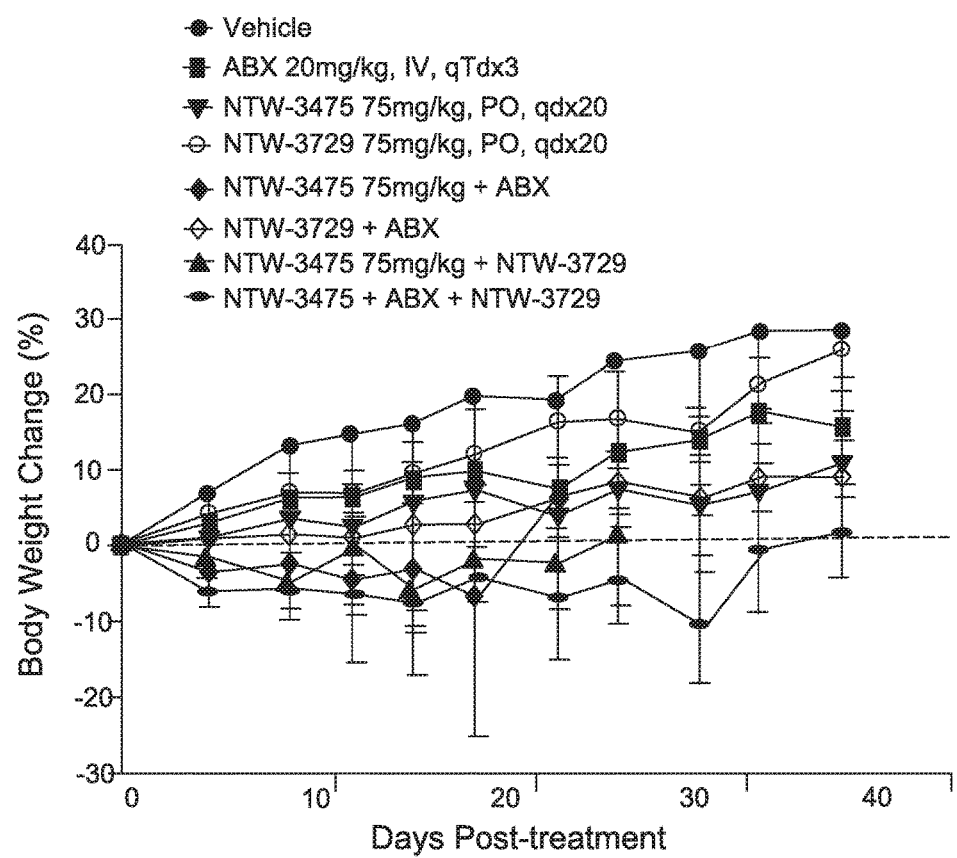
FIG. 18 depicts effect on animals' weight (a marker for overall toxicity) while undergoing Abraxane®-NTW-3475 combination therapy of Pancreatic Carcinoma using a xenograft model.
Figure 19:
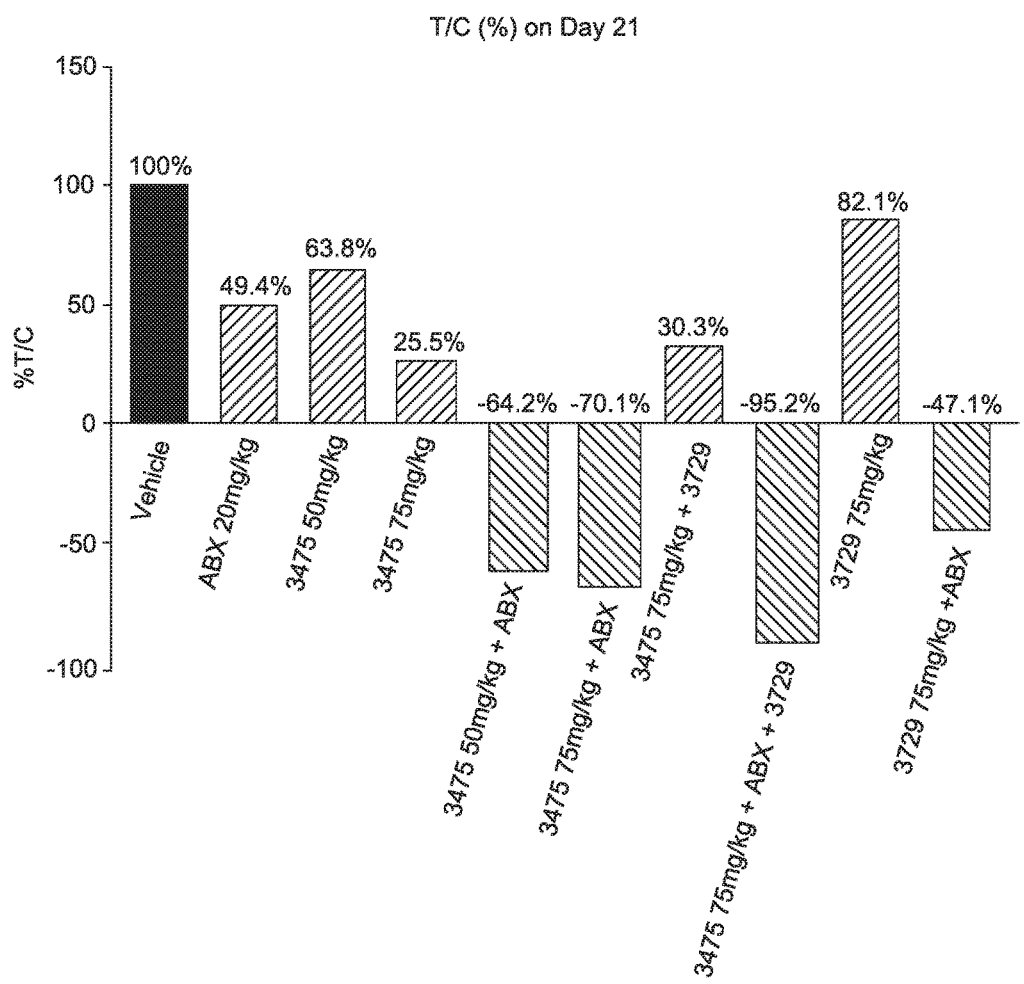
FIG. 19 depicts the % T/C for NTW-3475 and Abraxane®, in combination therapy using a xenograft model of Pancreatic Carcinoma.
Figure 27:
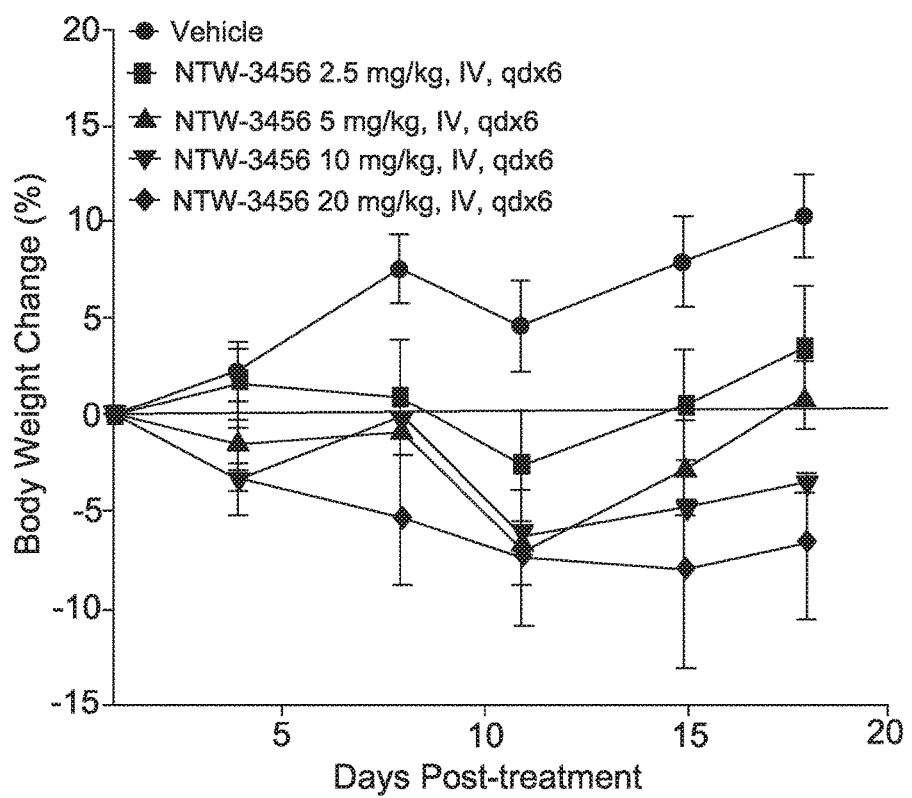
FIG. 27 depicts the animals' body weight change in the AMLxenograft with NTW-3456 (a marker for overall toxicity.)
Figure 28:
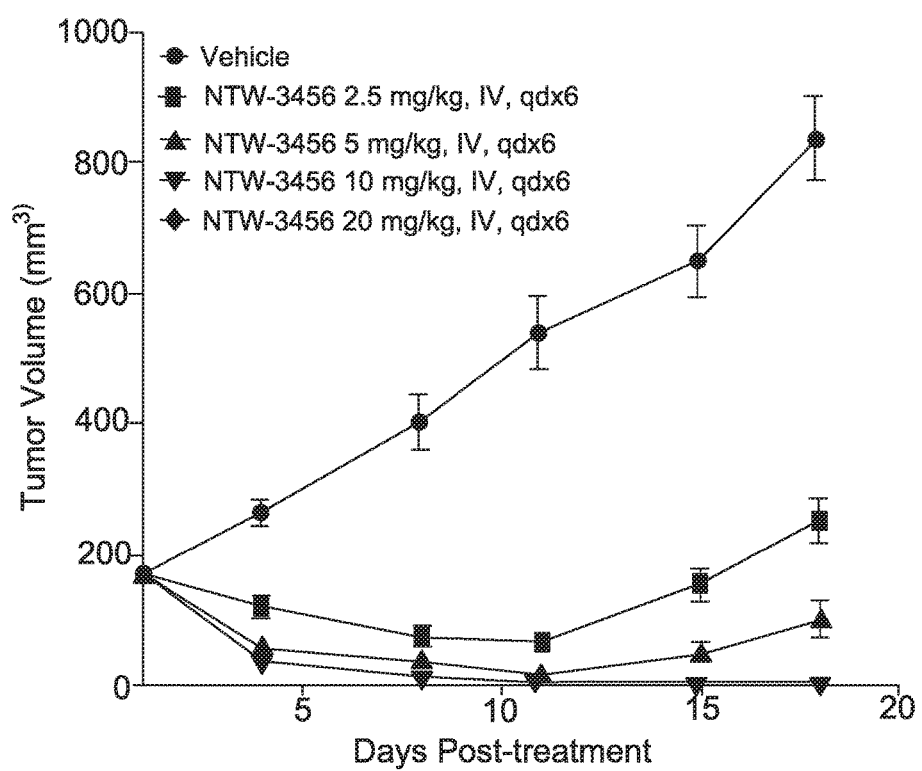
FIG. 28 depicts the tumor volume curve for NTW-3456 treated animals, showing anti-tumor activity in an AML model system.

NTW-3475 was similarly tested alone and in combination with Abraxane and the combination shown to have an anti-tumor effect in MIAPaCa-2 xenograft (FIGS. 17, 18 and 19).

Overall the kinase, proliferation, and xenografts studies indicate that NTW-3475 shows high cellular potency and targeting (FIG. 20) and NTW-3475 is active in vivo against AML, CML, thyroid, endometrial and some pancreatic carcinoma in xenograft model systems (FIG. 21).

Example 132

The embodiment of the invention disclosed in Example 87 (Compound 87), (also referred to herein as compound "NTW-3456") demonstrated strong inhibition of all the kinases in Example 128 and was chosen for further testing.

The first study was designed to assess the effect of NTW-3456 on kinase activity. Activity of NTW-3456 for a wide range of kinases and is shown FIGS. 22-24, including mutant kinases thought to play a large role in neoplastic transformation (FIGS. 23 and 24). In addition, NTW-3456 inhibited kinase activity in abl mutants for which no prior inhibitors have been FDA approved. In particular, NTW-3456 inhibits the 2 T315I mutant for which no kinase inhibitor had been known prior to NTW-3456.

Example 133

NTW-3456 was tested for its effect on in vitro proliferation using the protocol for the 60 NCI Cancer Cell Lines used to test NTW-3475.

The NCI-60 DTP Human Tumor Cell Line Panel was used to further evaluate the biochemistry of NTW-3475 (see Shoemaker: *The NCI60 human tumour cell line anticancer drug screen*, Nature Reviews Cancer 6, 813-823 (1 Oct. 2006)). The effect of NTW-3456 on kinase activity was tested for a wide range of kinases and is shown in FIG. 25. Overall, NTW-3456 inhibited both phosphorylation and proliferation. Anti-proliferative activity from NTW-3456 was seen against AML, CML, thyroid, enodmetrial, gastric, breast, and some pancreatic carcinoma cell lines (FIG. 26).

Example 134

This example studies the anti-tumor activity of NTW-3456 in xenograft model systems for AML, CML, thyroid, endometrial, pancreatic carcinomas.

Figure 29:
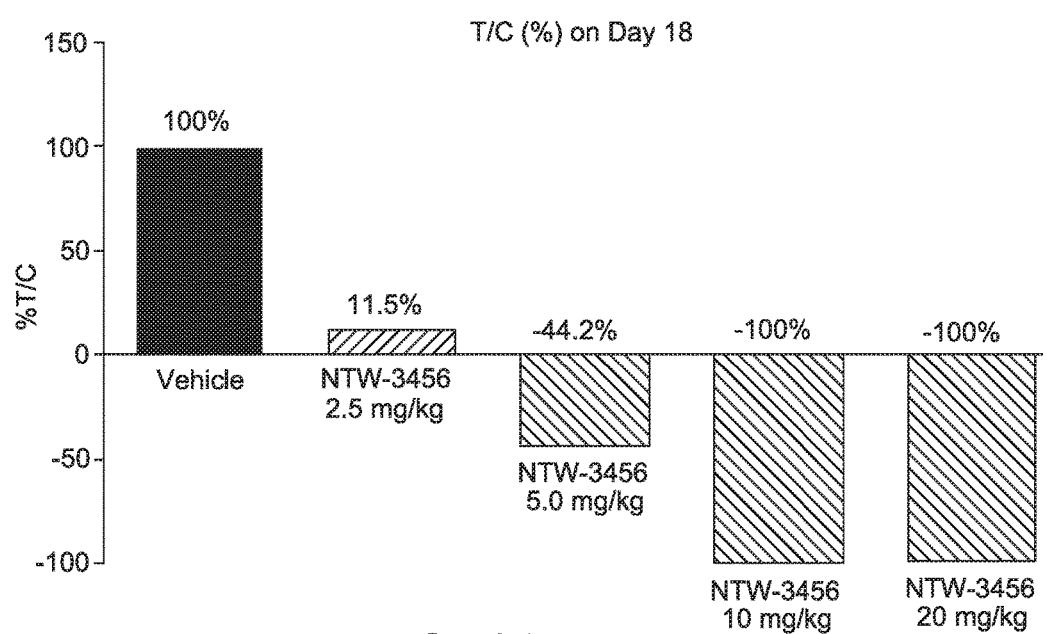
FIG. 29 depicts the antitumor activity of NTW-3456 in terms of tumor volume in treated/volume of tumor in untreated.
Figure 30:
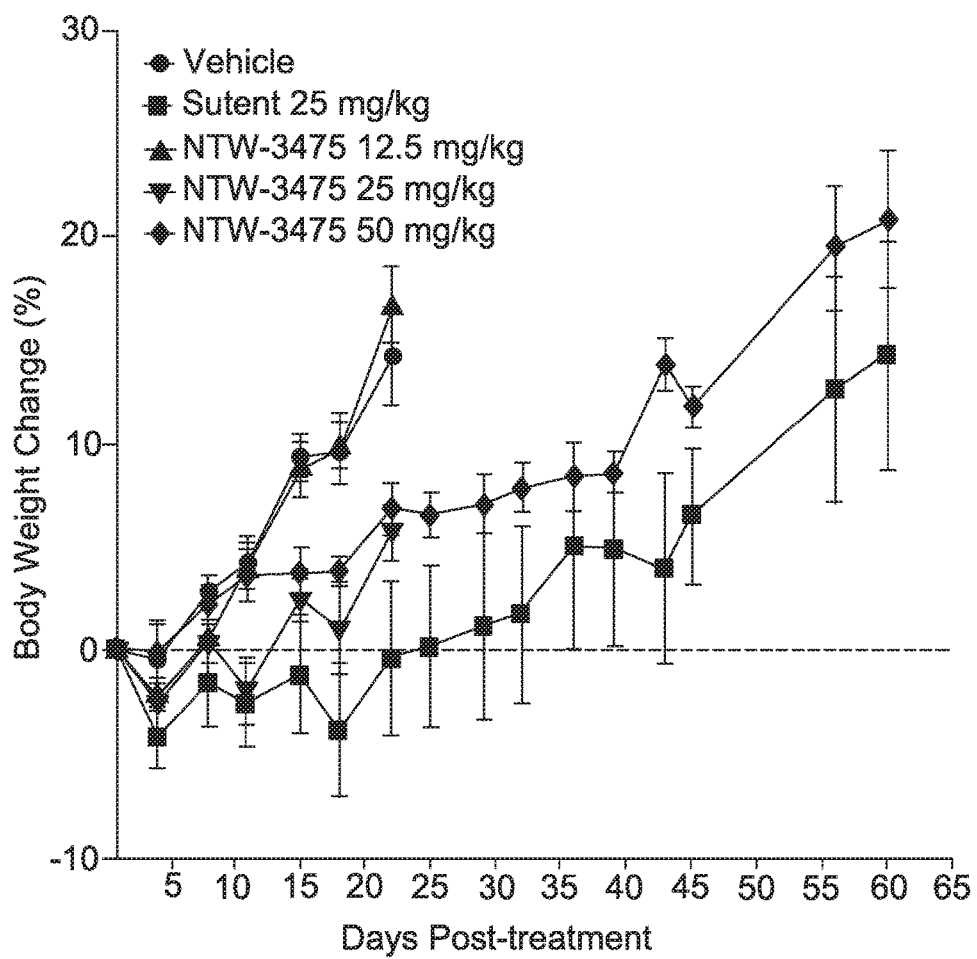
FIG. 30 depicts the animals' body weight change in the AMLxenograft with NTW-3456 (a marker for overall toxicity.)
Figure 31:
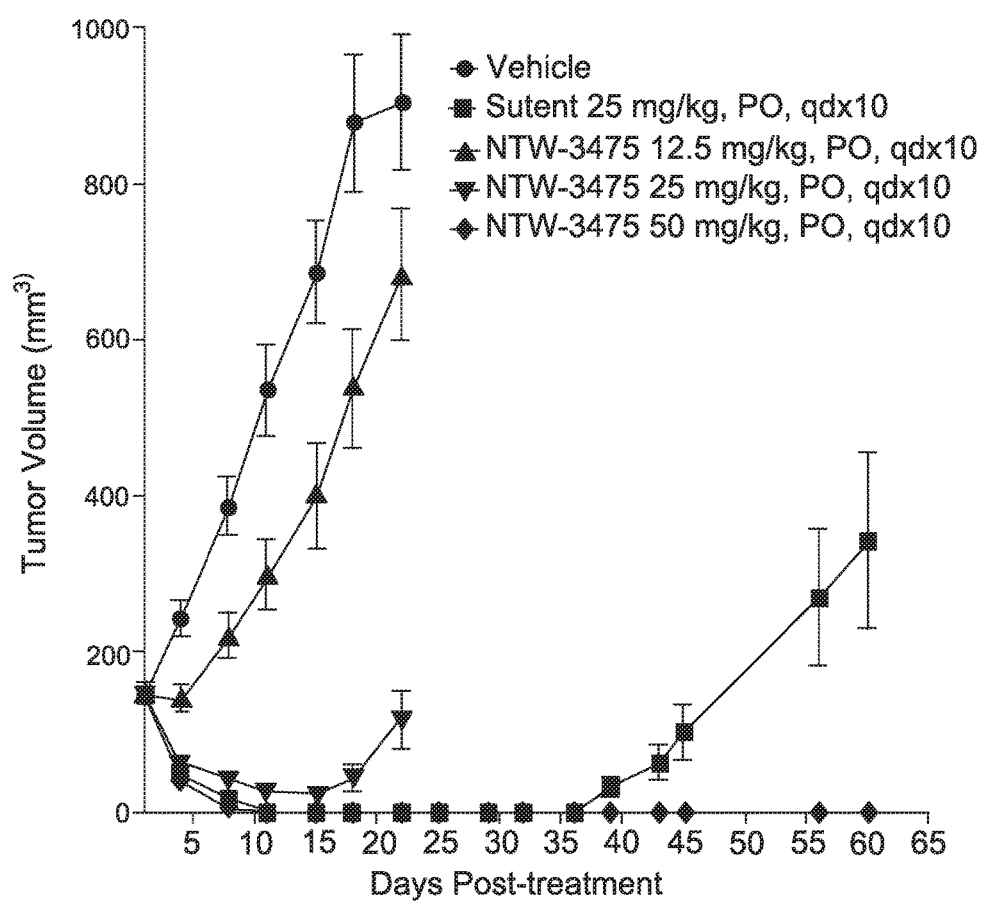
FIG. 31 depicts the tumor volume curve for NTW-3456 treated animals, showing anti-tumor activity in an AML model system.
Figure 32:
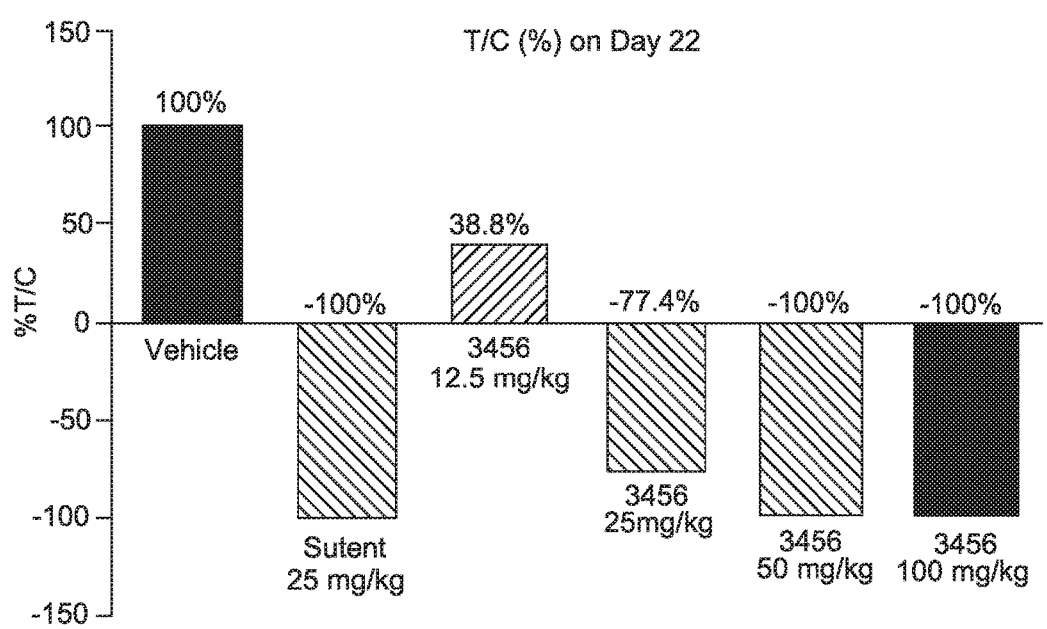
FIG. 32 depicts the tumor activity of NTW-3456 in terms of tumor volume in treated/volume of tumor in untreated.

FIGS. 27-32 depict the results of various concentrations of NTW-3456 on tumor growth in SCID mouse/xenograft model of AML using MV411 cells. In this model system, NTW-3456 demonstrates significant anti-tumor activity, especially at higher doses (FIGS. 29 and 32). This invention is characterized as it is here was a correlation between the inhibition of the pFLT3 kinase and growth control.

Figure 33:
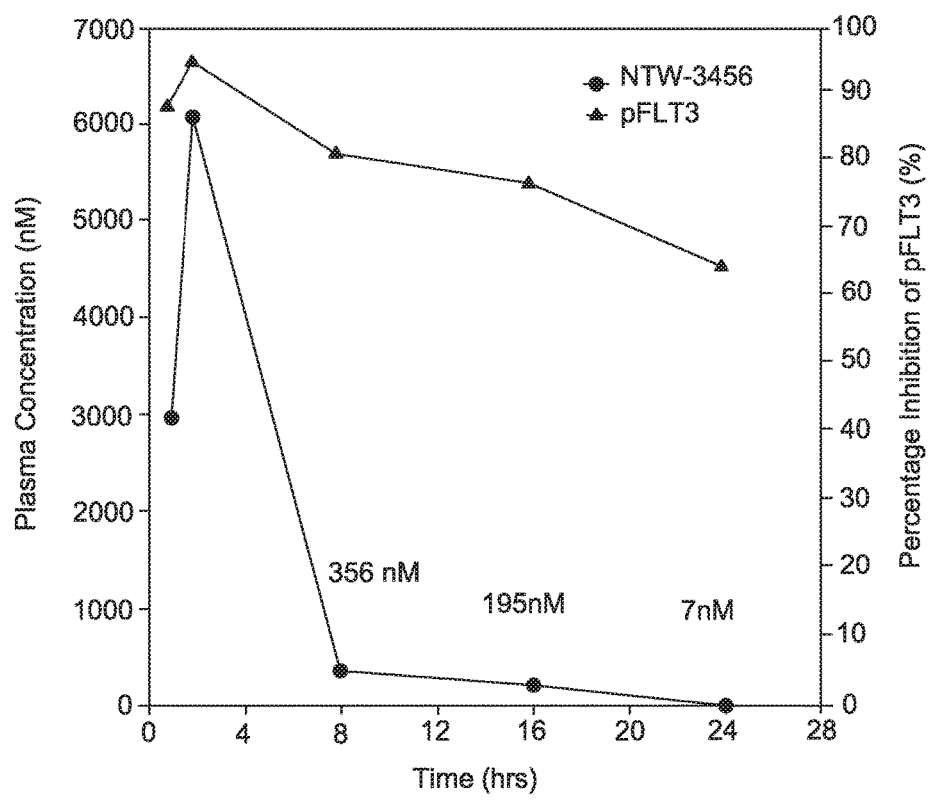
FIG. 33 demonstrates the correlation between PK and inhibition of pFlt3 in SCID mice bearing MV4-11 human acute myeloid leukemia following a single oral administration of 50 mg/kg NTW-3456.

The mice carrying the established MV4-11 tumor xenografts (tumor volume around 150 mm$^3$) were given an oral dose of 50 mg/kg NTW-3456. At 0, 1, 2, 8, 16, 24 hours after dosing, three were euthanized. The blood samples were collected and plasma was prepared with centrifuge for LCMS assay. And the tumors were harvested, homogenized in lysis buffer, immunoprecipitated with anti-FLT3 antibody FIG. 33.

The curve (solid dot) is the plot of plasma concentration-time profiles of NTW-3456 after oral administration of 50 mg/kg. The top curve (solid triangle) showed NTW-3456 inhibit FLT3 phosphorylation (pFLT3) of MV4-11 tumors after oral administration of 50 mg/kg NTW-3456 at indicated time.

NTW-3456 inhibits FLT3 phosphorylation in vivo and it is time-dependent. After 24 hour, NTW-3456 (7 nM in plasma) still inhibits more than 60% FLT3 phoseporylation of MV4-11 tumor.

Figure 34:
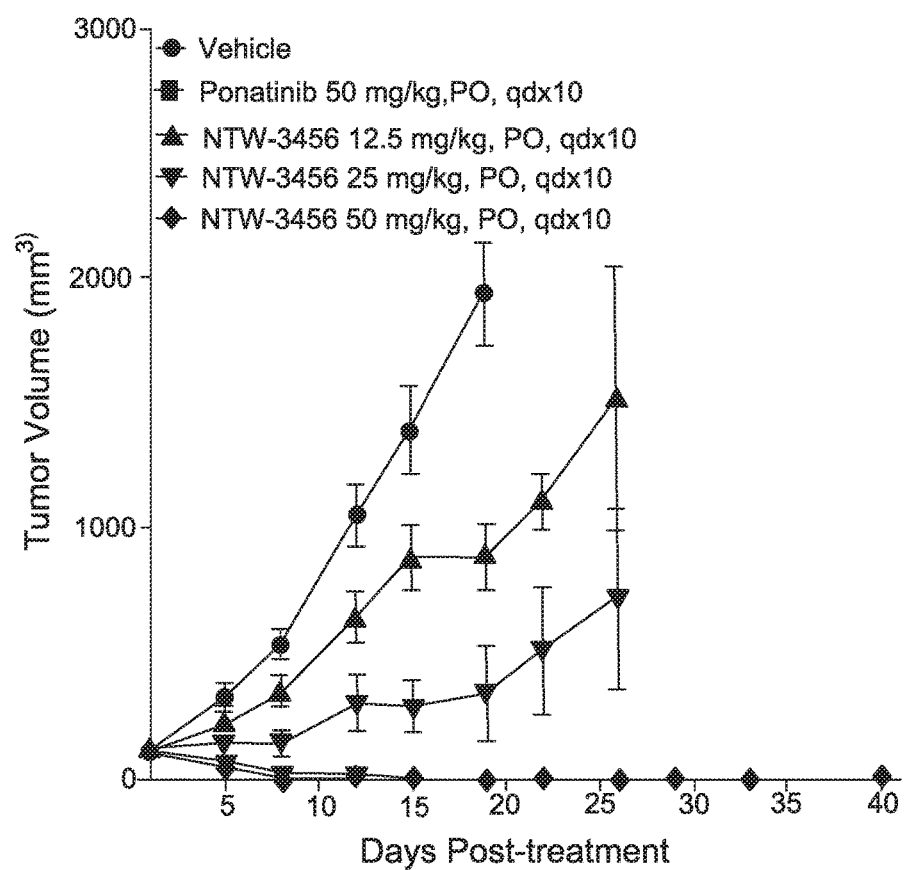
FIG. 34 depicts the tumor volume curve for NTW-3456 treated and control animals, showing anti-tumor activity in a CML model system.
Figure 35:
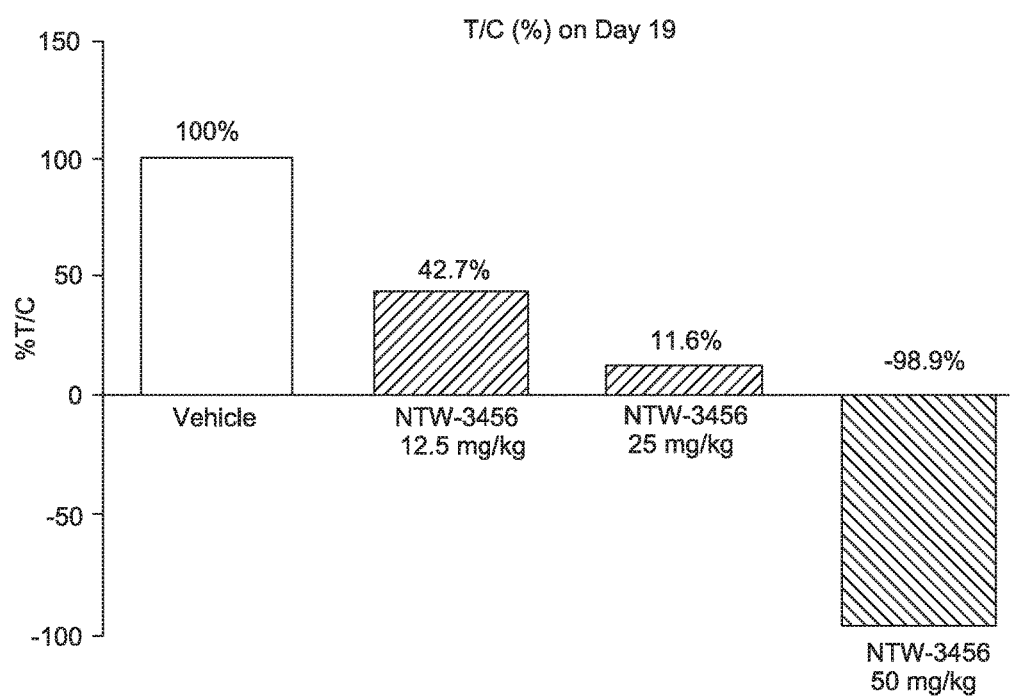
FIG. 35 depicts the tumor activity of NTW-3456 in terms of volume of tumor volume in treated/volume of tumor in controlin a CML model system.

FIGS. 34 and 35 depict the results of various concentrations of NTW-3456 on a SCID mouse/xenograft model of CML using K562 cells. In this model system, NTW-3456 demonstrates significant anti-tumor activity, especially at higher doses (FIG. 34).

Figure 36:
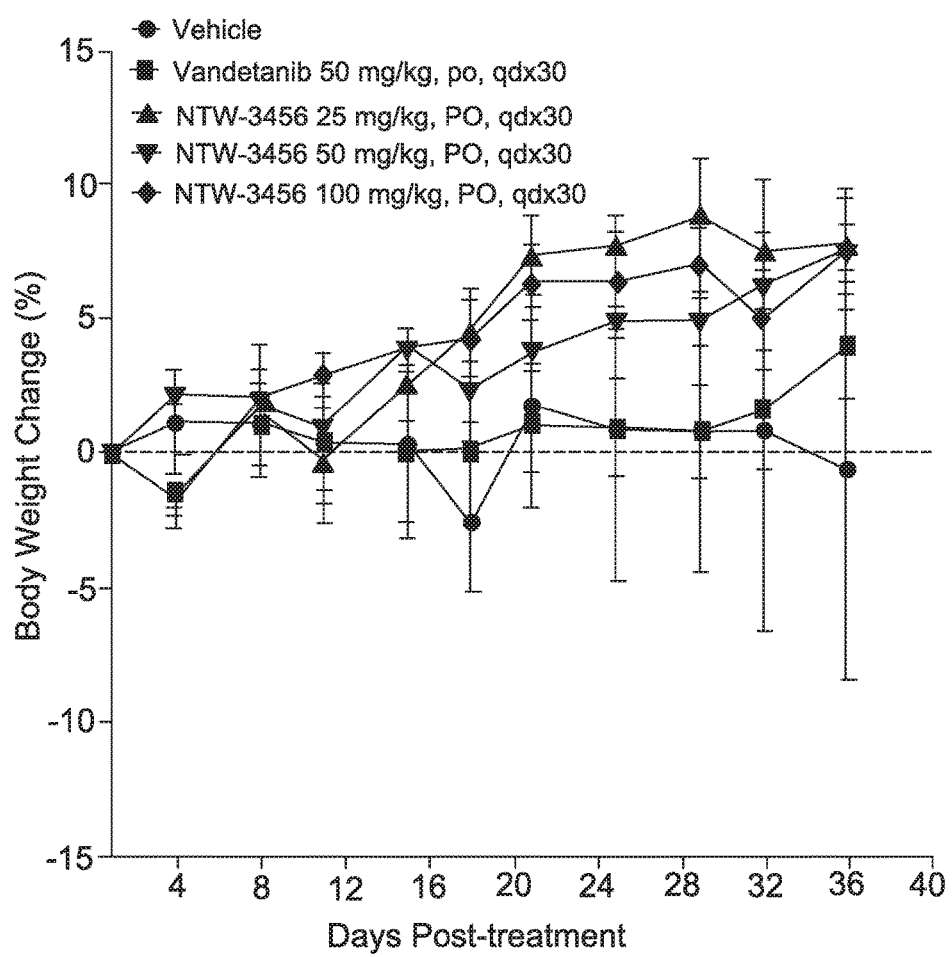
FIG. 36 depicts the weight time course for animals' weight while undergoing NTW-3456 (a marker for overall toxicity) in a thyroid carcinoma model system.
Figure 37:
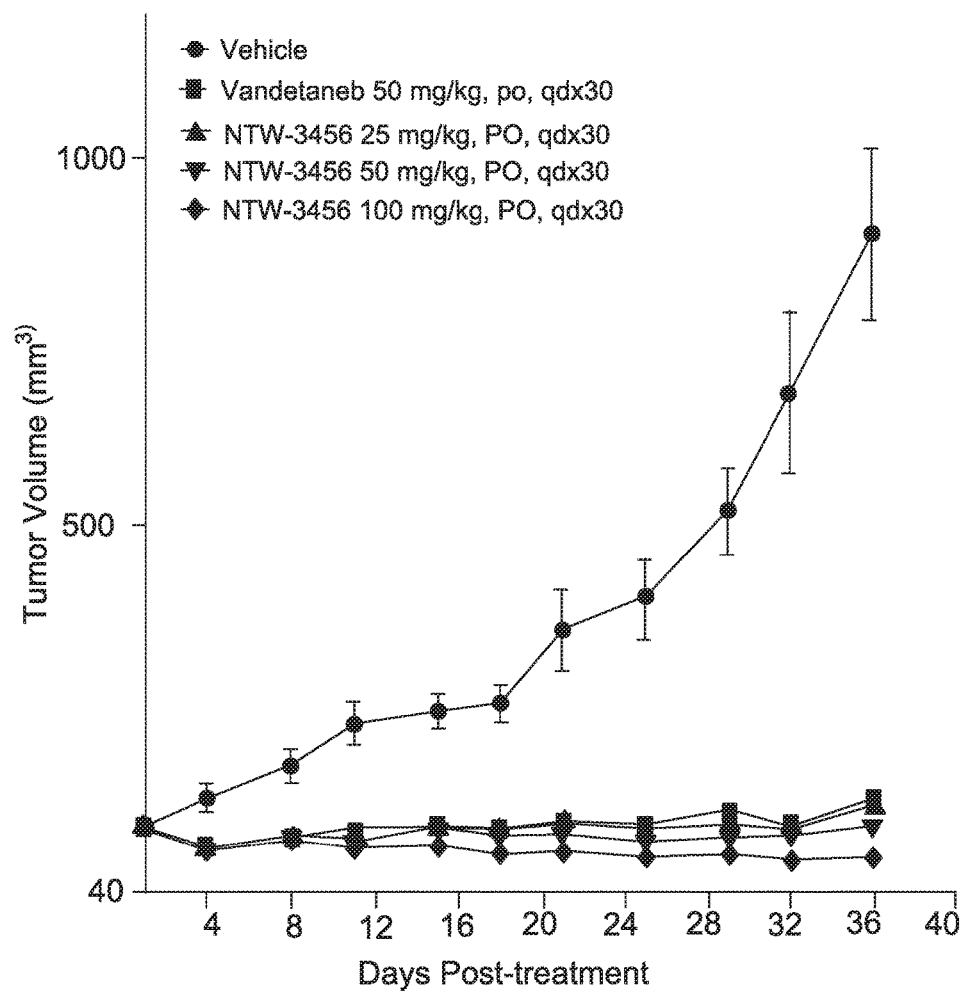
FIG. 37 depicts the tumor volume curve for NTW-3456 treated and control animals, showing anti-tumor activity in a thyroid carcinoma model system.
Figure 38:
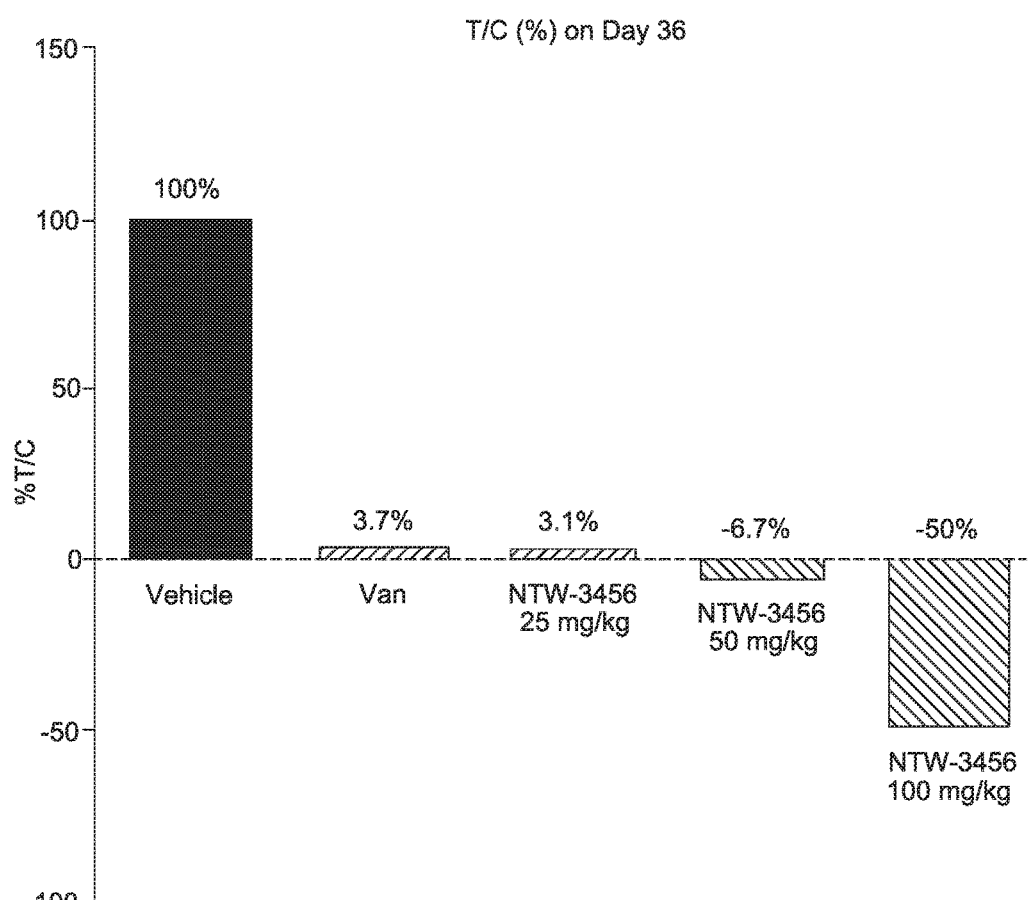
FIG. 38 depicts the tumor activity of NTW-3456 in terms of volume of tumor volume in treated/volume of tumor in control animals in a thyroid carcinoma model system.

FIGS. 36-38 depict the results of various concentrations of NTW-3456 on a nude mouse/xenograft the TT cell model of thyroid carcinoma. In this model system, NTW-3456 demonstrates significant anti-tumor activity, especially at higher doses (FIG. 38).

Figure 39:
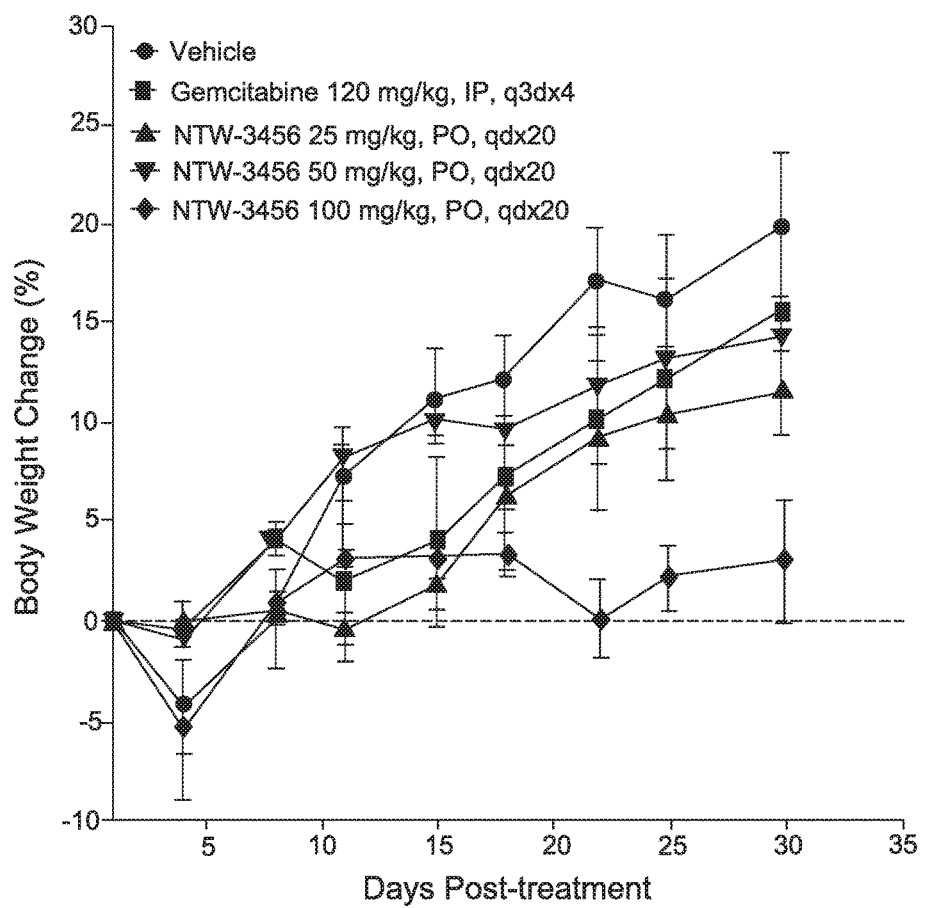
FIG. 39 depicts the weight time course for NTW-3456 (a marker for overall toxicity) in a endometrial carcinoma model system.
Figure 40:
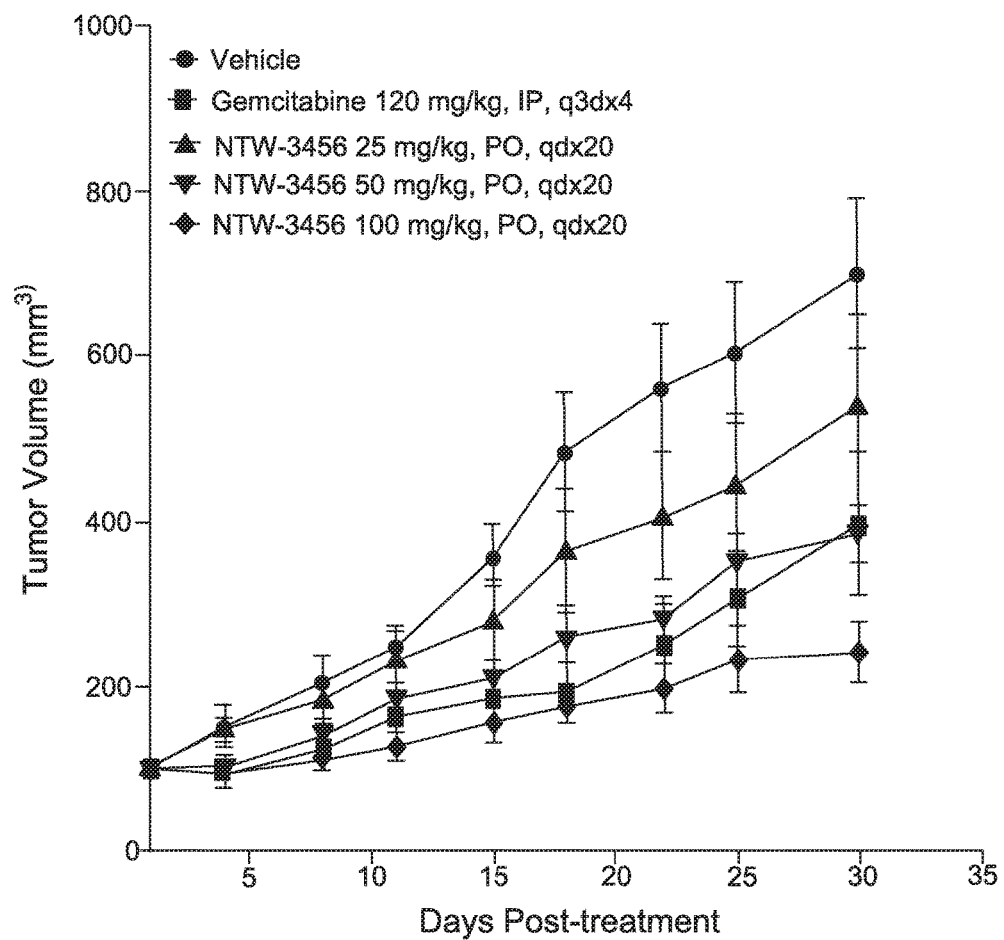
FIG. 40 depicts the tumor volume curve for NTW-3456 treated animals, showing anti-tumor activity in an endometrial carcinoma model system.
Figure 41:
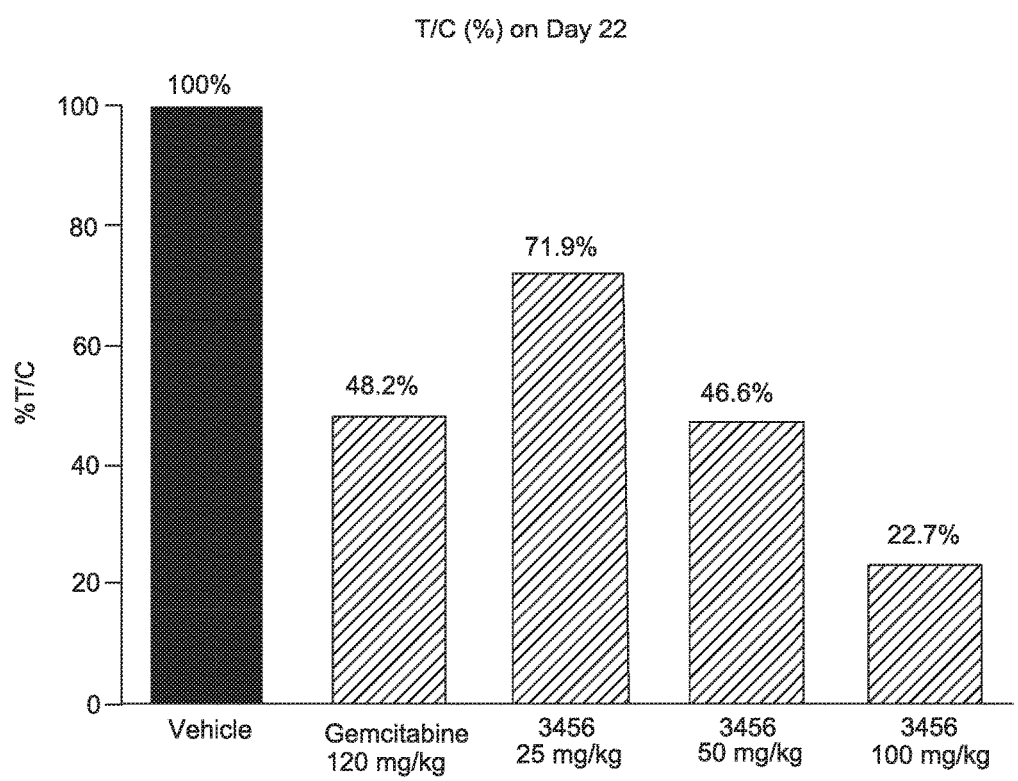
FIG. 41 depicts the tumor activity of NTW-3456 in terms of tumor volume in treated/volume of tumor in control animals in an endometrial carcinoma model system.

FIGS. 39-41 depict the results of various concentrations of NTW-3456 on the AN3 nude mouse/xenograft model of endometrial carcinoma. In this model system, NTW-3456 demonstrates significant anti-tumor activity, especially at higher doses (FIG. 41).

Figure 42:
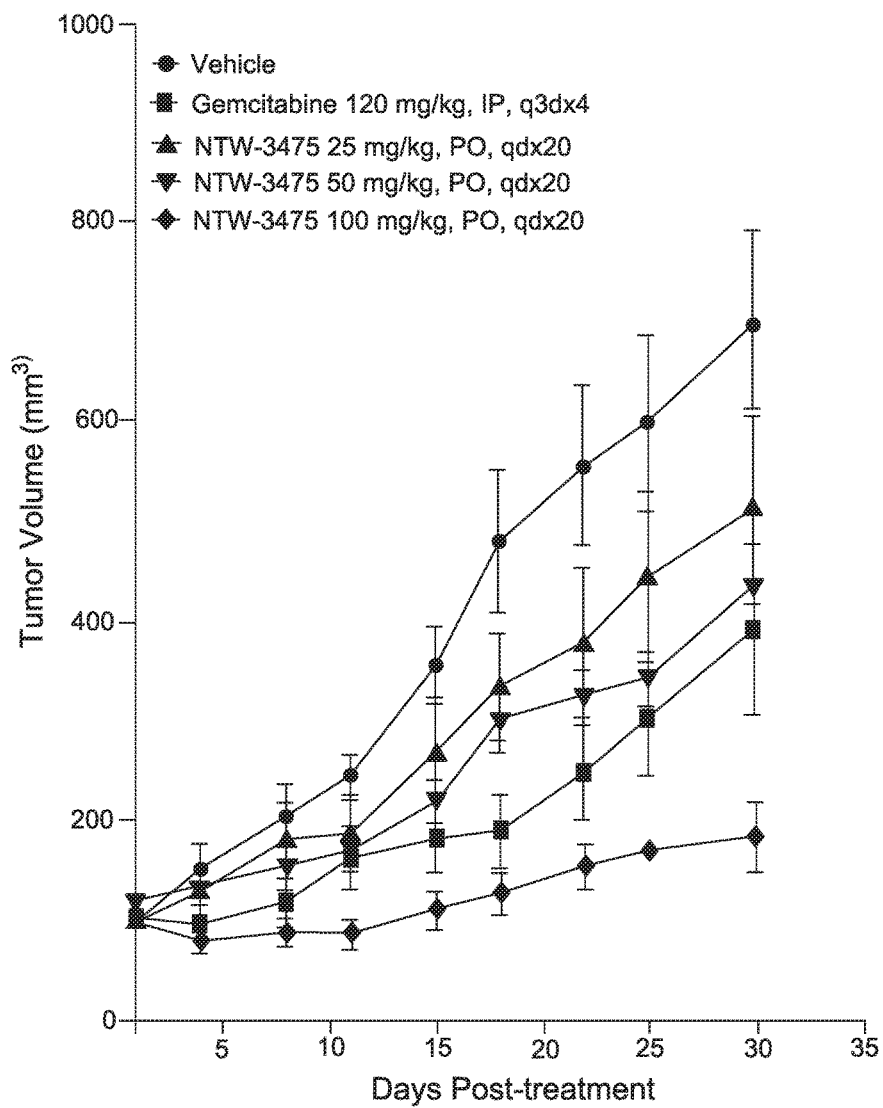
FIG. 42 depicts the weight time course for animals' weight while undergoing NTW-3456 (a marker for overall toxicity) in a pancreatic carcinoma model system.
Figure 43:
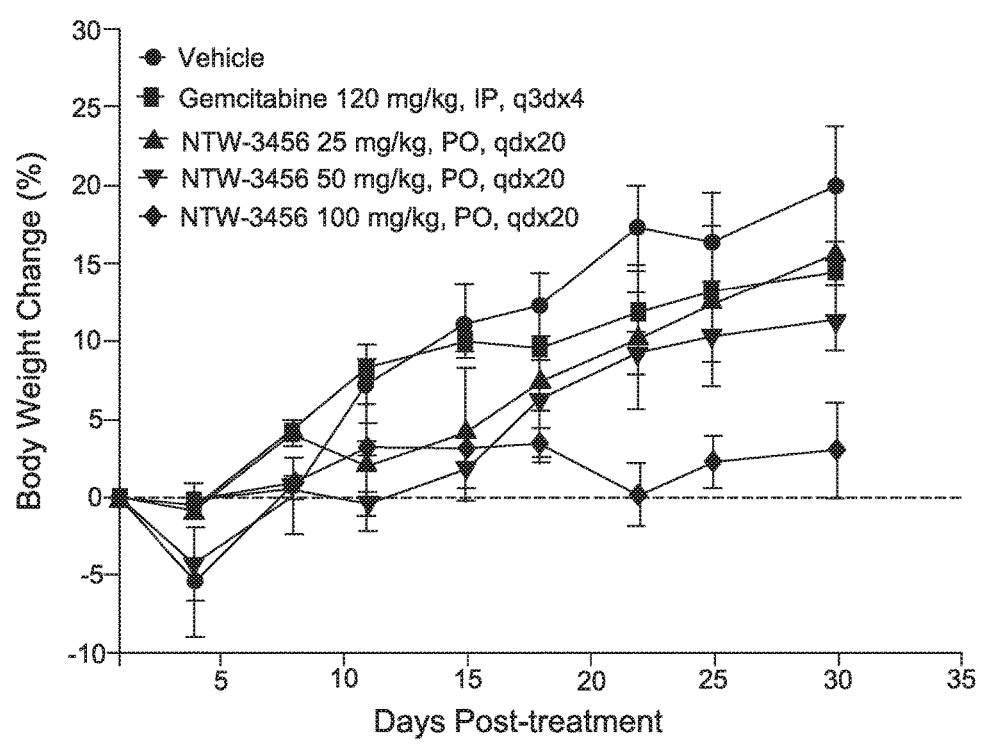
FIG. 43 depicts the tumor volume curve for NTW-3456 treated animals, showing anti-tumor activity in a pancreatic carcinoma model system.
Figure 44:
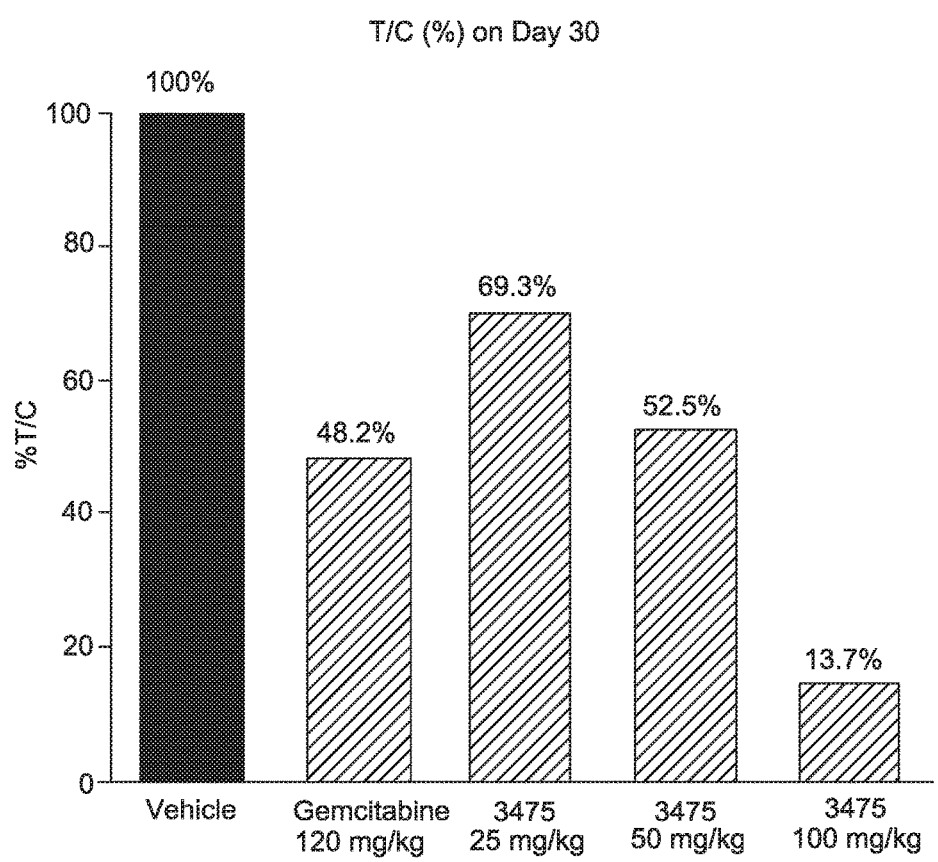
FIG. 44 depicts the tumor activity of NTW-3456 in terms of tumor volume in treated/volume of tumor in control animals in a pancreatic carcinoma model system.

FIGS. 42-44 depict the results of various concentrations of NTW-3456 on a nude mouse/xenograft the MIAPaCa-2 model of pancreatic carcinoma. In this model system, NTW-3456 demonstrates some anti-tumor activity in this model of pancreatic carcinoma.

Figure 45:
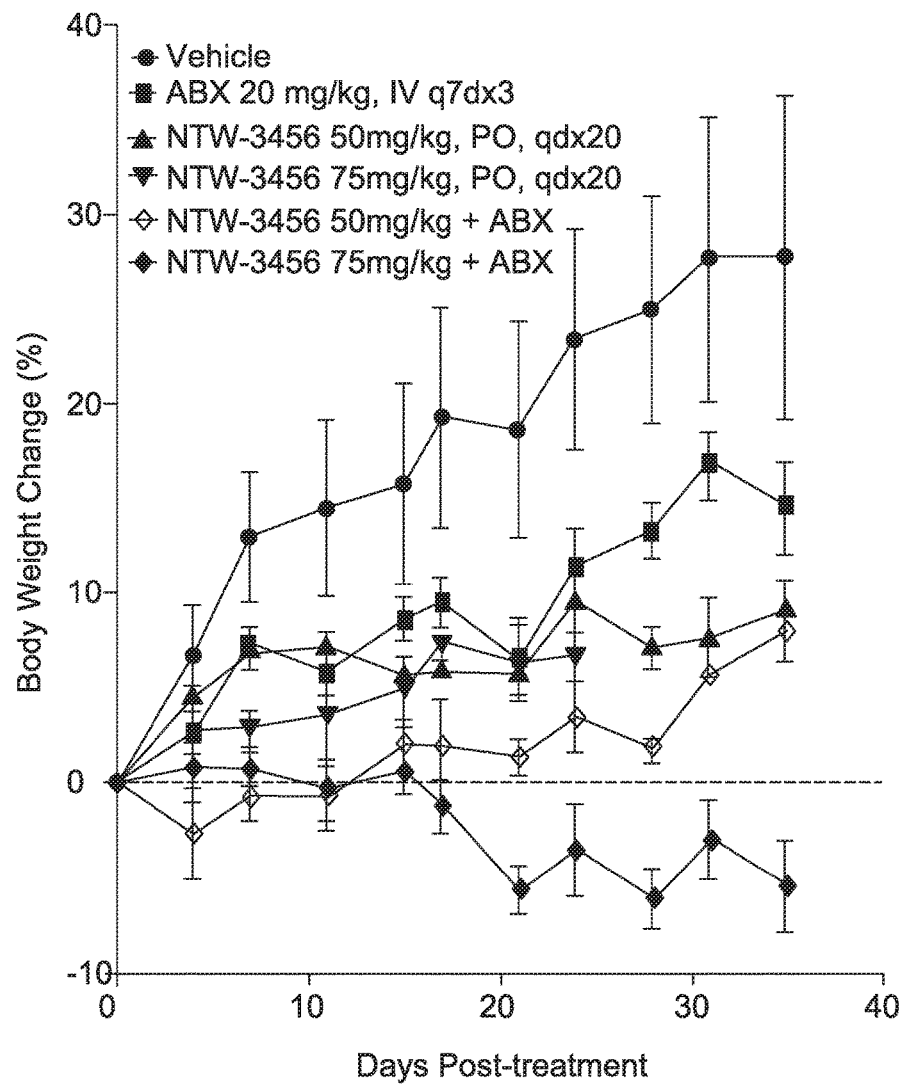
FIG. 45 depicts the weight time course for containing animals' weight while undergoing NTW-3456 single or dual agent therapy with Abraxane® (a marker for overall toxicity) in a MiaPaCa-2 pancreatic carcinoma model system.
Figure 46:
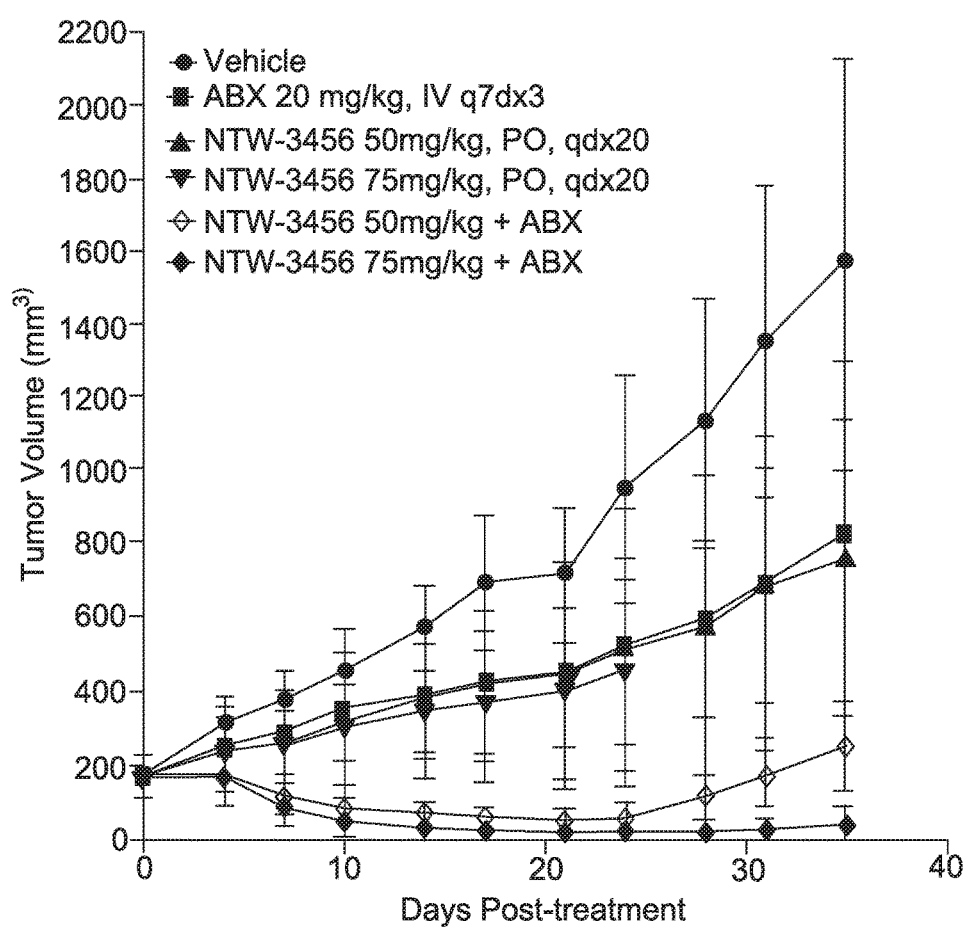
FIG. 46 depicts the tumor volume curve for NTW-3456 single or dual agent therapy with Abraxane treated and control animals, showing anti-tumor activity in a MiaPaCa-2 pancreatic carcinoma model system.
Figure 47:
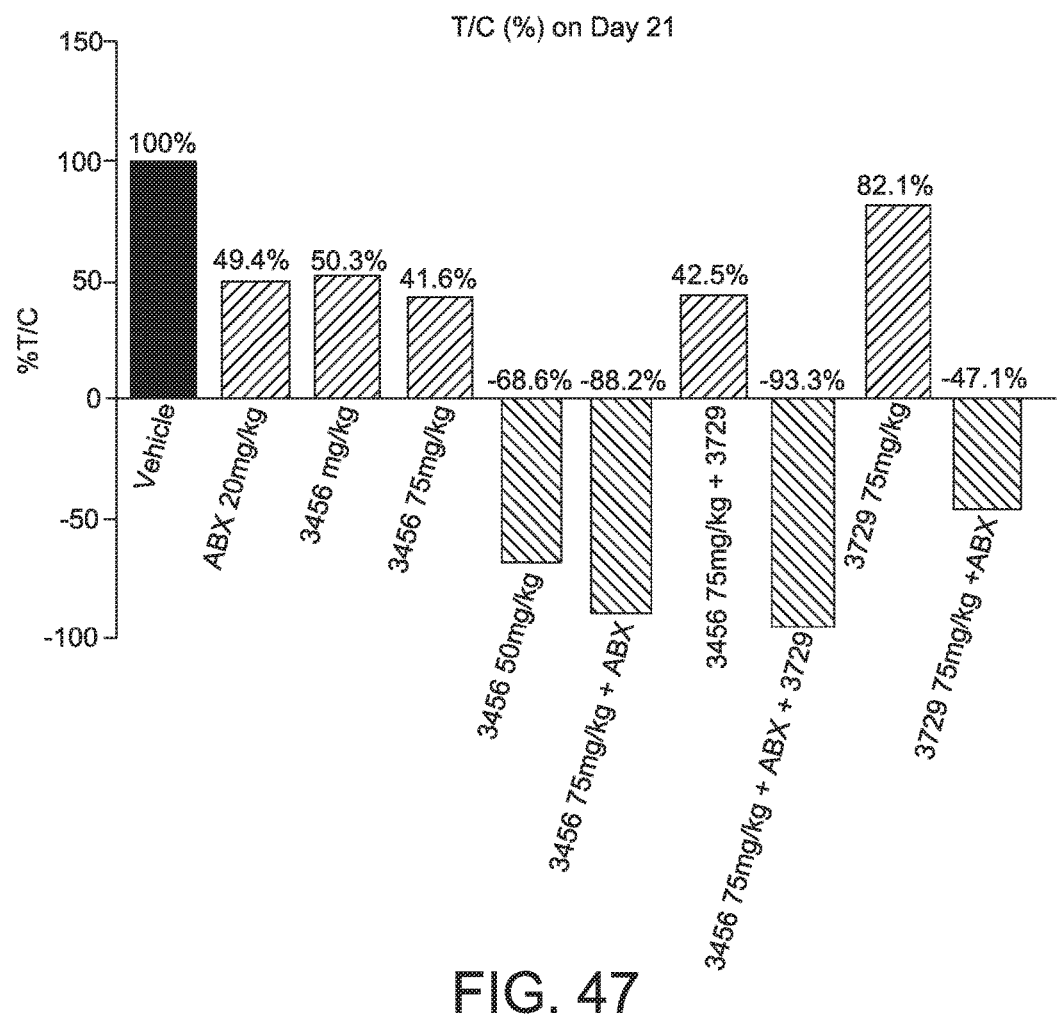
FIG. 47 depicts the antitumor activity of NTW-3456 alone or with Abraxane® in terms of tumor volume in treated/tumor volume in control animals in a MiaPaCa-2 pancreatic carcinoma model system.

FIGS. 45 and 46 depict the results of various concentrations of NTW-3456, with or without Abraxane on a MiaPaCa-2 model of pancreatic carcinoma. In this model system, NTW-3456 demonstrates significant anti-tumor activity, especially when used in combination with Abraxane (FIG. 47).

Figure 48:
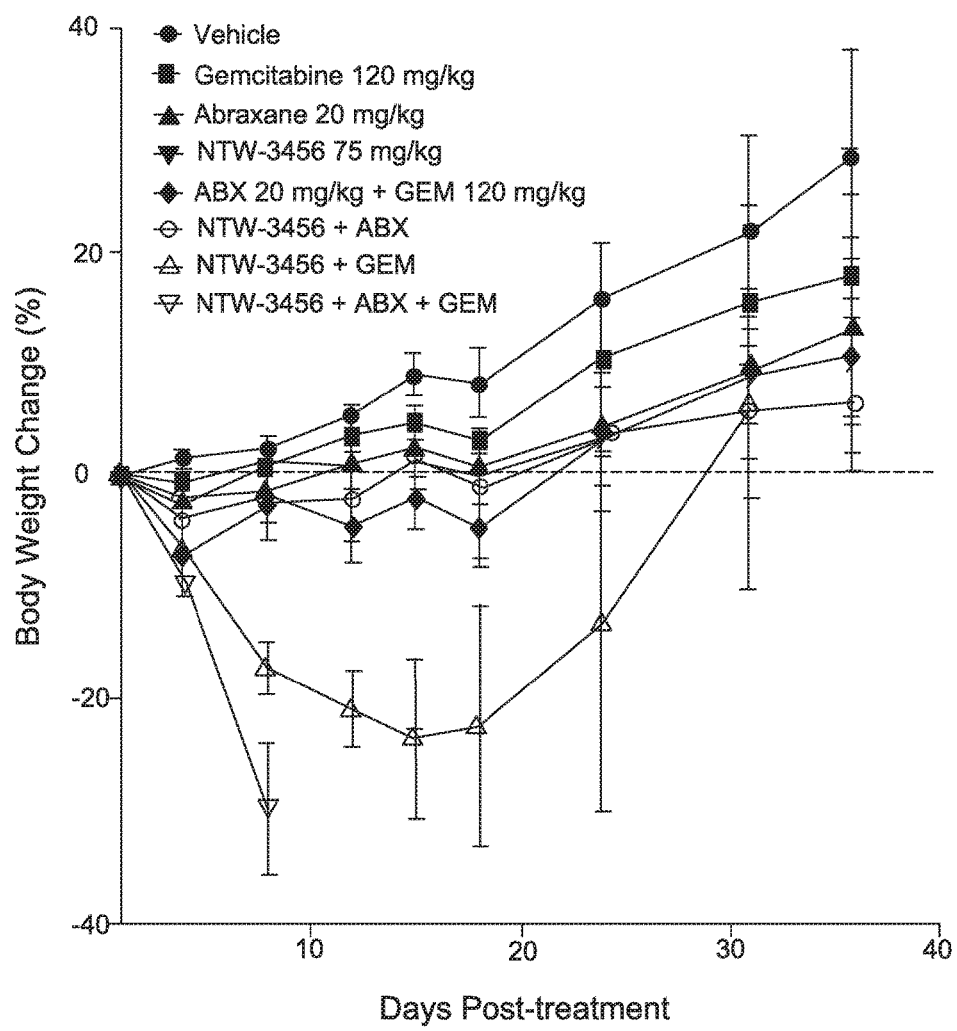
FIG. 48 depicts the weight time course for NTW-3456 single or dual agent therapy with Abraxane® (a marker for overall toxicity) in a Panc-1 pancreatic carcinoma model system.
Figure 49:
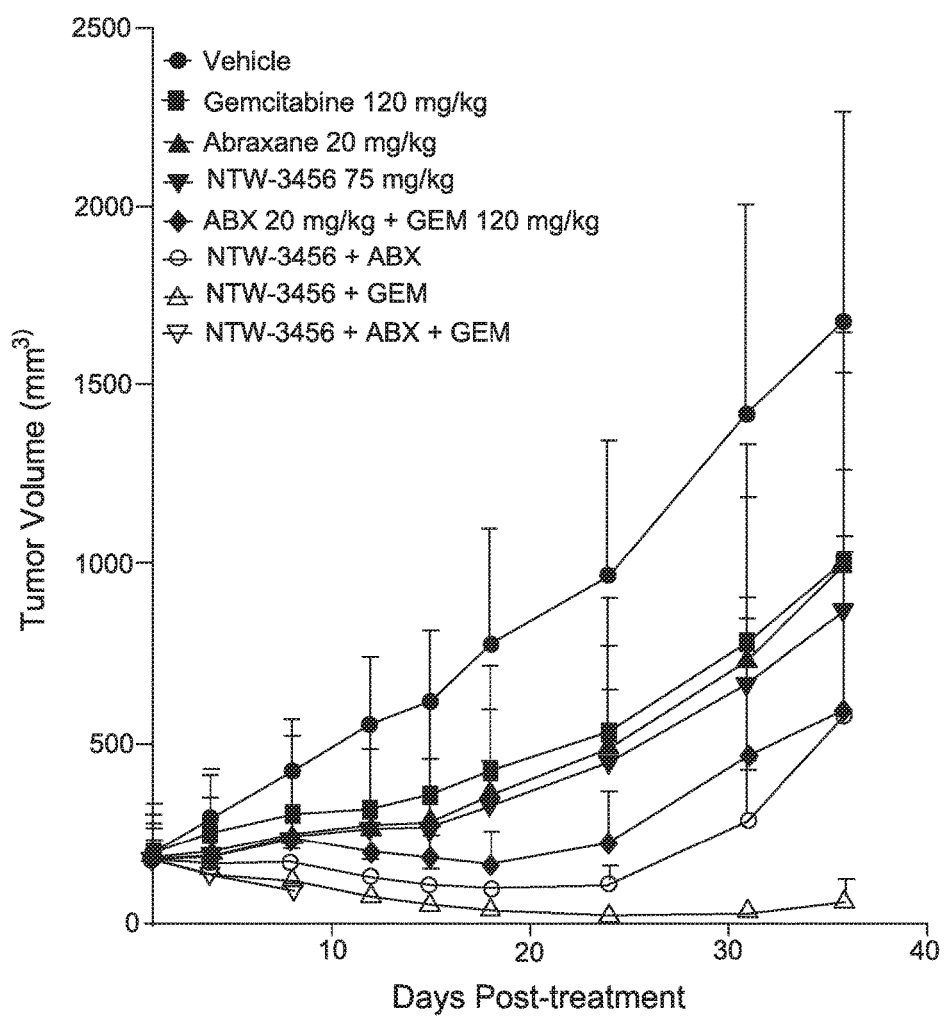
FIG. 49 depicts the tumor volume curve for control, NTW-3456 single or dual agent therapy with Abraxane® treated animals, showing anti-tumor activity in a Panc-1 pancreatic carcinoma model system.

FIGS. 48 and 49 depict the results of various concentrations of NTW-3456, with or without Abraxane on a Panc-1 model of pancreatic carcinoma. In this model system, NTW-3456 demonstrates significant anti-tumor activity, especially when used in combination with Abraxane FIG. 50 summarizes NTW-3456's anti-tumor activity in murine xenografts. Overall, these examples demonstrate the high specific activity seen with NTW-3456

Example 135

This example studies the biochemistry of NTW-3456 and NTW-3475 cells.

Figure 51A:
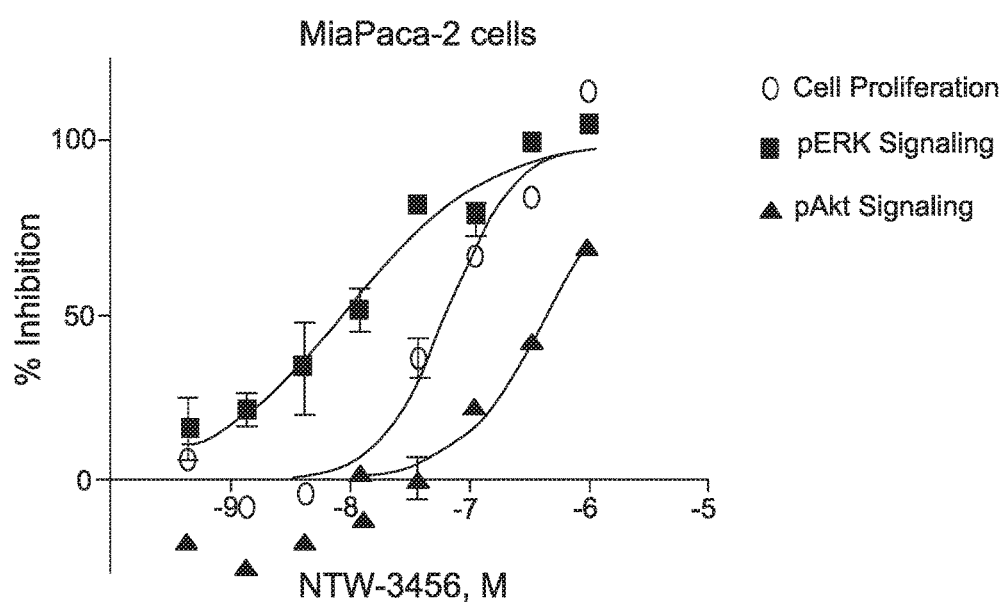
FIG. 51 shows the signal transduction effects of NTW-3456 on MiaPaCa-2 cells and BxPC3 cells.
Figure 51B:
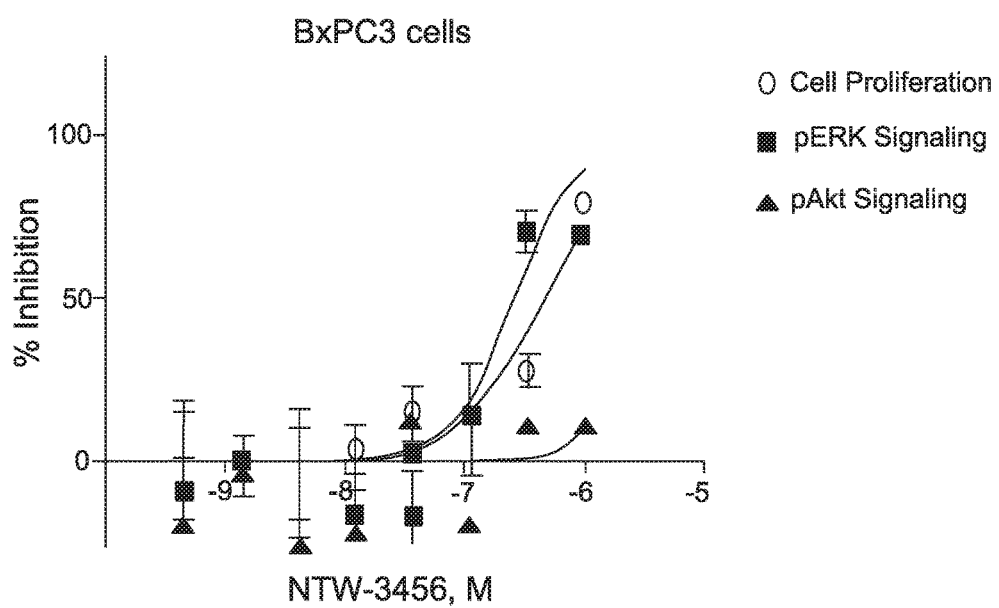
Figure 52A:
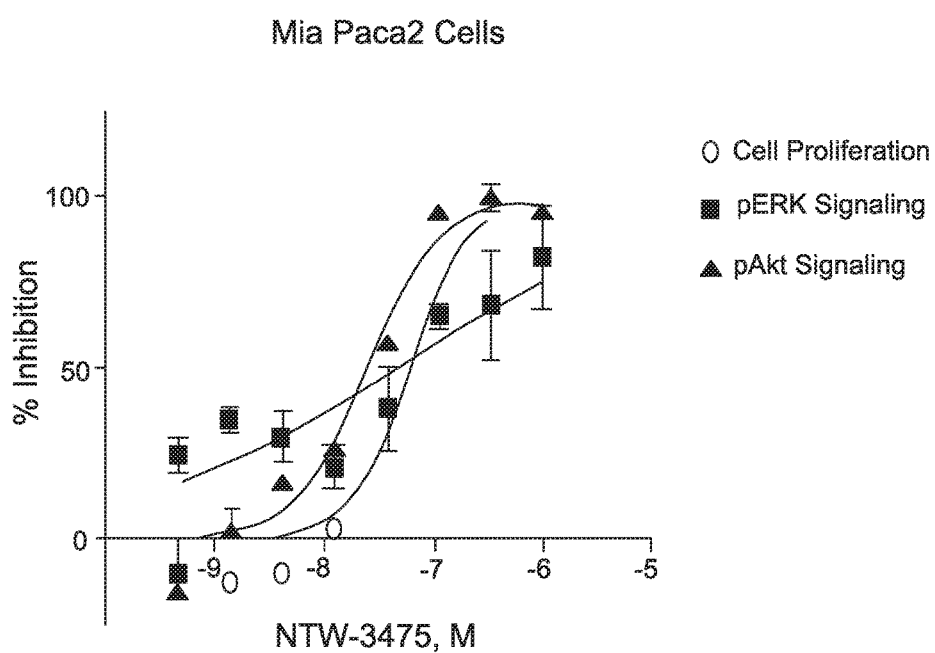
FIG. 52 shows the signal transduction effects of NTW-3475 in MiaPaCa-2 cells and BxPC3 cells.
Figure 52B:
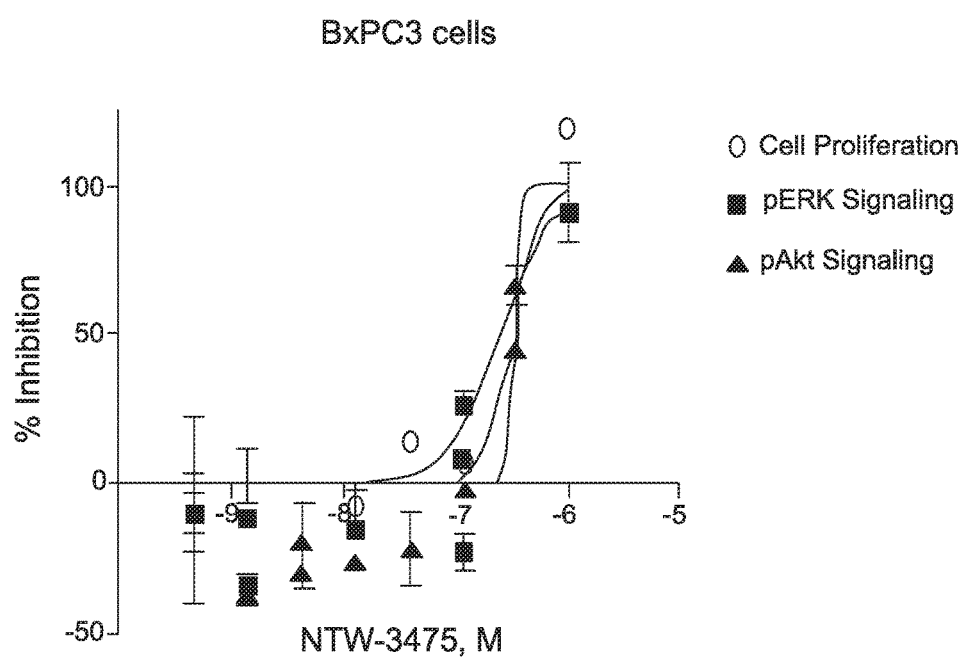

FIGS. 51 and 52 show the dose response curves for the inhibition of proliferation and pERK and pAKt signaling in MiaPaCa-2 and BaFC3 cells by NTE-3456, Nilotinib, Ponatinnib, Suntinib, and Imatinib. FIG. 53 summarizes this data.

Figure 54:
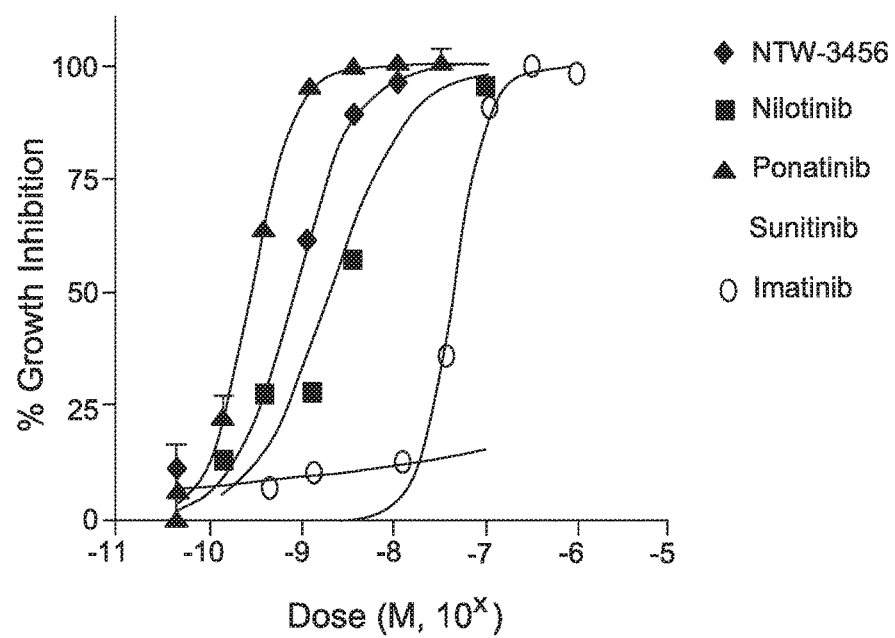
FIG. 54 depicts the inhibitory activities of NTW-3456 on the growth of K562 cells.
Figure 55:
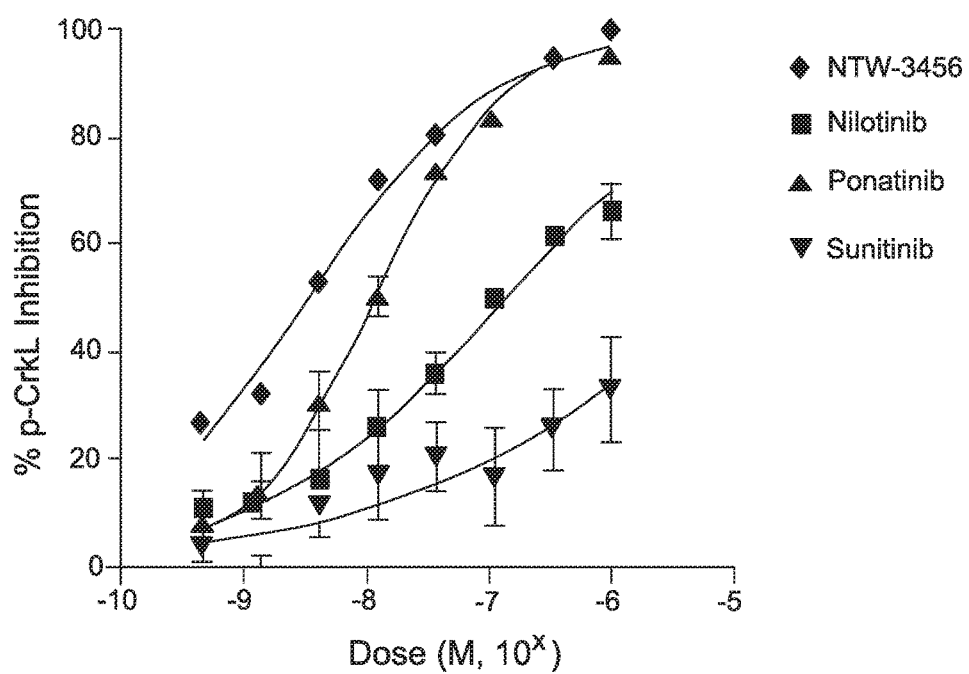
FIG. 55 depicts the inhibitory activities of NTW-3456 on pCrl inhibition in K562 cells.
Figure 56:
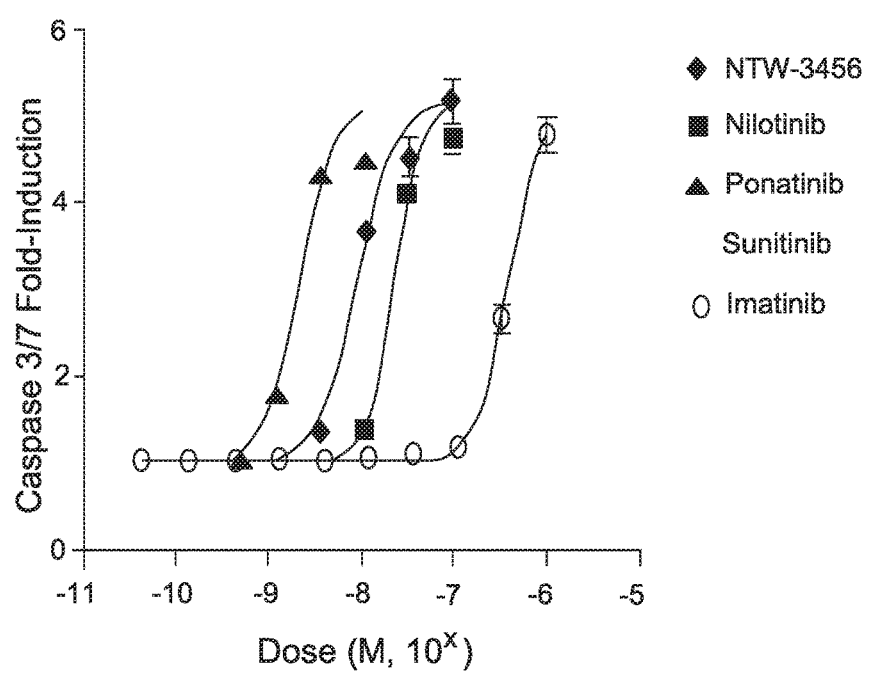
FIG. 56 depicts the inhibitory activities of NTW-3456 on caspase 3/7 induction in K562 cells.

FIG. 54 shows the dose response curves for the inhibition of in vitro growth in K562 cells by NTE-3456, Nilotinib, Ponatinnib, Suntinib, and Imatinib. FIG. 55 shows the dose response curves for the inhibition of p-Crl kinase activity in K562 cells by NTE-3456, Nilotinib, Ponatinnib, Suntinib, and Imatinib. FIG. 56 shows the dose response curves for the induction of Caspase 3/7 activity in K562 cells by NTE-3456, Nilotinib, Ponatinnib, Suntinib, and Imatinib. FIG. 57 summarizes this data.

Figure 58:
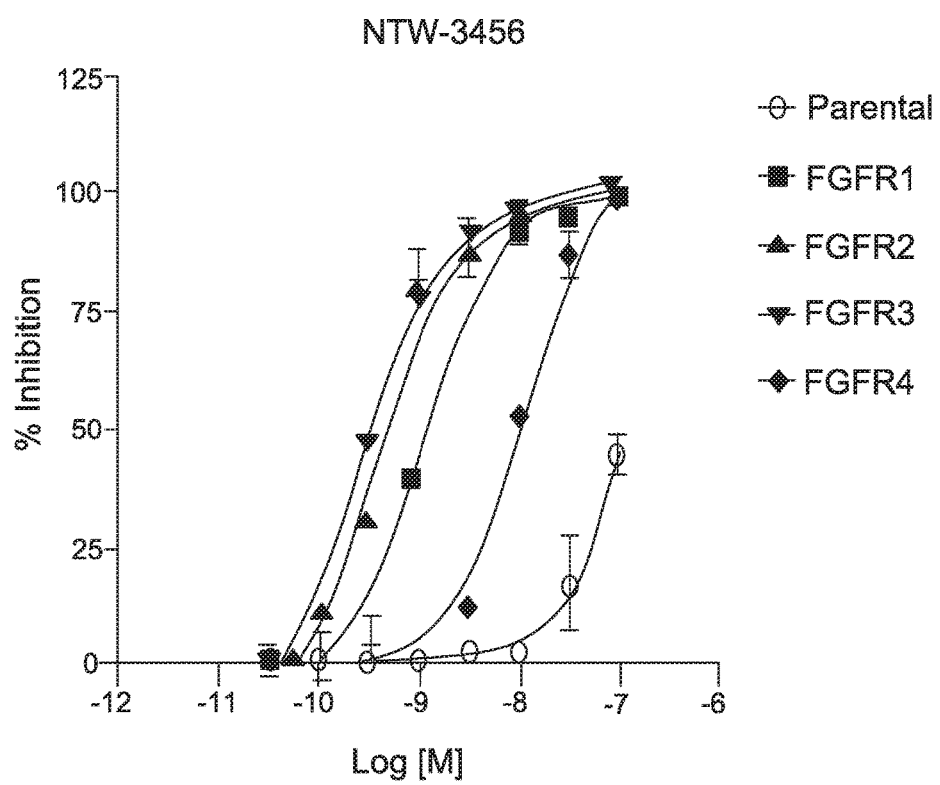
FIG. 58 shows the NTW-3456 dose response curve for the inhibition of the FGFR1-FGFR-4 in BaF3 cells.
Figure 60:
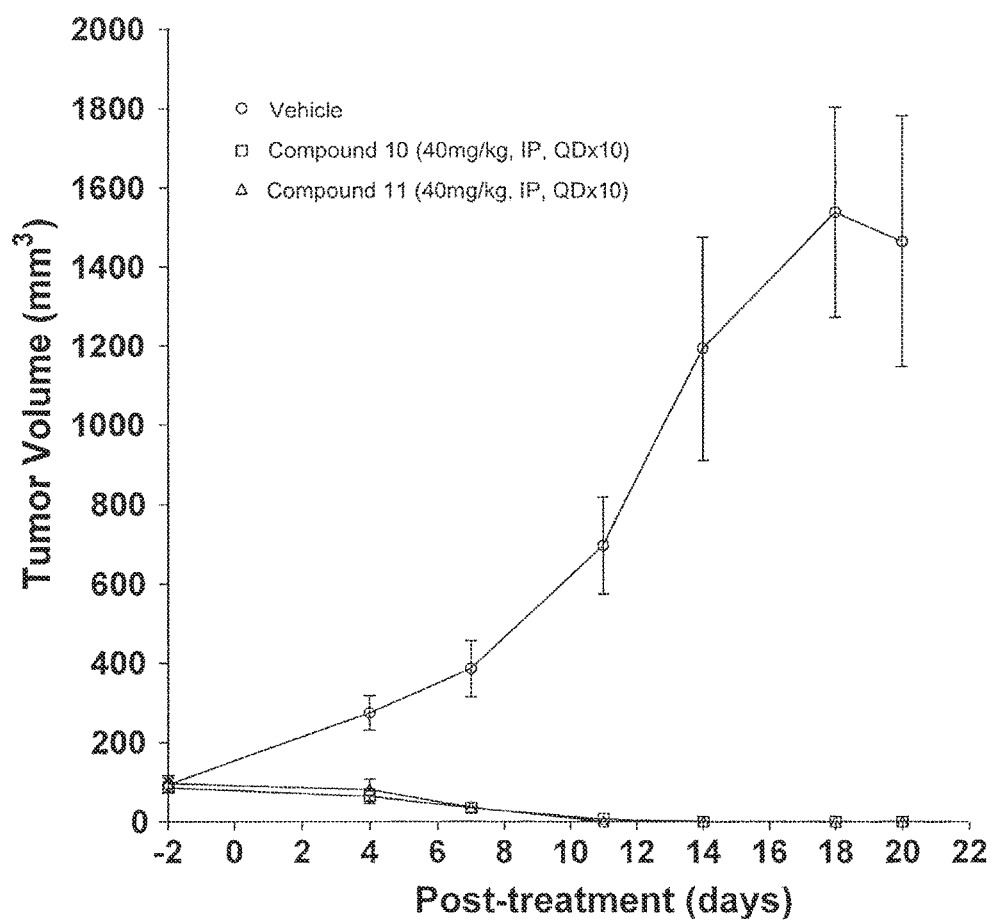
FIG. 60 depicts Compound 10 and 11 Inhibits Tumor Growth in K562 Human Chronic Myeloid Leukemia Xenograft (IP).
Figure 61:
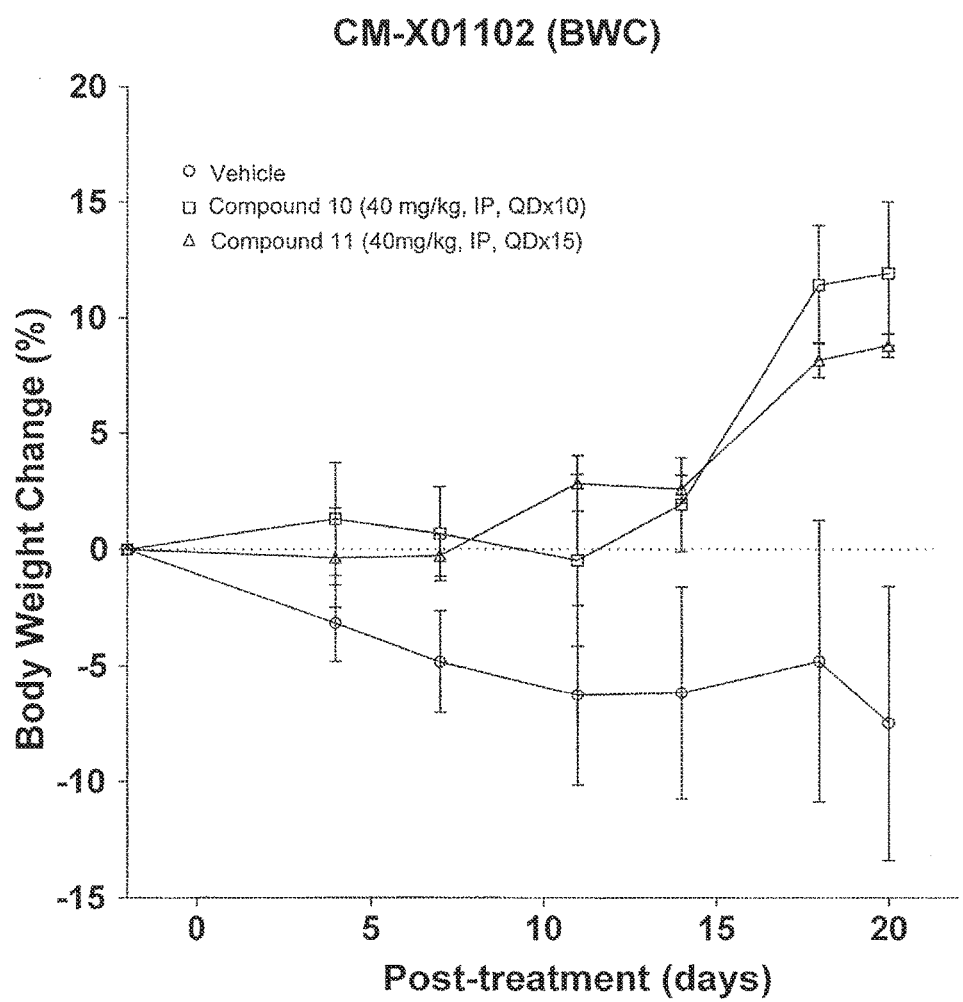
FIG. 61 depicts Body weight change for Compound 10 and 11 in K562 Human Chronic Myeloid Leukemia Xenograft (IP).
Figure 62:
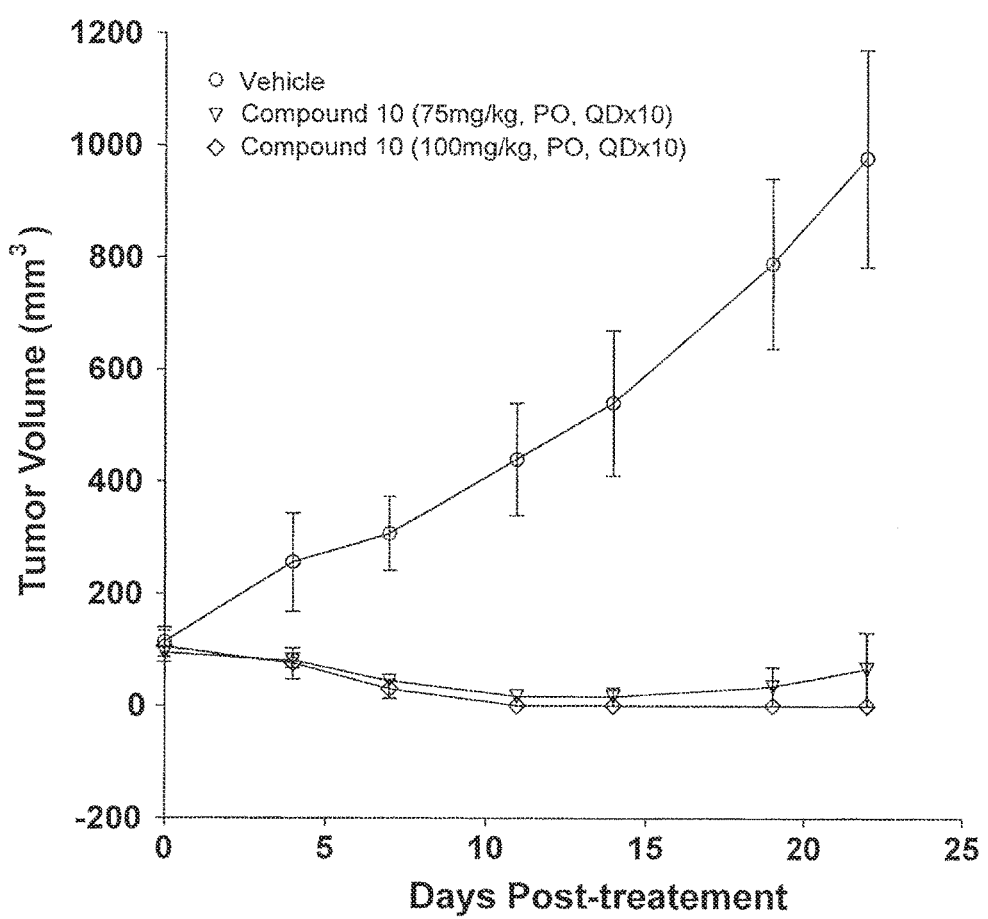
FIG. 62 depicts Compound 10 Inhibits Tumor Growth in K562 Human Chronic Myeloid Leukemia Xenograft (PO).
Figure 63:
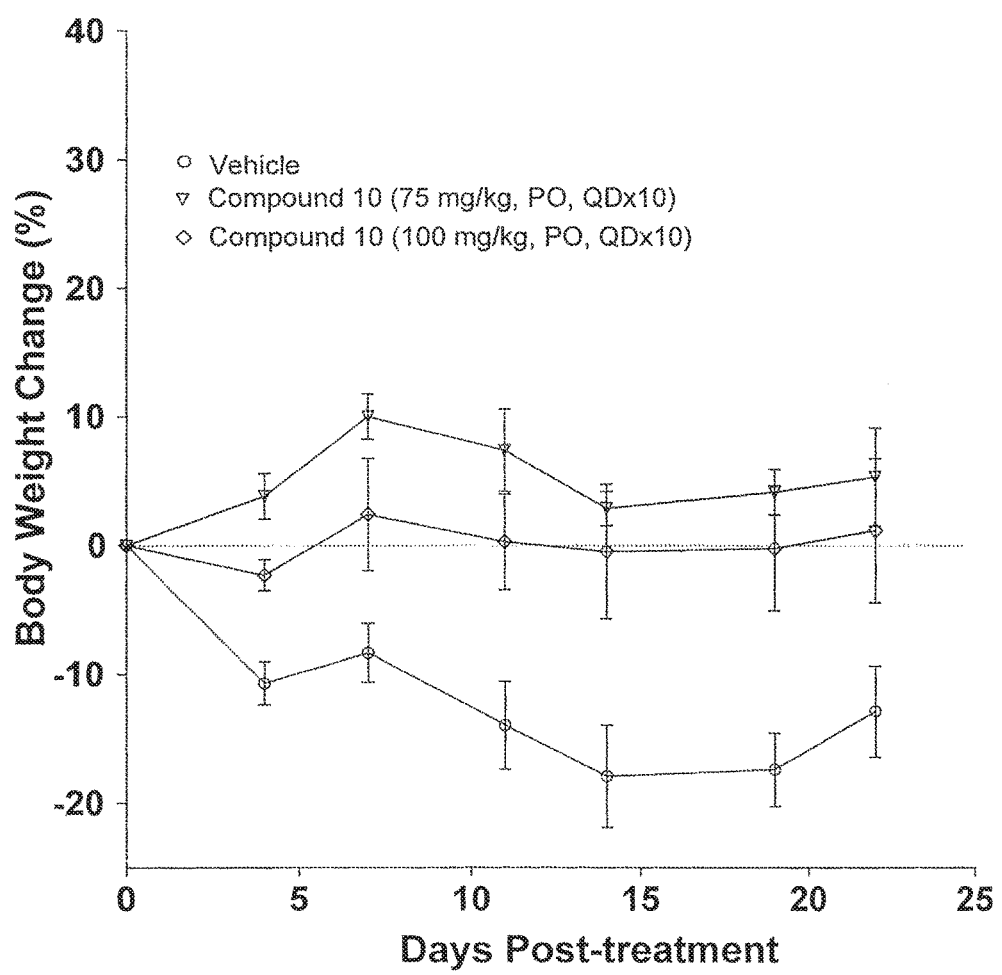
FIG. 63 depicts Body weight change for Compound 10 in K562 Human Chronic Myeloid Leukemia Xenograft (PO).

FIG. 58 shows the dose response curve for the inhibition of kinase activity in BaF3 cells by NTW-3456 from FGFR1, FGFR2, FGFR3, and FGFR4. FIG. 59 sets forth the NTW-3456 $IC_{50}$ levels for FGFR1, FGFR2, FGFR3, and FGFR4 driven BaF3 cells. Overall, the inhibition of proliferation, pERK pathway signaling in MIAPaca-2 and BxPC3 cells by NTW-3475 (FIG. 38) and NTW-3456 (FIG. 39) are similar. Further, these results suggest a correlation between and growth inhibition and the signaling inhibition.

Example 136

The effect of Compound 10 and 11 on kinase activity was tested for a wide range of kinases and is shown in Table 3.

TABLE 3

Kinase profile of Compound 10 and 11.

| Kinase | % inhibition @ 0.1 µM | |
|---|---|---|
| | Compound 10 | Compound 11 |
| Abl(h) | 110 | 108 |
| Abl(m) | 101 | 104 |
| Abl (H396P) (h) | 99 | 102 |
| Abl (M351T)(h) | 99 | 102 |
| Abl (Q252H) (h) | 99 | 102 |
| Abl(T315I)(h) | 101 | 102 |
| Abl(Y253F)(h) | 103 | 100 |
| ACK1(h) | 99 | 95 |
| ALK(h) | 87 | 86 |
| ALK4(h) | 77 | 81 |
| Arg(h) | 104 | 102 |
| AMPKα1(h) | 71 | 72 |
| AMPKα2(h) | 90 | 88 |
| Arg(m) | 99 | 102 |
| ARK5(h) | 99 | 95 |
| ASK1(h) | −14 | −17 |
| Aurora-A(h) | 98 | 99 |
| Aurora-B(h) | 97 | 98 |
| Aurora-C(h) | 54 | 67 |
| Axl(h) | 70 | 62 |
| Blk(h) | 94 | 94 |
| Blk(m) | 84 | 93 |
| Bmx(h) | 98 | 99 |
| BRK(h) | 54 | 73 |
| BrSK1(h) | 47 | 40 |
| BrSK2(h) | 60 | 48 |
| BTK(h) | 50 | 71 |
| BTK(R28H)(h) | 10 | −7 |
| CaMKI(h) | 2 | 7 |
| CaMKIIβ(h) | −5 | 8 |
| CaMKIIγ(h) | −8 | 22 |
| CaMKIδ(h) | 6 | 5 |
| CaMKIIδ(h) | −6 | 6 |
| CaMKIV(h) | −25 | −1 |
| CDK1/cyclinB(h) | 10 | −1 |
| CDK2/cyclinA(h) | 5 | 3 |
| CDK2/cyclinE(h) | 1 | 3 |
| CDK3/cyclinE(h) | 0 | 33 |
| CDK5/p25(h) | 24 | 26 |
| CDK5/p35(h) | 20 | 78 |
| CDK6/cyclinD3(h) | −5 | 11 |
| CDK7/cyclinH/MAT1(h) | 44 | 26 |
| CDK9/cyclin T1(h) | 22 | 32 |
| CHK1(h) | 16 | 0 |
| CHK2(h) | 11 | 4 |
| CHK2(I157T)(h) | 30 | −1 |
| CHK2(R145W)(h) | 22 | 6 |
| CK1γ1(h) | −4 | −10 |
| CK1γ2(h) | −20 | −16 |
| CK1γ3(h) | −12 | −9 |
| CK1δ(h) | −21 | −3 |
| CK1(y) | 17 | 4 |
| CK2(h) | 8 | 5 |
| CK2α2(h) | −13 | 8 |
| CLK2(h) | 29 | −3 |
| CLK3(h) | 16 | −14 |
| cKit(h) | 0 | 24 |
| cKit(D816V)(h) | 33 | 38 |
| cKit(D816H)(h) | 86 | 91 |
| cKit(V560G)(h) | 89 | 94 |
| cKit(V654A)(h) | 35 | 53 |
| CSK(h) | 12 | 5 |
| c-RAF(h) | 6 | 1 |
| cSRC(h) | 103 | 98 |
| DAPK1(h) | 0 | 3 |
| DAPK2(h) | −16 | −6 |
| DCAMKL2(h) | 16 | 15 |
| DDR2(h) | 80 | 83 |
| DMPK(h) | −4 | −16 |
| DRAK1(h) | 36 | 42 |
| DYRK2(h) | −6 | −1 |
| eEF-2K(h) | −15 | 10 |
| EGFR(h) | −8 | −6 |
| EGFR(L858R)(h) | −5 | 23 |

TABLE 3-continued

Kinase profile of Compound 10 and 11.

| Kinase | % inhibition @ 0.1 μM | |
|---|---|---|
| | Compound 10 | Compound 11 |
| EGFR(L861Q)(h) | 2 | 34 |
| EGFR(T790M)(h) | 17 | 30 |
| EGFR(T790M,L858R)(h) | 53 | 69 |
| EphA1(h) | 78 | 92 |
| EphA2(h) | 96 | 98 |
| EphA3(h) | 47 | 56 |
| EphA4(h) | 52 | 47 |
| EphA5(h) | 76 | 81 |
| EphA7(h) | 23 | 34 |
| EphA8(h) | 33 | 39 |
| EphB2(h) | 47 | 76 |
| EphB1(h) | 101 | 100 |
| EphB3(h) | −8 | −18 |
| EphB4(h) | 85 | 85 |
| ErbB4(h) | 13 | −5 |
| FAK(h) | 22 | 22 |
| Fer(h) | 38 | 45 |
| Fes(h) | 48 | 54 |
| FGFR1(h) | 100 | 100 |
| FGFR1(V561M)(h) | 101 | 101 |
| FGFR2(h) | 99 | 99 |
| FGFR2(N549H)(h) | 100 | 100 |
| FGFR3(h) | 100 | 101 |
| FGFR4(h) | 88 | 78 |
| Fgr(h) | 97 | 100 |
| Flt1(h) | 100 | 100 |
| Flt3(D835Y)(h) | 99 | 101 |
| Flt3(h) | 101 | 98 |
| Flt4(h) | 100 | 100 |
| Fms(h) | 91 | 95 |
| Fms(Y969C)(h) | 67 | 73 |
| Fyn(h) | 102 | 99 |
| GCK(h) | 79 | 85 |
| GRK5(h) | 18 | −2 |
| GRK6(h) | −5 | −14 |
| GRK7(h) | −4 | 0 |
| GSK3α(h) | 28 | 20 |
| GSK3β(h) | −15 | 19 |
| Haspin(h) | 0 | −11 |
| Hck(h) | 68 | 85 |
| Hck(h) activated | 90 | 84 |
| HIPK1(h) | −6 | −12 |
| HIPK2(h) | −2 | 0 |
| HIPK3(h) | −1 | −3 |
| IGF-1R(h) | 78 | 62 |
| IGF-1R(h), activated | 59 | 65 |
| IKKα(h) | −12 | −3 |
| IKKβ(h) | 1 | 5 |
| IR(h) | 83 | 84 |
| IR(h), activated | 73 | 71 |
| IRR(h) | 91 | 95 |
| IRAK1(h) | −2 | −9 |
| IRAK4(h) | 37 | 13 |
| Itk(h) | 31 | 54 |
| JAK2(h) | 92 | 99 |
| JAK3(h) | 86 | 86 |
| JNK1α1 (h) | −7 | 11 |
| JNK2α2(h) | −20 | −16 |
| JNK3(h) | −1 | −6 |
| KDR(h) | 93 | 92 |
| Lck(h) | 99 | 98 |
| Lck(h) activated | 97 | 100 |
| LIMK1(h) | 83 | 90 |
| LKB1(h) | 14 | −1 |
| LOK(h) | 73 | 86 |
| Lyn(h) | 100 | 99 |
| Lyn(m) | 98 | 101 |
| MAPK1(h) | −4 | −10 |
| MAPK2(h) | −8 | −13 |
| MAPK2(m) | −16 | 10 |
| MAPKAP-K2(h) | −7 | −10 |
| MAPKAP-K3(h) | 4 | −15 |
| MEK1(h) | 14 | 1 |
| MARK1(h) | 67 | 64 |
| MELK(h) | 69 | 87 |
| Mer(h) | 97 | 96 |
| Met(h) | 54 | 47 |
| Met(D1246H)(h) | 74 | 93 |
| Met(D1246N)(h) | 80 | 84 |
| Met(M1268T)(h) | 91 | 72 |
| Met(Y1248C)(h) | 57 | 95 |
| Met(Y1248D)(h) | 80 | 76 |
| Met(Y1248H)(h) | 69 | 91 |
| MINK(h) | 7 | 31 |
| MKK4(m) | −2 | −28 |
| MKK6(h) | −5 | −13 |
| MKK7β(h) | −26 | −16 |
| MLCK(h) | 0 | 0 |
| MLK1(h) | 84 | 86 |
| Mnk2(h) | 1 | −2 |
| MRCKα(h) | 2 | −3 |
| MRCKβ(h) | −6 | −16 |
| MSK1(h) | 96 | 9 |
| MSK2(h) | −7 | −5 |
| MSSK1(h) | 22 | 0 |
| MST1(h) | 78 | 74 |
| MST2(h) | 24 | 22 |
| MST3(h) | 85 | 80 |
| mTOR(h) | 25 | 18 |
| mTOR/FKBP12(h) | −14 | −9 |
| MuSK(h) | 30 | 20 |
| NEK2(h) | 6 | −7 |
| NEK3(h) | 18 | 16 |
| NEK6(h) | −11 | −11 |
| NEK7(h) | 8 | −5 |
| NEK11(h) | −8 | −6 |
| NLK(h) | −12 | −8 |
| p70S6K(h) | −10 | 2 |
| PAK2(h) | 16 | 0 |
| PAK4(h) | 29 | 23 |
| PAK5(h) | 60 | 68 |
| PAK6(h) | 0 | 35 |
| PAR-1Bα(h) | 75 | 66 |
| PASK(h) | 22 | −17 |
| PEK(h) | −4 | −8 |
| PDGFRα(h) | −3 | 29 |
| PDGFRα(D842V)(h) | 73 | 70 |
| PDGFRα(V561D)(h) | 86 | 72 |
| PDGFRβ(h) | 28 | 24 |
| PDK1(h) | 13 | 3 |
| PhKγ2(h) | 2 | 13 |
| Pim-1(h) | −21 | −9 |
| Pim-2(h) | −25 | 17 |
| Pim-3(h) | −1 | −4 |
| PKA(h) | 2 | −12 |
| PKBα(h) | −24 | −4 |
| PKBβ(h) | −35 | −9 |
| PKBγ(h) | −10 | −18 |
| PKCα(h) | 4 | −3 |
| PKCβI(h) | 2 | 5 |
| PKCβII(h) | 3 | −3 |
| PKCγ(h) | −8 | −5 |
| PKCδ(h) | 5 | 5 |
| PKCε(h) | −10 | 17 |
| PKCη(h) | −16 | −7 |
| PKCι(h) | 0 | −10 |
| PKCμ(h) | 7 | −7 |
| PKCθ(h) | 21 | −16 |
| PKCζ(h) | −7 | −14 |
| PKD2(h) | −5 | −1 |
| PKG1α(h) | −25 | −5 |
| PKG1β(h) | −11 | −2 |
| Plk1(h) | −9 | −10 |
| Plk3(h) | 1 | 1 |
| PRAK(h) | −24 | 6 |
| PRK2(h) | 51 | 51 |
| PrKX(h) | 13 | 35 |
| PTK5(h) | 72 | 72 |

TABLE 3-continued

Kinase profile of Compound 10 and 11.

| Kinase | % inhibition @ 0.1 μM | |
|---|---|---|
| | Compound 10 | Compound 11 |
| Pyk2(h) | 64 | 63 |
| Ret(h) | 102 | 100 |
| Ret (V804L)(h) | 103 | 102 |
| Ret(V804M)(h) | 96 | 101 |
| RIPK2(h) | 1 | 13 |
| ROCK-I(h) | −15 | −15 |
| ROCK-II(h) | 11 | 3 |
| ROCK-II(r) | 13 | 16 |
| Ron(h) | 34 | 43 |
| Ros(h) | 12 | 71 |
| Rse(h) | 3 | 11 |
| Rsk1(h) | −10 | 9 |
| Rsk1(r) | 16 | 14 |
| Rsk2(h) | 37 | 7 |
| Rsk3(h) | 63 | 63 |
| Rsk4(h) | 36 | 35 |
| SAPK2a(h) | 10 | −7 |
| SAPK2a(T106M)(h) | 2 | 3 |
| SAPK2b(h) | −2 | −6 |
| SAPK3(h) | −4 | −24 |
| SAPK4(h) | −13 | 3 |
| SGK(h) | −38 | −19 |
| SGK2(h) | −41 | −12 |
| SGK3(h) | −5 | 4 |
| SIK(h) | 50 | 56 |
| Snk(h) | 9 | 5 |
| Src(1-530)(h) | 101 | 101 |
| Src(T341M)(h) | 102 | 101 |
| SRPK1(h) | −11 | −14 |
| SRPK2(h) | 6 | 0 |
| STK33(h) | 8 | −4 |
| Syk(h) | 25 | 36 |
| TAK1(h) | 38 | 44 |
| TAO1(h) | 24 | 26 |
| TAO2(h) | 18 | 16 |
| TAO3(h) | 20 | 8 |
| TBK1(h) | 71 | 95 |
| Tec(h) activated | 46 | 20 |
| TGFBR1(h) | 66 | 47 |
| Tie2 (h) | 100 | 98 |
| Tie2(R849W)(h) | 88 | 93 |
| Tie2(Y897S)(h) | 91 | 93 |
| TLK2(h) | 69 | 70 |
| TrkA(h) | 102 | 100 |
| TrkB(h) | 103 | 100 |
| TSSK1(h) | 4 | 3 |
| TSSK2(h) | 5 | 2 |
| Txk(h) | 75 | 87 |
| ULK2(h) | 37 | 30 |
| ULK3(h) | 86 | 84 |
| WNK2(h) | −8 | −6 |
| WNK3(h) | 1 | 8 |
| VRK2(h) | 34 | 4 |
| Yes(h) | 99 | 101 |
| ZAP-70(h) | 3 | −13 |
| ZIPK(h) | 1 | 7 |
| PI3 Kinase (p110β/p85α)(h) | 0 | −1 |
| PI3 Kinase (p120γ)(h) | −2 | −1 |
| PI3 Kinase (p110δ/p85α)(h) | 2 | −1 |
| PI3 Kinase (p110α/p85α)(m) | 1 | −1 |
| PI3 Kinase (p110α/p65α)(m) | −1 | 2 |
| PI3 Kinase (p110α(E545K)/p85α)(m) | 0 | 1 |
| PI3 Kinase (p110α(H1047R)/p85α)(m) | −1 | 0 |
| PI3 Kinase (p110β/p85β)(m) | −1 | −1 |
| PI3 Kinase (p110β/p85α)(m) | 0 | 1 |
| PI3 Kinase (p110δ/p85α)(m) | −19 | 6 |
| PI3 Kinase (p110α(E542K)/p85α)(m) | 1 | 1 |
| PI3 Kinase (p110a/p85α)(h) | −1 | 5 |
| PI3 Kinase (p110α(E542K)/p85α)(h) | −1 | 0 |
| PI3 Kinase | −8 | −1 |

TABLE 3-continued

Kinase profile of Compound 10 and 11.

| Kinase | % inhibition @ 0.1 μM | |
|---|---|---|
| | Compound 10 | Compound 11 |
| (p110α(H1047R)/p85α)(h) | | |
| PI3 Kinase (p110α(E545K)/p85α)(h) | −2 | 2 |
| PI3 Kinase (p110α/p65α)(h) | −6 | −1 |
| PI3KC2α(h) | 15 | −5 |
| PI3KC2γ(h) | 27 | −2 |
| PIP4K2α(h) | 1 | −4 |
| PIP5K1α(h) | −2 | −3 |
| PIP5K1γ(h) | −8 | −5 |

Example 137

The compounds disclosed showed strong kinase inhibition for a wide range of kinases (Table 4 and 5).

Table 4 representative 1050 data for the inhibition of selected kinase.

| Example (compound) No. | IC50 (nM) | | | | | | |
|---|---|---|---|---|---|---|---|
| | Abl (h) | Auroro-A (h) | cSrc (h) | Flt3 (h) | KDR (h) | FGFR1 (h) | Ret (h) |
| 10 | 0.5 | 2 | 3 | 11 | — | 1 | 2 |
| 11 | 0.5 | <0.1 | 3 | 12 | 12 | 0.5 | 2 |
| 12 | 0.5 | 2 | 2 | 0.3 | — | — | 1 |
| 68 | 0.3 | 10 | 2 | 4 | 12 | 0.6 | 2 |
| 82 | 0.2 | 4 | 2 | 6 | 11 | 0.6 | 1 |
| 88 | 1 | 5 | 4 | 8 | 44 | 0.2 | 2 |

Compound 53 showed strong kinase inhibition for a wide range of kinases (Table 5), including mutant kinases wherein the mutations thought to be critical for their transformation of the cancer cells they isolated from were tested and, in particular, mutant abl kinases for which no inhibitors were known.

TABLE 5

Summary of kinase inhibition of Compound 53.

| Kinase | IC$_{50}$ (nM) |
|---|---|
| Aurora-A | 4.0 |
| cSrc | 2.0 |
| Flt3 | 13.0 |
| VEGFR1 | 3.0 |
| VEGFR2 | 16.0 |
| VEGFR3 | 2.0 |
| FGFR1 | 0.5 |
| FGFR2 | 2.0 |
| FGFR3 | 1.0 |
| FGFR4 | 13.0 |
| Ret | 2.0 |
| Ret(V804L mutation) | 10.0 |
| Ret(V804M mutation) | 6.0 |
| Abl | 0.6 |
| Abl(T315I) | 0.5 |
| Abl (H396P) | <0.1 |
| Abl(M351T) | 0.7 |
| Abl (Q252H) | 0.5 |
| Abl (Y253F) | 0.5 |

Example 138

Compound 53 was also tested for its antiproliferative potential using cell lines from the NCI 60 cancer cell line panel.

The NCI-60 DTP Human Tumor Cell Line Panel was used to further evaluate the biochemistry of Compound 53 (see Shoemaker: *The NCI60 human tumour cell line anticancer drug screen*, Nature Reviews Cancer 6, 813-823 (1 Oct. 2006)).

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 µL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 µg/ml gentamicin. Additional four, 10-fold or ½ log serial dilutions are made to provide a total of five drug concentrations plus control. Aliquots of 100 µl of these different drug dilutions are added to the appropriate microtiter wells already containing 100 µl of medium, resulting in the required final drug concentrations.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 µl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 µl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentrations levels. Percentage growth inhibition is calculated as:

[(Ti−Tz)/(C−Tz)]×100 for concentrations for which Ti>/=Tz

[(Ti−Tz)/Tz]×100 for concentrations for which Ti<Tz.

Three dose response parameters are calculated for each experimental agent. Growth inhibition of 50% (GI50) is calculated from [(Ti−Tz)/(C−Tz)]×100=50, which is the drug concentration resulting in a 50% reduction in the net protein increase (as measured by SRB staining) in control cells during the drug incubation.

As shown in Table 6, Compound 53 demonstrated the growth inhibition ($GI_{50}$) ranging from 0.01 to 1.89 µM.

TABLE 6

In-Vitro Testing Results for Compound 53.

| Caner type | Panel/Cell Line | GI50 (Molar) |
|---|---|---|
| Leukemia | CCRF-CEM | <1.00E−8 |
| | HL-60(TB) | 1.43E−6 |
| | K-562 | <1.00E−8 |
| | MOLT-4 | 4.81E−8 |
| | RPMI-8226 | 1.89E−6 |
| Non-Small Cell Lung Cancer | A549/ATCC | 3.88E−7 |
| | HOP-62 | 9.14E−8 |
| | HOP-92 | 2.24E−8 |
| | NCI-H226 | <1.00E−8 |
| | NCI-H23 | 1.53E−7 |
| | NCI-H322M | 9.15E−7 |
| | NCI-H460 | 8.69E−8 |
| | NCI-H522 | 7.22E−8 |
| Colon Cancer | COLO 205 | 8.59E−8 |
| | HCC-2998 | 1.42E−6 |
| | HCT-116 | 4.01E−8 |
| | HCT-15 | 3.97E−7 |
| | HT29 | 9.63E−8 |
| | KM12 | <1.00E−8 |
| | SW-620 | 4.41E−8 |
| CNS Cancer | SF-268 | 8.77E−8 |
| | SF-295 | 9.10E−8 |
| | SF-539 | 6.58E−8 |
| | SNB-19 | 2.05E−7 |
| | SNB-75 | 1.58E−8 |
| | U251 | 1.03E−7 |
| Melanoma | LOX IMVI | 3.43E−8 |
| | MALME-3M | 1.32E−7 |
| | M14 | 1.66E−7 |
| | MDA-MB-435 | 3.54E−7 |
| | SK-MEL-2 | 1.42E−6 |
| | SK-MEL-28 | 3.42E−7 |
| | SK-MEL-5 | 1.27E−6 |
| | UACC-257 | 3.88E−7 |
| | UACC-62 | 5.02E−7 |
| Ovarian Cancer | IGROV1 | 4.72E−8 |
| | OVCAR-3 | 1.07E−6 |
| | OVCAR-4 | 1.55E−6 |
| | OVCAR-5 | 1.71E−7 |
| | OVCAR-8 | 1.87E−7 |
| | NCI/ADR-RES | 1.54E−6 |
| | SK-OV-3 | 4.21E−7 |
| Renal Cancer | 786-0 | 9.72E−8 |
| | A498 | <1.00E−8 |
| | ACHN | 1.90E−7 |
| | CAKI-1 | 9.01E−7 |
| | RXF 393 | 1.84E−8 |
| | SN12C | 4.87E−8 |
| | UO-31 | 8.10E−8 |
| Prostate Cancer | PC-3 | 1.27E−6 |
| | DU-145 | 2.88E−7 |
| Breast Cancer | MCF7 | <1.00E−8 |
| | MDA-MB-231/ATCC | 2.27E−7 |
| | HS 578T | 1.30E−8 |
| | BT-549 | 2.68E−7 |
| | T-47D | 1.03E−6 |
| | MDA-MB-468 | 3.92E−8 |

Compound 53 demonstrated strong antiproliferative activity, and this anti-proliferative effect was seen a range of cell lines including cell lines from leukemia, lung, colon, CNS, renal and breast carcinomas.

Example 139

This example illustrated the proliferating cell growth inhibition of selected compounds from this invention. To do this, the cells were seeded into fresh Iscove's growth medium at a density of 0.4e6 cells/ml and grown in log phase for 24 hr. Cells were then resuspended in their fresh respective growth media at $0.1e^6$ cells/ml and plated into 384 well black, clear-bottom microplates at 36 μl/well. Test compounds and controls were initially dissolved in DMSO at the desired concentration, then serially diluted to the assay buffer. These solutions were added and cells were incubated for 72 hours at 37° C. CellTiterBlue (Promega cat# G7572) was added on the Beckman FX. Plates were returned to the 37° C. $CO_2$ incubator for 4 hr and then fluorescence was determined on the Victor plate reader. Data were processed using Microsoft Excel, and $GI_{50}$ values were generated using Prism (GraphPad Software, San Diego, Calif.).

Table 7 shows representative $GI_{50}$ data for the cell growth inhibition of K562, TT, KU812, MV4.11, RS4.11, AN3.CA and Kato III proliferations.

| Example (compound) No. | $GI_{50}$ (nM) | | | | | | |
|---|---|---|---|---|---|---|---|
| | K562 | TT | KU812 | MV4.11 | RS4.11 | AN3.CA | Kato III |
| 10 | 0.19 | 8.3 | <0.025 | 0.19 | 3.22 | 3.00 | 0.07 |
| 11 | 0.41 | — | 1.61 | 0.29 | 3.16 | — | — |
| 12 | 0.28 | — | 0.27 | 0.41 | 3.22 | — | — |
| 53 | 0.69 | 3.5 | 0.24 | 0.15 | 10.98 | 0.78 | 0.06 |
| 68 | 0.26 | 1.9 | — | 0.16 | — | 0.88 | — |
| 82 | 0.31 | — | 0.75 | 0.28 | 2.65 | — | — |
| 83 | 0.55 | — | 0.67 | 0.40 | 3.30 | — | — |
| 88 | 0.60 | 3.4 | 0.71 | 0.16 | 3.71 | 0.31 | 0.06 |
| 90 | 0.85 | 3.8 | 0.90 | 0.13 | 5.07 | 2.00 | — |

Example 140

This example illustrated antitumor activities of Compound 10 and 11 in human K562 chronic myelogenous leukemia (CML) xenograft model in female SCID mice.

Four to six animals were randomly assigned to study groups. Each animal was weighed, and then injected subcutaneously in the left and right flank area with 0.1 ml of $8.0 \times 10^7$ K562 cells per mL.

Each test or control animal was on a 5-day on, two-day off for two cycles treatment schedule. Tumor growth was measured with a digital hand held caliper twice weekly (once tumor emerges) prior to the first dosing and then two to three times weekly until euthanized. Animals were weighed prior to tumor cell injection, prior to dosing, two to three times weekly with tumor growth measurements, and prior to euthanasia. The results are shown in FIGS. 60 to 63. The results show that Compound 10 and 11 have a strong anti-tumor effect against CML in this model system and no body weight lost.

On the appropriate days, each animal in an appropriate group will receive a specific amount of test article either at 75 or 100 mg/kg, and the dosing volume is 10 ml/kg by oral gavage as indicated. Dosing schedule will be once daily for 10 days (qd×10, 5 days on and 2 days off for 2 cycles).

Figure 64:
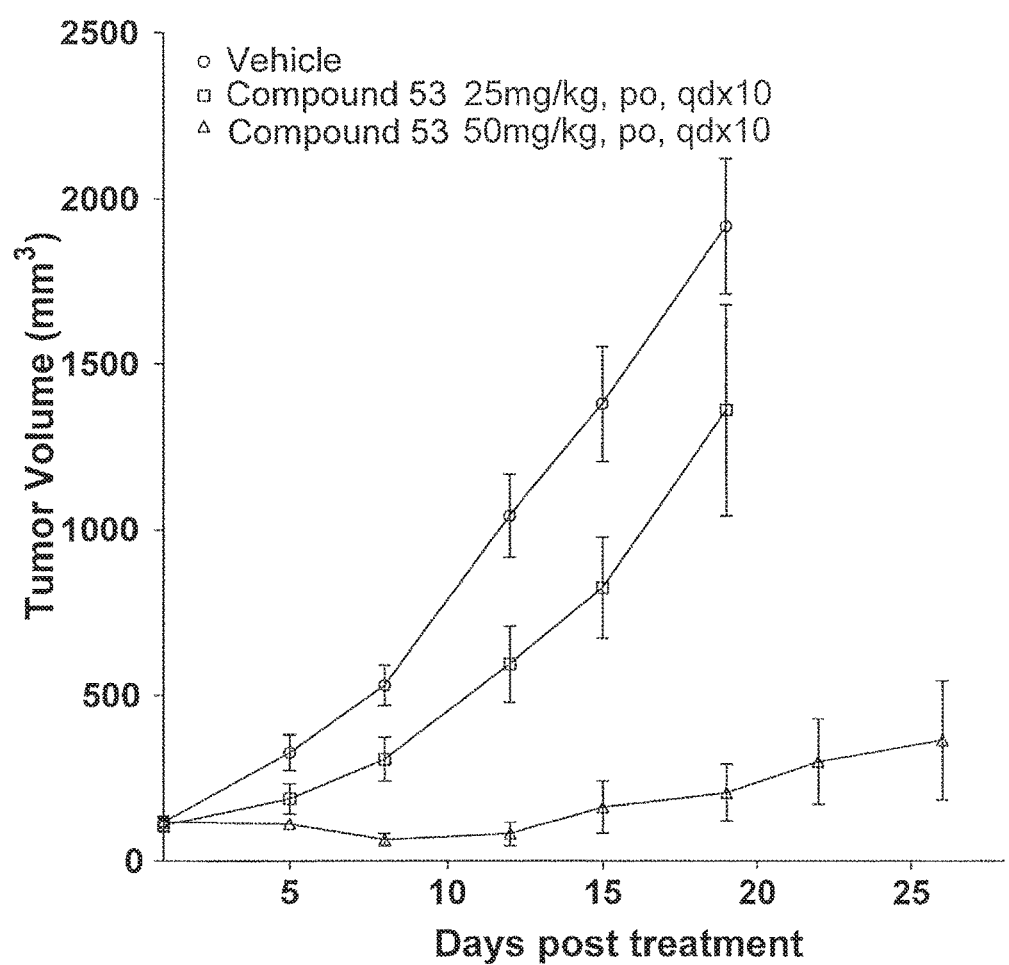
FIG. 64 depicts Compound 53 Inhibits Tumor Growth in K562 Human Chronic Myeloid Leukemia Xenograft (PO).

Compound 53 was similarly tested and shown to have an anti-tumor effect in the in K562 Human Chronic Myeloid Leukemia Xenograft model in mice (FIG. 64).

Example 141

This example assesses Compound 10, 53 and 88's anti-tumor activity using a SCID mouse xenograft models for TT human Thyroid carcinoma xenograft (FIGS. 65 to 69.)

Figure 65:
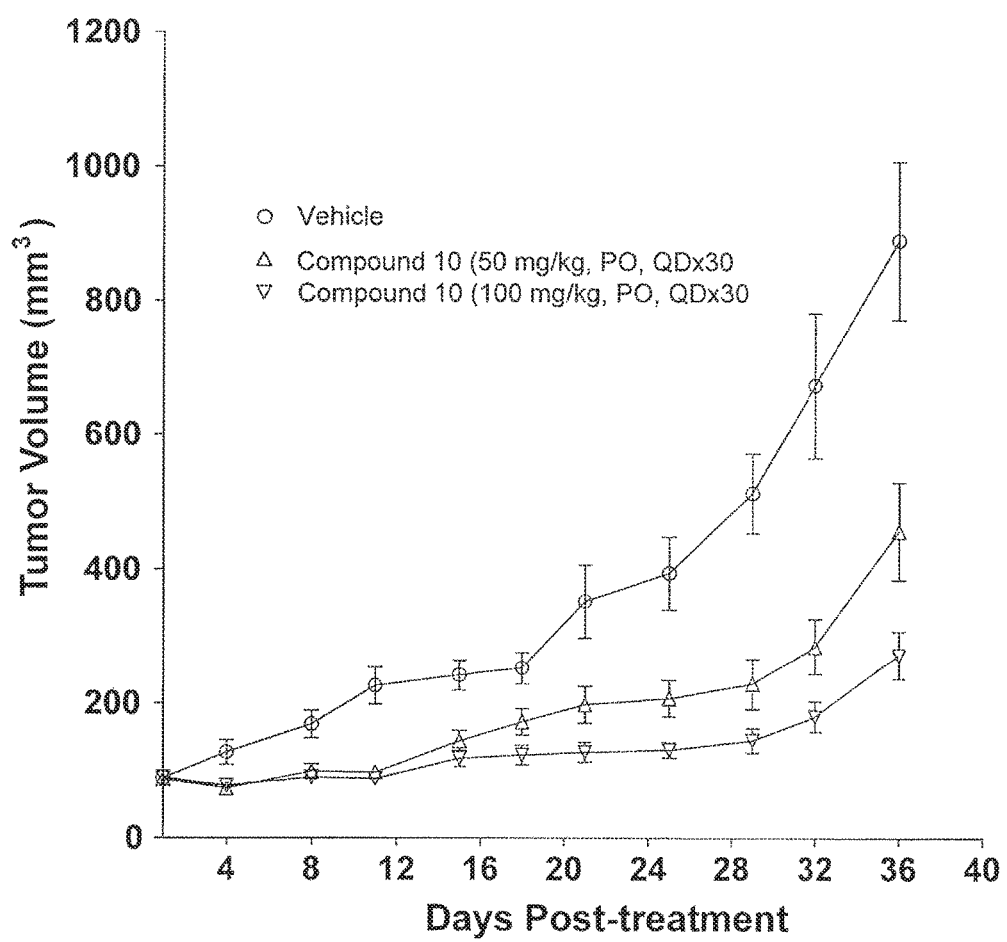
FIG. 65 depicts Compound 10 Inhibits Tumor Growth in TT Human Thyroid Carcinoma Xenograft (PO).
Figure 66:
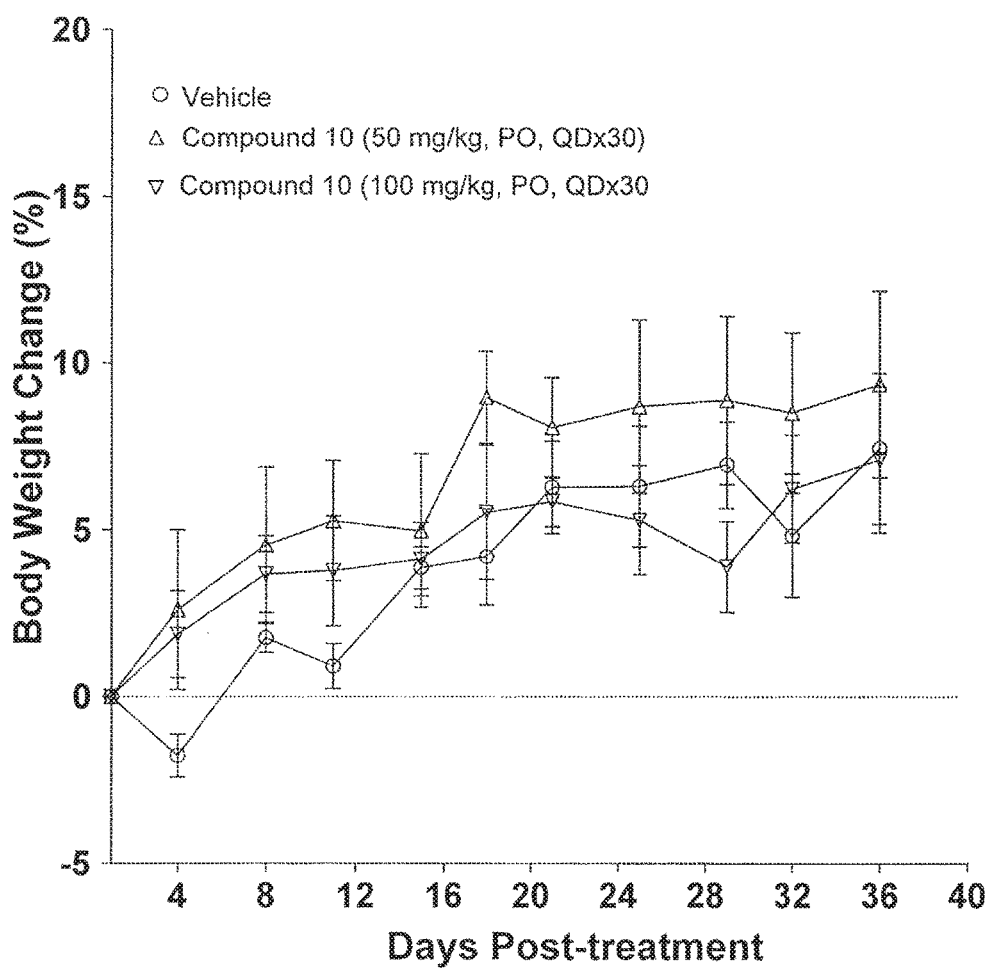
FIG. 66 depicts Body weight change for Compound 10 in Tumor Growth in TT Human Thyroid Carcinoma Xenograft model in nude mice (PO).
Figure 67:
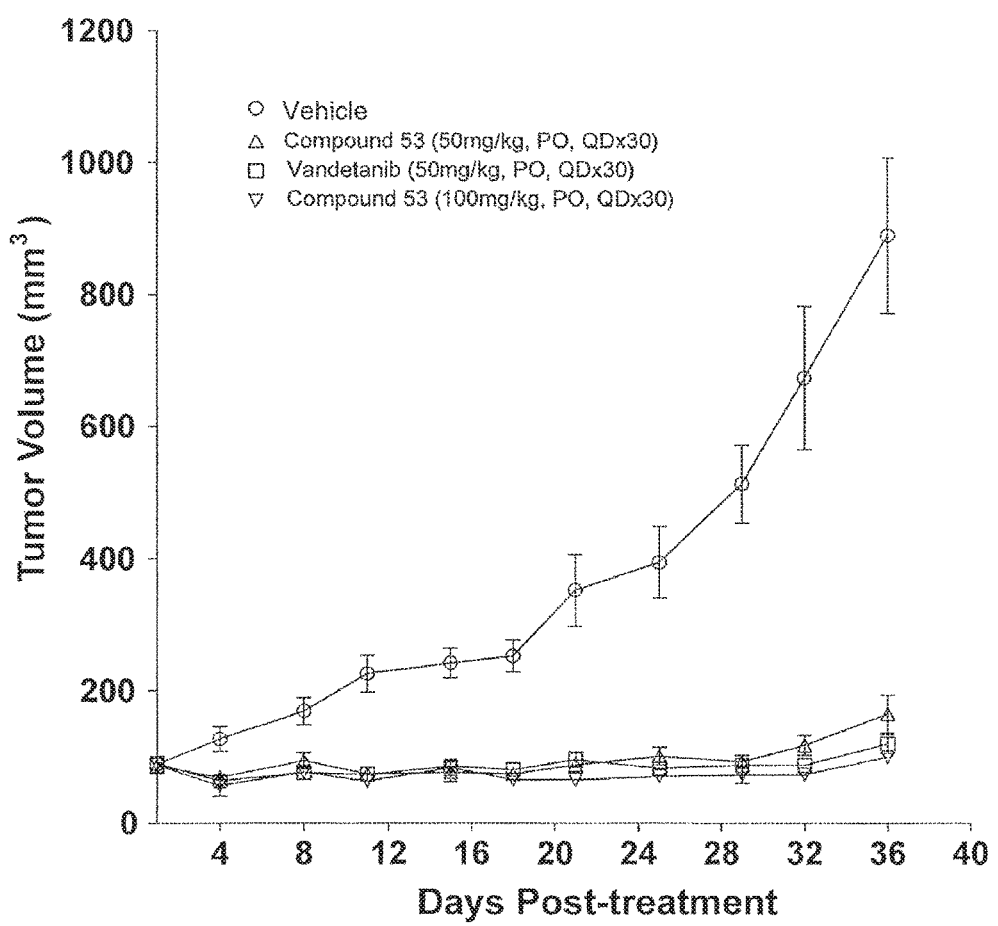
FIG. 67 depicts Compound 53 Inhibits Tumor Growth in TT Human Thyroid Carcinoma Xenograft (PO) in nude mice.
Figure 68:
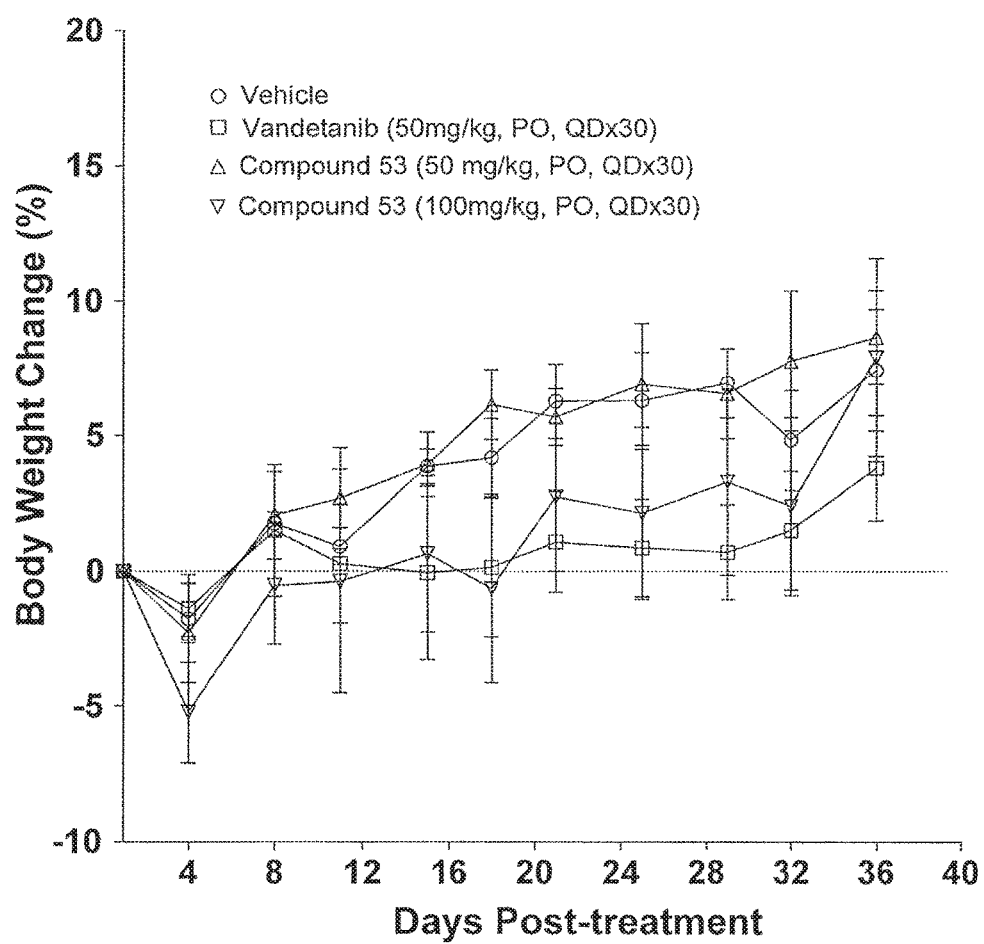
FIG. 68 depicts Body weight change for Compound 53 in Tumor Growth in TT Human Thyroid Carcinoma Xenograft model in nude mice (PO).
Figure 69:
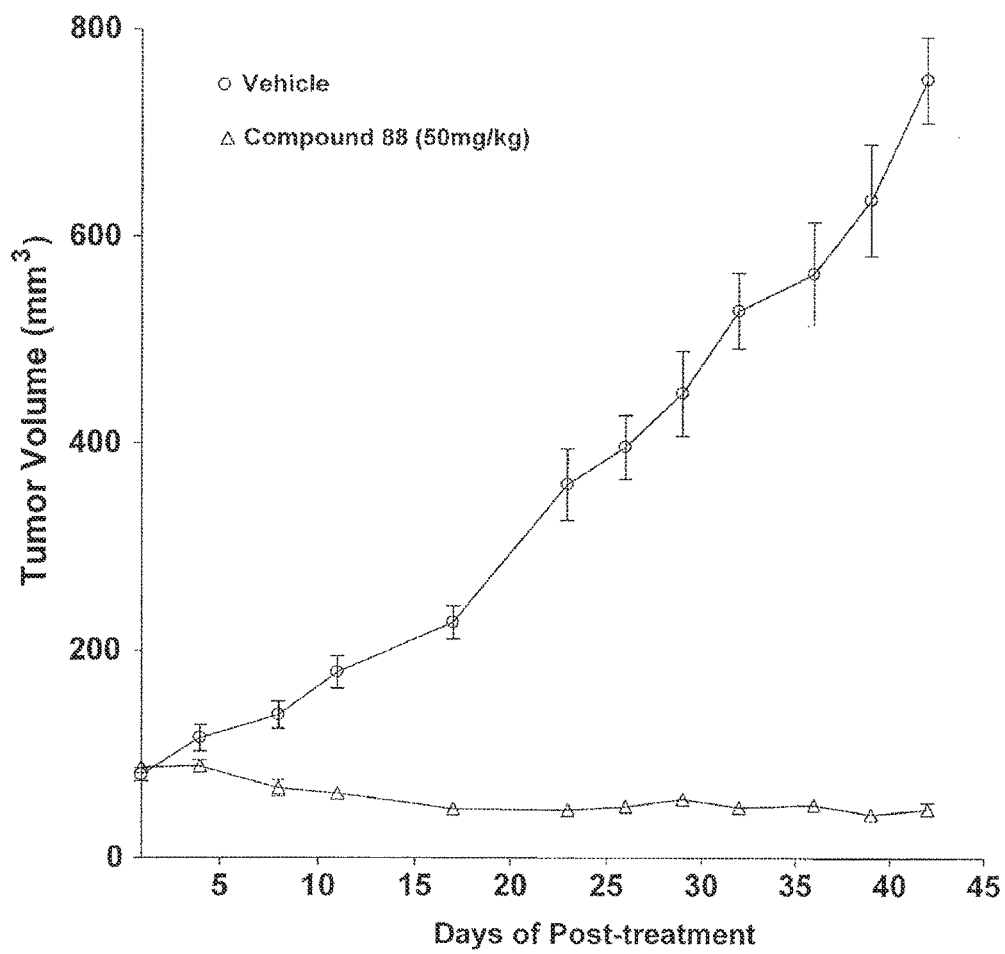
FIG. 69 depicts Compound 88 Inhibits Tumor Growth in TT Human Thyroid Carcinoma Xenograft.

Compound 10 was tested and shown to have an anti-tumor effect in TT human Thyroid carcinoma xenograft (FIGS. 65 and 66). On the appropriate days, each animal in an appropriate group will receive a specific amount of Compound 10 either at 50 or 100 mg/kg, and the dosing volume is 10 ml/kg by oral gavage as indicated. Dosing schedule will be once daily for 30 days.

On the appropriate days, each animal in an appropriate group will receive a specific amount of Compound 53 either at 50 or 100 mg/kg, and the dosing volume is 10 ml/kg by oral gavage as indicated. Dosing schedule will be once daily for 30 days.

On the appropriate days, each animal in an appropriate group will receive a specific amount of Compound 88 either at 50 mg/kg, and the dosing volume is 10 ml/kg by oral gavage as indicated. Dosing schedule will be once daily for 30 days.

Example 142

The objective of the first study was to evaluate antitumor activities of the novel multiple-kinase inhibitor Compounds 11, 68, and 82 against human MV411 human acute myelogenous leukemia (AML) xenograft model in female SCID mice.

Four or six animals were randomly assigned to each study group. Each animal was injected subcutaneously in the left and right flank area with 0.1 ml of $1.0 \times 10^8$ MV411 cells per mL.

Each test or control animal was placed on a 5-day on, two-day off for two cycles of vehicle negative control or 25, 50 mg/kg of compound. Tumor growth was measured with a digital hand held caliper twice weekly (once tumor emerges) prior to the first dosing and then two to three times weekly until euthanized. Animals were weighed prior to tumor cell injection, prior to dosing, two to three times weekly with tumor growth measurements, and prior to euthanasia.

Figure 70:
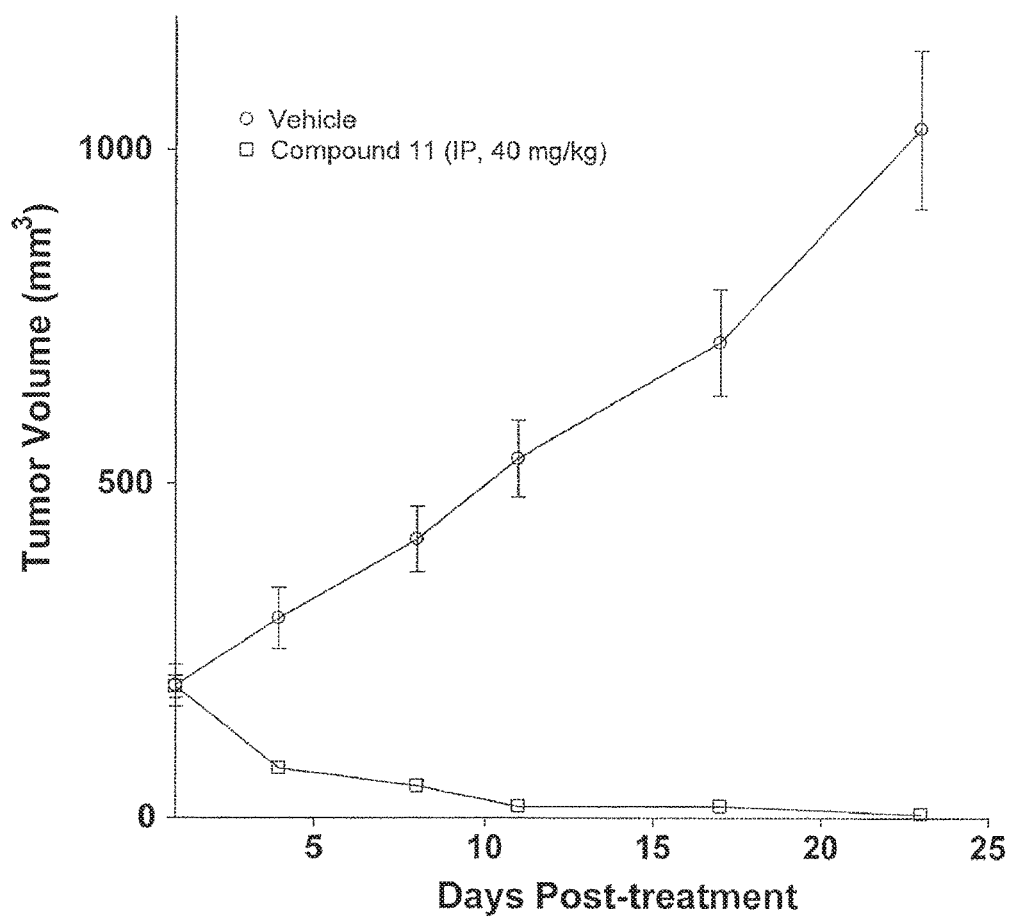
FIG. 70 depicts Compound 11 Inhibits Tumor Growth in MV-4-11 Human Acute Myeloid Leukemia (AML) Xenograft Model (IP).
Figure 71:
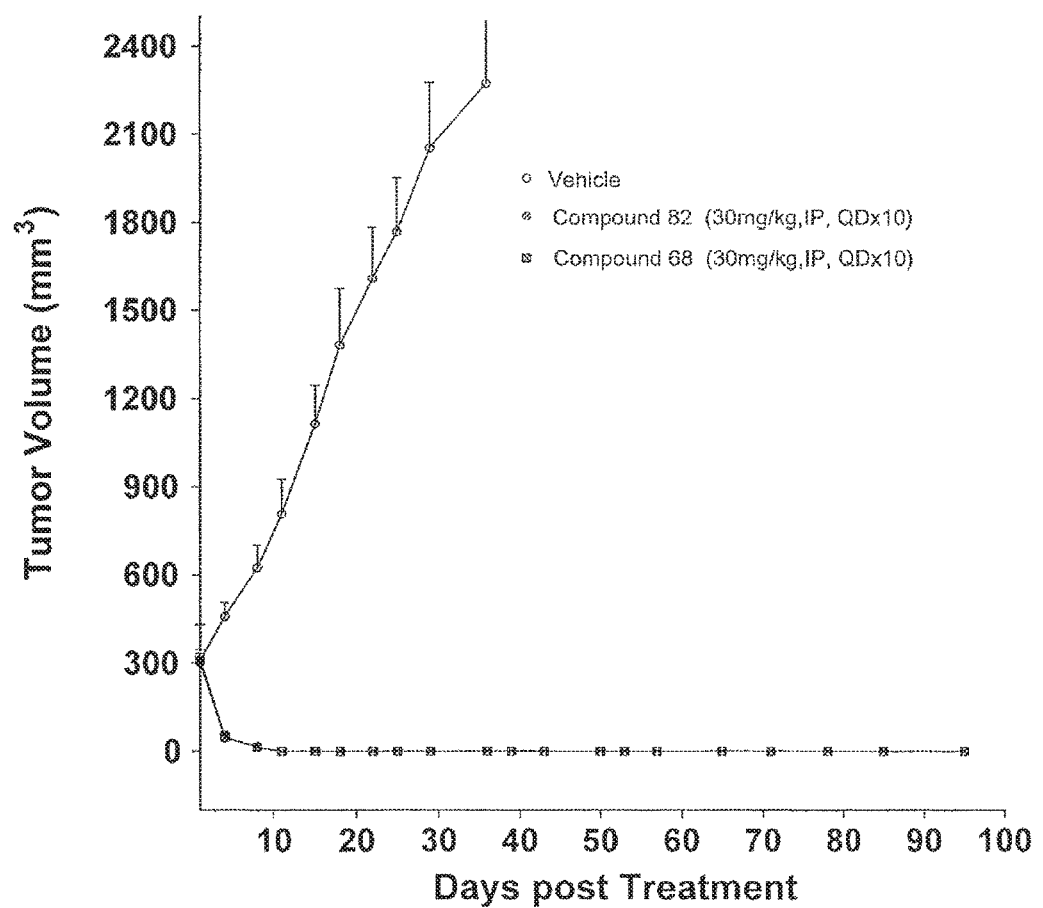
FIG. 71 depicts Compound 68 and Compound 82 Inhibits Tumor Growth in MV-4-11 Human Acute Myeloid Leukemia (AML) Xenograft Model.

The results are shown in FIGS. 70-71. The results indicate that Compounds 11, 68 and 82 have a strong anti-tumor effect against AML with minimal body weight lost.

Example 143

The objective of the third study was to evaluate antitumor activities of novel multiple-kinase inhibitor Compound 10, 11, 12, 53, 68, 82, 83, 88, and 90 in human MIAPaCa-2 pancreatic carcinoma xenograft in athymic nude-Faxn1 mice.

Four animals were randomly assigned to study groups. Each animal was weighed, and then injected subcutaneously in the left and right flank area with 0.1 ml of $5.0 \times 10^7$ MIAPaCa-2 cells per mL.

Each test or control animal was on a 5-day on, two-day off for three cycles treatment schedule with negative control vehicle or 40 mg/kg of Compound 10, 11, 12, 53, 68, 82, 83, 88 and 90. Tumor growth was measured with a digital hand held caliper twice weekly (once tumor emerges) prior to the first dosing and then two to three times weekly until euthanized.

Figure 72:
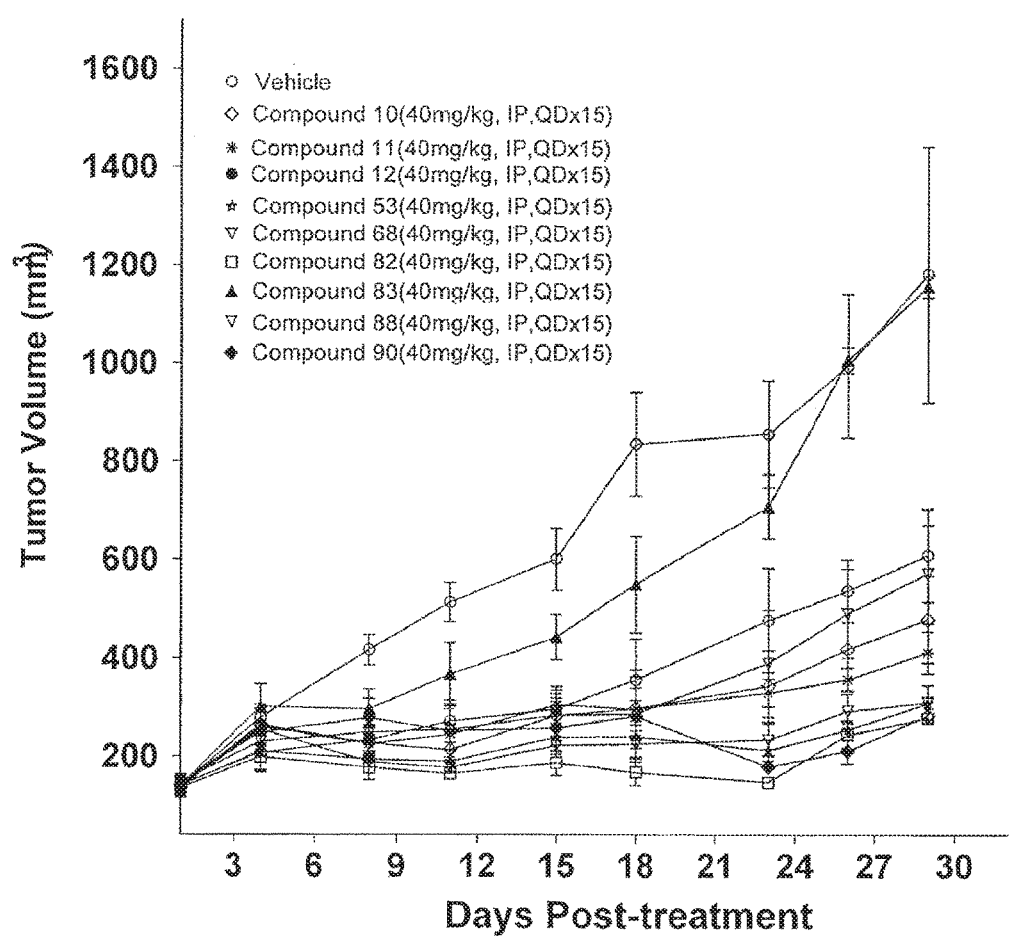
FIG. 72 depicts Compounds Inhibits Tumor Growth of MiaPaCa-2 Human Pancreatic Carcinoma Xenograft (IP) in nude mice (CM-X01303).
Figure 73:
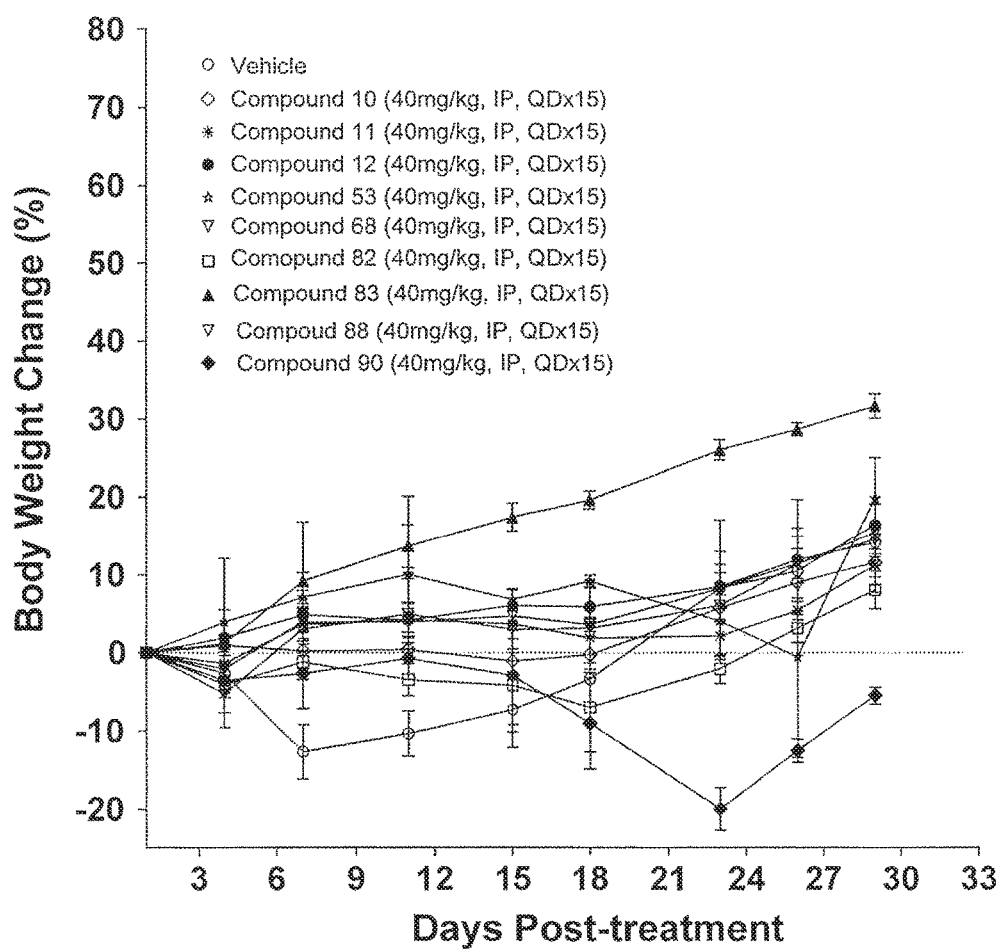
FIG. 73 depicts Body weight change of Compounds for Tumor Growth of MiaPaCa-2 Human Pancreatic Carcinoma Xenograft (IP) in nude mice.
Figure 74:
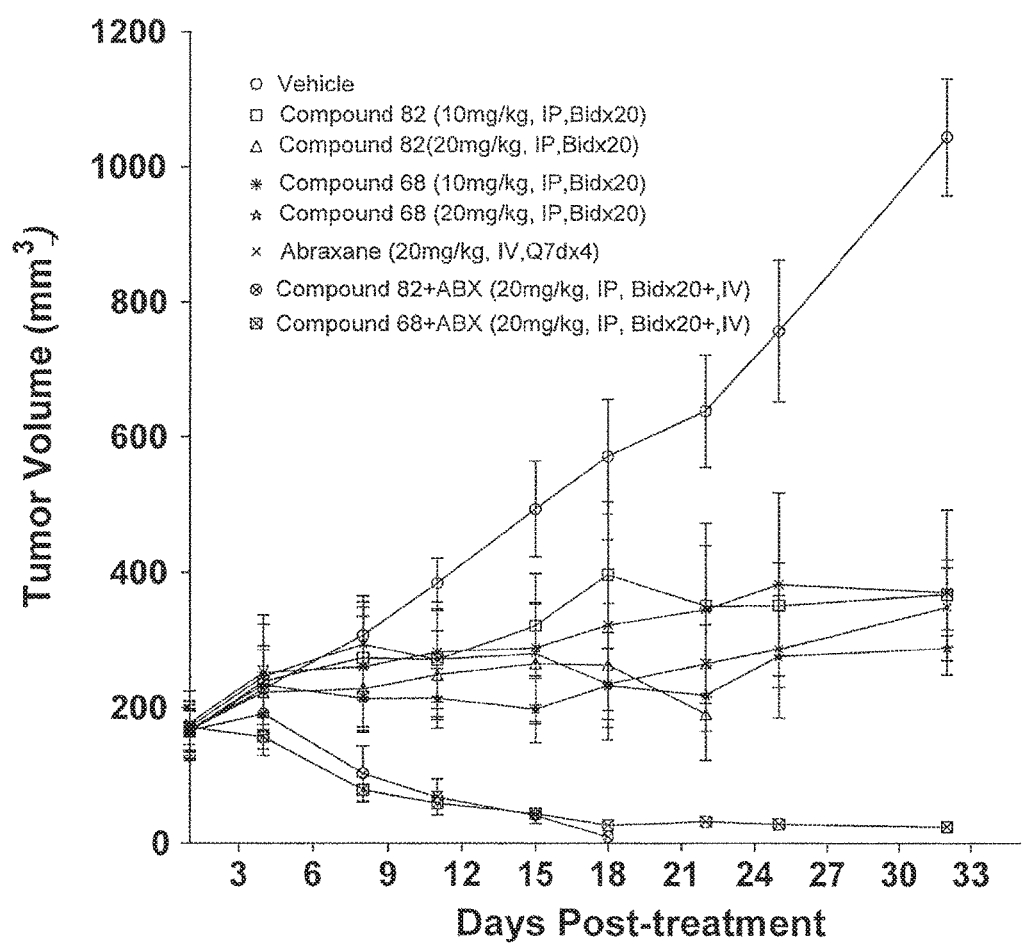
FIG. 74 depicts Efficacy of Compound 68 and 82 as single agents and their combination with Abraxane in MiaPaCa-2 Human Pancreatic Carcinoma Xenograft in nude mice.
Figure 75:
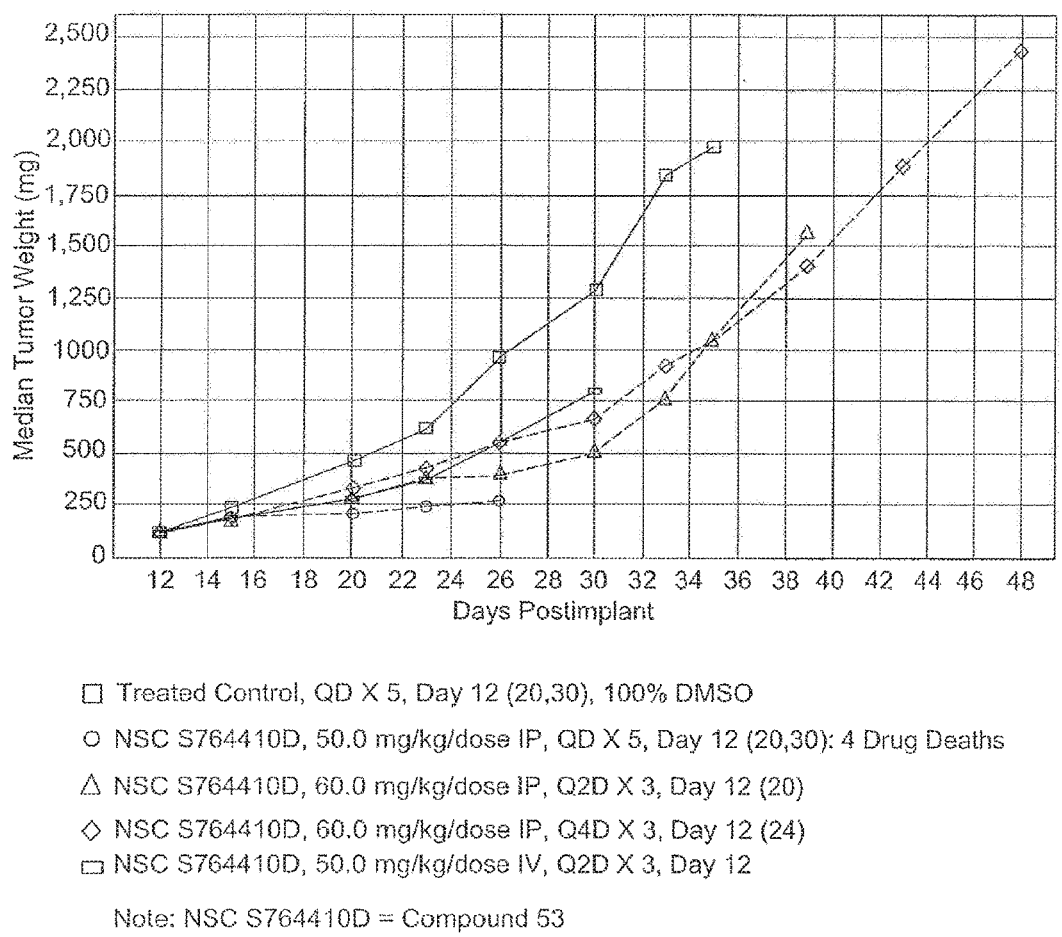
FIG. 75 depicts efficacy of Compound 53 in U251 Human CNS Carcinoma Xenograft in nude mice.

The results are shown in FIGS. 72, 73, and 74 which indicate that Compounds 10, 11, 12, 53, 68, 82, 83, 88, and 90 have a strong anti-tumor effect against pancreatic carcinoma cells in this model system. The combination of Compounds 68 and 82 with Abraxane showed significant anti-tumor efficacy.

Example 144

The in vivo anti-tumor efficacy of Compound 53 has been studied using U251 human CNS tumor xenograft model in nude mice (FIG. 16). This was a subcutaneous early stage experiment (defined as a median tumor staging size less than 200 mg). Compound 53 or vehicle control was administered by Intraperitoneal injection for various days with different doses. Compound 53 showed significant antitumor activities at dose of 60 mg/kg with the value of treat/control (T/C), 40% on day 30 when used dosing schedule of Q2Dx3. Compound 53 was well tolerated at this doses with maximum body weight lose 3.4%.

Example 145

Figure 76:
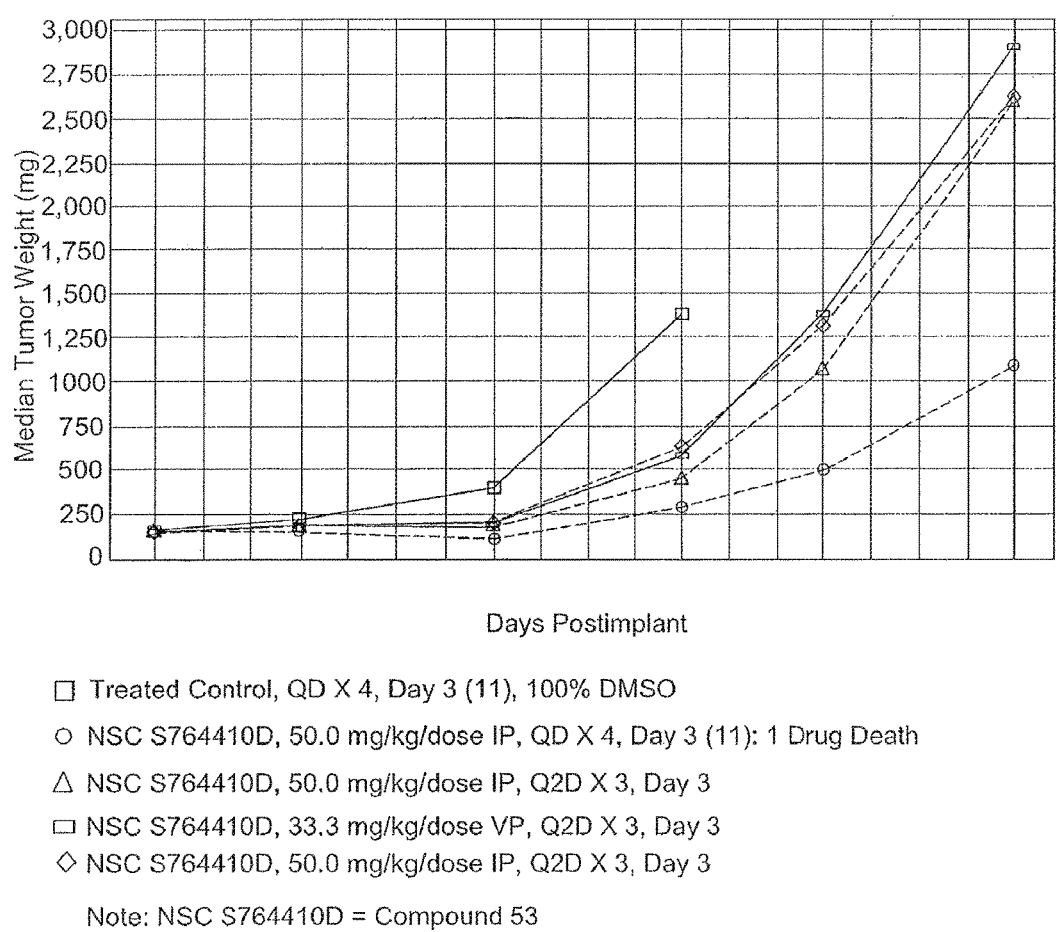
FIG. 76 depicts efficacy of Compound 53 in SC LOX IMVI Human Melanoma Carcinoma Xenograft in nude mice.

The in vivo anti-tumor efficacy of Compound 53 has been studied using SC LOX IMVI Melanoma Xenografts model in nude mice (FIG. 76). This was a subcutaneous early stage experiment (defined as a median tumor staging size less than 200 mg). Compound 53 or vehicle control was administered by Intraperitoneal injection for various days with different doses. Compound 53 showed significant antitumor activities at dose of 50 mg/kg with the value of treat/control (T/C), 21% on day 13 when used dosing schedule of QDx4. Compound 53 was well tolerated at this doses with maximum body weight lose 10.3%.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A compound of the formula (I)

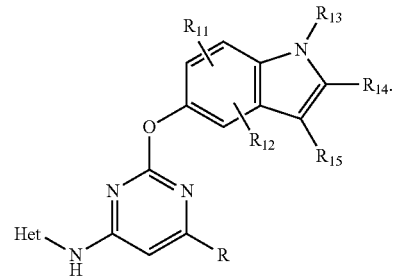

or its pharmaceutically acceptable salts, hydrates, solvates, and individual diastereomers thereof, wherein;
R is selected from:
(i) hydrogen, amino, alkyl amino;
(ii) C1-C6 alkyl, C2-C6 alkenyl, C2-C6 alkynyl;
(iii) K—Ar;
Ar represents heteroaryl or aryl, each of which is substituted with from 0 to 4 substituents independently chosen from:
(1) halogen, hydroxy, amino, amide, cyano, —COOH, —SO2NH2, oxo, nitro and alkoxycarbonyl; and
(2) C1-C6 alkyl, C1-C6 alkoxy, C3-C10 cycloalkyl, C2-C6 alkenyl, C2-C6 alkynyl, C2-C6 alkanoyl, C1-C6 haloalkyl, C1-C6 haloalkoxy, mono- and di-(C1-C6 alkyl)amino, C1-C6 alkylsulfonyl, mono- and di-(C1-C6alkyl) sulfonamido and mono- and di-(C1-C6 alkyl) aminocarbonyl; phenyl C0-C4 alkyl and (4- to 7-membered heterocycle) C0-C4 alkyl, each of which is substituted with from 0 to 4 secondary substituents independently chosen from halogen, hydroxy, cyano, oxo, imino, C1-C4 alkyl, C1-C4 alkoxy and C1-C4 haloalkyl;
K is selected from
a) O, S, SO, SO2;
b) (CH2)m, m=0-3, —O(CH2)p, p=1-3, —S(CH2)p, p=1-3, —N(CH2)p, p=1-3, —(CH2)pO, p=1-3;
c) NR1
R1 represents hydrogen, alkyl, cycloalkyl, alkenyl, alkynyl, alkylthio, aryl, arylalkyl;
(iv) groups of the formula (Ia);

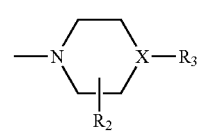

(Ia)
wherein:
R2 represents hydrogen, C1-C4 alkyl, oxo;
X is CH, when R3 is hydrogen; or X—R3 is O; or X is N, R3 represents groups of hydrogen, C1-C6 alkyl, C2-C6 alkenyl, C2-C6 alkynyl, C3-C10 aryl or heteroaryl, (C3-C7cycloalkyl)C1-C4alkyl, C1-C6 haloalkyl, C1-C6 alkoxy, C1-C6 alkylthio, C2-C6 alkanoyl, C1-C6 alkoxycarbonyl, C2-C6 alkanoyloxy, mono- and di-(C3-C8 cycloalkyl)aminoC0-C4alkyl, (4- to 7-membered heterocycle)C0-C4alkyl, C1-C6 alkylsulfonyl, mono- and di-(C1-C6 alkyl) sulfonamido, and mono- and di-(C1-C6alkyl)aminocarbonyl, each of which is substituted with from 0 to 4 substituents independently chosen from halogen, hydroxy, cyano, amino, —COOH and oxo;

Het is selected from any heterocycle, which is substituted with from 0 to 4 substituents independently chosen from:
(i) C1-C6 alkyl, C2-C6 alkenyl, C2-C6 alkynyl;
(ii) halogen, hydroxy, amino, amide, cyano, —COOH, —SO2NH2, oxo, nitro and alkoxycarbonyl,
(iii) aryl;

R11 and R12 are independently selected from: Hydrogen, F, Cl, Br, CN, C1-C4 alkyl, C1-C6 alkoxy;

R13, R14 and R15 are independently selected from Hydrogene, C1-C4 alkyl, C2-C6 alkenyl, C2-C6 alkynyl, C3-C10 aryl or heteroaryl, C1-C6 alkoxy, C1-C6 alkylthio, C2-C6 alkanoyl, C1-C6 alkoxycarbonyl, C2-C6 alkanoyloxy.

2. A pharmaceutical composition comprising at least one compound of claim 1 or its pharmaceutically acceptable salts, hydrates, solvates, and individual diastereomers thereof, and a pharmaceutically acceptable carrier.

3. The composition according to claim 2, further comprising one or more additional therapeutic agents.

4. The compound with the formula:

or its pharmaceutically acceptable salts, hydrates, solvates, and individual diastereomers thereof.

5. A pharmaceutical composition comprising the compound of claim 4 or its pharmaceutically acceptable salts, hydrates, solvates, and individual diastereomers thereof, and a pharmaceutically acceptable carrier.

6. The composition according to claim 5, further comprising one or more additional therapeutic agents.

7. The compound with the formula:

or its pharmaceutically acceptable salts, hydrates, solvates, and individual diastereomers thereof.

8. A pharmaceutical composition comprising the compound of claim 7 or its pharmaceutically acceptable salts, hydrates, solvates, and individual diastereomers thereof, and a pharmaceutically acceptable carrier.

9. The composition according to claim 8, further comprising one or more additional therapeutic agents.

10. The compound with the formula:

or its pharmaceutically acceptable salts, hydrates, solvates, and individual diastereomers thereof.

11. A pharmaceutical composition comprising the compound of claim 10 or its pharmaceutically acceptable salts, hydrates, solvates, and individual diastereomers thereof, and a pharmaceutically acceptable carrier.

12. The composition according to claim 11, further comprising one or more additional therapeutic agents.

13. The compound with the formula:

or its pharmaceutically acceptable salts, hydrates, solvates, and individual diastereomers thereof.

14. A pharmaceutical composition comprising the compound of claim 13 or its pharmaceutically acceptable salts, hydrates, solvates, and individual diastereomers thereof, and a pharmaceutically acceptable carrier.

15. The composition according to claim 14, further comprising one or more additional therapeutic agents.

16. The compound with the formula:

or its pharmaceutically acceptable salts, hydrates, solvates, and individual diastereomers thereof.

17. A pharmaceutical composition comprising the compound of claim 16 or its pharmaceutically acceptable salts, hydrates, solvates, and individual diastereomers thereof, and a pharmaceutically acceptable carrier.

18. The composition according to claim 17, further comprising one or more additional therapeutic agents.

19. The compound with the formula:

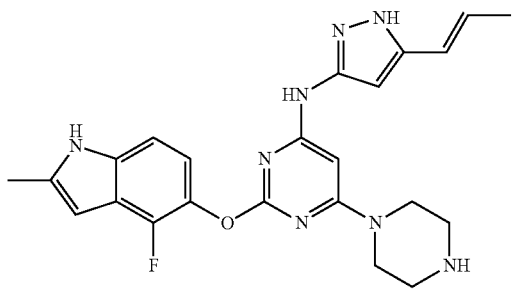 [SMILES: C/C=C/c1cc(Nc2cc(N3CCNCC3)nc(Oc3ccc4[nH]c(C)cc4c3F)n2)n[nH]1]

or its pharmaceutically acceptable salts, hydrates, solvates, and individual diastereomers thereof.

20. A pharmaceutical composition comprising the compound of claim 19 or its pharmaceutically acceptable salts, hydrates, solvates, and individual diastereomers thereof, and a pharmaceutically acceptable carrier.

21. The composition according to claim 20, further comprising one or more additional therapeutic agents.

22. The compound with the formula:

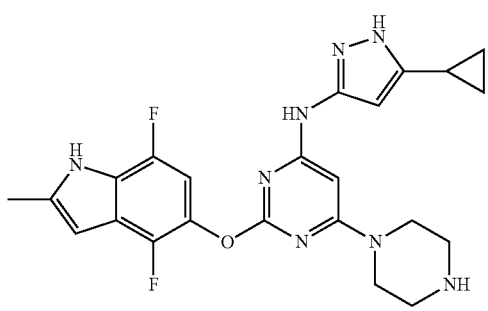 [SMILES: Cc1cc2c(F)c(Oc3nc(Nc4cc(C5CC5)[nH]n4)cc(N4CCNCC4)n3)cc(F)c2[nH]1]

or its pharmaceutically acceptable salts, hydrates, solvates, and individual diastereomers thereof.

23. A pharmaceutical composition comprising the compound of claim 22 or its pharmaceutically acceptable salts, hydrates, solvates, and individual diastereomers thereof, and a pharmaceutically acceptable carrier.

24. The composition according to claim 23, further comprising one or more additional therapeutic agents.

25. The compound with the formula:

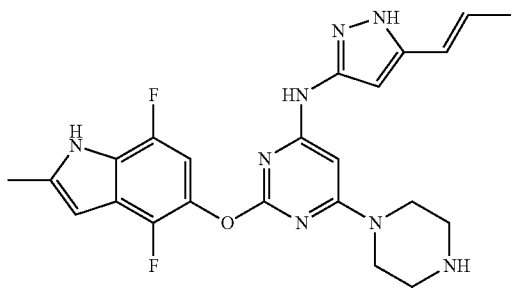 [SMILES: C/C=C/c1cc(Nc2cc(N3CCNCC3)nc(Oc3cc(F)c4[nH]c(C)cc4c3F)n2)n[nH]1]

or its pharmaceutically acceptable salts, hydrates, solvates, and individual diastereomers thereof.

26. A pharmaceutical composition comprising the compound of claim 25 or its pharmaceutically acceptable salts, hydrates, solvates, and individual diastereomers thereof, and a pharmaceutically acceptable carrier.

27. The composition according to claim 26, further comprising one or more additional therapeutic agents.

28. The compound with the formula;

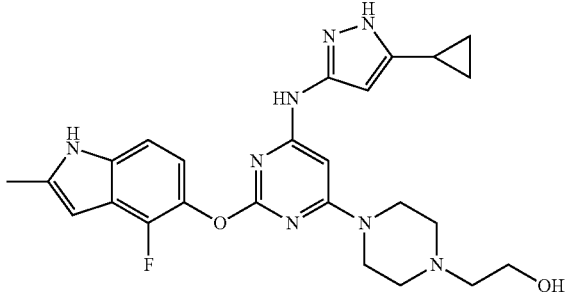 [SMILES: Cc1cc2c(F)c(Oc3nc(Nc4cc(C5CC5)[nH]n4)cc(N4CCN(CCO)CC4)n3)ccc2[nH]1]

or its pharmaceutically acceptable salts, hydrates, solvates, and individual diastereomers thereof.

29. A pharmaceutical composition comprising the compound of claim 28 or its pharmaceutically acceptable salts, hydrates, solvates, and individual diastereomers thereof, and a pharmaceutically acceptable carrier.

30. The composition according to claim 29, further comprising one or more additional therapeutic agents.

31. The compound with the formula:

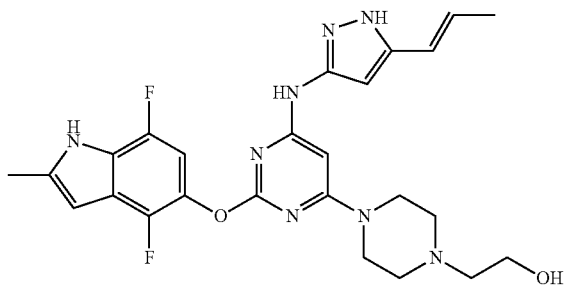 [SMILES: C/C=C/c1cc(Nc2cc(N3CCN(CCO)CC3)nc(Oc3cc(F)c4[nH]c(C)cc4c3F)n2)n[nH]1]

or its pharmaceutically acceptable salts, hydrates, solvates, and individual diastereomers thereof.

32. A pharmaceutical composition comprising the compound of claim 31 or its pharmaceutically acceptable salts, hydrates, solvates, and individual diastereomers thereof, and a pharmaceutically acceptable carrier.

33. The composition according to claim 32, further comprising one or more additional therapeutic agents.

34. The compound with the formula:

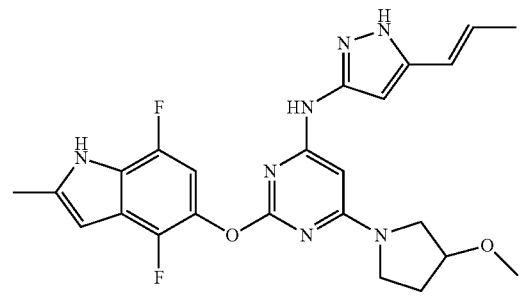

or its pharmaceutically acceptable salts, hydrates, solvates, and individual diastereomers thereof.

35. A pharmaceutical composition comprising the compound of claim 34 or its pharmaceutically acceptable salts, hydrates, solvates, and individual diastereomers thereof, and a pharmaceutically acceptable carrier.

36. The composition according to claim 35, further comprising one or more additional therapeutic agents.

37. A method of inhibiting kinase activity, comprising contacting a kinase with a compound of claim 1 whereby kinase activity is inhibited.

38. A method of treating cancer, comprising contacting the tumor cell with a compound of claim 1, wherein the cancer is a leukemia, lung cancer, colon cancer, CNS cancer, melanoma, ovarian cancer, renal cancer, prostate cancer, or breast cancer.

39. A method of claim 38, in which the concentration of the pharmaceutical composition of resulting in a 50% reduction in the net tumor volume increase in xenograft models is from 0.01, to 1.9 μM.

40. A method of claim 38, in which the leukemia is chronic myeogenous leukemia (CML).

\* \* \* \* \*